US006949105B2

(12) United States Patent
Bryan et al.

(10) Patent No.: US 6,949,105 B2
(45) Date of Patent: Sep. 27, 2005

(54) METHOD AND APPARATUS FOR STEREOTACTIC IMPLANTATION

(75) Inventors: Vincent Bryan, Mercer Island, WA (US); Alex Kunzler, LaQuinta, CA (US); Robert Conta, Mercer Island, WA (US); Randy Allard, Germantown, TN (US); Richard J. Broman, Monroe, WA (US); Anthony Finazzo, Lake Forest Park, WA (US); Carlos E. Gil, Collierville, TN (US); Jeffrey P. Rouleau, Maple Grove, MN (US); Leonard Tokish, Jr., Issaquah, WA (US); David Yager, Monroe, WA (US)

(73) Assignee: SDGI Holdings, Inc., Wilmington, DE (US)

( * ) Notice: Subject to any disclaimer, the term of this patent is extended or adjusted under 35 U.S.C. 154(b) by 149 days.

(21) Appl. No.: 09/923,891

(22) Filed: Aug. 7, 2001

(65) Prior Publication Data

US 2002/0161446 A1 Oct. 31, 2002

Related U.S. Application Data

(63) Continuation-in-part of application No. 09/783,860, filed on Feb. 13, 2001, now abandoned, and a continuation-in-part of application No. 09/783,910, filed on Feb. 13, 2001, now abandoned.
(60) Provisional application No. 60/223,863, filed on Aug. 8, 2000, and provisional application No. 60/265,218, filed on Jan. 31, 2001.

(51) Int. Cl.[7] .............................................. A61B 19/00
(52) U.S. Cl. ..................................................... 606/130
(58) Field of Search .................................. 606/130, 108, 606/79, 80, 61, 86, 96; 604/116, 164.11; 623/17.15, 17.11, 17.16; 128/898; 600/426, 427, 429, 411

(56) References Cited

U.S. PATENT DOCUMENTS

| 2,677,369 A | 5/1954 | Knowles |
| 3,486,505 A | 12/1969 | Morrison |

(Continued)

FOREIGN PATENT DOCUMENTS

| DE | 2263842 | 7/1974 |
| DE | 2804936 | 8/1979 |
| DE | 30 23 353 A1 | 4/1981 |

(Continued)

OTHER PUBLICATIONS

Brain et al.; "The Neurological Manifestations of Cervical Spondylosis;" Brain: A Journal of Neurology, vol. 75; Macmillan & Co.; 1952; pp. 187–225.
Buttner–Janz et al.; "Biomechanics of the SB Charite Lumbar Intervertebral Disc Endoprosthesis;" International Orthopedics; vol. 13; 1989; pp. 173–176.

(Continued)

Primary Examiner—Pedro Philogene
(74) Attorney, Agent, or Firm—Haynes and Boone, LLP

(57) ABSTRACT

The invention relates to a technique for precisely locating a line containing a predetermined point within the surgical site using a series of levels and plumb lines and internal anatomical features of the surgical site, using this location to precisely position and temporarily affix a site preparation scaffold relative to the patient's anatomy so that site preparation instruments can be introduced into the site at precise locations governed by the scaffold geometry and patient anatomy. This precise positioning of the scaffold also provides a way for the surgeon to use patient anatomical features to reliably and precisely prepare the surgical site. Scaffolds having angling features further increase the precise preparation of the surgical site. This increased precision in site preparation increases the probability of a successful procedure, and decreases the likelihood that additional surgery may be needed.

21 Claims, 82 Drawing Sheets

U.S. PATENT DOCUMENTS

| | | |
|---|---|---|
| 3,875,595 A | 4/1975 | Froning |
| 3,876,728 A | 4/1975 | Stubstad |
| 4,023,572 A | 5/1977 | Weigand et al. |
| 4,116,200 A | 9/1978 | Braun et al. |
| 4,179,810 A | 12/1979 | Kirsch |
| 4,309,777 A | 1/1982 | Patil |
| 4,349,921 A | 9/1982 | Kuntz |
| 4,386,602 A * | 6/1983 | Sheldon et al. ............. 600/102 |
| 4,599,086 A | 7/1986 | Doty |
| 4,645,507 A | 2/1987 | Engelbrecht et al. |
| 4,714,469 A | 12/1987 | Kenna |
| 4,743,256 A | 5/1988 | Brantigan |
| 4,757,983 A | 7/1988 | Ray et al. |
| 4,759,766 A | 7/1988 | Buettner-Janz et al. |
| 4,759,769 A | 7/1988 | Hedman et al. |
| 4,766,328 A | 8/1988 | Yang |
| 4,777,942 A | 10/1988 | Frey et al. |
| 4,800,639 A | 1/1989 | Frey et al. |
| 4,834,757 A | 5/1989 | Brantigan |
| 4,863,476 A | 9/1989 | Shepperd |
| 4,863,477 A | 9/1989 | Monson |
| 4,874,389 A | 10/1989 | Downey |
| 4,878,915 A | 11/1989 | Brantigan |
| 4,887,595 A | 12/1989 | Heinig et al. |
| 4,904,260 A | 2/1990 | Ray et al. |
| 4,904,261 A | 2/1990 | Dove et al. |
| 4,908,032 A | 3/1990 | Keller |
| 4,908,036 A | 3/1990 | Link et al. |
| 4,911,718 A | 3/1990 | Lee et al. |
| 4,917,704 A | 4/1990 | Frey et al. |
| 4,932,969 A | 6/1990 | Frey et al. |
| 4,932,975 A | 6/1990 | Main et al. |
| 4,946,378 A | 8/1990 | Hirayama et al. |
| 4,955,908 A | 9/1990 | Frey et al. |
| 4,978,355 A | 12/1990 | Frey et al. |
| 4,997,432 A | 3/1991 | Keller |
| 5,002,576 A | 3/1991 | Fuhrmann et al. |
| 5,015,247 A | 5/1991 | Michelson |
| 5,035,716 A | 7/1991 | Downey |
| 5,047,055 A | 9/1991 | Bao et al. |
| 5,059,193 A | 10/1991 | Kuslich |
| 5,059,194 A | 10/1991 | Michelson |
| 5,071,437 A | 12/1991 | Steffee |
| 5,080,662 A | 1/1992 | Paul |
| 5,084,048 A | 1/1992 | Jacob et al. |
| 5,108,438 A | 4/1992 | Stone |
| 5,122,130 A | 6/1992 | Keller |
| 5,123,926 A | 6/1992 | Pisharodi |
| 5,171,280 A | 12/1992 | Baumgartner |
| 5,171,281 A | 12/1992 | Parsons et al. |
| 5,176,708 A | 1/1993 | Frey et al. |
| 5,192,326 A | 3/1993 | Bao et al. |
| 5,192,327 A | 3/1993 | Brantigan |
| 5,234,431 A | 8/1993 | Keller |
| 5,236,460 A | 8/1993 | Barber |
| 5,246,458 A | 9/1993 | Graham |
| 5,257,998 A * | 11/1993 | Ota et al. .................... 606/130 |
| 5,258,031 A | 11/1993 | Salib et al. |
| 5,261,911 A | 11/1993 | Carl |
| 5,261,913 A | 11/1993 | Marnay |
| 5,306,308 A | 4/1994 | Gross et al. |
| 5,314,477 A | 5/1994 | Marnay |
| 5,314,478 A | 5/1994 | Oka et al. |
| 5,320,644 A | 6/1994 | Baumgartner |
| 5,370,697 A | 12/1994 | Baumgartner |
| 5,383,933 A | 1/1995 | Keller |
| 5,389,101 A * | 2/1995 | Heilbrun et al. ............. 606/130 |
| 5,401,269 A | 3/1995 | Buttner-Janz et al. |
| 5,403,314 A | 4/1995 | Currier |
| 5,425,772 A | 6/1995 | Brantigan |
| 5,425,773 A | 6/1995 | Boyd et al. |
| 5,443,514 A | 8/1995 | Steffee |
| 5,456,719 A | 10/1995 | Keller |
| 5,458,638 A | 10/1995 | Kuslich et al. |
| 5,458,642 A | 10/1995 | Beer et al. |
| 5,484,437 A | 1/1996 | Michelson |
| 5,489,307 A | 2/1996 | Kuslich et al. |
| 5,489,308 A | 2/1996 | Kuslich et al. |
| 5,496,318 A | 3/1996 | Howland et al. |
| 5,507,816 A | 4/1996 | Bullivant |
| 5,514,180 A | 5/1996 | Heggeness et al. |
| 5,527,315 A | 6/1996 | Jeanson et al. |
| 5,534,028 A | 7/1996 | Bao et al. |
| 5,534,029 A | 7/1996 | Shima |
| 5,534,030 A | 7/1996 | Navarro et al. |
| 5,545,229 A | 8/1996 | Parsons et al. |
| 5,549,679 A | 8/1996 | Kuslich |
| 5,556,431 A | 9/1996 | Buttner-Janz |
| 5,562,738 A | 10/1996 | Boyd et al. |
| 5,571,189 A | 11/1996 | Kuslich |
| 5,593,409 A | 1/1997 | Michelson |
| 5,609,636 A | 3/1997 | Kohrs et al. |
| 5,645,598 A | 7/1997 | Brosnahan |
| 5,649,926 A | 7/1997 | Howland |
| 5,658,285 A | 8/1997 | Marnay et al. |
| 5,662,158 A | 9/1997 | Caldarise |
| 5,674,294 A | 10/1997 | Bainville et al. |
| 5,674,295 A | 10/1997 | Ray et al. |
| 5,674,296 A | 10/1997 | Bryan et al. |
| 5,676,701 A | 10/1997 | Yuan et al. |
| 5,683,464 A | 11/1997 | Wagner et al. |
| 5,702,450 A | 12/1997 | Bisserie |
| 5,713,899 A | 2/1998 | Marnay et al. |
| 5,716,415 A | 2/1998 | Steffee |
| 5,720,748 A | 2/1998 | Kuslich et al. |
| 5,722,977 A | 3/1998 | Wilhelmy |
| 5,723,013 A | 3/1998 | Jeanson et al. |
| 5,741,253 A | 4/1998 | Michelson |
| 5,782,830 A | 7/1998 | Farris |
| 5,782,832 A | 7/1998 | Larsen et al. |
| 5,797,909 A | 8/1998 | Michelson |
| 5,824,093 A | 10/1998 | Ray et al. |
| 5,824,094 A | 10/1998 | Serhan et al. |
| 5,865,846 A | 2/1999 | Bryan et al. |
| 5,865,848 A | 2/1999 | Baker |
| 5,885,300 A | 3/1999 | Tokuhashi et al. |
| 5,888,197 A | 3/1999 | Mulac et al. |
| 5,888,226 A | 3/1999 | Rogozinski |
| 5,897,087 A | 4/1999 | Farley |
| 5,902,233 A | 5/1999 | Farley et al. |
| 5,928,284 A | 7/1999 | Mehdizadeh |
| 5,947,971 A | 9/1999 | Kuslich et al. |
| 5,964,761 A * | 10/1999 | Kambin ....................... 606/61 |
| 5,976,187 A | 11/1999 | Richelsoph |
| 5,984,865 A | 11/1999 | Farley et al. |
| 5,989,291 A | 11/1999 | Ralph et al. |
| 6,001,130 A * | 12/1999 | Bryan et al. .............. 623/17.16 |
| 6,017,008 A | 1/2000 | Farley |
| 6,022,376 A | 2/2000 | Assell |
| 6,033,363 A | 3/2000 | Farley et al. |
| 6,059,790 A | 5/2000 | Sand et al. |
| 6,059,829 A | 5/2000 | Schlapfer et al. |
| 6,063,121 A | 5/2000 | Xavier et al. |
| 6,066,174 A | 5/2000 | Farris |
| 6,080,155 A | 6/2000 | Michelson |
| 6,083,228 A | 7/2000 | Michelson |
| 6,086,595 A | 7/2000 | Yonemura et al. |
| 6,096,038 A | 8/2000 | Michelson |
| 6,139,579 A | 10/2000 | Steffee et al. |
| 6,156,067 A | 12/2000 | Bryan et al. |
| 6,162,252 A | 12/2000 | Kuras et al. |

| | | | |
|---|---|---|---|
| 6,175,758 B1 * | 1/2001 | Kambin | 600/426 |
| 6,179,874 B1 | 1/2001 | Cauthen | |
| 6,228,022 B1 | 5/2001 | Friesem et al. | |
| 6,228,026 B1 | 5/2001 | Rull et al. | |
| 6,231,609 B1 | 5/2001 | Mehdizadeh | |
| 6,517,544 B1 * | 2/2003 | Michelson | 606/80 |
| 6,575,899 B1 * | 6/2003 | Foley et al. | 600/114 |

FOREIGN PATENT DOCUMENTS

| | | | |
|---|---|---|---|
| DE | 37 41 493 A1 | 6/1989 | |
| DE | 90 00 094.3 | 4/1990 | |
| EP | 0176728 | 4/1986 | |
| EP | 00560140 A1 | 9/1993 | |
| SU | 895433 | 1/1982 | |
| SU | 1560184 | 4/1990 | |
| WO | WO96/03087 | * 2/1996 | 606/130 |
| WO | WO 00/04839 | 2/2000 | |
| WO | WO 00/04851 | 3/2000 | |
| WO | WO 00/13619 | 3/2000 | |
| WO | WO 00/13620 | 3/2000 | |

OTHER PUBLICATIONS

Edeland; "Some Additional Suggestions for an Intervertebral Disc Prosthesis;" Dept. of Occupational Health; Vdvo PV AB; S–40508; Goteborg; Sweden; 1985 Butterworth & Co. Publishers Ltd.

Enker et al.; "Artificial Disc Replacement;" Spine; vol. 18; No. 8; 1993; pp. 1061–1070.

Hawkins et al.; "Shear Stability of an Elastomeric Disk Spacer Within an Intervertebral Joint: A Parametric Study;" Journal of Biomechanical Engineering Technical Briefs; vol. 114; Aug. 1992; pp. 414–415.

Hedman et al.; "Design of an Intervertebral Disc Prosthesis;" Spine; vol. 17; No. 6; 1991; pp. S256–S260.

Hellier et al.; "Wear Studies for Development of an Intervertebral Disc Prosthesis;" Spine; vol. 17; No. 6 Supplement; 1992; pp. S86–S96.

Hodd; "Far Lateral Lumbar Disc Herniations;" Neurosurgery Clinics of North America; vol. 4, No. 1; Jan. 1993; pp. 117–124.

Langrana et al.; "Finite–Element Modeling of the Synthetic Intevertebral Disc;" Spine; vol. 16; No. 6: 1991; pp. S245–S252.

Lee et al.; "Development of a Prosthetic Intervertebral Disc;" Spine; vol. 16; No. 6; 1991; pp. S253–S255.

Lee et al.; "Natural History & Prognosis of Cervical Spondylosis;" British Medical Journal; Dec. 28, 1963; British Medical Association, London, England; Copyright 1963; pp. 1607–1610.

Long; "Failed Back Surgery Syndrome;" Neurosurgery Clinics of North America; vol. 2, No. 4; Oct. 1991; pp. 899–919.

Ray; "The Artificial Disc—Introduction, History and Socioeconomics;" Clinical Efficacy and Outcome in the Diagnosis and Treatment of Low Back Pain; Raven Press, Ltd., NY; 1992; pp. 205–280.

Robinson et al.; The Results of Anterior Interbody Fusion of the Cervical Spine, The Journal of Bone & Joint Surgery; vol. 44–A, No. 8, Dec. 1962; pp. 1569–1587.

Simeone and Rothman; "Cervical Disc Disease;" Pennsylvania Hospital & University of Pennsylvania; 1975; pp. 387–433.

Solini et al.; "Metal Cementless Prosthesis for Vertebral Body Replacement of Metastatic Malignant Disease of the Cervical Spine;" Journal of Spinal Disorders; vol. 2; No. 4; 1989; pp. 254–262.

Taylor, Collier;, "The Occurrence of Optic Neuritis in Lesions of the Spinal Cord, Injury, Tumor, Melitis;" Brain: A Journal of Neurology; vol. 24; Macmillian & Co. Ltd., 1901; pp. 532–550.

Tie–sheng et al.; "Lumbar Intervertebral Disc Prosthesis;" Chinese Medical Journal, 104–(5); 1991; pp. 381–386.

Artificial Disc, Market Potential and Technology Update, Viscogliosi Bros., LLC, Feb. 2000, pp. 1–65.

Boning–Up, The Musculoskeletal Healthcare Industry, Industry Commentary & Review of 1999, Viscogliosi Bros., LLC, Mar. 10, 2000, pp. 1–33.

Bryan Total Cervical Disc Prosthesis, Single Level Surgical Technique Manual, SPINALdynamics Corporation, 2000, 01080–004, pp. 29.

Spine Industry Dynamics, Viscogliosi Bros., LLC, Mar. 10, 2000, pp. 1–4.

* cited by examiner

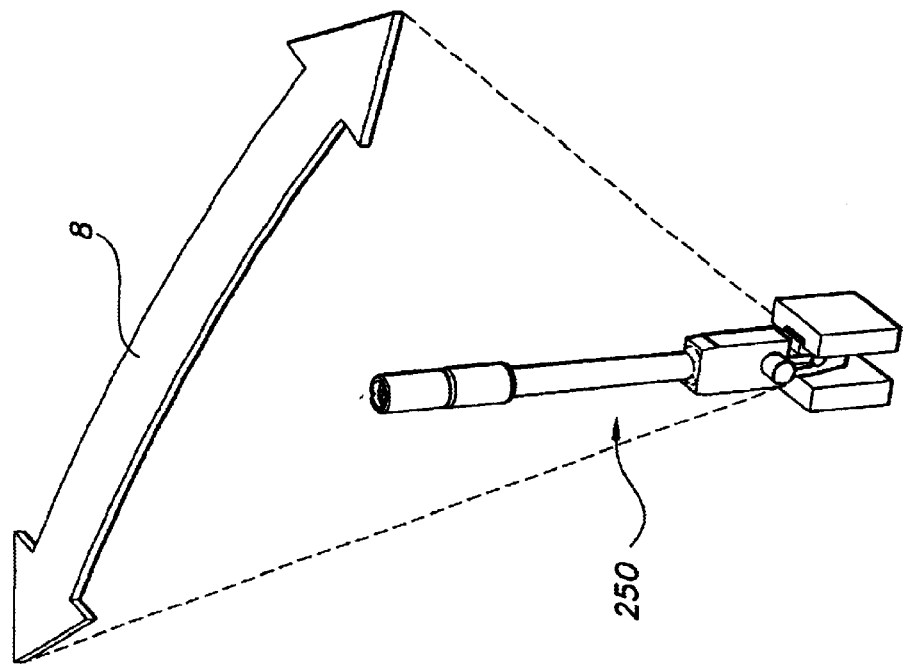
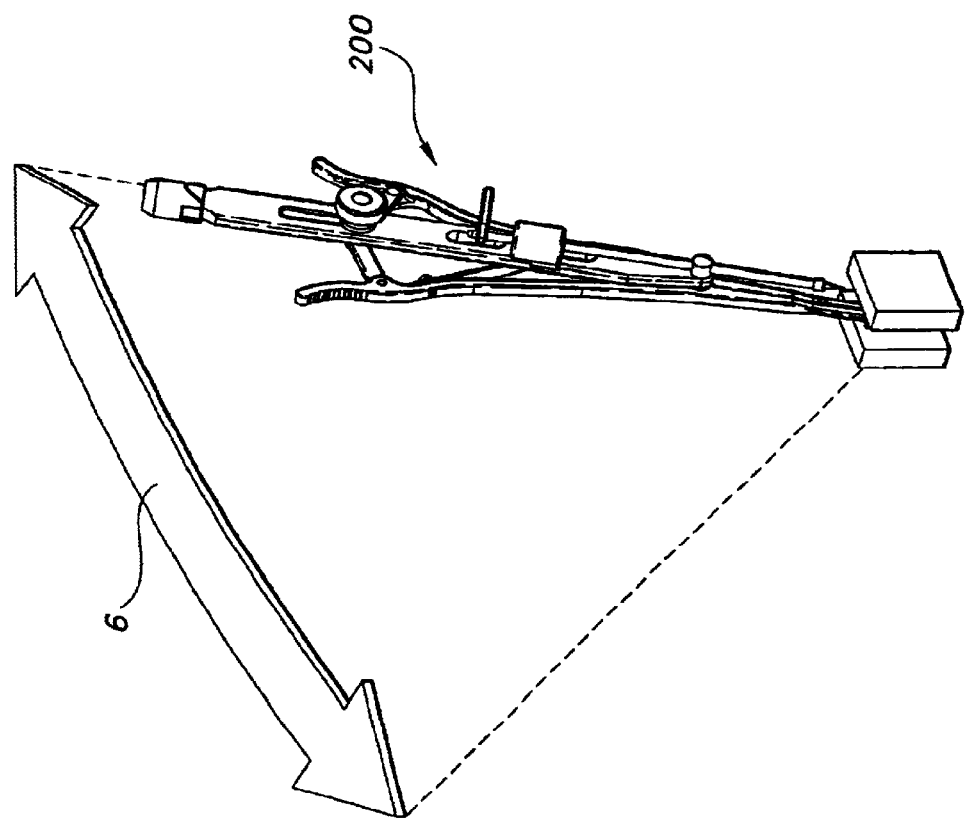
FIG 1A
FIG 1B

FIG 3A  FIG 3B

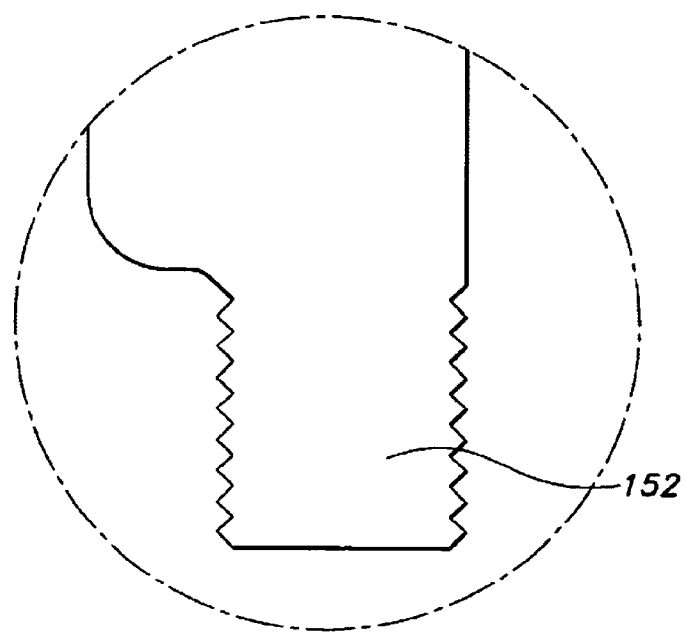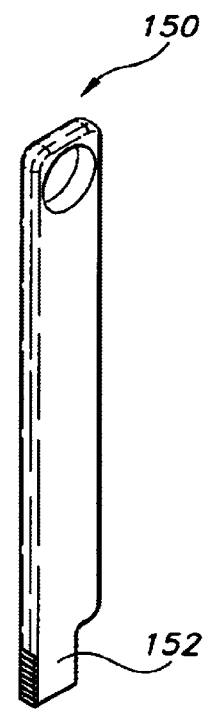
FIG 20B  FIG 20A

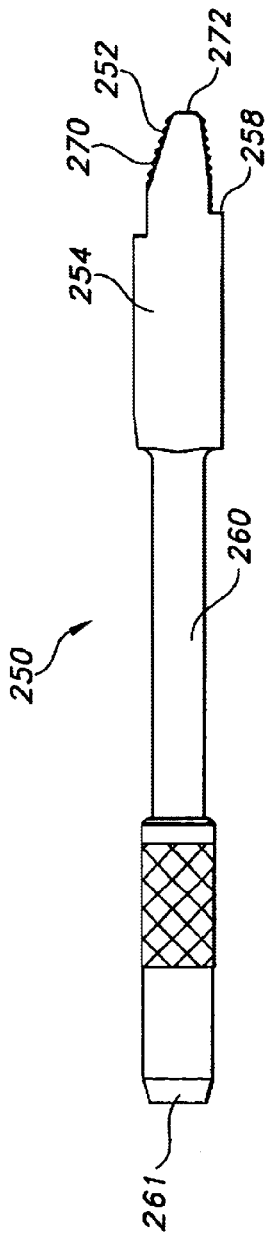
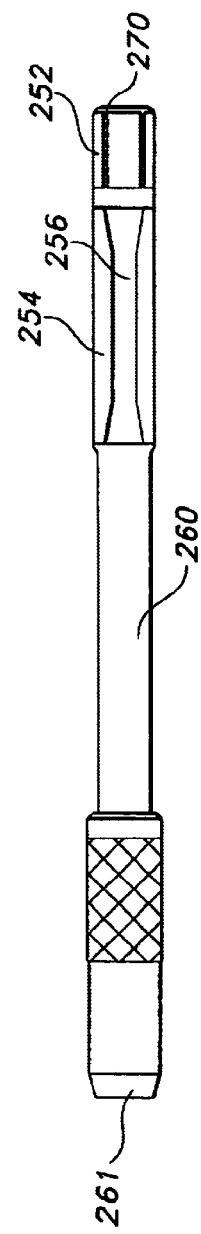
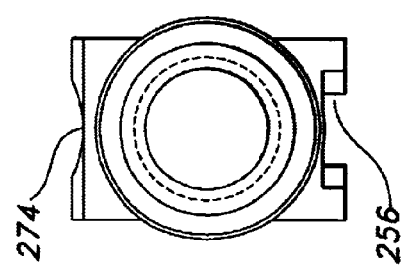
FIG 28B
FIG 28A
FIG 28C

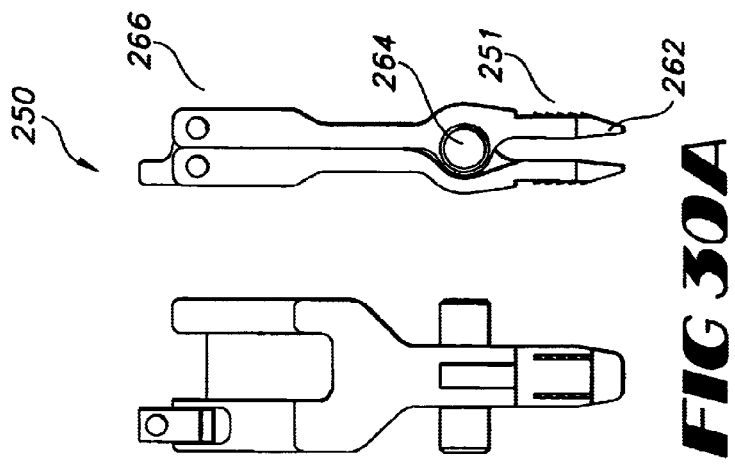
FIG 30B
FIG 30A
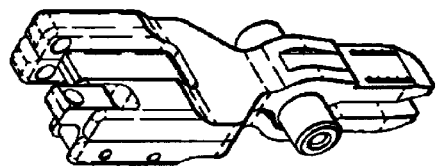
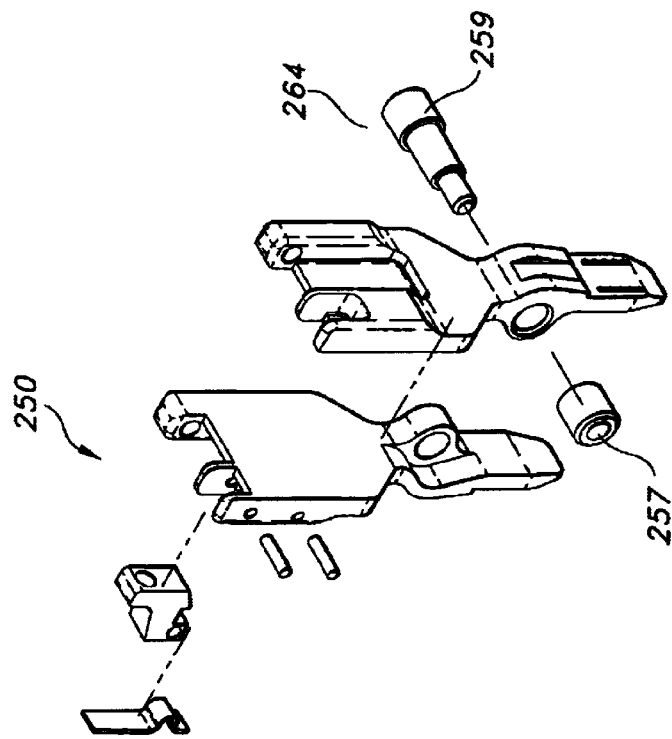
FIG 30C

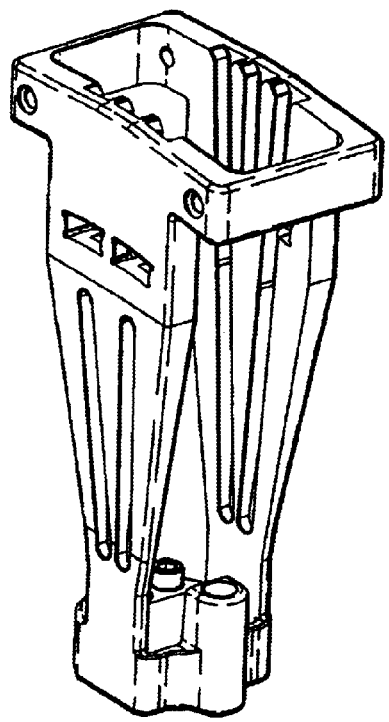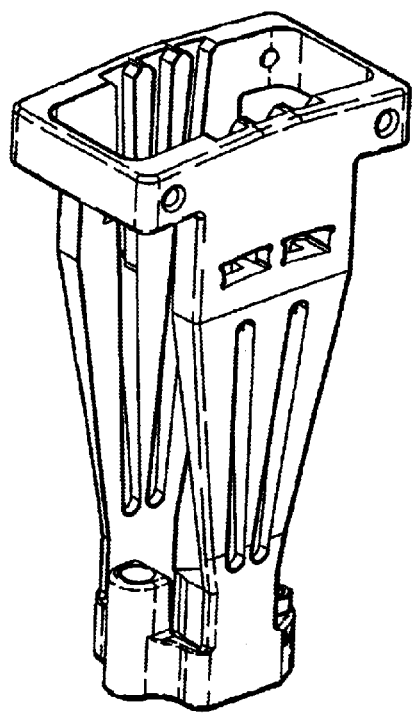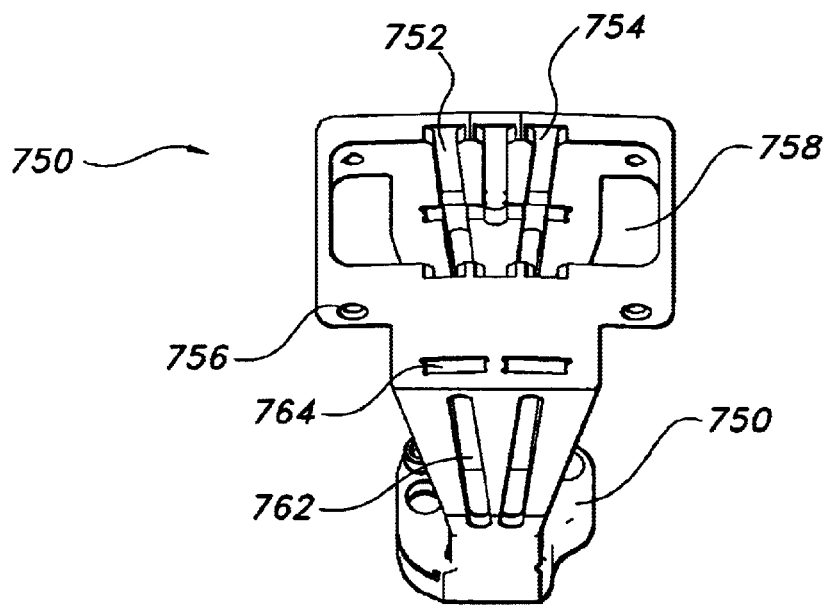
FIG 36C  FIG 36D
FIG 36A

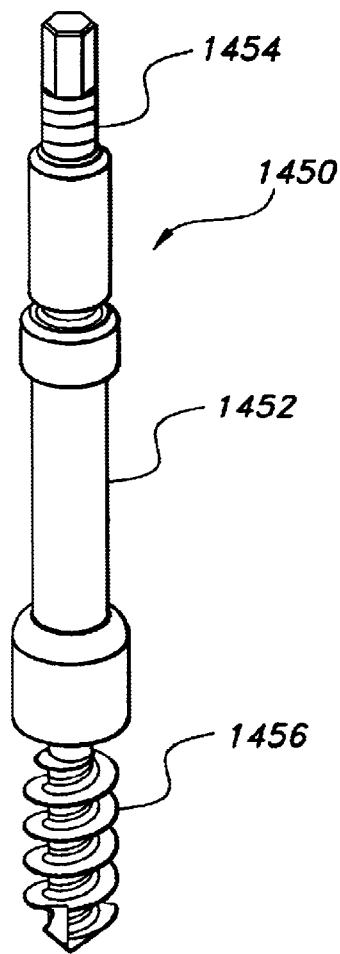
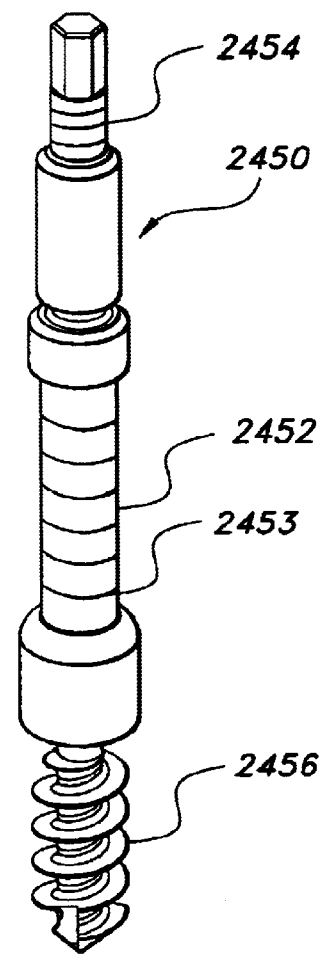
FIG 39B      FIG 39C

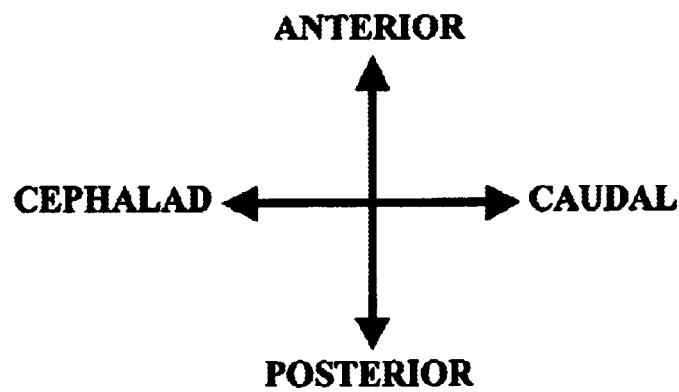
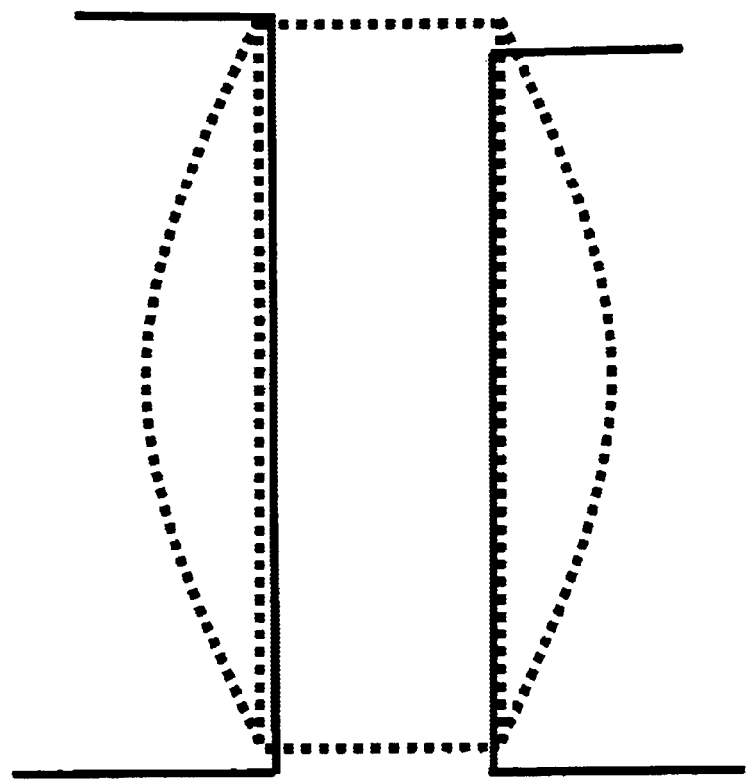
FIGURE 59

METHOD AND APPARATUS FOR STEREOTACTIC IMPLANTATION

This application is a continuation-in-part of U.S. Pat. application Ser. No. 09/783,860, filed on Feb. 13, 2001, now abandoned having the title "METHOD AND APPARATUS FOR STEREOTACTIC IMPLANTATION," and a continuation-in-part of U.S. Pat. application Ser. No. 09/783,910, filed on Feb. 13, 2001, now abandoned, having the title "IMPLANTABLE JOINT PROSTHESIS," both of which claim benefit under 35 U.S.C. § 119(e) of Provisional U.S. Ser. No. 60/223,863, filed Aug. 8, 2000, and entitled "INSTRUMENTATION AND METHOD FOR IMPLANTING A PROSTHETIC INTERVERTEBRAL BODY" and of Provisional U.S. Ser. No. 60/265,218 entitled "GRAVITY ASSISTED LOCALIZATION SYSTEM," filed Jan. 31, 2001, all of which are hereby incorporated herein by this reference.

BACKGROUND OF THE INVENTION

1. Field of the Invention

The invention relates to methods and associated instrumentation for stereotactically locating the site of a prosthetic implant in a body, and in particular to methods and associated instrumentation for stereotactically locating and preparing the site for an intervertebral endoprosthesis, and to precisely implanting the endoprosthesis.

2. Description of Related Art

The proper location of any endoprosthetic implant is a key element of the success of the implantation procedure in improving patient quality of life. In spinal implants, for example, properly locating the endoprosthesis ensures among other benefits that the patient will enjoy the full range of motion offered by the implant.

The use of intervertebral implants (arthroplasty) has, in recent years, attained increasing acceptance as a preferable alternative to spinal fusion (arthrodesis) as a method for treating patients where discectomy is indicated. This is in part due to recent advances in implant technology, and in part due to the increasing appreciation of the advantages provided by implantation, including increased range of motion, decreased post-operative damage to adjacent intervertebral discs (which can result from the decreased range of motion at the level of the fusion), decreased risk of harvest site morbidity, etc. This increasing acceptance seems likely to continue for the foreseeable future, and more and more implantation procedures will likely be performed.

Surgical implantation of prostheses into the intervertebral space may be done using a posterior approach or an anterior approach. The posterior approach has the disadvantage of requiring dissection of muscle tissue of the back, which causes patient discomfort and increased healing time. An anterior surgical approach is often preferable for this and other reasons, and is quite practical for implantation between cervical vertebrae, in particular. Irrespective of the surgical approach, precisely locating the desired implant position, and precise positioning of cavity preparation tools and of the implant at that location are essential. Errors in positioning of the implant or in positioning of the devices used to prepare the intervertebral space to receive the implant can be catastrophic to the patient, given the proximity of the surgical site to the spinal cord, vertebral arteries, etc.

Similar considerations apply in other areas of surgery, in particular in neurosurgery. For example, during surgery on the brain, the surgeon often anchors a frame to the sides of the patient's head, which provides constant reference points during surgery, irrespective of how the patient's head or neck is positioned or moved during the procedure. This level of stereotactic precision in location and placement is also desirable for other medical and surgical procedures, such as in spinal surgery, where the margin for error is very small due to the proximity to the spinal cord and other neuro and vascular structures. However, in most procedures used for spinal surgery, as well as surgery to other body parts, it is impossible (or at least impracticable or undesirable) to secure an external frame to the patient's skeleton or soft tissues to provide constant reference points.

Electronic systems exist for stereotactic positioning of medical instruments during surgical procedures. However, these systems are extremely expensive, requiring significant computing power, are highly complex, and require specialized software, and are not always available, particularly in smaller health care systems or in less developed countries.

Accordingly, there remains a need in the art for a method and apparatus for stereotactically locating targeted implantation positions, for precisely positioning tools for preparing the implantation site, and for precisely inserting the implant in the desired position that is simple, safe, that does not require expensive electronic or computerized tracking of medical instrumentation, and that can be used with conventionally available imaging technologies.

Furthermore, there is a need in the art to provide a method and instrumentation that will allow a surgeon to revise two fused vertebra and interpose an articulating implant therebetween.

Examples of procedures for introducing intervertebral implants are described in U.S. Pat. Nos. 5,674,296 and 5,865,846, the entire contents of each of which are hereby incorporated by reference. These patents generally disclose the steps of determining which size and shape prosthetic vertebral body disc unit a patient needs and implanting that prosthetic into the patient's spine. More specifically, the surgeon or medical technician determines the size, shape, and nature of a patient's damaged vertebral body by viewing images of the patient's spine, such as radiographs, CT and/or other MRI scans. Based upon that information, an appropriate size prosthetic disc unit is constructed by a specialized laboratory in conformity with the information provided by the surgeon or medical technician. The prosthetic units are described as having concaval-convex elements.

When the units are received, the patient is prepared and the damaged natural spinal disc material is removed. The surgeon forms holes in the bone structure using a measuring instrument centered in the excavated natural intravertebral disc space. These holes are tapped to form female threads and anchors are implanted therein to form an imaginary platform of reference points with respect to the patient's spine. A bone surface machining jig is then affixed to the anchors and used to form the desired concave surfaces on the inferior and superior surfaces of opposing vertebral bodies, using a milling head or bit of a predetermined size.

After the bone surface machining jig is removed, a prosthetic disc unit, having corresponding concaval surfaces, is inserted between the distracted and milled vertebral bodies. The concaval-convex elements are then attached by the same anchors to the bone, insuring a mate between the bone surface and the concaval-convex elements.

While these methods are certainly sufficient to achieve a successful intervertebral implantation, there remains a need for improved techniques and instruments that provide even more precise localization, such as improved stereotactic location of the desired site of the implant, the precision positioning of milling, burring, and other tools and instruments for conducting the procedure, and the implantation of the endoprosthesis into the prepared site.

SUMMARY OF THE INVENTION

The methods and apparatus of the invention satisfy this need by providing a technique for precisely locating a preferred location for positioning a device, such as a joint prosthesis. There are numerous ways to describe and characterize the techniques outlined herein, either in terms of locating and positioning with regard to various reference points, lines or planes. In accordance with one such characterization, generally, the desired preferred location is found by precisely locating a line containing a predetermined point within the surgical site using a series of levels and plumb lines and internal anatomical features of the surgical site, using this location to precisely position and temporarily affix a site preparation machining jig or scaffold relative to the patient's anatomy so that site preparation instruments can be introduced into the site at precise locations governed by the scaffold geometry and patient anatomy. The surgical site may be, for example, a target disc space having a damaged spinal disc, or a site created by removal of bone growth associated with an earlier fusion of two vertebrae. This precise positioning of the scaffold also provides a way for the surgeon to use patient anatomical features to reliably and precisely prepare the surgical site. This increased precision in site preparation increases the probability of a successful procedure, and decreases the likelihood that additional surgery may be needed.

Because the position of the patient with respect to gravity is used in conjunction with the patient's anatomical features to precisely locate a predetermined point within the surgical site, there is no need to place the patient in a particular orientation relative to the surgeon or operating table, or to vary that position during surgery. For instance, for anterior cervical discectomy and arthroplasty, the patient is merely immobilized with the patient's spine in its preoperative lordosis, in a position suitable for a normal anterior approach. An image of the patient's spine can be taken to ensure that the spinous processes of the relevant vertebrae are as close as possible to midway between the facet joints. However, once the patient is immobilized in an appropriate position, there is no need to move the patient or the operating table to accommodate the procedure.

In a general sense then, the invention relates to the use of internal anatomical features in or near the surgical site, a plumb or vertical line showing the relationship of the patient's anatomy to vertical (while immobilized on the operating table), and various leveling tools, such as spot or bubble levels, protractors, and goniometers to define a particular line passing through a predetermined point in the surgical site. This line can then be used to position a temporary machining jig or scaffold that precisely locates the various instruments used to prepare the surgical site and to conduct the procedure. The result is a precision implantation procedure that requires relatively inexpensive instrumentation, and is widely applicable to different patients without significant variation in the procedure or instruments.

In general terms, an instrument is used to precisely locate features within the surgical target area, and the instrument is then rotated about a fulcrum located in or near the surgical target area. The end of the instrument distal to the surgical target area describes a first arc above the horizontal as the result of that rotation, and a level can be used to determine when the end of the instrument is at the apogee of that arc. This fixes the transverse midpoint of the surgical target area. An instrument (which may be the same or different) is positioned with a fulcrum at this midpoint and rotated through a second arc that is orthogonal to the first arc and passes through the apogee of the first arc. A line passing through a point on the second arc and a predetermined point in the surgical target area, and having a predetermined angle from the vertical (which may be zero) is used to precisely position a scaffold that will guide other surgical instruments. In one embodiment of the invention, this line is located by placing a protractor fitted with a level on the distal end of an instrument positioned at the transverse midpoint, and orienting the instrument so that its axis defines a line having the desired angle (indicated by the protractor) from vertical (indicated by the level). The instrument can then be used as a reference line for subsequent surgical activities.

Alternatively, the method of the present invention can be generally described as follows. A plane containing the desired line passing through the predetermined point in the surgical site is first located, e.g., by using anatomical features near the surgical site, and a level or protractor. The particular desired line in that plane is then located, e.g. by referencing a line in the plane connecting two anatomical features near the surgical site (the reference line) and measuring the angle between this reference line (or a line normal to it, also in the plane) and vertical. For convenience, the plane is often a vertical one, and can be laterally located by reference to anatomical features near the surgical site, and its angular orientation determined with a bubble or other level.

In a particular embodiment of the invention, the procedure relates to introducing an intervertebral endoprosthesis. With respect to this embodiment, the procedure uses internal features of the patient's intervertebral space, as well as the relationship between the patient's spinal anatomy and a vertical line (determined, e.g., using inclinometers, levels, and simple protractors) to precisely locate instruments to prepare the disc space and introduce the implant. These internal features are subject to considerably less variation between patients than are other external anatomical features that are more remote from the site of the implant, including the various spinal processes. Moreover, once the patient is immobilized for surgery, the relationship between the patient's spinal anatomy and vertical is fixed for the duration of the procedure.

More specifically, an important feature of this embodiment of the invention is the process of locating a particular reference line (defined by two points) passing through a predetermined point in the target disc space. In accordance with one embodiment, this is done by (1) locating a first arc above the horizontal centered around the predetermined point in the target disc space by reference to internal structures within the disc space, (2) locating the apogee of that first arc using a level, (3) locating a second arc orthogonal to the first, also centered around the predetermined point in the target disc space, and passing through the apogee of the first arc, and (4) locating a line passing through the predetermined point in the target disc space and a point on the second arc, and making a predetermined angle with respect to a vertical line.

Put another way, the method involves (1) locating a sagitally extending vertical plane that contains the predetermined point in the target disc space and (2) locating a line in that plane that (a) contains the predetermined point in the target disc space and (b) is normal to a line connecting a point in the plane on the posterior inferior edge of the caudal vertebral body and a point in the plane on the posterior superior edge of the cephalad vertebral body.

In either case, this line forms an axis for positioning a machining fixture or scaffold, upon which can be mounted the instruments for preparing a cavity in the endplates adjacent the target disc space. This cavity can then be used to receive the implant. Once the implantation cavity is precisely prepared using instruments located as described herein, the shape of the cavity and the corresponding shape and features of the prosthesis can serve to appropriately position the prosthesis, and maintain such positioning.

In another embodiment, this procedure relates to providing instruments that are adapted to enhance the surgeon's ability to prepare the disc space to receive an endoprosthesis having two articulating outer shells. More specifically, the instruments enhance the surgeon's ability to position the shells such that they are substantially parallel to one another within the disc space when the patient's spine assumes a normal position while standing without flexion or extension. In some instances, to achieve parallel shell positions when the patient is standing in a neutral position, it is preferable to prepare the vertebral body endplates at an angle relative to the machining instrument. Such an angle is useful to compensate for any deviation from the normal lordosis or kyphosis of the spine (i.e. curvature while standing in a neutral position) caused by the horizontal positioning of the patient on the operating table or non parallel positioning of the vertebral bodies resulting from distraction. It is thus desirable to provide a procedure that allows for machining the vertebral body endplates at a controlled specified angle, and that provides instruments adapted to accommodate such angled machining processes. In another embodiment, this invention relates to a method for machining the vertebral body endplates at an angle to prepare the inter-vertebral disc space for receiving the endoprosthesis and to instruments facilitating this method.

Additionally, this invention also relates to a surgical procedure and associated instruments, wherein an intervertebral endoprosthesis is implanted within more than one disc space of the spine. In this embodiment, a first intervertebral endoprosthesis is placed according to the methods described herein, and a second endoprosthesis or a plurality of endoprostheses are subsequently placed at levels or disc spaces immediately adjacent to the level of the first endoprosthesis. A modified machining fixture is used in the second or subsequent procedures. As with the standard machining fixture, the modified machining fixture facilitates precise placement of the instruments. The multiple-level technique and instrumentation can be used to implant multiple endoprostheses during a single surgery, or they may be used to implant an endoprosthesis at an adjacent level during a second surgery.

A modified machining fixture is beneficial for this procedure because it allows reuse of a fixation device used to secure the machining fixture during the first procedure. This eliminates the need to drill additional holes to accommodate the fixation device in the common vertebral body between the two adjacent target disc spaces. If multiple holes are drilled there is a chance that the second hole would intersect with and unnecessarily enlarge the first hole already formed, which would likely cause the machining fixture fixation device, and thus the machining fixture, to become unstable during the procedure.

BRIEF DESCRIPTION OF THE DRAWINGS

FIG. 1A is a schematic perspective diagram illustrating the transverse arc described by a transverse centering tool in accordance with the present invention. FIG. 1B is a schematic perspective diagram illustrating the sagittal arc described by a sagittal centering tool in accordance with the present invention.

FIG. 4 shows generally a horizontal measuring arm that is positioned from a posterior point on the superior vertebral body of the cephalad vertebrae to a posterior point on the inferior vertebral body of the caudal vertebrae at the targeted disc space, and vertical measuring arm that is placed over a radiographic image showing the patient's spinal anatomy and the gravity indicator of the inclinometer of FIG. 2 or FIG. 3.

FIG. 20 is a perspective view (A) of one embodiment of a sagittal retainer or spacer of the invention, having a heel portion shown in detail in (B) that maintains the separation achieved by the distractor of FIG. 19.

FIG. 28 is a front view (A), side plan view (B), and top plan view (C) of one embodiment of a sagittal centering tool of the present invention, showing generally a handle, nose and a neck that defines a keyway. The sagittal centering tool is adapted to receive a centering level at one end.

FIG. 30 is a side plan view (A), a perspective view (B), and an exploded view (C) of another embodiment of a sagittal centering tool of the present invention, showing generally a nose that is defined by lever actuated prongs and which distracts the posterior aspects of the vertebral bodies.

FIG. 28B shows more particularly the base having a foot, a drill guide opening, and a locking screw. FIG. 28C illustrates an adjustable bushing and locking screw included in the base.

FIG. 36 includes various views of a multi-track machining fixture. FIG. 36A is a top perspective view of a multi-track machining fixture adapted to position instruments for angled machining. FIG. 36C and FIG. 36D are side perspective views of the multi-track machining fixture of FIG. 36A.

FIG. 39B and FIG. 39C are perspective views of alternative embodiments of a fixation device, which are adapted to be flexible and are particularly useful with the multi-level machining fixture of FIG. 34 or FIG. 35.

FIG. 57 illustrates reference points used to measure the angles accommodated by the various machining fixtures.

FIG. 59 is a schematic drawing illustrating the preferred anterior-posterior prosthesis position in accordance with the present invention.

DETAILED DESCRIPTION OF SPECIFIC EMBODIMENTS

Figure 2:
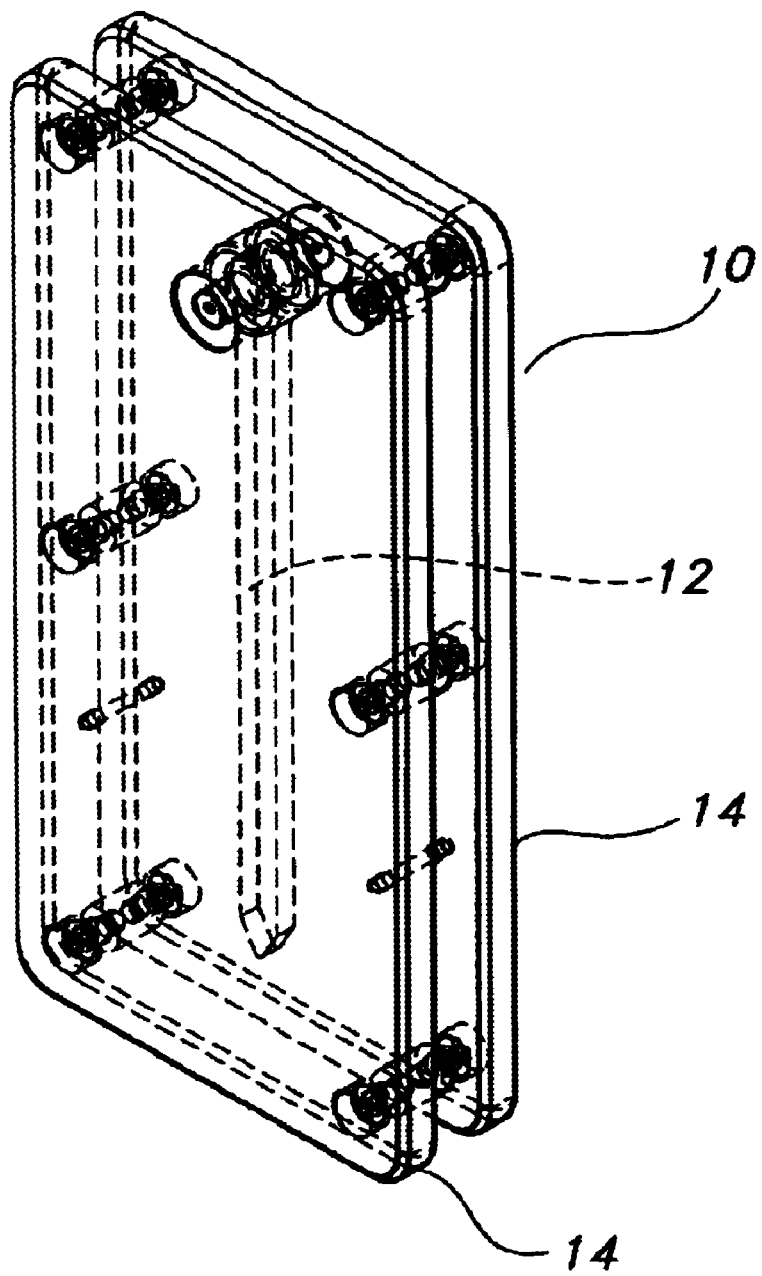
FIG. 2 is a perspective view of a reference point device or inclinometer according to one embodiment of the invention, which shows generally a gravity indicator pointing vertically downward (in direction of gravity).

It will be understood from the description above that the techniques of this invention are applicable to a wide variety of surgical procedures where stereotactic precision is required. The described procedure and instruments generally provide a system and method for locating and targeting a precise location. The description that follows focuses on one embodiment of the invention, namely the implantation of an intervertebral endoprosthesis, and in particular, to the implantation of such an endoprosthesis in the intervertebral space between cervical vertebrae using an anterior approach. Those of skill in the art will recognize that the procedure described below can be varied or modified to be applicable to other spinal implants such as fusion implants or to other approaches, or to lumbar or thoracic vertebral implants, to implants in other parts of the body, such as hips, knees, elbows, or other joints, and to other procedures that do not involve implantation.

1. Brief Overview of Procedure

The primary goal of the surgical procedures of the present invention is to provide a method of precisely forming a cavity of predetermined geometry at a precise location within a skeletal joint. This cavity can then be used to implant a joint prosthesis to restore proper functioning of the joint and/or alleviate pain in the vicinity of the joint. The geometry of the cavity closely approximates the geometry of the implant, and thereby serves to keep the implant in a given position.

In the context of implanting an intervertebral disc prosthesis into an intervertebral disc space of a patient, the method of the present invention generally includes the following steps:

(1) determining the appropriate size prosthesis;

(2) taking an orientation image of the spine in the area of the target intervertebral disc space with a gravity direction indicator visible in the image field;

(3) quantifying the relationship between the orientation of the spine and a gravitational vector shown by the gravity direction indicator visible on the image;

(4) distracting the target disc space;

(5) using a transverse positioning tool to locate the preferred transverse position for the center of the prosthesis;

(6) using the preferred transverse position to position a sagittal positioning tool;

(7) aligning a fixture 300 over the sagittal positioning tool 250;

(8) using the quantified relationship between the orientation of the spine and the gravitational vector to adjust the position of the sagittal positioning tool 250 to a preferred sagittal position for the center of the prosthesis;

(9) securing fixture 300 to the vertebral bodies;

Regarding step of quantifying the relationship between the orientation of the spine and a gravitational vector, this involves determining a spine orientation angle that is equal to the angle between an anatomic reference line and the gravitational vector. In accordance with a preferred embodiment, the anatomic reference line is a line normal to a line connecting the posterior inferior edge of the vertebral body caudal to the target disc space and the posterior superior edge of the vertebral body cephalad to the target disc space. This quantified relation ship may be used to position the sagittal positioning tool by positioning the sagittal positioning tool such that the angle of the sagittal positioning tool's axis relative to the gravitational vector is equal to the spine orientation angle.

More particularly, the method of the present invention may be described as follows. A radio graphic image (such as, for example, a fluoroscopic image) of the target implantation site is typically taken as part of the preoperative assessment of the patient. In accordance with the present invention, a radio-opaque pendulum or other device for providing a radiographic image of a vertical or plumb line is positioned near the immobilized patient's spine or on the image intensifier of the fluoroscope. The image of the vertebral or plumb line represents a gravitational vector.

A radiograph or other image is then taken that includes both the vertical or plumb line image and the area of spine where the implantation will occur (it will be understood that other imaging techniques can be used, provided that the plumb line or pendulum can be imaged by those techniques), namely the target site, e.g. the target disc space. For purposes of the discussion herein, references to the target disc space shall include an artificial target disc space created by the removal of a fused bone segment. This provides an image of the relationship between the patient's spinal anatomy and a vertical line. Features of the patient's spinal anatomy visible on the radiographic image (discussed in more detail below) are used to determine a reference angle between a line passing through a predetermined reference point in the target disc space and a vertical line.

After discectomy, a transverse centering tool, e.g., having retractable laterally extending prongs, is used to feel for anatomical landmarks of the surgical site, for example, the intersection of the annulus fibrosus and the uncinate process on either side of the intervertebral space. The handle of the transverse centering tool is fitted with a bubble level. The bubble is laterally centered by tilting or rotating the centering tool laterally to define a first vertical transverse arc, and positioning the tool at the apogee of that arc (when the bubble level is centered). The transverse centering tool and the arc defined thereby are illustrated in FIG. 1 A. At this point, a pointer or other device, preferably mounted on the transverse centering tool, is used to mark (or guide a marking tool which marks) the transverse center of the anterior surface of one of the vertebral bodies, and in accordance with a preferred embodiment, the anterior surface of the cephalad vertebral body.

After distraction of the intervertebral space, the mark is used to position a sagittal centering tool. The sagittal centering tool is inserted into the distracted space to the appropriate depth (as determined by, e.g., a stop or flange that contacts the anterior surface of the caudal vertebral body).

The end of the sagittal centering tool is then rotated about a predetermined reference point in the target disc space to describe a second arc that is orthogonal to the first arc. The second arc is also shown schematically in FIG. 1B. The line formed by the shaft of the sagittal centering tool can be precisely positioned at an appropriate angle from vertical by attaching a protractor to the end of the sagittal centering tool and placing a level on the end of the protractor and centering the level when the protractor is set to the appropriate angle. The appropriate angle between the line defined by the sagittal centering tool and a vertical line corresponds to the angle between the vertical line provided by the inclinometer and the line perpendicular to the reference line taken from the patient's spinal anatomy, as determined from the radiograph and described above.

The inserted sagittal centering tool is then used to position a machining fixture (also referred to herein as a milling scaffold), e.g., by sliding the machining fixture or milling scaffold over the sagittal centering tool. This positioning may be accomplished by any interfacing, mating or locking or engaging mechanism, e.g., a key on one of the devices that engages a key-way on the other device. The determination of the angle between the sagittal centering tool and vertical can be made or remade during positioning of the machining fixture.

When properly situated, the machining fixture can be affixed to the anterior surfaces of the cephalad and caudal vertebral bodies using a fixation device. The sagittal centering tool can then be removed. At this point, the machining fixture has been positioned such that it is centered around a line passing through the predetermined reference point in the disc space between the vertebral bodies.

After the machining fixture is properly positioned, it is used to facilitate tissue machining processes— an optional preliminary machining process, and a profile machining process. Prior to the tissue machining, gauges are used to determine the appropriate machining positions. In particular, a gauge is used to determine the posterior limit for the transverse burring. A second gauge is used to determine the appropriate anterior-posterior position for milling the implant profile into the vertebral body endplate.

The optional preliminary machining process is typically done to provide adequate space within the intervertebral space to facilitate insertion of the profile machining instrumentation. Although this step is included within a preferred embodiment of the method of the present invention, those skilled in the art may find it unnecessary in certain applications if adequate access already exists. The preliminary machining process may included one or more of a transverse centered machining process or transverse off-set machining processes using transverse machining tools, such as for example transverse burring tools.

Transverse burring tools remove debris and tissue from the intervertebral space, and in some cases bone from the surfaces of the vertebral plates, in a pattern that permits a milling tool to be inserted. The transverse burring tool is inserted into the disc space, and axially guided by a transverse burring block mounted on the machining fixture. In one embodiment, the transverse burring tool pivots within the machining fixture, and the transverse burring block limits the motion of the transverse burring tool by limiting the depth and arc distance of the cuts made by the transverse burring tool. The resulting opening in the intervertebral space is sufficient to receive a profile milling tool that performs the second tissue machining process.

The transverse burring tool can then be removed, and the transverse burring block removed from the machining fixture. A profile milling tool can then be combined with or inserted into the machining fixture and the cephalad and caudal vertebral endplates milled to a cephalad-caudal depth and shape adapted to receive the implant. The cephalad-caudal depth of the cut can be guided by, e.g., a stop on the machining fixture, and the anterior posterior position of the cut can be regulated by adjusting the length of the milling attachment, e.g., by using the depth determined with the depth gauge.

The invention also provides angled machining instrumentation that can be used for a variety of machining operations including, for example, cutting, milling, abrading or burring. In general, the angled machining instrumentation allows for the positioning of various instruments at various angles relative to the target disc space or its adjacent vertebral endplates. For purposes of the discussion herein, references to the adjacent vertebral endplates shall include adjacent vertebral bone surfaces created as result of the removal of a fused bone segment to create an artificial target disc space. The angulation may be achieved by virtue of design features of the machining instruments themselves and/or design features of the machining scaffold.

Once the disc cavity has been milled, the implant can be inserted using, if necessary, an appropriate insertion tool. If the machining fixture is configured to allow the implant and insertion tool to fit within it, then the scaffold and the scaffold fixation devices can be removed after implant insertion. If the implant and insertion tool will not fit within the machining fixture, the disc space can be distracted, e.g., by using the scaffold fixation device, insertable distractors, or a combination thereof, the machining fixture removed, the implant inserted, and distraction released. The scaffold fixation device can then be removed and the resulting holes filled with graft or fill material.

There are also provided methods and instrumentation for multi-level adjacent procedures. In a multi-level adjacent procedure, a second endoprosthesis is implanted in a disc space immediately adjacent to a disc space in which a first endoprosthesis has been implanted. In accordance with this aspect of the present invention, the methods described herein with regard to a single level procedure are repeated using a machining fixture that is adapted specifically for use in adjacent multi-level procedures.

In particular, a multi-level machining fixture will be positioned and fixed over the first disc space during the procedure at the first level. Thereafter the multi-level machining fixture will be repositioned and fixed over the adjacent second disc space during the procedure at the second level. In each procedure a fixation device will be used to secure a machining fixture to the common vertebral body lying between the two adjacent target disc spaces. In accordance with a preferred embodiment a hole must be drilled in the common vertebral body to accommodate the fixation device. Thus, it is desirable to use the same fixation device hole for both procedures, rather than drilling a new hole for the second procedure. The multi-level machining fixture of the present invention is adapted to use the existing fixation device in the existing hole if the two levels are done during a single surgery. If the second level is done during a subsequent surgery, the multi-level machining fixture of the present invention is adapted to use a fixation device that utilizes the hole in the common vertebral body that was previously used to position the machining fixture during the first level surgery. As described in greater detail below, in certain embodiments of the present invention, it is preferable that the fixation device be flexible to facilitate placement and movement of the multi-level machining fixture.

The description below provides a more detailed overview of the procedure used to implant an intervertebral endoprosthesis.

2. Detailed Overview of Procedure

The appropriate size implant can be selected and determined preoperatively, as explained in more detail below, by imaging the relevant vertebral bodies using radiography, MRI, CT scanning, or other appropriate imaging technique. The patient's head and/or upper body is immobilized on a table or other operating surface so that the portion of the spine to be implanted has a lordotic angle similar to the patient's neutral position, and so that the spinous processes are midway between the facets (as determined, e.g., by an anterior-posterior radiograph). As used herein, the neutral position of the spine is hereby defined as the post-operative position that a spine assumes when the patient is standing without any flexion or extension, and which can be approximated by the patient's analogous pre-operative position of the spine.

A disc space reference angle is determined. The disc space reference angle is an angle representing the position of the patient's target disc space relative to vertical. Generally, a lateral radiograph or fluoroscopic image is prepared showing the immobilized patient's spinal anatomy with respect to a pendulum or inclinometer that is radio-opaque and indicates a plumb line relative to the patient's spinal anatomy. A vertebral body orienting tool is used to determine the angle between (a) the vertical line indicated by the inclinometer image on the radiograph, and (b) an angle reference line that is normal to a line connecting the image of the posterior inferior edge of the caudal vertebral body adjacent the target disc space, and the posterior superior edge of the cephalad vertebral body adjacent the target disc space. The latter line is assumed to be parallel to the target disc space. The vertebral body orienting tool may be a protractor, goniometer or radiographic (C-arm) fluoroscope angle calculator.

A rigid frame is mounted on the operating table or surface to provide reference points during surgery and to secure retractors and other surgical instruments to be used during the procedure. The positions of the patient's head and neck remain constant with respect to the mounted frame. The frame could be secured to any surface that will remain stable during the surgery. As an example, in a particular embodiment described in more detail below, this can be done by attaching an adjustable frame assembly to the side rails of an operating table. The surgical instruments can then be secured to the frame and stabilized relative to the patient.

Once the patient and frame have been positioned, the surgeon is ready to begin the procedure. An incision is made in the neck, the spinal column is exposed by suitable soft tissue retraction, and a discectomy is performed to expose the interior of the intervertebral space into which a prosthesis will fit (any bony protrusions that obstruct access to the intervertebral space can be removed). The intervertebral space is distracted without damaging either the remaining soft tissue or the bony endplates of the vertebral bodies.

A predetermined reference point within the disc space is selected. This predetermined point represents the point where the approximate center of the prosthesis will be located once it is properly positioned within the disc space. This predetermined point is then used as a reference to precisely position a scaffold, which in turn will serve to properly position a variety of instruments used to prepare the opposing vertebral bodies to receive the prosthesis. This predetermined point is generally a point within the disc space that is substantially centered in the lateral-medial direction between the opposing uncinate processes. It should be noted, however, that one skilled in the art may select a point that is off center depending upon clinical considerations.

The predetermined point is substantially centered in the caudal-cephalad direction between the two opposing vertebral bodies. In accordance with the preferred embodiment, the anterior-posterior position of this predetermined point is selected based on an anticipated positioning of the prosthesis such that its anterior end is substantially aligned with or tangent to the anterior surface of the most anteriorly extending vertebral body adjacent the target disc space. Specifically, preferably the anterior-posterior position of the predetermined point is located a distance from the anterior surface of the most anteriorly extending vertebral body that is equal to one-half of the prosthesis' anterior-posterior dimension. Those skilled in the art will appreciate that the anterior-posterior position of the predetermined point can be varied based on the extent to which one desires the prosthesis to extend within the disc space.

To facilitate proper positioning of the instruments used to prepare the opposing vertebral bodies, a positioning reference line is located that substantially parallels the target disc space and passes through the predetermined reference point in the target disc space. This reference line is located as follows.

First, a transverse centering tool having a distal end and a proximal end is used. The distal end of the transverse centering tool is inserted into the disc space, and the proximal end is laterally pivoted. The pivotal movement of the proximal end of the transverse centering tool describes a transverse arc, and the apogee of that arc is located. A bubble level or other leveling device is placed on the proximal end of the transverse centering tool. The apogee of the transverse arc described by pivotal movement of the tool in the lateral direction is determined by centering the level. A mark is then made on the anterior surface of one of the vertebral bodies, preferably by using a marking device or pointer on the transverse centering tool. This mark is contained within a vertical plane laterally bisecting the target disc space. The distal end of the transverse centering tool is then removed from the disc space.

The mark on the anterior surface of the vertebral body is used to laterally position the distal end of a sagittal centering tool within the target disc space. The sagittal centering tool is designed such that when properly positioned within the disc space, its central axis is substantially congruent with the positioning reference line. The sagittal centering tool is properly positioned by rotating the proximal end of the sagittal centering tool to define an additional arc orthogonal to the first transverse arc, and intersecting the first transverse arc at the apogee thereof. The angle between the line formed by the axis of the sagittal centering tool and vertical is adjusted using a level and protractor, so that it corresponds to the disc space reference angle described above. When properly adjusted, the axis of the sagittal centering tool will locate the positioning reference line, and provide the axis about which the scaffold will be oriented, and along which instruments for measuring and preparing the intervertebral space will be guided.

After the sagittal centering tool has been adjusted in the manner described (with its axis positioned congruent with the positioning reference line), a machining fixture or scaffold is precisely placed with respect to the positioning reference line, and such that it indicates the predetermined point in the target disc space. The machining fixture is positioned to rest on the anterior surfaces of the vertebral bodies and is temporarily immobilized with respect to the anterior surfaces of the vertebral bodies. The machining fixture is then temporarily, but rigidly, affixed to the anterior surfaces of the vertebral bodies and more securely clamped to the adjustable frame for added stability.

In other words, the sagittal centering tool serves to position the machining fixture in place, so that the machining fixture can be properly oriented around the desired axis, which is the positioning reference line. For instance, the machining fixture can slide over the sagittal centering tool so that a key or other orienting interface on the machining fixture or sagittal centering tool cooperates with a keyway or orienting interface on the other device.

The machining fixture is adapted to receive instruments and stabilize them relative to the frame and the patient. The machining fixture also holds the vertebral bodies apart, and precisely positions and stabilizes the instruments that will be used to prepare the vertebral bodies to receive the implant. The machining fixture can be slid over the sagittal centering tool before the angle of the sagittal centering tool is adjusted. Alternatively, the angle of the sagittal centering tool can be adjusted, the machining fixture introduced, and the angle rechecked prior to immobilization of the machining fixture.

The dimensions of the target space are determined. Specifically, the distance to the anterior-most portion of the targeted vertebral body is determined, as well as the depth to which the vertebral bodies will be milled to receive the implant. Measuring instruments are used to perform and verify these measurements. Desirably, some or all of the measuring instruments are adapted to cooperate with the machining fixture, so that the machining fixture provides a fixed reference point from which distances into the intervertebral space can be measured. The machining fixture itself is secured to the vertebral bodies and secured to the adjustable frame. After the dimensions have been confirmed as correct, burring instruments are used to remove bone and enlarge the space between the vertebral bodies to provide space for the milling instruments and the prosthesis. The superior surface of the caudal vertebral body and the inferior surface of the cephalad vertebral body, which will support the prosthesis, are then milled to receive and support the prosthesis, and to expose cancellous bone to the prosthesis surfaces.

The machining fixture, in conjunction with the instruments themselves and other positioning devices, positions the instruments so that machining is done at the appropriate positions. For instance, in one embodiment of the invention, the measuring, burring and milling instruments (collectively referred to as "site preparation instruments"), and the machining fixture have specialized stabilizing and stopping mechanisms, such as pins and slots, that regulate the distance that the site preparation instruments extend into the intervertebral space, and restrict their range of motion when inserted therein. The machining fixture cooperates with site preparation instruments so that when they are positioned, they are secured in a precise location in relation to the machining fixture.

During the procedure, site preparation instruments are inserted through the machining fixture, which catches or stops the instruments at the desired position. For example, the machining fixture may have slots that cooperate with corresponding pins or keys on the site preparation instruments. The pins or keys contact the bottom of the slots, which act as a stop when the measuring or milling instruments are inserted through the entryway of the machining fixture. This prevents the instruments from penetrating too far into the intervertebral space and stabilizes them in their desired positions, which can be set by adjusting either the machining fixture or the instrument. The slots may also include specific slots that allow the instruments to be maneuvered within a prescribed range of motion, so that the depth or position of any cutting, burring, or milling is pre-set and precisely controlled.

In alternate embodiments, the machining fixture and the site preparation instruments may have any other interfacing structure. For example, the machining fixture may have keys and the site preparation instruments have slots. The keys of the machining fixture would catch the slots of site preparation instruments in the above-described manner. Other mechanical interfacing mechanisms, including other locking and sliding mechanisms, may be used and should be considered within the spirit of this invention, so long as the machining fixture or brace cooperates with site preparation instruments so that the range of motion and depth of penetration of the instruments is limited.

In even further embodiments, the machining fixture is provided with various configurations, such as pre-determined angulation or variable angulation options. This offers the surgeon flexibility in the machining of the vertebral body endplates to ensure a more accurate placement of the implant.

After the vertebral bodies have been prepared to receive the prosthesis, the distance between the vertebral bodies is appropriately maintained, while the prosthesis is prepared for insertion. Suitable prostheses include those described in U.S. Ser. No. 09/783,910, filed Feb. 13, 2001, the entire contents of which are hereby incorporated by reference. In a particular embodiment, the prosthesis is filled with lubricating fluid, compressed, and positioned between the vertebral bodies in the machined spaces for a secure fit. No additional screws or fasteners are needed to secure the prosthesis. The carefully measured and milled surfaces in the vertebral bodies, which mate with the geometry of the prosthesis, hold the prosthesis in the correct position. Retaining elements on the prosthesis also help keep the prosthesis in position and prevent posterior migration.

It is also possible to perform additional procedures to place additional endoprostheses in nearby intervertebral spaces. If an endoprosthesis is to be placed at a target disc space adjacent to a disc space already containing an endoprosthesis, the invention provides instruments to facilitate the adjacent level procedure, including a special machining fixture and a special machining fixture fixation device that is a flexible anchor post.

The specifics of patient preparation, as well as further details of an embodiment of the procedure itself and embodiments of the instruments used therein are provided in more detail below.

3. Detailed Description of Procedure and Instruments

A. Preoperative Procedures

Desirably, the surgeon determines the appropriate size of the prosthesis to be implanted prior to commencing the surgical procedure. (For the purposes of this document, "surgeon" means doctor, operating surgeon or physician, medical technician, nurse, veterinarian, training technician, or person otherwise providing the medical services or performing the described procedures.) To do this, the surgeon views images, such as radiographs, computer tomography (CT) scans, magnetic resonance image (MRI) scans, or the like, of the area in which the prosthesis is to be implanted, and particularly views and examines the appropriate anterior-posterior (AP) views of the endplates of the vertebral bodies superior and inferior to the target disc space. The surgeon should determine the smaller of the two vertebral body endplates at the target disc space to analyze and choose the largest prosthesis that will fit that vertebral body. Any spurs or ridges that will be removed during subsequent burring or milling processes need not be included in the determination.

Because the images used by the surgeon may be at different magnification factors, it may be necessary for the surgeon to take this into account when determining the appropriate size implant, e.g., by using a template that scales an image of the various implant sizes to the commonly used magnification factors, and which the surgeon can simply place over the image. Prostheses may be offered in a range of sizes. For example, a system of prostheses for use in humans as described above typically range in diameter from 14 mm to 18 mm, generally in 1 mm increments. Alternatively, the diameters may range from 12 mm to 18 mm. It is generally desirable for the surgeon to choose the largest prosthesis that would fit in the target space, while still allowing at least 1 mm of additional bone on the posterior side of the intervertebral space. In other words, the size of the prosthesis is selected such that when the prosthesis is positioned within the disc space, the posterior edge of the prosthesis is positioned at least 1 mm anterior to the posterior edge of each adjacent vertebral body endplate. In addition, the prosthesis may be placed such that its anterior surface is substantially tangent to the anterior surface of the anteriorly superior vertebral body. This allows for a "cushion" of additional bone to help reduce the possibility of the prosthesis migrating in the posterior direction and contacting the spinal cord.

B. Patient Positioning and Preparation

The patient should be positioned on the operating table supine in the AP position with the head supported, so that the neck is relatively parallel to the table, and the cervical vertebrae assumes its neutral position, as defined herein. The patient should be positioned in such a way that allows C-arm fluoroscopy to be performed on the target disc space. This may require that an extension be used to support the patient's head. An AP radiograph is typically taken to ensure that spinous processes are as close to midway between the facets as possible. The patient is immobilized on the operating table, with special attention paid to the head and neck areas, using surgical tape and other restraining techniques known to those familiar with the art of spinal surgery, discectomy, etc. The head is typically placed on a donut-shaped pad, without a roll under the shoulders, and the chin extended, in order to more closely reproduce the spine's neutral position.

Figure 3:
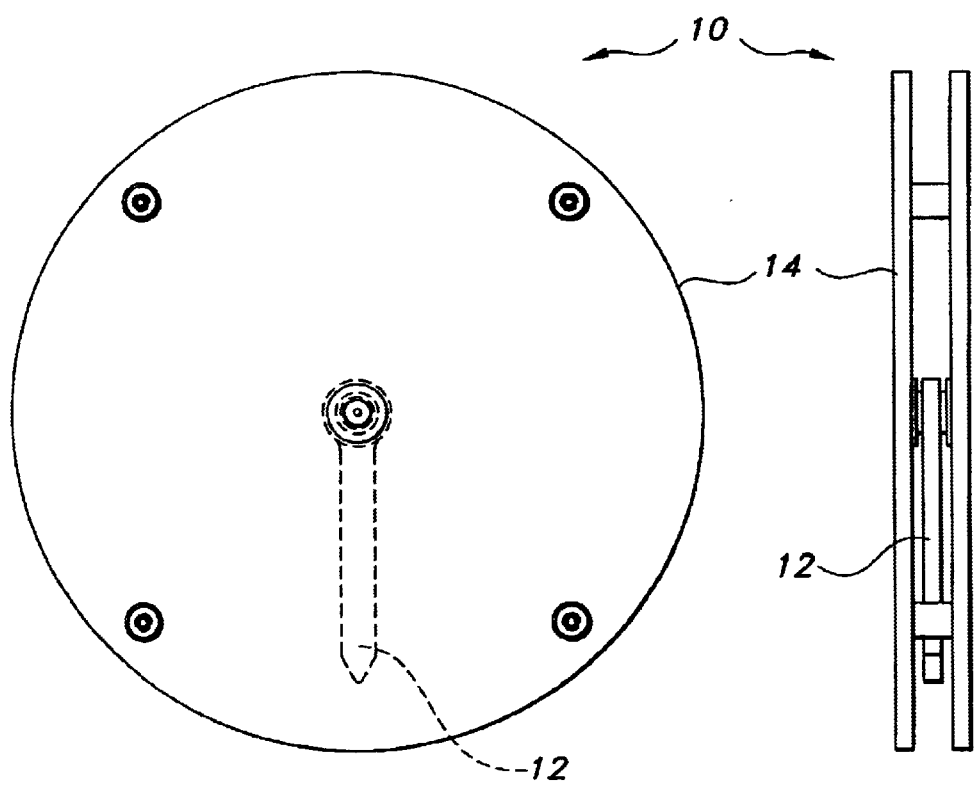
FIG. 3 is a plan view (A) and side view (B) of another embodiment of an inclinometer according to the invention.

A lateral radiograph is then taken of the spine in the area of the target intervertebral space, with the inclinometer 10, shown in FIG. 2 and FIG. 3, visible to the fluoroscope. Inclinometer 10 is an apparatus for stereotactically positioning a subject comprising an image producer for producing an image of tissue that is beneath the subject's skin surface; a gravity indicator 12 mounted within the field of view of the image producer, wherein said gravity indicator 12 is made from a material that is visible on images produced by the image producer. The image producer may be a radiographic image producer and the gravity indicator 12 may be a radio-opaque pendulum.

Desirably, inclinometer 10 should be attached, e.g., by magnets, suction cups, tape, or the like, to the image intensifier of the C-arm fluoroscope so that it is visible on the display screen with the lateral image of the patient's spine, and so that the inclinometer can operate to indicate a plumb line without interference from the fluoroscope. Inclinometer 10 is generally a weighted, radio-opaque pendulum that provides a radiographic image of a plumb line on the same radiograph as the patient's immobilized spine. Inclinometer 10 acts as a direction indicator and its use allows the surgeon to determine the relationship between anatomical features of the spine and a vertical line or gravitational vector. It also allows the surgeon to assess the angle between the plumb line and a line passing through a predetermined reference point in the target disc space. This angle can be used later to precisely position various instruments relative to the target disc space and/or its adjacent vertebral body endplates.

In one embodiment, inclinometer 10 is an image producer that has an arrow-shaped gravity indicator 12 that is pivotally mounted in a housing and hangs straight down, no matter what position inclinometer shell 14 assumes. Gravity indicator 12 may also be mounted in a partial housing. As illustrated best in FIG. 3B, in order to provide a free space in which gravity indicator 12 can move and change its orientation relative to gravity changes, inclinometer shell 14 preferably comprises two shell units that are bolted or otherwise connected together, providing a space having a depth greater than the thickness of gravity indicator 12. In this embodiment, the gravity indicator 12 is removable and pivotably mounted within the field of view of the image producer. Gravity indicator 12 may be an arrow-shaped weight.

Figure 4:
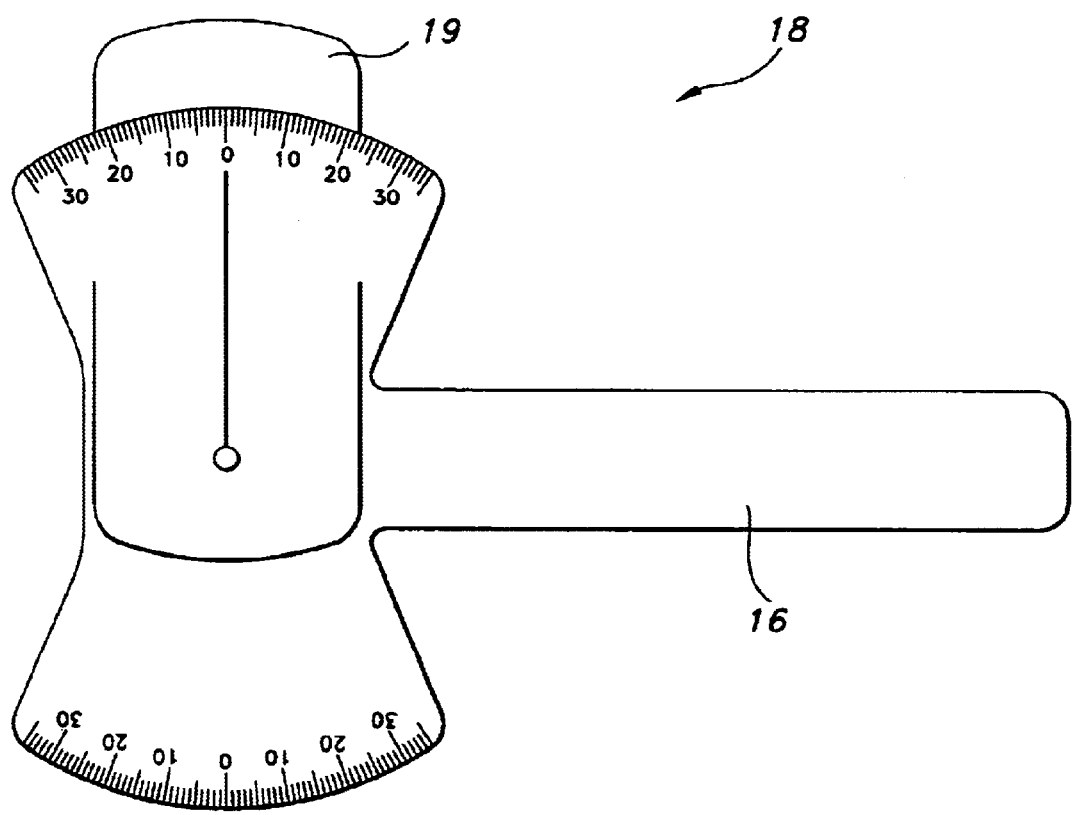
FIG. 4 is a front plan view of a goniometer, which is specific embodiment of a vertebral body orienting tool in accordance with the present invention.

The lateral radiographic image of the patient's spine and inclinometer 10 is displayed. The surgeon should then quantify the relationship between the orientation of the spine and the vertical line shown by the inclinometer image. Typically this is done by measuring the angle made by (a) a reference line that passes through a predetermined reference point in the intervertebral space, and (b) the vertical line made by the inclinometer image. The reference line is located as follows. A vertebral body orienting tool is used to measure the angle between the reference line and the vertical line. The vertebral body orienting tool is preferably a goniometer 18, having indicia which is shown in FIG. 4, a protractor, or another device or combination of devices that can measure the angle between two lines relatively accurately. It has been found that a line normal to the line connecting the posterior inferior edge of the caudal vertebral body and posterior superior edge of the cephalad vertebral body is a suitable reference line. A measuring reference, such as horizontal arm 16 of goniometer 18, shown in FIG. 4, is then positioned along this connecting line. The line normal to the reference line can then be transferred, using the goniometer 18, to the vicinity of the inclinometer image, and the angle between the line normal to the reference line and the vertical line indicated by the inclinometer image can then be determined.

This indicates to the surgeon the angle between a line through the predetermined point in the target disc space and the vertical line reference. For example, a movable angle measuring portion, such as vertical arm 19 of goniometer 18, is positioned so that it lies over the image of inclinometer 10 shown on the fluoroscope image. The angle between the line normal to the reference line is measured by means of the horizontal arm 16 and the gravity indicator 12 and is recorded. The recorded angle represents the desired angle between the vertical line and the line that will form the axis of the machining fixture.

C. Attaching Frame Assembly

Figure 5:
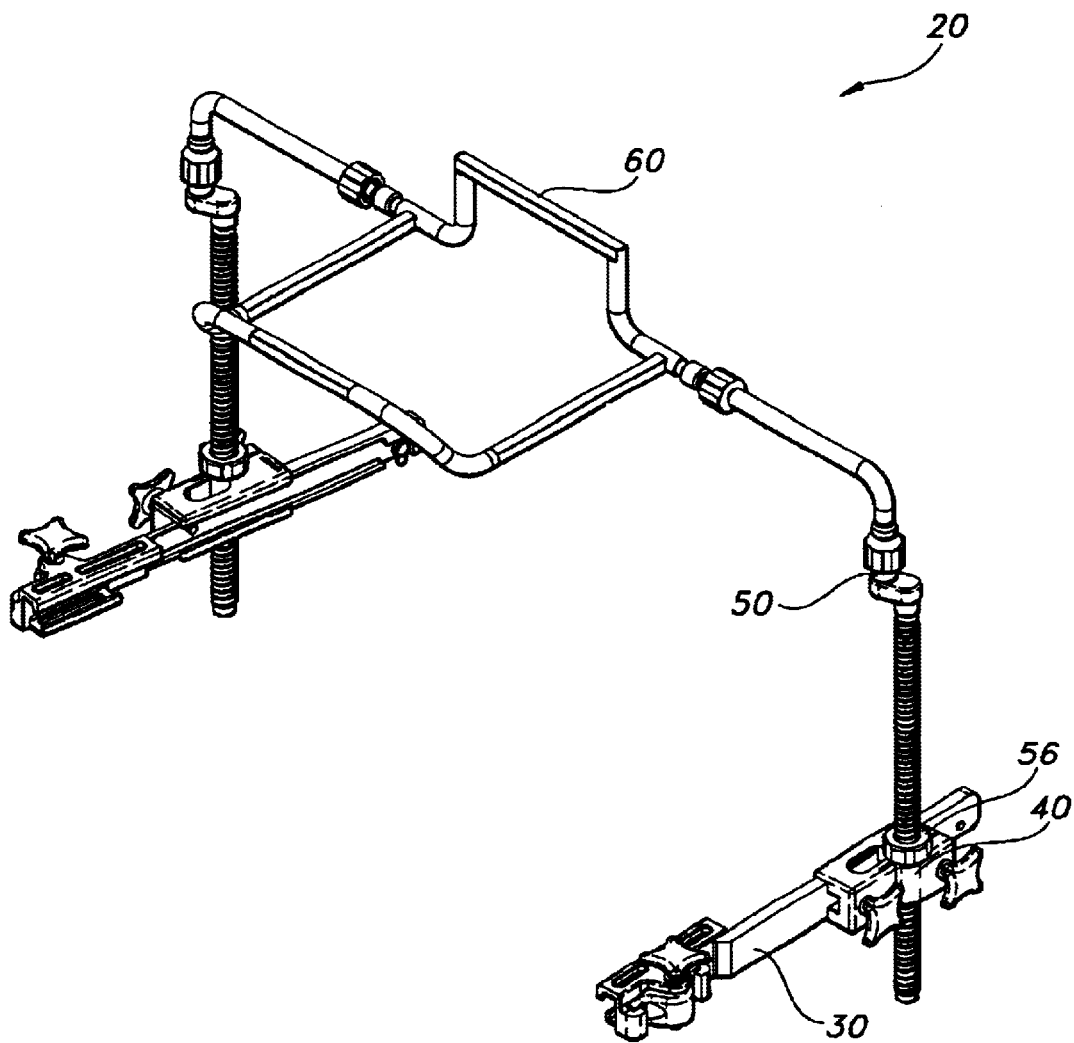
FIG. 5 is a perspective view of an assembled frame assembly, showing generally rail extensions, clamps, vertical rods, and rigid frame.

Once the patient is stabilized, prepared, and draped, and the position of the spine relative to gravity has been ascertained, adjustable frame assembly 20 shown completely assembled in FIG. 5 is attached to the operating table. Frame assembly 20 may be a one-piece assembly or may comprise several modular components that can be disassembled and packaged for storage and/or sterilization and then erected during the procedure. This multi-component embodiment saves storage space in operating rooms, autoclaves, and distributors. One feature of frame assembly 20 is that it can be used with a variety of different surgical tables and can accommodate various dimensions of side rails.

An exemplary embodiment of frame assembly 20 comprises side rail extensions 30, vertical rod clamps 40, vertical rods (also called vertically extending rods) 50, rod collars 56, and rigid frame (also called open frame) 60. Standard operating room tables have side rails along the sides, which are used to provide a base for the frame assembly 20. Once frame assembly 20 is erected, each side rail will have a side rail extension 30, vertical rod clamp 40, and vertical rod 50, attached thereto. The vertical rods 50 support the rigid frame 60.

Generally, side rail extensions 30 are adapted to clamp onto the operating room table side rails and to receive vertical rod clamps 40. Vertical rods 50 and optional rod collars 56 are adapted to cooperate with vertical rod clamps 40. Rigid frame 60 is secured to vertical rods 50. Side rail extensions 30 can accommodate operating room tables having side rails of various dimensions. They are slideable along the side rails, and provide a base for the frame assembly 20. In the particular embodiment shown, side rail extensions 30 are configured to clamp onto the side rails without tearing sterile drapes.

Figure 6:
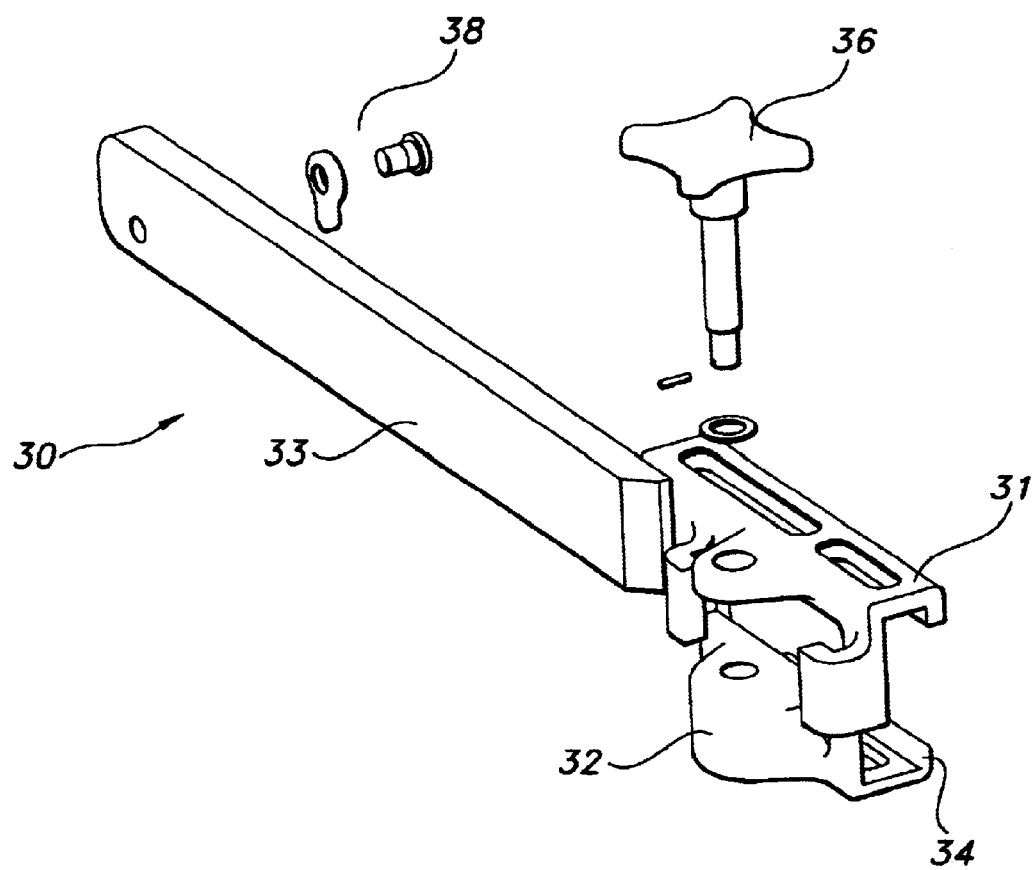
FIG. 6 is an exploded perspective view of one embodiment of a side rail extension, showing generally adjustable foot portion, clamp, and safety catch.

As shown in more detail in FIG. 6, in a particular embodiment, each side rail extension 30 has stationary hook 31 at its distal end and extension arm 33 at its proximal end. (In this description, "distal" denotes the direction toward the patient's feet and "proximal" denotes the direction toward the patient's head.) Stationary hook 31 cooperates with the top of the table side rail. Extending below and substantially parallel to stationary hook 31 is movable hook 34, which is part of adjustable foot portion 32, which is adapted to slide over or otherwise cooperate with the table side rail. Side rail extension clamp 36, which in use is attached to adjustable foot portion 32, can be positioned to adjust and secure the movable hook 34 against the bottom of the table side rail for a tight fit of extension 30 against the operating table side rail. It should be noted that in other embodiments, stationary hook 31 and movable hook 34 may have alternate positions, i.e., stationary hook 31 may cooperate with the bottom of the table side rail and the movable hook 34 may cooperate with the top. Additionally, adjustable clamping mechanisms other than those specifically shown can be used to secure extensions 30 in place.

Figure 7:
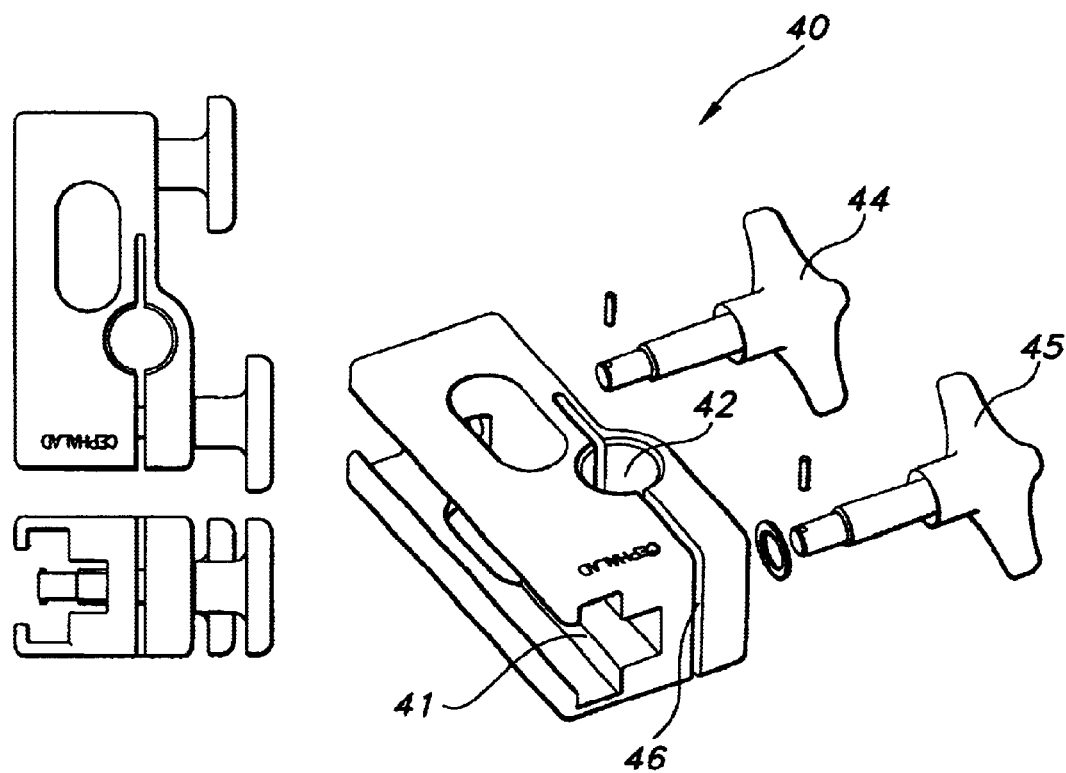
FIG. 7 is an exploded perspective view of one embodiment of a vertical rod clamp, adapted to connect to the side rail extension of FIG. 6 and receive a vertical rod.

As shown in FIG. 5, vertical rod clamps 40 attach to extension arm 33 of side rail extension 30. Vertical rod clamp 40, which is shown in detail in FIG. 7, cooperates with extension arm 33 via a groove 41 located on one side of vertical rod clamp 40. Vertical rod clamps 40 slideably engage the extension arm 33 via groove 41. The proximal ends of side rail extensions 30 optionally have safety catch mechanism 38, shown in FIG. 6, which extends slightly below the lower edge of extension arm 33. When vertical rod clamp 40 is placed onto extension arm 33, safety catch 38 would extend and prevent the vertical rod clamp 40 from disengaging from extension arm 33. It thus operates to prevent the vertical rod clamp 40 from accidentally slipping off during the procedure if, for example, the patient needs to be redraped and the side rail extensions are removed.

Referring again to FIG. 7, vertical rod clamps 40 also include rod receiving portion 42 adapted and sized to receive a vertical rod 50, as shown in FIG. 5. Rod receiving portion 42 is a bore that may be threaded or smooth. In addition, vertical rod clamps 40 include slot 46 that segments clamps 40 and intersects rod receiving portion 42. As described below slot 46 act as part of the clamp's locking mechanism.

Vertical rod clamps 40 also include knobs 44 and 45, which may be conveniently located on the side opposite groove 41. As one or both of these knobs are tightened, they force extension arm 33 against the sides of groove 41, and thereby lock the position of clamp 40 relative to extension 30. It should be noted that the extension arms 33 and the side surface of groove 41 may be serrated to enhance the locking mechanism. Similarly, as one or both of the knobs are tightened, the clamp segments adjacent slot 46 are forced closer together, thereby compressing rod receiving portion 42 against the surface of the vertical rod 50 and securing the position of rod 50 relative to clamp 40.

In the embodiment illustrated, knob 44 secures the vertical rod clamp 40 to the side rail, while knob 45 secures the vertical rod 50 in place. Although two knobs 44 and 45 are shown in the illustrated embodiment, other embodiments may contain one knob or more than two knobs.

To position extension 30 on operating room side rails, it is preferable that the adjustable foot portion 32 be completely lowered to prevent tearing of the sterile drape. Once the extension 30 is in place, the clamp can be tightened so that stationary hook 31 and adjustable foot portion 32 clamp against the table side rail. When extensions 30 are positioned on both sides of the operating table, the proximal portion of each vertical rod clamp 40 is preferably flush with the end of the operating room table.

Figure 8:
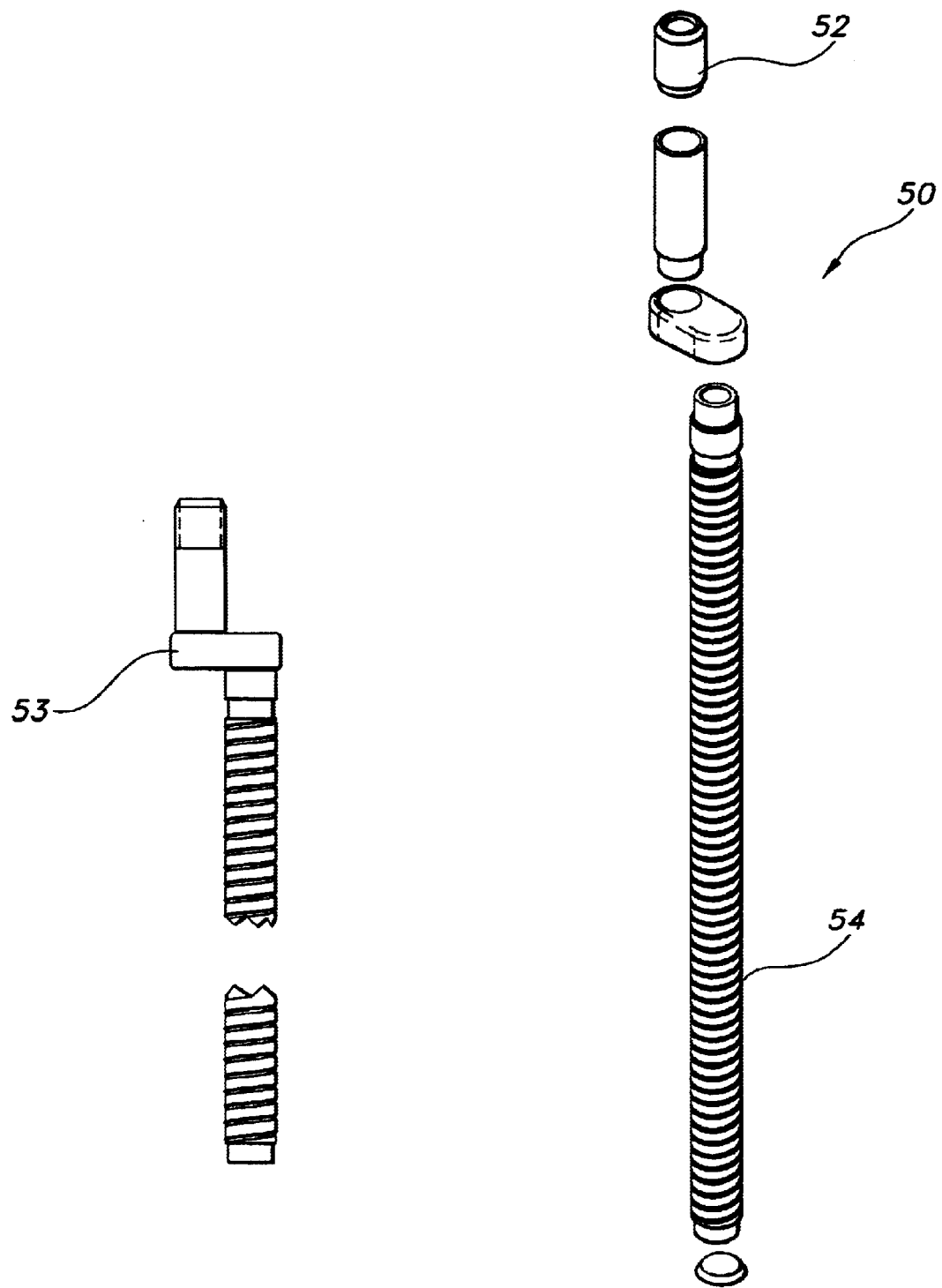
FIG. 8 is an exploded perspective view of one embodiment of a vertical rod, showing generally threaded portions and the offset or S-curve of the vertical rod.

Vertical rods 50 shown in FIG. 8 are then placed into the rod receiving portions 42 of the vertical rod clamps 40. Once positioned, the vertical rod 50 is tightly secured by a knob on the vertical rod clamp 40. Vertical rods 50 preferably have upper and lower threaded portions 52 and 54. The lower threaded portion 54 can control and determine the height and placement of vertical rod 50. For example, threaded portion 54 of vertical rod 50 may optionally be threaded into a threaded rod receiving portion 42. Alternatively, threaded portion 54 does not threadably engage the rod receiving portion 42, but instead threadably cooperates with a vertical rod collar 56, shown in FIG. 5. Vertical rod collar 56 has a threaded bore that enables it to engage lower threaded portion 54 of vertical rod 50. When vertical rod collar 56 is placed on vertical rod 50, an optional threaded bore on vertical rod collar 56 (not shown) may cooperate with lower threaded portion 54 of vertical rod 50 to control the height of vertical rod relative to the operating table. Essentially, in use, vertical rod collar 56 contacts the surface of vertical rod clamp 40 and secures vertical rod 50 at the desired height.

As shown in FIG. 8, upper and lower threaded portions 52 and 54 may be separated by an S-curve 53 in either or both vertical rods. S-curve 53 (traditionally called an offset or an axial offset and which may particularly be a vertical offset) is optional, but helps provide and adjust for variability between operating tables and allows interoperative rotation of the frame, e.g. if the patient is not perfectly centered on the table. S-curve 53 provides the surgeon with a means for maneuvering rods 50 side to side if necessary for proper positioning. Thus, once vertical rods 50 are erected on both sides of the operating room table and rigid frame 60 (described below) is attached, the surgeon may wish to rotate the vertical rods 50 to alter the location of connecting portions 64 (also described below). S-curve 53 allows the movement of vertical rods 50 to affect these adjustments without moving the side rail extensions or the patient.

Figure 9:
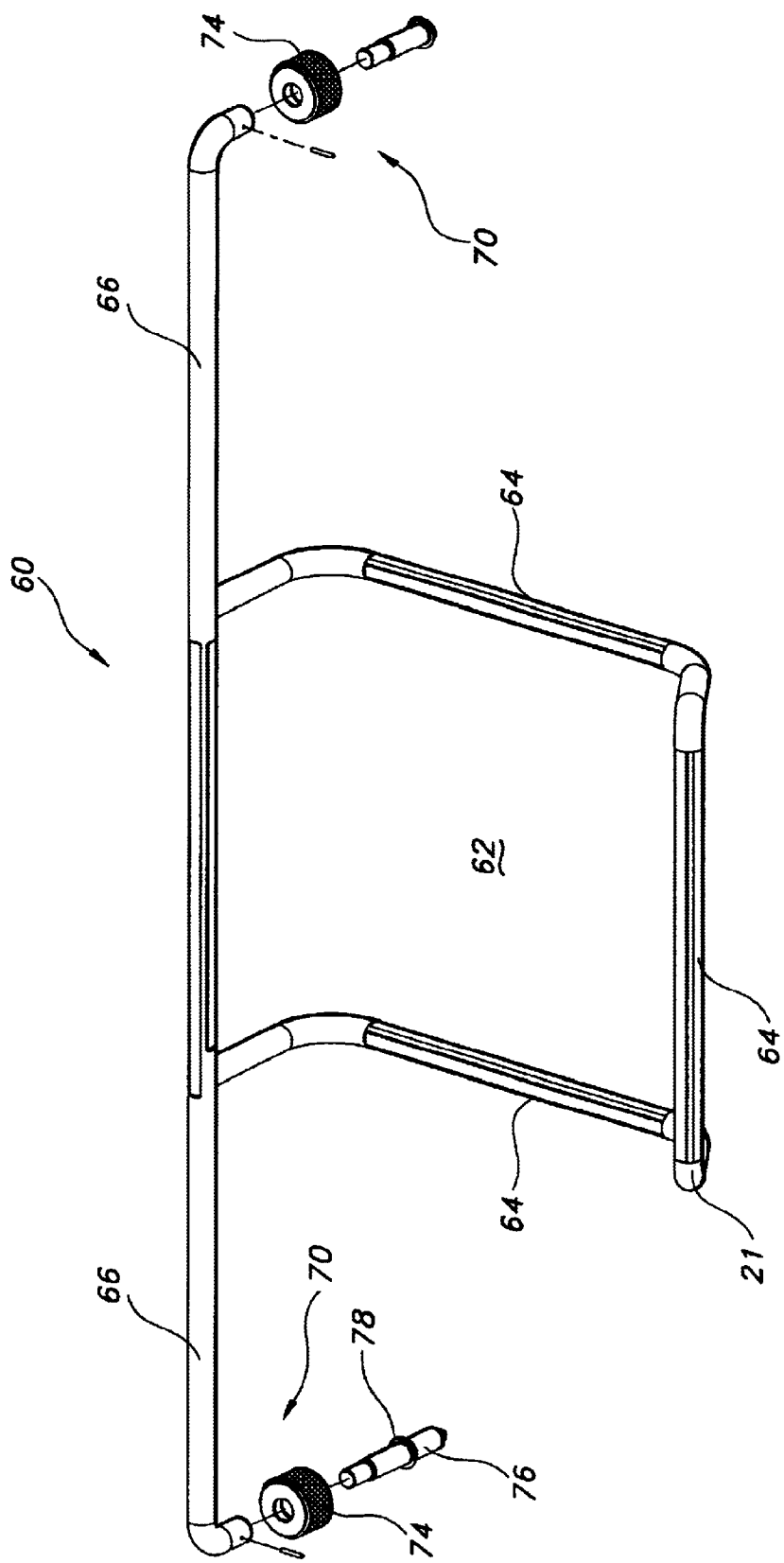
FIG. 9 is an exploded perspective view of one embodiment of a rigid frame, showing generally a one piece assembly adapted to attach to the vertical rods of FIG. 8.
Figure 10:
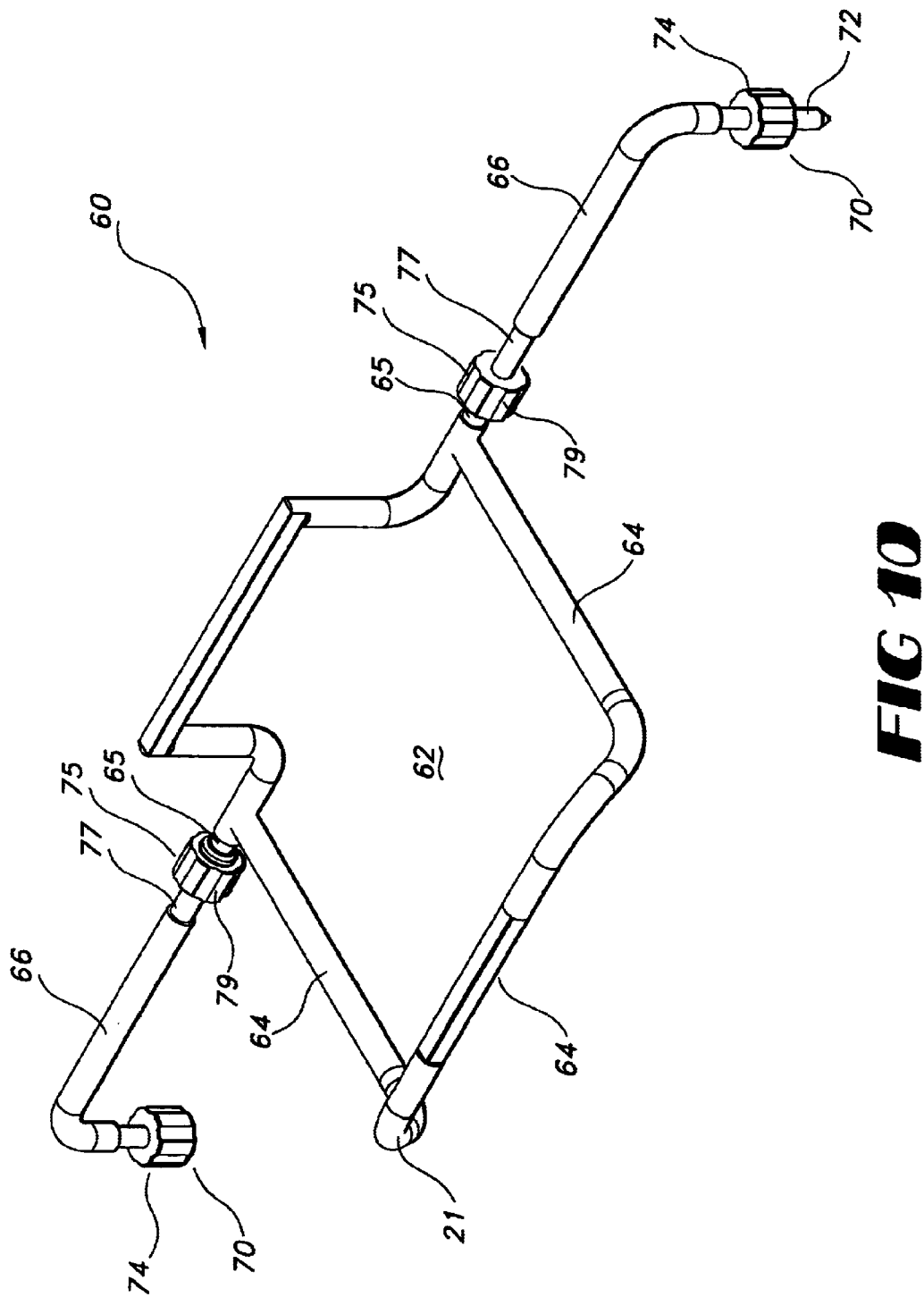
FIG. 10 is a perspective view of another embodiment of a rigid frame, showing generally a multi-piece assembly having arms, a frame square, and connecting mechanisms.
Figure 11:
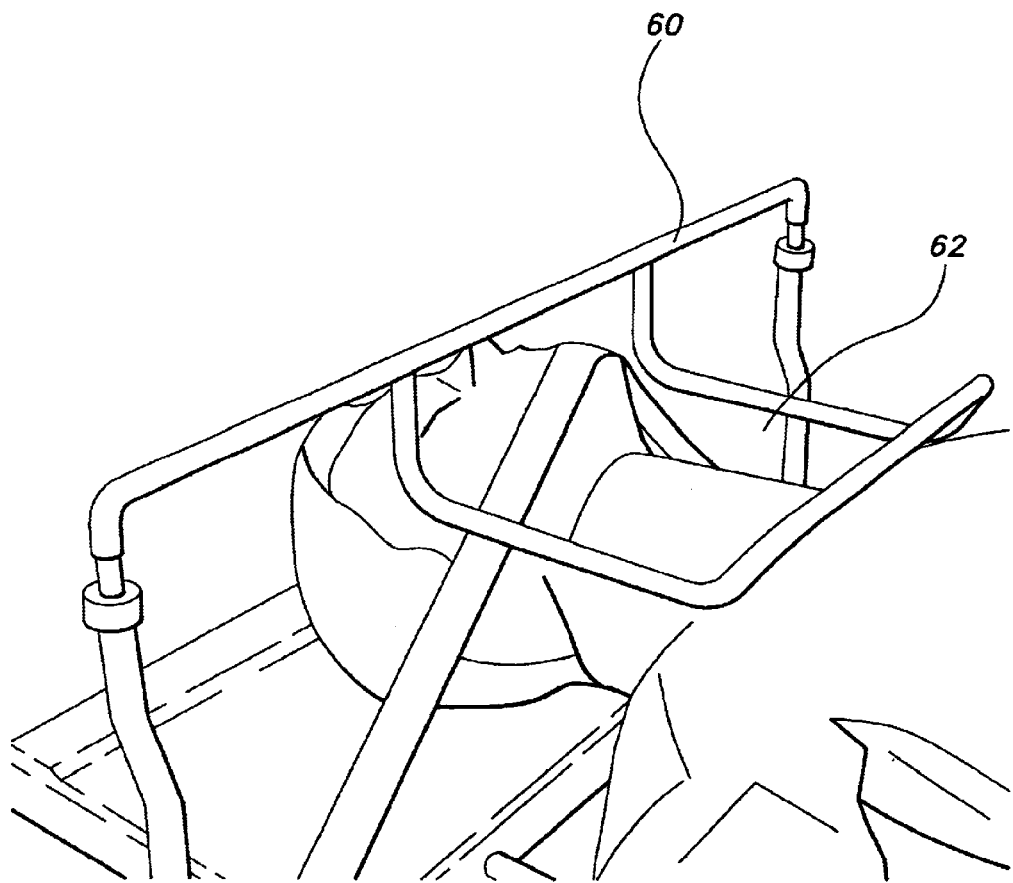
FIG. 11 is an illustration of the proper positioning of the frame assembly of the present invention relative to a patient.

To complete the positioning of frame assembly 20, rigid frame 60 shown in FIG. 9 and FIG. 10, is secured to the vertical rods 50. Rigid frame 60 may be a one-piece assembly, as shown in FIG. 9, or it may have multiple components, as shown in FIG. 10. A multiple component arrangement allows frame assembly 20 to be more easily stored and sterilized, since it can be separated into pieces that will fit into a sterile cassette. Generally, as illustrated in FIG. 11, rigid frame 60 has an aperture 62 that should be positioned approximately over the target disc space, and relatively close to the patient. Aperture 62 is defined by three or more connecting portions 64, which will ultimately serve as a support for instruments and a reference point during the procedure. Connecting portions 64 optimally collectively form a frame square 21 (or rectangle). Connecting portions 64 may specifically be substantially horizontal lateral side portions, a s/h cephalad portion and a s/h caudal portion.

Rigid frame 60 also contains arms (or side arms) 66 that connect to vertical rods 50. If rigid frame 60 is a multiple piece assembly as shown by FIG. 10, arms 66 can be separate items that are removably attachable to vertical rods 50 and to the central portion of rigid frame 60. In this multiple-piece embodiment, the central portion of rigid frame 60 has optional frame extensions 65 that cooperate with and facilitate attachment of the arms 66 to the rigid frame 60.

Arms 66 are illustrated having an L-shape, and cooperate with upper threaded portions 52 of vertical rods and, in a multipiece embodiment, with frame extensions 65 of rigid frame 60. In use, arms 66 orient rigid frame 60 so that aperture 62 is substantially perpendicular to vertical rods 50. If arms 66 are removably attachable, as in the embodiment shown in FIG. 10, they have attachment mechanisms 70 and 75 at each end, which cooperate with vertical rod 50 and with frame extensions 65, respectively. If arms 66 are integral with rigid frame 60, as in the embodiment shown in FIG. 9, then only the end intended to cooperate with vertical rod 50 has attachment mechanism 70.

Attachment mechanism 70 is adapted to cooperate with vertical rod 50 and attachment mechanism 75 is adapted to cooperate with frame extensions 65. The attachment mechanisms 70 and 75 may use the same or different connecting means. Additionally, corresponding mechanisms 70 or 75 on separate arms 66 may use the same or different connecting mechanisms. The interface between the mechanisms 70 and 75, the vertical rod 50, and the rigid frame 60 is accomplished most effectively through male and female connections, but may also be accomplished via tapers, magnetic mechanisms, etc.

Attachment mechanisms 70 and 75 preferably have slideable nuts 74 and 79 that are rotatable. They are optionally integrally connected to arms 66 so as not to slip off or otherwise provide additional components for the surgeon to keep track of in an operating room. This is preferably achieved by using an expanded lip portion 78 on the arm tip 76 shown if FIG. 9. Arm tip 76 may be integral with arm 66, or may be removably attached as suggested by FIG. 9.

In one embodiment, upper threaded portion 52 of rod 50 (see FIG. 8) comprises an outer threaded male portion and a hollow female cavity nested therein. The corresponding mechanism 70 comprises a male portion 72 (se FIG. 10) that cooperates with the hollow female cavity. The mechanism 70 also has a slideable female threaded sleeve nut or coupling 74 that slides down over the male portion 72 to cooperate with the threaded male portion 52 of the vertical rod 50 and secure the arm 66 to the vertical rod 50.

At the other end of the arm, attachment mechanism 75, which is adapted to connect to frame extension 65, comprises a male portion 77. Attachment mechanism 75 also has a slideable female threaded sleeve nut 79. Frame extension 65 comprises an outer threaded male portion and a hollow female cavity nested therein. The male portion 77 of the corresponding mechanism 75 cooperates with the hollow female cavity. In accordance with an embodiment of the present invention any of the interconnecting components of the frame assembly may include self orienting mating geometric features that limit orientation in which the components may be interconnected. For example, optionally male portion 77 may have a D-shaped cross section, and female cavity may have a corresponding D-shaped cross section to ensure that arm 66 is positioned in the correct orientation and can be arranged only one way. Once male portion 77 is mated with the hollow female cavity, slideable threaded nut 79 engages threaded male portion 77.

Note that it is possible to provide simpler male and female connectors or simpler threaded bore adapters. The combination described above merely provides more stability for the frame assembly 20 but is not intended to limit the scope of the invention. In an alternate embodiment, the female and male threaded portions are reversed.

If the rigid frame 60 is of multiple-piece construction, the arms 66 should generally be attached to the frame extensions 65 before the rigid frame is attached to the vertical rods 50. In one embodiment, each arm 66 may be somewhat different from the other. For example, one arm 66 may have a longer male portion 72 than the other arm, as illustrated in FIG. 10. This enables the longer male portion 72 to be placed into a hollow female cavity of one of vertical rods 50 before the arm with the shorter male portion, in order to provide for easier set up by the surgeon, who can start threading one side before the other. Before the frame assembly 20 is located in place via vertical rod claps 40, the surgeon should make sure the frame square 21 is positioned over and surrounds the target area as illustrated in FIG. 11.

In a specific embodiment, the frame is a system for positioning and stabilizing surgical instruments, comprising: a substantially horizontal rectangular open frame adapted to be positioned over an operating area and to support surgical instruments, having two substantially horizontal lateral side portions, a substantially horizontal cephalad portion, and a substantially horizontal caudal portion; two laterally extending side arms, each having a proximal end adapted to connect to at least one side of the open frame and a distal end adapted to connect to a vertically extending rod; two vertically extending rods, each having a proximal end adapted to connect to one distal end of a side arm, and a distal end adapted to be engaged by a clamp; two clamps, each adapted to releasably engage one distal end of a vertically extending rod and releasably engaging a rail or rail extension of an operating table.

Figure 12:
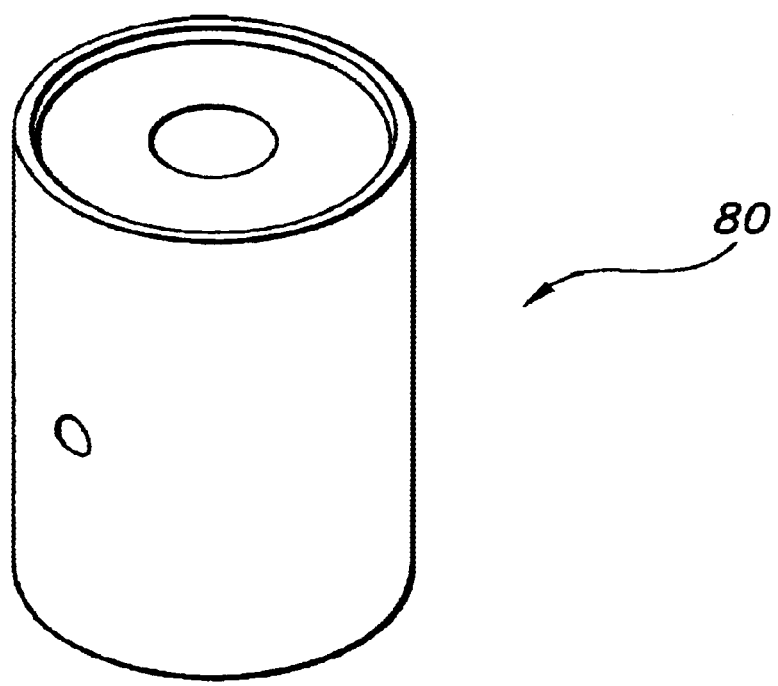
FIG. 12 is a perspective view of a centering or bubble level according to one embodiment of the invention.

Once assembled, to ensure that the frame assembly 20 is appropriately erected, a centering level 80, shown in FIG. 12, should be placed on the rigid frame 60, i.e., on one of the connecting portions 64. The surgeon should then adjust the frame assembly as necessary in order to ensure that the frame is level in the lateral direction by adjusting and tightening the vertical rod collars 56 and vertical rod clamps 40 to raise and/or lower the vertical rods 50.

The centering level 80 shown in FIG. 12 is merely illustrative; any level or location-measuring device that is small enough to fit on any surgical instrument can be used. Centering level 80 may have a female connecting portion, male connecting portion, screw threads, screw bore, magnetic surface, clip surface, or any other connector by which it can be reliably attached to the intended instrument.

Likewise, the instrument should have the appropriate corresponding connecting structure.

In accordance with an alternative embodiment of the present invention, the frame assembly 20 may include an angling mechanism that allows the surgeon to set the angle of rod 50 relative to square 20 at a predetermined angle. The angling mechanism may include a lockable hinge incorporated into the connection of arm 66 to rod 50. Such an angling mechanism may be used to select and control the angle of various instruments that are subsequently attached to the frame assembly, and in particularly control the angle of such instruments relative to the target disc space and/or its adjacent vertebral body endplates.

D. Exposing Surgical Site

Once frame assembly 20 is in position, the surgeon prepares the surgical site much as he would for an anterior cervical discectomy (ACD). The transverse curvilinear incision location will be marked approximately at the level of the targeted disc space and extended one centimeter contralateral to the side of the operating surgeon. It is possible, however, for the surgeon to make any type of incision he/she usually prefers to use for an ACD. After the surgeon makes a routine anterior exposure at the target disc level, he/she should confirm that the proper target location is exposed. Confirmation is preferably made by imaging a probe or needle placed adjacent to the target disc, and viewing the probe or needle under fluoroscopy.

Figure 13:
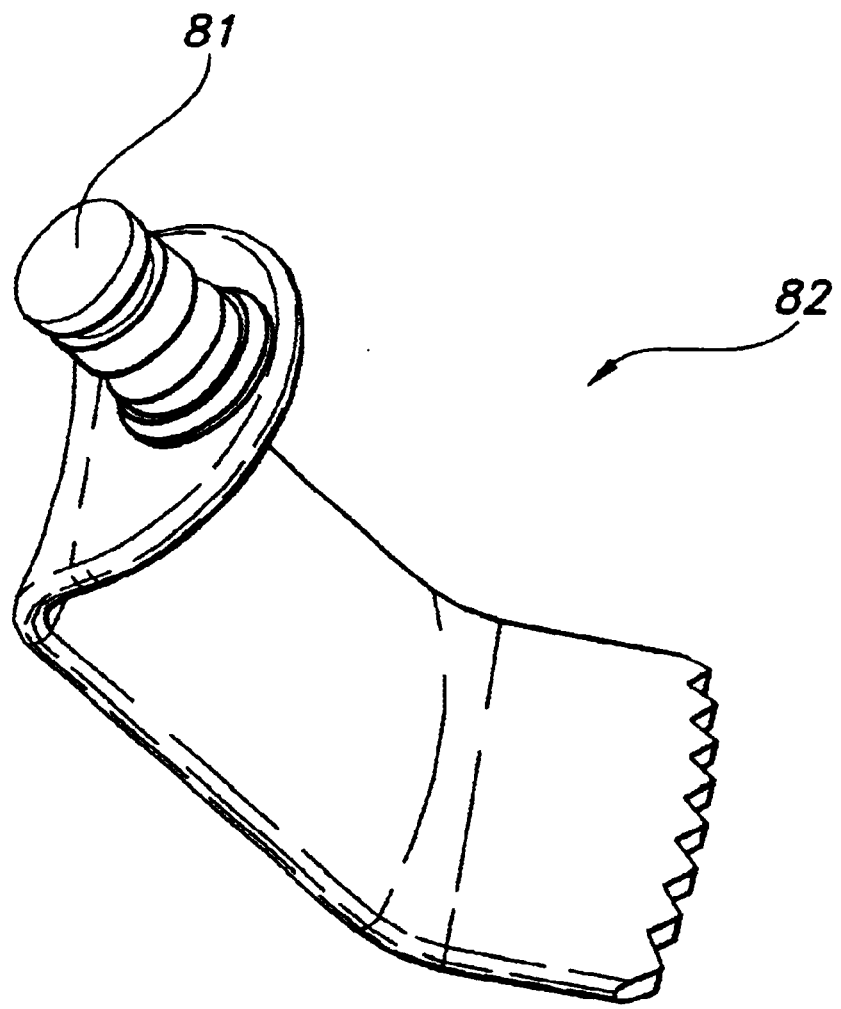
FIG. 13 is a perspective view of one embodiment of a retractor blade of the invention, adapted to interface with a retractor blade holder illustrated in FIG. 14.
Figure 16:
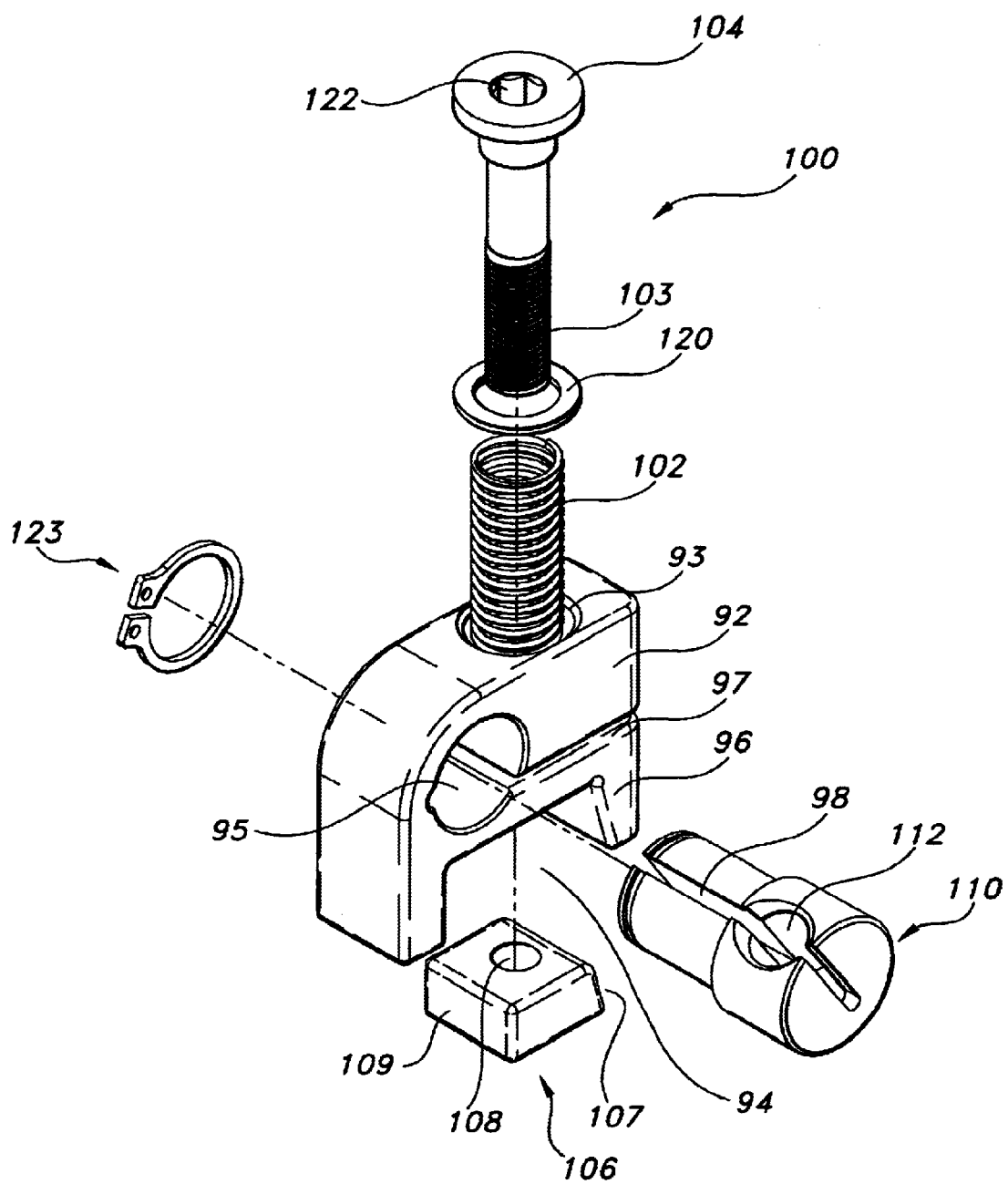
FIG. 16 is an exploded perspective view of the Kunzler clamp of FIG. 15.
Figure 17:
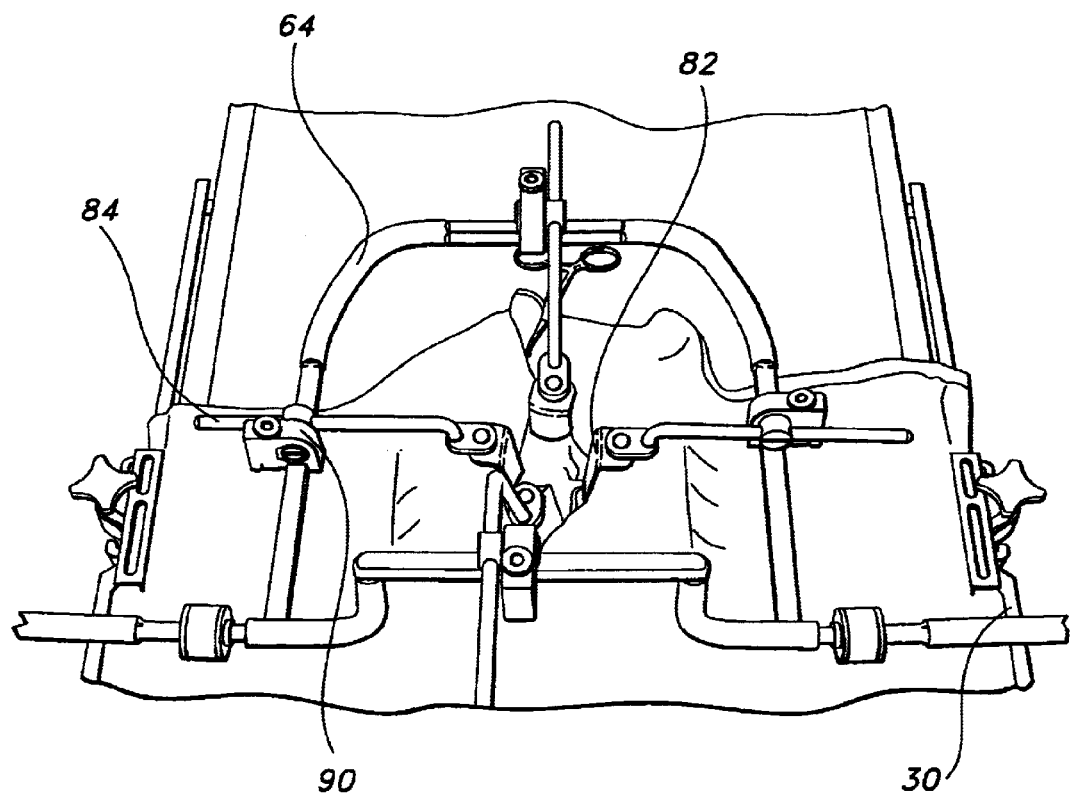
FIG. 17 is a top perspective view of the frame assembly, Kunzler clamps, retractor blades and retractor blade holders in accordance with the present invention, and illustrates how these components are attached to one another.

Near the level of the target space, the surgeon inserts a retractor blade 82, shown in FIG. 13, to retract each of the longus colli muscles, and other soft tissue, such as the trachea. To maintain the retracted position, the surgeon needs to join the retractor blade 82 to frame assembly. In one embodiment, the surgeon inserts a retractor blade holder 84, shown in FIG. 14, into Kunzler clamp 90, shown in FIG. 15 and FIG. 16, joins retractor blade 82 to the face of retractor blade holder 84, and secures the Kunzler clamp to the rigid frame 60 with a Kunzler clamp hex driver (not shown). The complete assembly is shown in FIG. 17.

More particularly, retractor blade 82 may be toothed or smooth and is provided in a plurality of shapes and sizes. Retractor blade 82 has a typical retracting portion as well as a connecting portion, such as knob 81, shown in FIG. 13.

Retractor blade holder 84 has a face 86 with a connecting portion, such as aperture 87, shown in FIG. 14, which connects to the connecting portion of retractor blade 82, such as knob 81. Retractor blade holder 84 has handle 85 that may be angled (as shown) or straight (not shown).

Figure 14A:
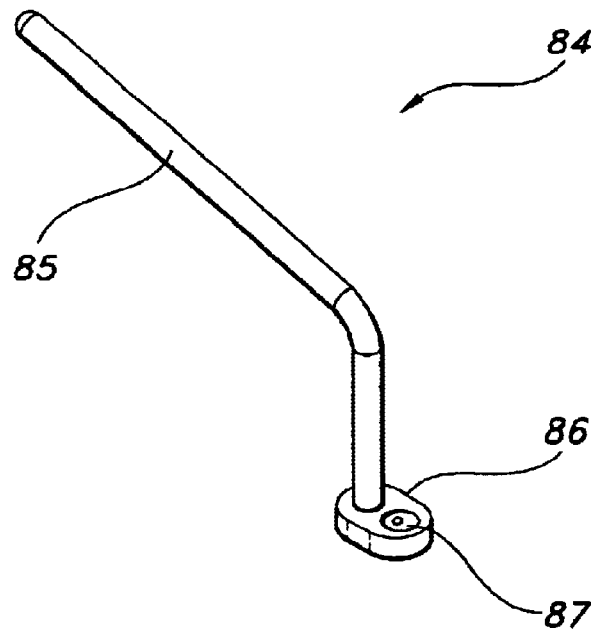
FIG. 14 includes a perspective view (A), a side plan view (B), and a bottom plan view (C) of one embodiment of a retractor blade holder, which receives the retractor blade of FIG. 13.
FIG. 14D is a perspective view of another embodiment of a retractor blade holder of the invention.
FIG. 14E is an exploded perspective view of the retractor blade holder of FIG. 14D.
Figure 14B:
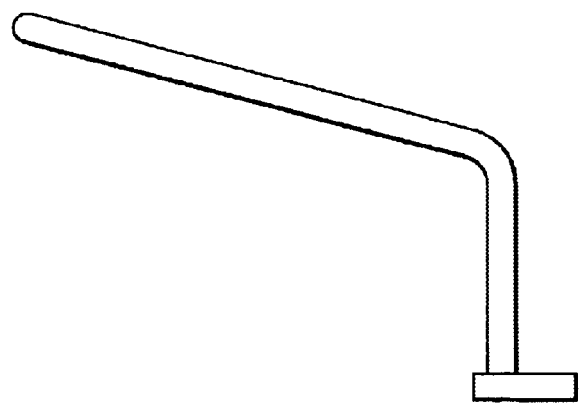
Figure 14C:
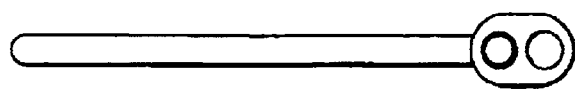
Figure 14E:
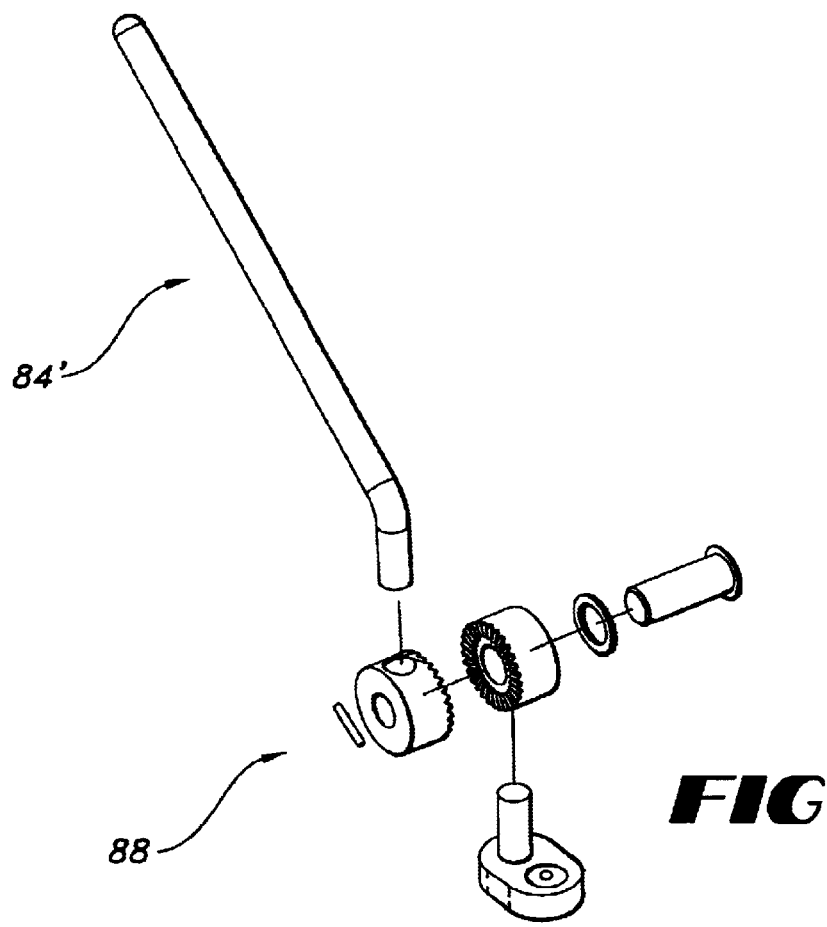
Figure 14D:
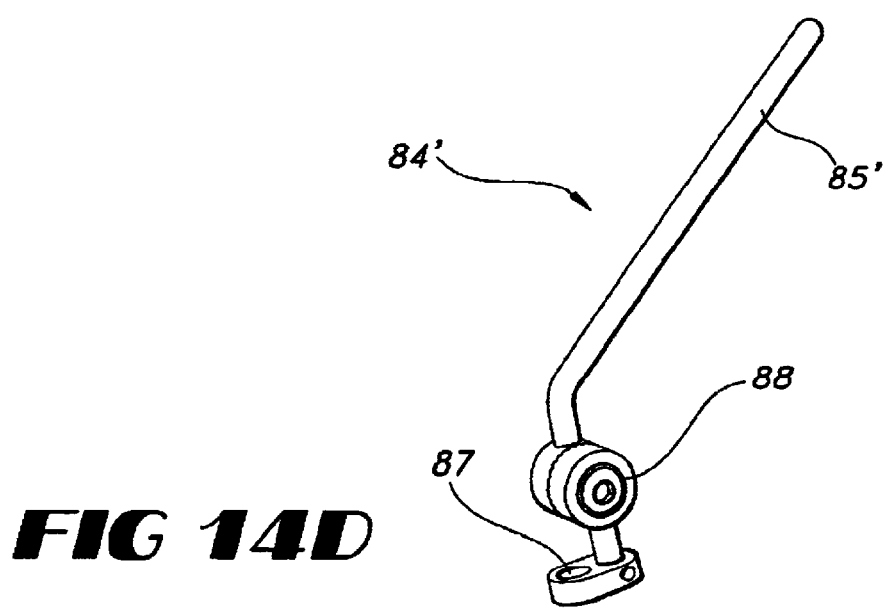

An alternate embodiment of retractor blade holder 84; has face 87 and a modified handle 85'. Modified handle 85' includes a hinge 88, adapted to change the position of the face 87 with respect to the modified handle 85'. FIG. 14E is an exploded perspective view, showing one embodiment of hinge 88 in greater detail, although it should be understood that any mechanism that can re-position face 87 with respect to handle falls with the spirit of a hinge 88 of modified handle 85'. For the purposes of this document, any reference to retractor blade holder includes all embodiments shown in FIGS. 14A–E.

Kunzler clamp 90 cooperates with frame assembly 20 and receives retractor blade 82 and retractor blade holder 84 to stabilize them with respect to frame assembly. Kunzler clamp 90 is tightened onto the frame assembly with hex driver so that Kunzler clamp 90 is stable and secure. In other words, it grips retractor blade holder 84 tightly, and is secured to frame assembly 20, so that clamp 90 and holder 84 are stationary. Since the Kunzler clamp 90 simultaneously grips the holder 84 and frame assembly 20, it alleviates the need for two separate locking devices. The surgeon retracts the longus colli muscles with this retracting system to expose the target disc space.

Figure 15:
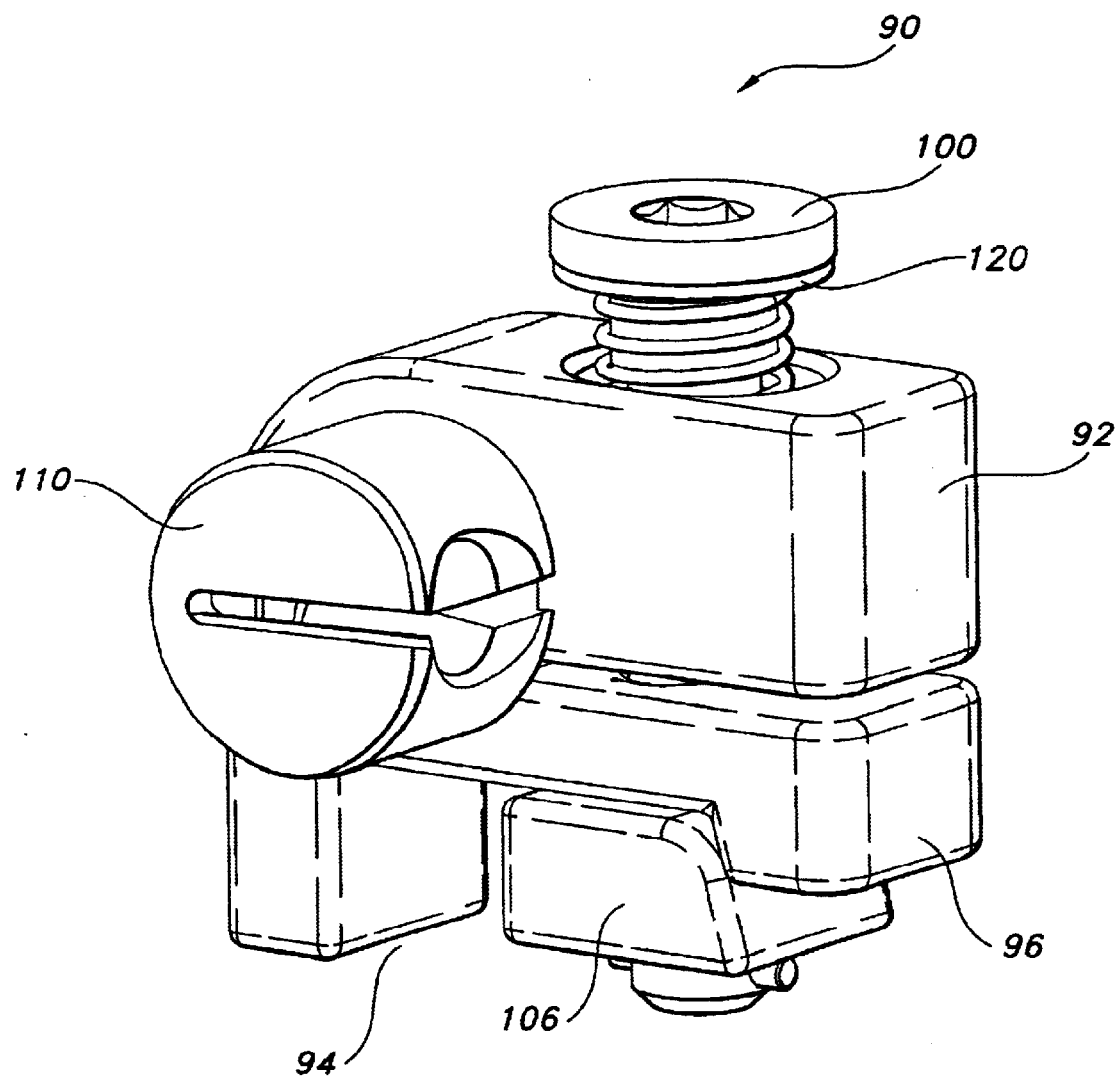
FIG. 15 is a perspective view of one embodiment of a Kunzler clamp, showing generally a main body, throughpin, securing block, and receiving protrusion, and which is adapted to be secured to the rigid frame of FIG. 9 and FIG. 10, and which is capable of receiving the retractor blade holder of FIG. 14 and securing it to the rigid frame.

As shown in FIG. 15, Kunzler clamp 90 has main body 92 with upper, lower, and lateral sides with main body 92 supporting throughpin 100, securing block 106, and an instrument holder or receiving protrusion 110. Main body 92, detailed in FIG. 16, has a groove or cut out portion 94 on its lower side that is adapted to cooperate with connecting portions 64 (shown in FIG. 9 and FIG. 10) of the frame assembly 20. Groove 94 is defined by sides, at least one of the sides forming a main body foot 96. Main body 92 also has channel 97, shown in FIG. 16, extending from an outer surface of main body 92 to an aperture 95 (also called a first aperture) in inner portion of main body 92 separating main body into a first and second portion. Channel 97 in part secures instrument holder or receiving protrusion 110 when Kunzler clamp 90 is tightened.

Throughpin 100 extends through an aperture 93 in main body 92 and cooperates with securing block 106. Throughpin 100, as shown in the exploded view of FIG. 16, is a bolt having a straight portion 103 and a head portion 104. Straight portion 103 is threaded at its lower portion to facilitate connection with securing block 106. Throughpin 100 may optionally be associated with washer 120 that protects the interface between the head portion 104 and main body 92. It may also be associated with a spring 102 that biases throughpin 100 upward and facilitates upward movement of the throughpin 100 through aperture 93. In a one embodiment, the spring is a coil spring disposed in the second aperture, and the throughpin passes through the coil spring.

In use, straight threaded portion 103 interfaces and cooperates with securing block 106. Securing block 106 has a threaded bore 108 that receives straight threaded portion 103. Securing block 106 has at least sides 107 and 109. Side 107 may be beveled and corresponds to and interfaces with the main body foot 96 and side 109 is adapted to contact connecting portion 64 of the rigid frame 60.

In use, securing block 106 fits into groove 94. Particularly, side 107 of securing block 106 fits into and interfaces with main body foot 96. Side 107 is beveled and foot 96 has a corresponding bevel. This angle configuration makes the Kunzler clamp 90 less prone to slipping once the throughpin 100 is tightened. To tighten the Kunzler clamp 90 and drive the straight threaded portion 103 into the threaded bore 108, a Kunzler clamp hex driver (not shown) engages head portion 104 of throughpin 100. Head portion 104 has a hexagonal opening 122 corresponding to a pattern on hex driver, quite similar to a hexagonal head screw driver/screw combination. As the clamp is tightened, the bevel on side 107 moves up the corresponding bevel on foot 96, which causes side 109 to move toward connecting portion 64 of frame assembly 20, securing the clamp to the frame.

Beveled side 107 and spring 102 provide a quick release mechanism for clamp 90. In general, throughpin 100 can be tightened just enough to secure connecting portion 64 of the rigid frame 60 within groove 94. The clamp can then be quickly and easily released from connecting portion 64 by simply pressing down on the biased throughpin 100. Block 106 will move down, and because of beveled surface 107, block 109 will translate toward foot 96 thereby increasing the width of groove 94 and releasing the clamp's lock on frame connecting portion 64. Clamp 90 can then be repositioned along connecting portion 64 and the pressure on the top of throughpin 100 released. This will cause the side 109 to again clamp against connecting portion 64. Kunzler clamp 90 also has an instrument holder 110 that is positioned within aperture 95. Instrument holder 110 has an opening 112 that receives surgical instruments that the surgeon desires to secure to the frame, e.g. retractor blade holder 84. Instrument holder 110 is rotatably positioned within aperture 95, and is secured by retaining ring 123. Instrument holder 110 swivels to provide a proper angle of the opening 112 with respect to the retractor blade holder 84. Tightening the throughpin 100 causes the sides defining channel 97 to compress as securing block 106 moves upward. This causes the internal surfaces adjacent aperture 95 to press against and immobilize instrument holder 110 with respect to the clamp main body 92. Receiving protrusion 110 also has slot 98 that extend from opening 112 to an exterior surface of instrument holder 110. Consequently, as the internal surfaces of adjacent aperture 95 press against instrument holder 110, the sides defining slot 98 are compressed, thereby compressing the sides of aperture 112 onto any instrument inserted therein. This prevents any translational motion within slot 112 of any instrument inserted therein. In other words, when the throughpin is rotated in one direction, its threads urge the securing block against the lower side of the main body, simultaneously compressing the channel and constricting the first aperture, which in turn compresses the slot and constricts the opening of the instrument holder, and narrows the support channel.

Thus clamp 90 provides a mechanism to that will loosely temporarily hold two components (e.g. frame 60 and holder 84) relative to one another, such that they can still be repositioned along one or more of three degrees of movement (e.g., (1) translation of holder 84 along connecting portion 64, (2) translation of holder 84 within opening 112, and (3) rotation of holder 84 relative to frame 60 by rotating receiving protrusion 110 within aperture 95). Upon obtaining the proper positioning of the two components relative to one another, clamp 90 provides a simple means of locking that position along each of the three degrees of movement by actuating a single mechanism, e.g. rotating throughpin 100.

Once the retractor blade holder 84 is secured to Kunzler clamp 90, preferably by sliding handle 85 of the holder 84 into opening 112, the surgeon joins the retractor blade holder 84 to retractor blade 82. (Note that these steps may be conducted in any order, based upon the surgeon's preference.) This connection may be accomplished in a number of ways. One connection embodiment provides a retractor blade holder 84 having a face 86 with an aperture 87 that interfaces with a knob 81 of retractor blade 82. The surgeon retracts tissues and muscles and attaches Kunzler clamp 90 to the rigid frame 60 and secures Kunzler clamp 90 to both the frame and the retractor blade holder with the hex driver.

These retracting and positioning steps are repeated for the opposite side of the incision, as well as the cephalic and caudal aspects of the incision. This system and method allow the surgeon to create the maximum symmetrical exposure at the target disc space, and free his hands for the surgical procedure. In addition, the rigid frame provides a completely rigid retraction system that allows the retraction of both midline and lateral structures, which offer differing resistances to retraction, without movement of the frame relative to the patient.

E. Excision of the Target Disc

Next, the surgeon will remove a portion of the target disc. The surgeon performs a discectomy, removing the nucleus pulposus as well as any material that has been expelled from the disc space by herniation or rupture, while leaving in place as many of the ligamentous support structures as possible. As with a number of the procedures described herein, the specific order of steps and tools used may vary from surgeon to surgeon.

Figure 18:
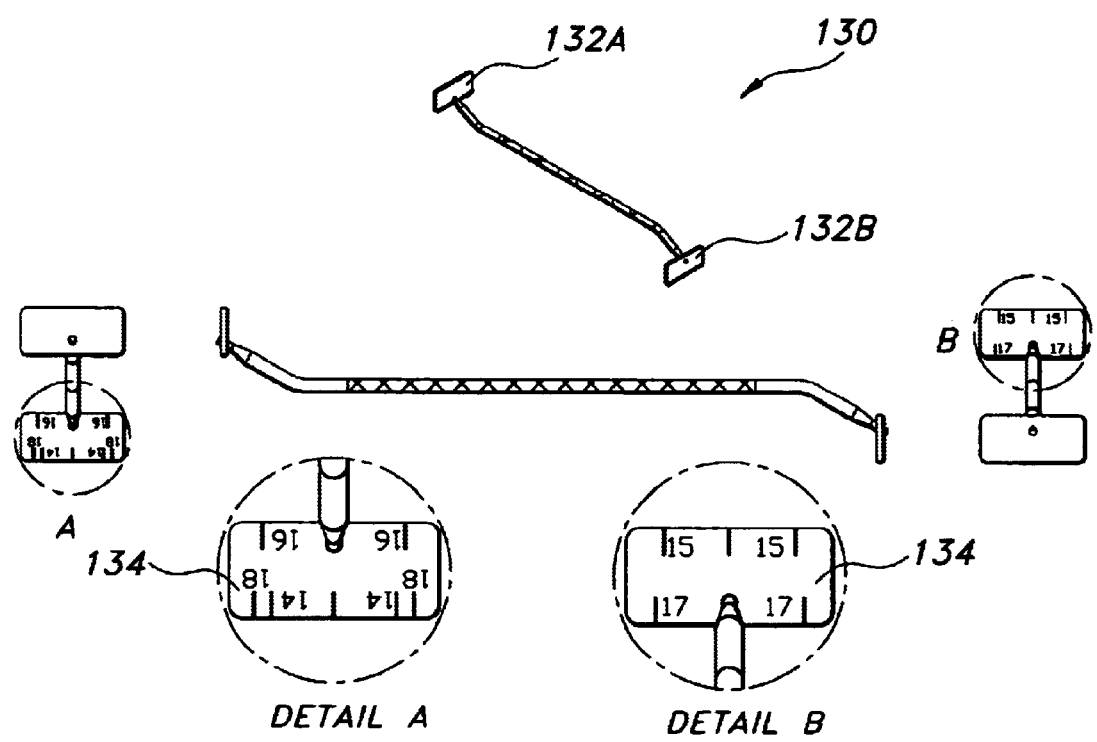
FIG. 18 is a perspective view of one embodiment of an incision template of the invention, showing generally scale marks on the opposing faces of the incision template, which help locate the predetermined point in target space for a particular pre-selected prosthesis.

The surgeon marks the estimated midline of the target disc space with sterile ink. An incision template 130, shown in FIG. 18, is placed onto the anterior surface of the target disc space, with the center of the template aligned with the estimated lateral midline of the target disc space. Incision template 130 has faces 132 A and B with scale marks 134. Scale marks 134 include a mark the center of each face 132, and marks corresponding to preferred lateral incision positions for various sizes of prosthesis. The surgeon uses the scale marks 134 associated with the pre-determined prosthesis size as a distance guide, and excises a portion of the annulus fibrosis that corresponds to the size of the pre-determined prosthesis. The surgeon removes as much as possible of the nucleus pulposus and soft interior portion of the annulus fibrosis using forceps, ronguers, and curettes, leaving the densely fibrotic portion of the annulus fibrosis intact. Generally, incision template 130 allows the surgeon to limit the cut of the annulus fibrosis to the approximate size of the prosthesis. This minimizes the amount of tissue removed and minimizes the damage to surrounding connective tissues.

Before or after the nucleus pulposus and a portion of the annulus fibrosis has been removed, the surgeon may need to manually remove spondylotic osteophytes and/or ridges with, e.g., a Kerrison rongeur or a burr to allow adequate access to the intervertebral space to perform the discectomy, and to create a level surface for the machining fixture base that will be placed on the anterior surface of the vertebral bodies.

F. Distraction of the Vertebral Bodies

Figure 19:
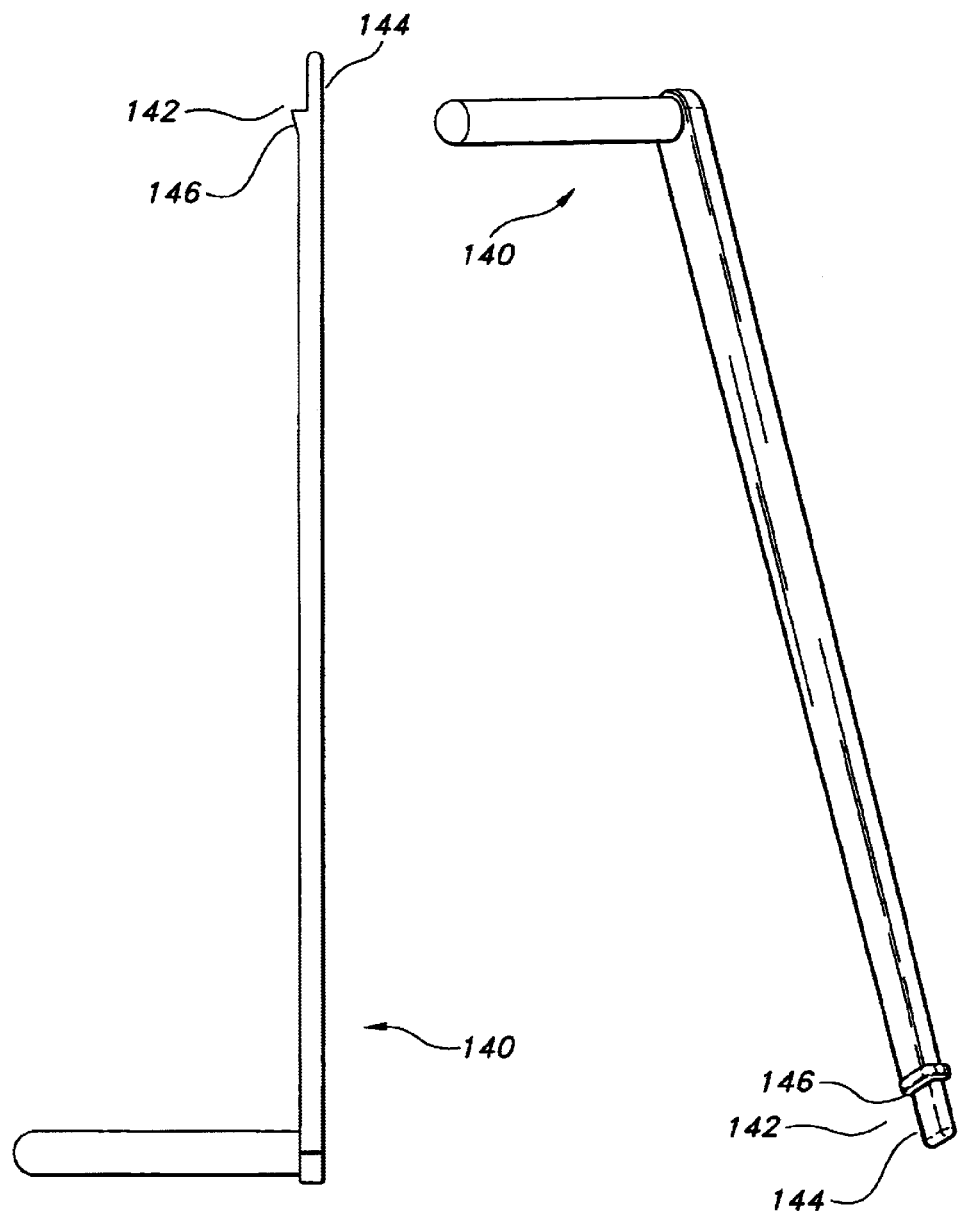
FIG. 19 is a perspective view (A) and a side view (B) of one embodiment of a cam distractor of the invention, having a base that is adapted to distract the space between two vertebral bodies.

Referring now to FIG. 19, the surgeon next distracts the vertebral bodies to expose the target space by sequentially using cam-action distractors 140 of increasing widths. Each distractor 140 has a substantially blunt, substantially flat, blade-shaped proximal end or base 142 that is shaped to fit between the vertebral bodies. In one embodiment, base 142 has a longitudinally extending flat blade portion 144 that is adapted to extend into the target space, and a laterally projecting stop 146 that contacts the face of one of the vertebral bodies. More specifically, proximal end or base 142 comprises a system for separating and maintaining separation of the bones of a joint, comprising: a cam-action distractor comprising a proximal end, a distal end, and an intermediate length, wherein the proximal end comprises a substantially blunt, substantially flat, longitudinally extending blade adapted for insertion into the joint, the blade comprising a leading edge, a first and second opposed face, and opposed lateral edges; and a laterally projecting stop located at a distal end of the blade and adapted to contact one or more joint surfaces and limit the penetration of the blade into the joint; the distal end comprises a handle extending substantially orthogonal to the intermediate length, and adapted for gripping and turning; wherein when the handle is turned, the opposed lateral edges of the blade bear against the bones of a joint and force them apart. In accordance with alternative embodiments, stop 146 may extend 180° around distractor 140 or 360° around distractor 140.

Distractors 140 are provided in various sizes, for example, 4.5 mm, 6.5 mm, and 8.5 mm. The ultimate goal of the distracting step is to distract the space so that it is wide enough to receive a prosthesis (in most cases, 8.5 mm), or wide enough to receive additional instruments to prepare the disc space to receive the prosthesis. Accordingly, a stepped-up range of distractors 140 is used to slowly distract the space at various levels. The smallest distractor 140 is used first. The surgeon distracts the disc space by inserting the flat blade into the intervertebral space, and turning the distractor, using a slow rotary motion, alternating between counter-clockwise and clockwise motions, so that the width of the blade forces the vertebral bodies apart by a camming action. This rotation slowly stretches the ligaments. In one embodiment, it is possible to use a plurality of cam distractors of increasing widths on opposite lateral sides of the target disc space, for example, there may be at least three distractors wherein the distance between said first edge and said second edge is 4.5 mm, 6.5 mm, and 8.5 mm.

To maintain the separation of the vertebral bodies obtained by using distractor 140, optional sagittal retainers 150 of increasing sizes may be inserted at the sides of the disc space prior to removing distractor 140. Sagittal retainers 150, shown in FIG. 20, are also provided in increasing widths. Each retainer 150 is preferably about 0.5 mm smaller in width than the width of each distractor 140, for example 4 mm, 6 mm, and 8 mm. After the smallest distractor 140 (e.g., a distractor having a blade width of 4.5 mm) is used, the smallest sagittal retainer 150 (e.g., having a width of 4 mm) is inserted into the intervertebral space to hold the vertebral bodies apart as the surgeon removes the distractor and inserts a larger one. Retainer 150 has heel 152 that spaces the vertebral bodies apart. In one embodiment, the retaining spacer may comprise a heel having first and second edges, adapted for insertion into the distracted joint, wherein the first and second edges contact the bones of the joint and maintain their distance apart when the cam action distractor is removed. The first and second edges may be serrated. Once a distraction of 8.5 mm is reached, an 8 mm retainer 150 can be placed between the vertebral bodies to maintain that distance.

In general, a maximum distraction of 8.5 mm is desired for implantation. If, for some reason, the disc space is over-distracted, then the implantation procedure can be aborted and a fusion procedure conducted, or a larger prosthesis (i.e., a thicker prosthesis, e.g., having thicker shells) constructed and implanted.

G. Positioning Machining Fixture Relative to Target Disc Space

The surgeon should next locate a line passing through a predetermined reference point in the surgical site, that is in a sagittally extending vertical plane, and that forms an angle with a vertical line that corresponds to the angle measured using the inclinometer image and the vertebral body orienting tool. This is done using a series of levels, plumb lines, and tools that are adapted to measure a patient's internal anatomical features and position relative to the gravity vector. The line passing through the predetermined reference point in the target disc space is used to precisely position instruments to prepare the disc space, so that the placement of the prosthesis occurs at a precise location.

1) Transverse Centering System and Method

The present invention also provides a method for positioning surgical instruments relative to a reference line within a target location in a patient, comprising:

(a) determining the position of the reference line relative to a gravitational vector;

(b) determining a first point relative to a first plane intersecting the target location;

(c) using the first point to position an instrument that is adapted to locate a second plane intersecting the target location;

(d) positioning a fixture relative to the instrument;

(e) using a position locating device to align the fixture along the intersection of the first and second planes, wherein such intersection is substantially congruent with the reference line;

(f) securing the fixture in place; and (g) using the fixture the position other instruments within the target location relative to the reference line.

First, to locate the transverse arc, the surgeon uses a transverse centering tool. This instrument has two laterally extendable/retractable prongs or tips, which when extended, allow the surgeon to feel, through the resistance to lateral extension of the prongs, the intersection between the bone of the uncinate processes and the remaining material of the annulus fibrosus. The prongs are retracted during insertion and removal from the disc space. Once the surgeon inserts the instrument into the intervertebral space, he expands the prongs, and locates the intersection on either side of the disc space. One skilled in the art will appreciate that when disc disease is present such anatomical landmarks may not be discernable or may not provide the preferred symmetrical reference points. In such cases, the surgeon may instead use as a reference point the intersection between the annulus fibrosus and the larger of the two uncinate processes. The surgeon then places a leveling device, such as a centering level, which may be a bubble level as shown in FIG. 12, on the end of the instrument which has a member adapted to cooperate with the leveling device. Using the bubble level as a guide, the surgeon rotates the instrument in the lateral or transverse direction, until the bubble level is laterally centered, indicating the location of the apogee of the transverse arc. The surgeon then deploys a marker, which is centered between the extendible prongs, to the anterior surface of one of the vertebral bodies, usually the superior vertebral body, and marks the anterior surface of the vertebral body, indicating the sagittally extending vertical plane, which bisects the intervertebral space, and intersects the vertebral body surface. Exemplary embodiments of various transverse centering tools 200 are shown in FIG. 21-FIG. 27. Similar structural features are indicated by like numerals, even though the embodiments depicted can operate somewhat differently.

Transverse centering tool 200 has opposed, retractable tips 204, which have blunt ends, and which extend laterally after insertion to contact the sides of the intervertebral space, marking device 206, and main shaft 207. Tips 204 are retractable and expandable laterally, so that the tool can be inserted into the intervertebral space through the opening created during discectomy. End 210 of the tool is adapted to receive bubble level 80 (shown in FIG. 12), which can be used to orient the tool so that its end is located at the apogee of a transverse arc 6 defined by the lateral swing of the end of the tool as illustrated in FIG. 1. Once this point is located, marking device 206, typically in the form of a pointed pin, is lowered to the anterior surface of the vertebral body. A mark is placed on the surface, either by the marking device 206 itself, or using a sterile marker and using the marking device 206 as a locator. The marking device may be releasable, i.e., it may detach from the tool and remain in place to indicate the location on the anterior surface until removed by the surgeon. It may be lowered by the surgeon sliding the pin downward to the bone surface, or may be spring loaded and lowered when the surgeon releases the spring. Alternatively, it may be spring loaded, but biased in its non-marking position so that it returns to that position after the surgeon makes his mark. Marking device 206 may be a pin, anchor, pointer dye marker, sterile ink pen, biocompatible dye or other marking means that either physically remains in the area marked or leaves an indication on the area marked.

Figure 21:
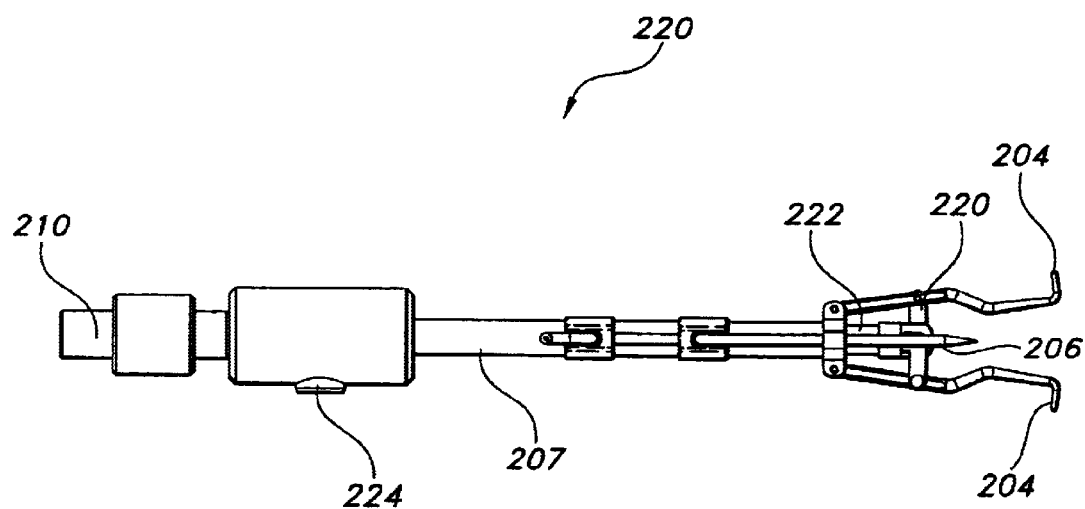
FIG. 21 is a side plan view of one embodiment of a transverse centering tool of the invention, showing generally a main shaft that houses tips, a marking device, and a securing button, and which is used to locate and mark a point on the anterior surface of a vertebral body which point corresponds to the apogee of the first arc. One end of the tool is adapted to receive a centering level.
Figure 22:
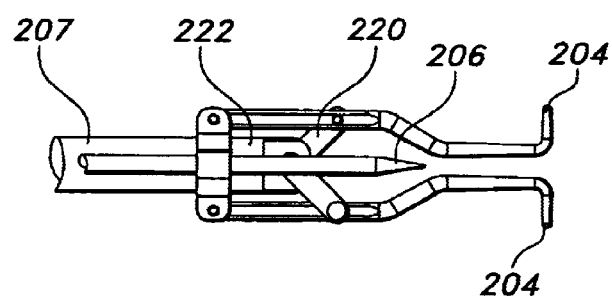
FIG. 22 is a magnified side plan view of the end of the transverse centering tool of FIG. 21.

In the embodiment of the transverse centering tool shown in FIG. 21, the retraction and extension of the tips 204 are controlled by movement of an inner, adjustment shaft 222, which moves equalizing connecting bars 220, levering tips 204 around fulcrums formed where the tips are hinged to main shaft 207. Details of the connections between tips, connecting bars, the main shaft, and the adjustment shaft are shown in FIG. 22. In one embodiment, the shaft 222 is substantially centrally located between the ends of the expandable tips 204 at all possible positions of the tips 204. The appropriate degree of extension of the tips can be set by releasing a simple spring loaded adjustment button 224 that stops adjustment shaft 222 from moving relative to main shaft 207. Marking device 206 slides along main shaft 207, and is lowered by the surgeon.

Figure 23:
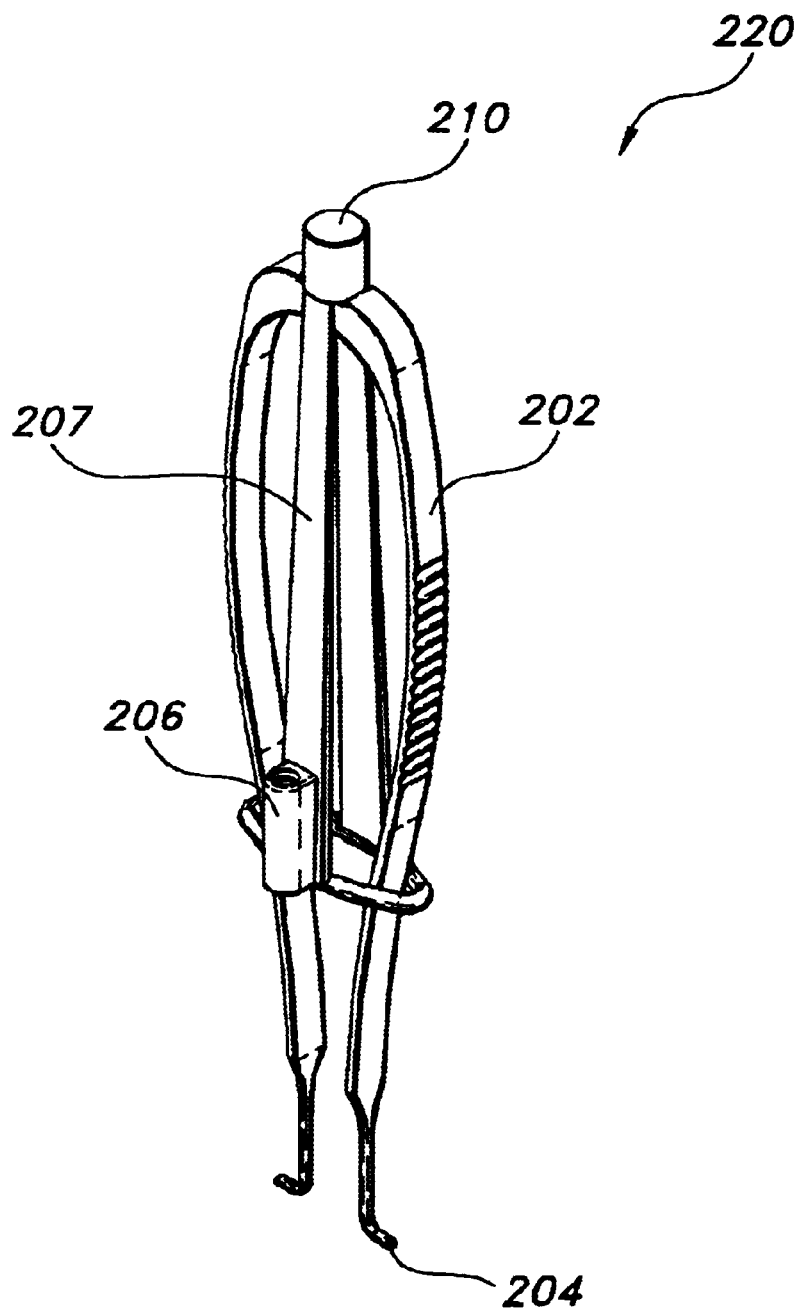
FIG. 23 is a perspective view of another embodiment of a transverse centering tool of the invention, showing generally a handle that terminates at tips and that also houses a marking device and is adapted to receive a centering level at one end.
Figure 24:
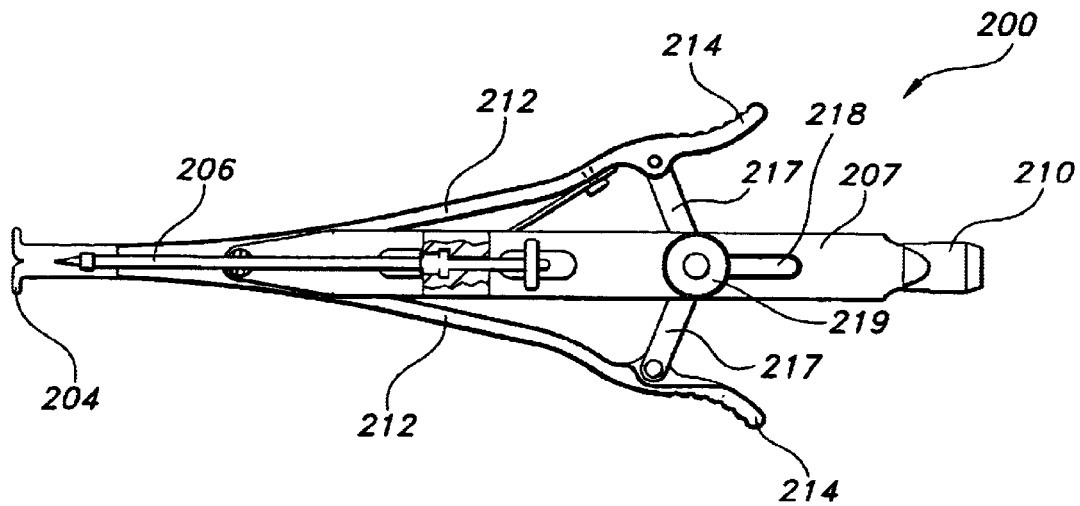
FIG. 24 is a top plan view of another embodiment of a transverse centering tool of the present invention, showing generally a main shaft having extensions that terminate at tips, a securing knob, and a thumb-activated platform, and that is adapted to receive a centering level at one end.
Figure 25:
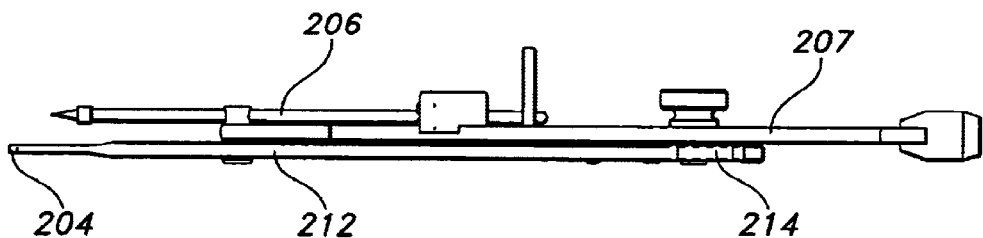
FIG. 25 is a side plan view of the transverse centering tool of FIG. 22.
Figure 26:
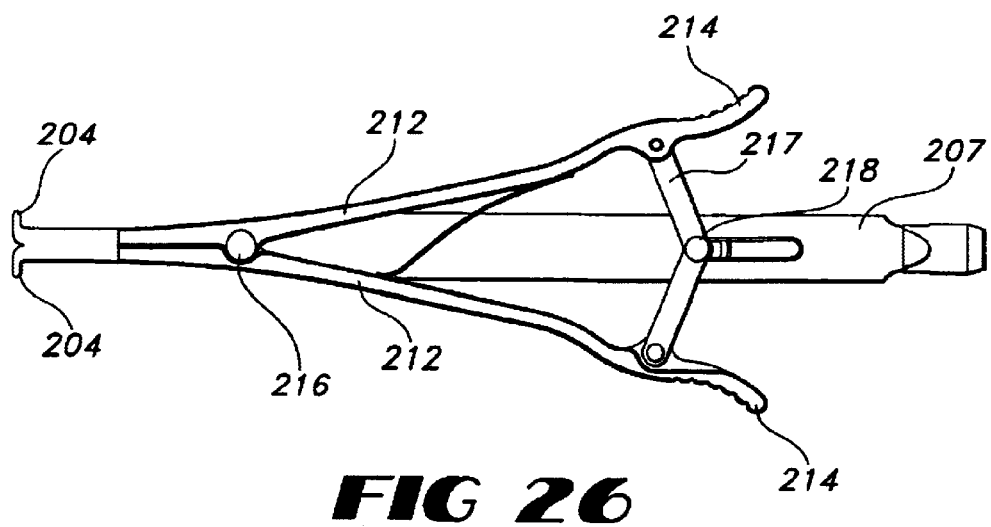
FIG. 26 is a bottom plan view of the transverse centering tool of FIG. 22.
Figure 27:
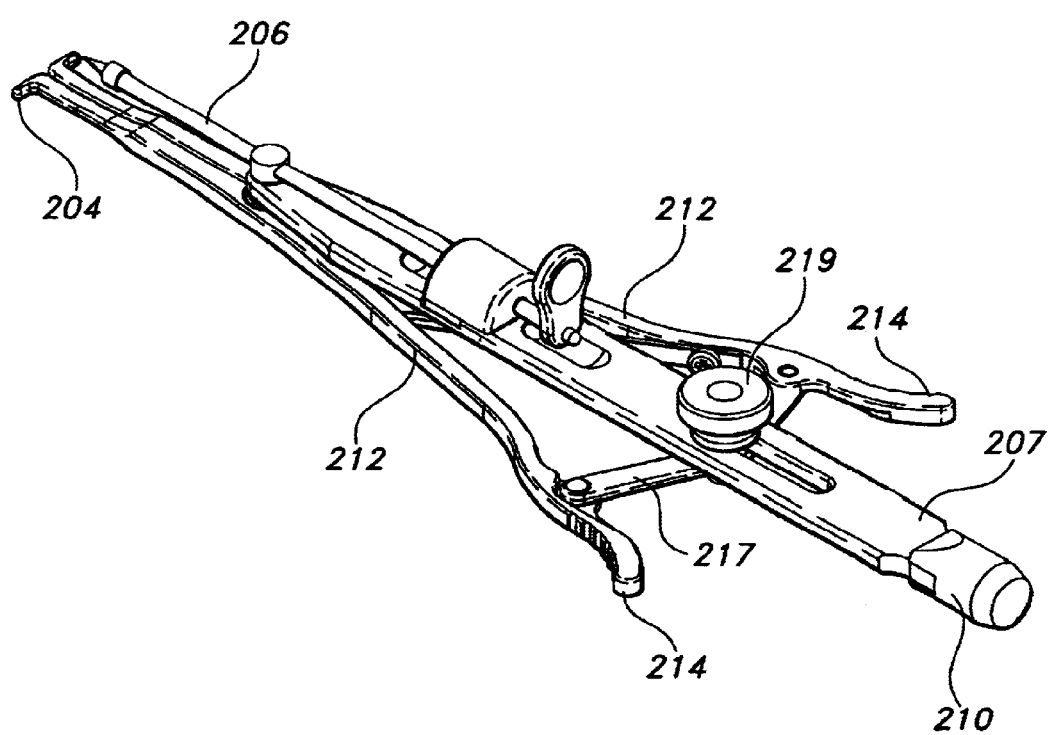
FIG. 27 is a perspective view of the transverse centering tool of FIG. 22.

Referring to FIG. 23, tips 204 may alternatively be connected to handle 202 to form an integrated forcep or tweezer. When sides of handle 202 are compressed, tips 204 are also compressed and can be inserted into the target disc space. Once inserted, the surgeon relaxes the pressure, allowing tips 204 to spread apart and contact the sides of the disc space. Marking device 206 may automatically release or may be manually lowered by the surgeon.

Alternatively, as shown in FIG. 24-FIG. 27, tips 204 may have integral extensions 212 which are manipulated by the surgeon to extend the tips by squeezing the ends of extensions 212 together. The surgeon inserts tool 200 into the target disc space without pressure on extensions 212, and then squeezes extensions 212 together to expand tips 204. Extensions 212 may be of any suitable length and may have any type of grasping surface 214. Grasping surface 214 may be straight, curved, angled, or flat surfaces. Of particular use is grasping surface 214 that is slightly curved or indented at the ends, providing the surgeon with a convenient place to rest his finger and thumb when using tool 200.

Extensions 212 are hinged to the main shaft at a first fulcrum 216 near tips 204 and also hinged to equalizing connecting bars 217, which in turn are hinged to main shaft 207 at second fulcrum 218 closer to grasping surfaces 214. Fulcrums 216 and 218 provide for a smooth movement of tips 204, facilitating more precise measurement. Second fulcrum 218 also has a securing knob 219, which secures the location of second fulcrum 218 with respect to main shaft 207 so that the degree of extension of tips 204 may be set in place once the appropriate anatomical features have been located.

2) Sagittal Centering System and Method

Next, the surgeon may use the first point to position an instrument that is adapted to locate a second plane comprising:

(a) positioning the instrument relative to the first point;
(b) rotating the instrument through an arc, and thereby defining the second plane, wherein said second plane is substantially perpendicular to the first plane; and
(c) using a leveling device to position the instrument at the apogee of the arc, wherein the intersection of the first and second planes at said apogee is congruent with the reference line.

More specifically, in one embodiment, the surgeon laterally positions a sagittal centering tool by using the point marked on the vertebral body using transverse centering tool 200. Sagittal centering tool is then rotated through an arc orthogonal to the transverse arc described by the transverse centering tool, as illustrated in FIG. 1. The sagittal centering tool can then be oriented at a predetermined angle relative to vertical using a bubble level and a protractor, as described above. Preferably, the predetermined angle used is typically that determined using the inclinometer and goniometer. Exemplary embodiments of sagittal centering tool 250 are shown in FIG. 28–FIG. 31.

Note that it is possible to use a single instrument as the transverse centering tool and the sagittal centering tool, although not necessarily preferable. Thus, although the remainder of the discussion will address the tools as separate instruments, this is not intended to be limiting. Any tool that will perform the functions described is possible for use in conjunction with the present invention.

Sagittal centering tool 250 is oriented in the target disc space, between the targeted vertebral bodies. To place sagittal centering tool 250, the surgeon lines up the mark on the vertebral body with a reference point on sagittal centering tool 250, such as depression 274, shown in FIG. 28C. This establishes the lateral position of the sagittal centering tool, and ensures that its end describes an arc orthogonal to the transverse arc described by the transverse centering tool. The surgeon uses a leveling device at a second end 261 of the tool 250 to determine the apogee of the orthogonal arc (also called the second arc or the second plane.) In the embodiment shown in FIG. 28A and FIG. 28B, the caudal side of tool 250 has keyway 256 and step 258. Keyway 256 is adapted to interface with key 310 of machining fixture or scaffold 300, described below. When tool 250 is in use, step 258 contacts the anterior surface of one of the vertebral bodies.

In the embodiment shown in FIG. 28A and FIG. 28B, sagittal centering tool 250 has nose 252, keyway 256, and handle 260. Handle 260 may have threaded bore top portion 261 that cooperates with puller 475 (described below) to help ease the removal of tool 250, if necessary. Nose 252 can have teeth 270 that secure tool 250 in place between vertebral bodies. Teeth 270 may be a jagged edge of nose 252, a layer of jagged material integral with nose 252, or individual teeth (or bumps) that are clearly defined on the surface of nose 252. Nose 252 has a shape that allows it to be inserted easily between vertebral bodies, preferably thinner at tip 272 of nose 252.

Nose 252 also contains step 258. Step 258 contacts a surface of a vertebral body, preferably the anterior surface of the caudal vertebral body, and secures tool 250 from sliding too far into the intervertebral space while maintaining a midline position. Nose 252 is connected to neck 254. On one side of neck 254 is keyway 256 that stabilizes the relationship between sagittal centering tool 250 and scaffold 300 (described below). Neck 254 may be integral with nose 252, as shown in FIG. 28A and FIG. 28B.

Figure 29:
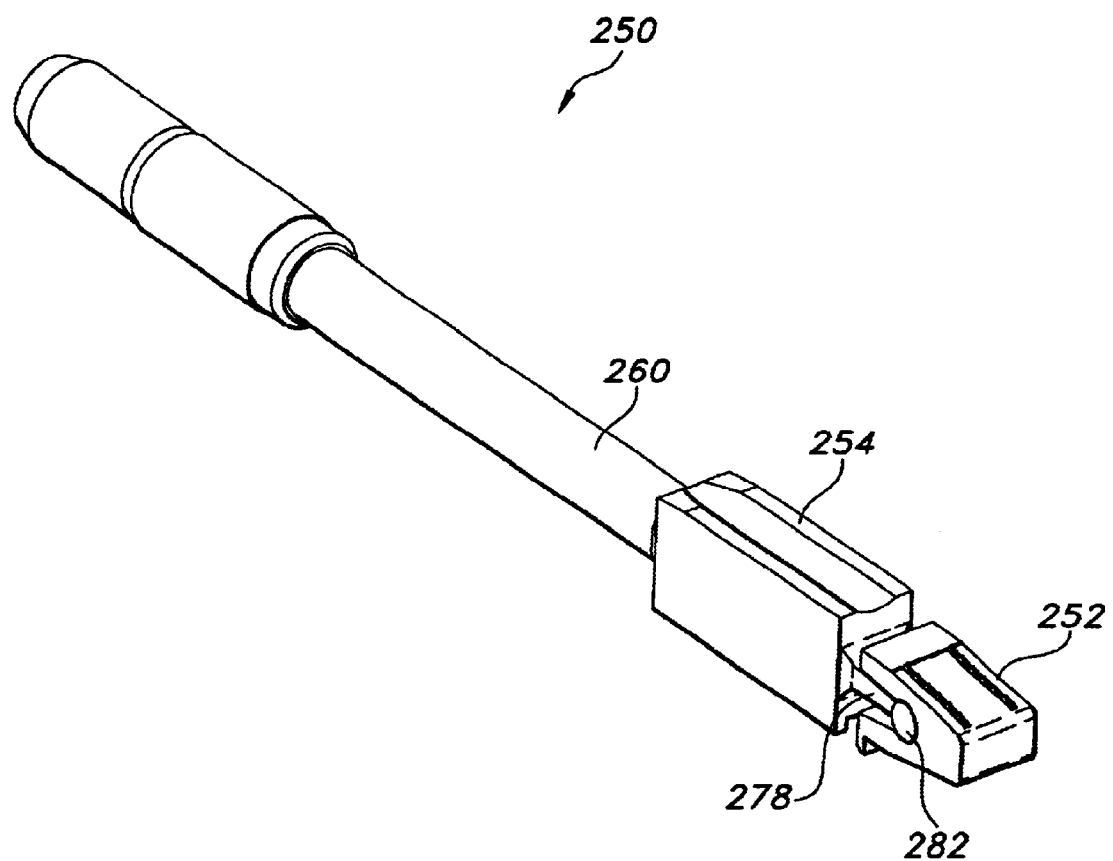
FIG. 29 is a perspective view of another embodiment of a sagittal centering tool of the present invention, showing generally a post that allows a hinged connection between the nose and neck.
Figure 31:
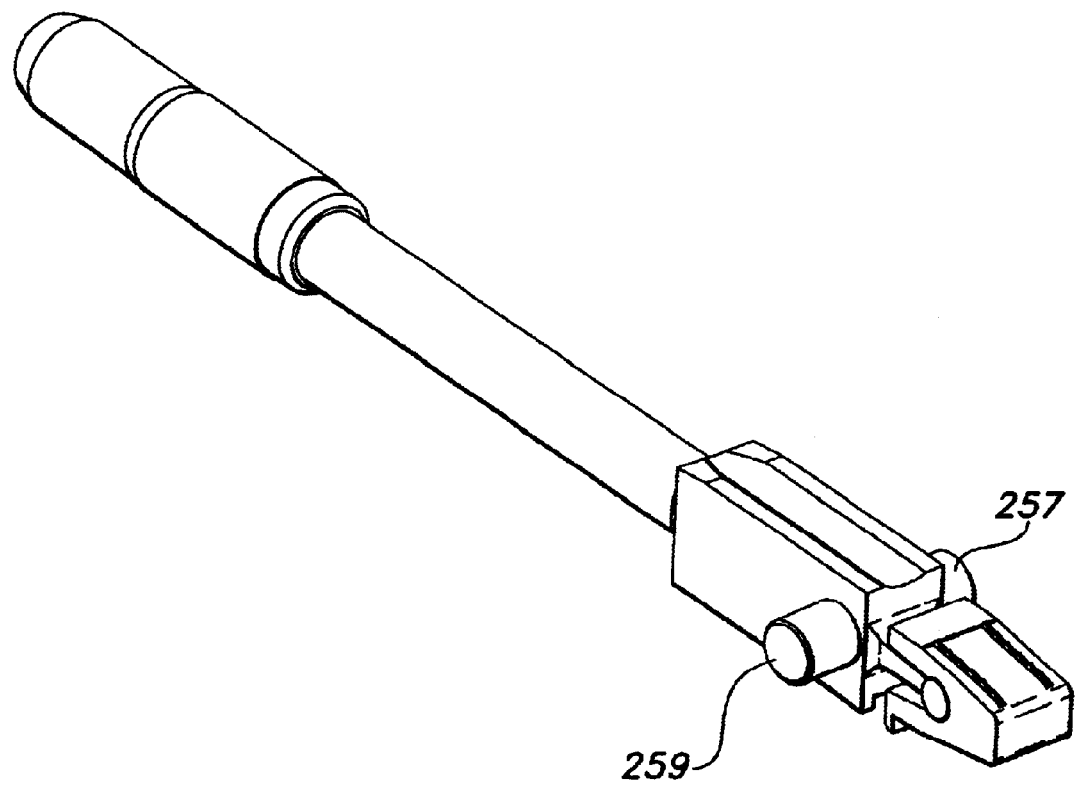
FIG. 31 is a perspective view of another embodiment of a sagittal centering tool of the present invention, showing an alternative centering mechanism.

Alternatively, nose 252 may be separated from neck 254 by post 278, which allows nose 252 and neck 254 to be in hinged relation to one another, as shown in FIG. 29 and FIG. 31. Hinge 282 may allow motion in one plane, or may allow complete rotation of neck 254 relative to nose 252. In other words, in use, nose 252 remains in its stable position between vertebral bodies, and handle 260 is maneuvered to change the orientation of handle 260 and neck 254 relative to stabilized nose 252. This permits the surgeon to more easily maneuver tool 250 in order to place it at the appropriate angle relative to vertical without disturbing the positions of the vertebral bodies relative to one another.

Another embodiment of sagittal centering tool 250 has a clothespin-like nose 251 shown in FIG. 30. Clothespin-like nose has two prongs 262 connected at fulcrum 264. This embodiment has a modified handle 266 that operates to control prongs 262. This embodiment has the additional advantage of providing distraction at the posterior portion of the vertebral bodies.

In yet another embodiment of the sagittal centering tool (not shown), the handle of the tool is removable, so that it can be disengaged from nose 252 and/or neck 254.

3) Machining Fixture System and Method

Once sagittal centering tool 250 is positioned, the surgeon aligns scaffold or machining fixture. In one embodiment, this comprises removably placing the fixture over the instrument; and using a position locating device to adjust the position of the fixture to correspond to the pre-determined position of the reference line. Another way to characterize the placement of the machining fixture is that the fixture is positioned such that it is collinear with a reference line, and such that said fixture may be used to position instruments for preparation of the target location for implantation of the prosthesis at the prosthesis at the preferred position. The fixture is then temporarily affixed in position to one or more of the patient's vertebrae bodies, a brace, or a rigid structure not secured to the patient. The present invention also provides a system for guiding site preparation instruments to a surgical site during spinal surgery, comprising:

(a) a set of locating instruments for locating a specific position of the surgical site into which a site preparation instrument is to be guided;

(b) a guiding structure adapted to be temporarily affixed to vertebral bodies to define the specific position located by the set of locating instruments, the guiding structure having a first set of features adapted to receive and guide a site preparation instrument; and (c) a corresponding site preparation instrument having a second set of corresponding features, wherein the first set of features can be aligned with the second set of corresponding features in order to guide a site preparation instrument to the surgical site.

Figure 32A:
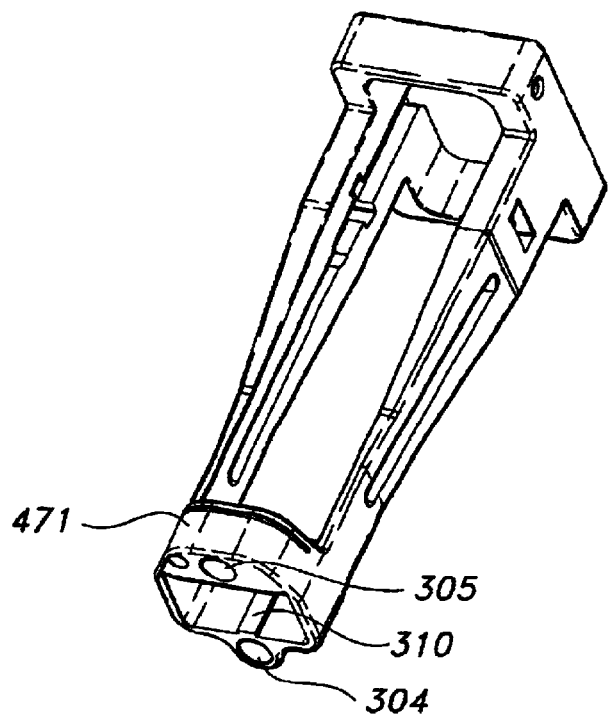
FIG. 32 illustrates three perspective views (A, B, and C) of one embodiment of a scaffold that is adapted to receive, align, and secure various surgical instruments. The scaffold generally has a torso that is defined by an entryway, sides having slots, and a base.
Figure 32B:
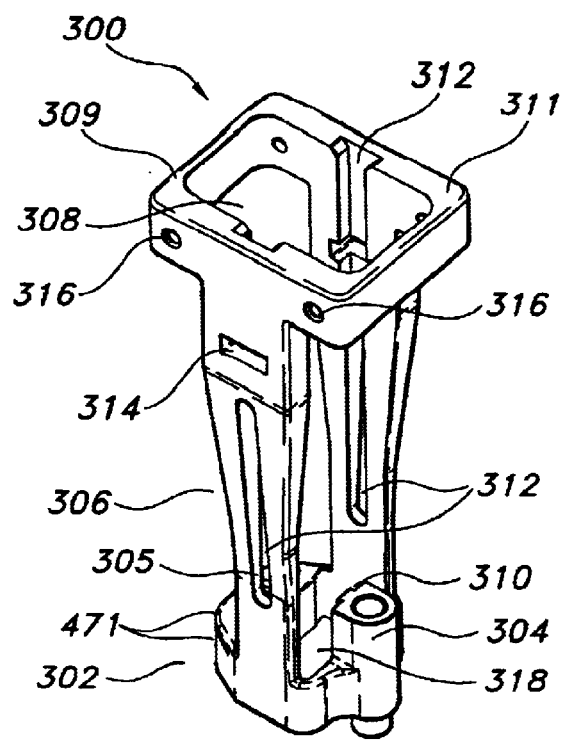
Figure 32C:
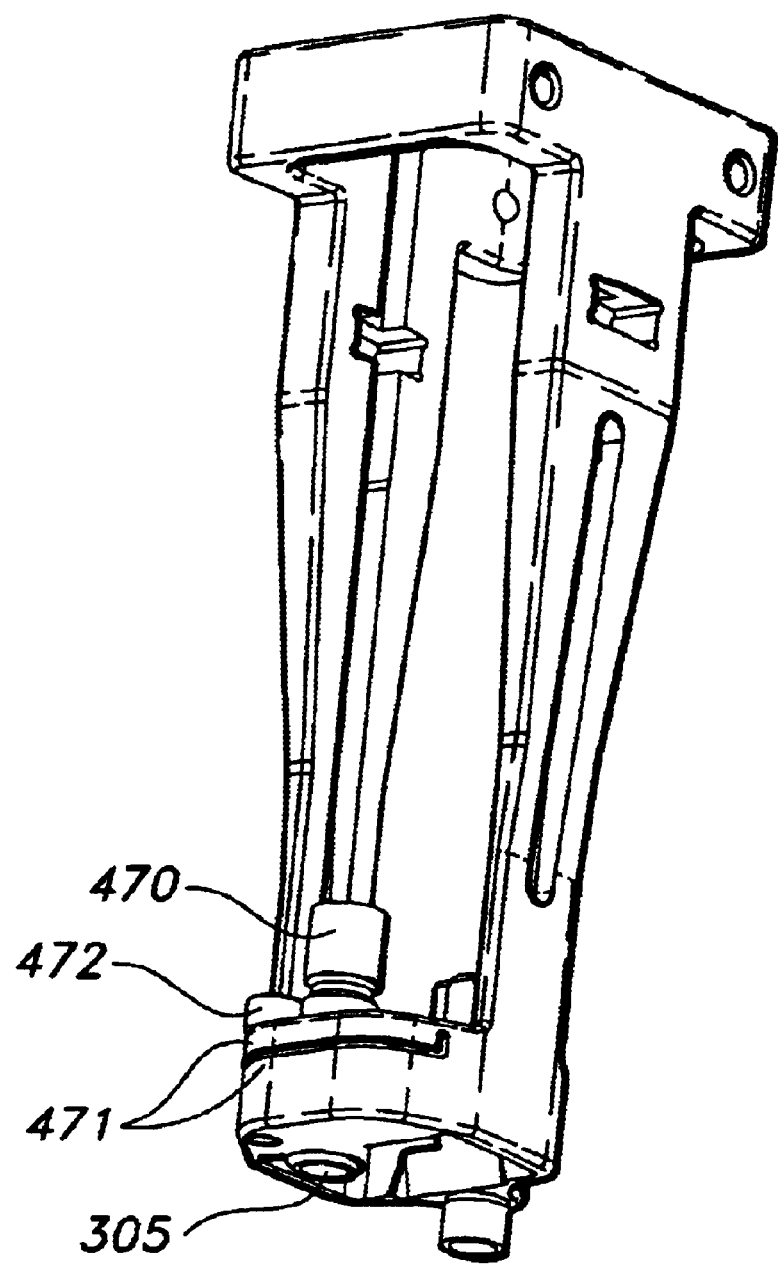

Various embodiments of machining fixtures in accordance with the present invention are shown in FIG. 32–FIG. 36. It should be noted that throughout this document, reference to scaffold or machining fixture 300, which is shown in FIG. 32, incorporates a reference to all the various machining fixture embodiments disclosed herein and discussed in greater detail below, including machining fixture 700, machining fixture 900, multi-track machining fixture 750, machining fixture 800, or machining fixture 780.

As described below, centering tool 250 and machining fixture 300 include features to facilitate proper positioning of these instruments relative to one another. It should be noted that the alternative embodiments of the machining fixture may include similar centering tool positioning features as machining fixture 300.

Referring to FIG. 32, machining fixture 300 has base 302, torso 306, entryway 308, and slots 312. Base 302 of machining fixture 300 defines an aperture 318 that allows machining fixture 300 to slide over sagittal centering tool 250. It has foot 304 and drill guide opening 305, through which a fixation device (not shown in this figure) is inserted to secure machining fixture 300 to the vertebral bodies.

Foot 304 and guide opening 305 may have threaded or smooth openings, which may be simply holes in base 302 or one or both may be adjustable bushings. Preferably, when machining fixture 300 is in place, foot 304 faces the caudal direction and drill guide 305 faces the cephalad direction. This directional positioning of the machining fixture is arbitrarily selected in this preferred embodiment in view of the directional aspects of various instruments that interact with machining fixture 300. In the embodiment illustrated in FIG. 32A, foot 304 is stationary (i.e. does not include an adjustable bushing) and has an aperture through which drill bit 430 (shown in FIG. 38) and fixation device 450 (shown in FIG. 39) can be individually inserted to secure machining fixture 300 in place with respect to the caudal vertebral body. As seen best in FIG. 32C, guide opening 305 includes an extendable bushing or adjustable guide 470 containing an aperture through which drill bit 430 and a fixation device 450 can be individually inserted. Adjustable guide 470 is extendable so that base 302 of machining fixture 300 can be positioned to meet the cephalad vertebral body prior to securing machining fixture 300. As illustrated best in FIG. 32C, base 302 of machining fixture 300 also has plates 471 that help secure adjustable guide 470 by means of locking screw 472. In use, as locking screw 472 is tightened, plates 471 are compressed together thereby binding the threads of adjustable guide 470 and locking it into its position.

As noted above, centering tool 250 and machining fixture 300 include features to facilitate proper positioning of these instruments relative to one another. In accordance with one embodiment of the present invention as illustrated in FIG. 28 and FIG. 32, the interior surface of base 302 has key 310 that is adapted to cooperate and interface with keyway 256 of sagittal centering tool 250. Key 310 and keyway 256 may be any combination of elements that allow slideable movement of machining fixture 300 with respect to sagittal centering tool 250, as well as secure alignment of tool 250 and machining fixture 300 once they are in place. For example, key and keyway may be tongue and groove attachments, or other similar cooperating attachment structures. Although key 310 is described as an element of machining fixture 300 and keyway 256 is described as an element of sagittal centering tool 250, it should be understood that they may be reversed. For instance, sagittal centering tool 250 may have key 310, and machining fixture 300 may have keyway 256.

As illustrated in FIG. 31, in accordance with an alternative embodiment of the present invention, sagittal centering tool 250 may include laterally extending centering posts 257 and 259. In general, this embodiment functions similar to centering tool 250, except it does not include a keyway. Instead, when the machining fixture 300 is placed over the sagittal centering tool 250', the two centering posts 257, 259 extend to the interior surfaces of base 302 of machining fixture 300, thereby maintaining the sagittal centering tool in the lateral-medial center of machining fixture 300.

Referring back to the sagittal centering tool 250 shown in FIG. 28–FIG. 30, in use aperture 318 of base 302 of machining fixture 300 is placed over handle 260 of sagittal centering tool 250 and slid down until key 310 of foot 304 engages keyway 256 of sagittal centering tool 250. The main shaft of sagittal centering tool 250 will extend from entryway 308 of machining fixture 300, which is defined by sides 309. Holes 316 are also provided on machining fixture 300, which facilitate the securing of machining fixture 300 to frame 60, described below.

Torso 306 of machining fixture 300 has two slots 312 on opposing sides that extend the substantial length of the interior of torso 306, and may extend up to entryway 308. Each slot 312 has a pivot arc slot 314, which may be substantially perpendicular to the length of slot 312. Pivot arc slots 314 provide a mechanism by which the movements of the instruments described below can be controlled in machining fixture 300 over a predetermined distance, while remaining stable at a particular anterior-posterior position.

4) Alignment Block System and Method

Figure 40A:
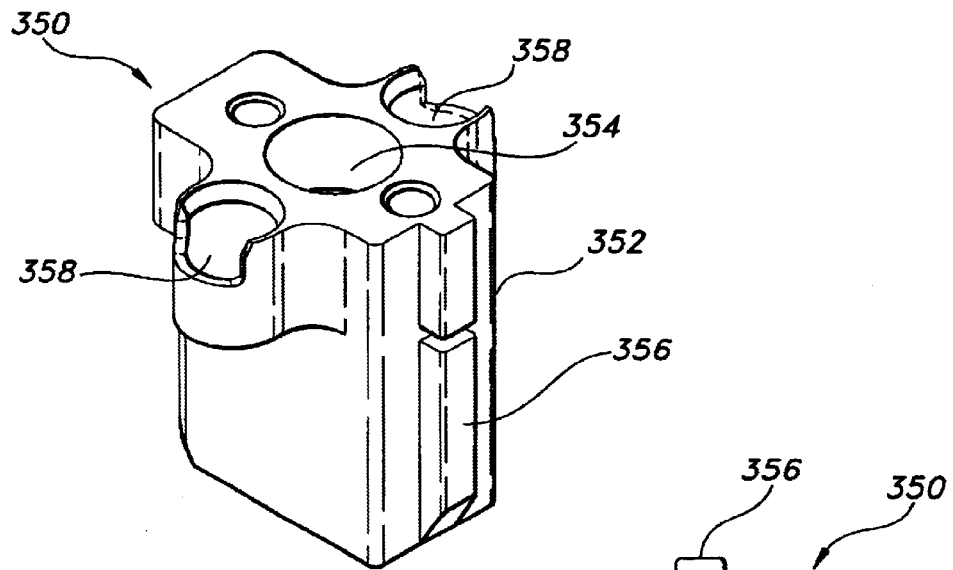
FIG. 40 is a perspective view (A), top plan view (B) and side plan view (C) of one embodiment of an alignment block of the present invention, showing generally body portion, aperture, and centering apertures. Alignment block is adapted to fit on the scaffold of FIG. 32.
Figure 40B:
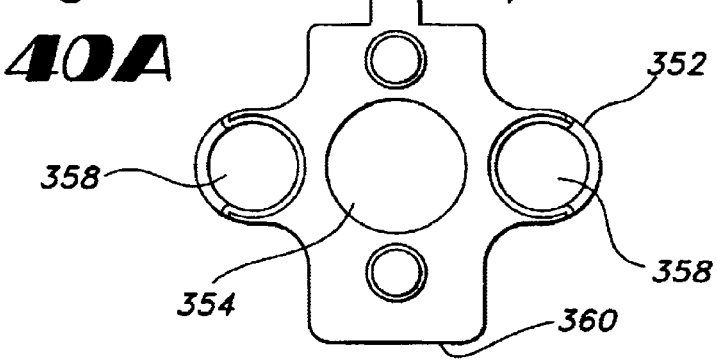
Figure 40C:
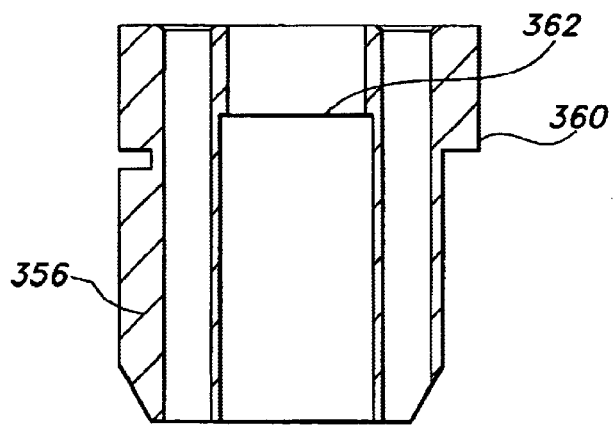

Once scaffold 300 is placed over sagittal centering tool 250, alignment block 350 shown in FIG. 40 is placed over the scaffold 300/sagittal centering tool 250 combination. Alignment block 350 stabilizes sagittal centering tool 250 in relation to scaffold 300 and provides support and guidance for instruments, such as drills and anchor post drivers, that will be used to secure scaffold 300 to the vertebral bodies. The alignment block is used to secure the sagittal centering tool and the machining fixture in relation to one another during the step of aligning the fixture along the intersection of the first and second planes described above. Alignment block 350 has body portion 352, aperture 354, protrusion 356, and centering apertures 358. Aperture 354 slides over and receives an aligning instrument such as handle 260 of sagittal centering tool 250. Protrusion 356 extends from one side of body portion 352 and fits into one of slots 312 of scaffold 300. This secures alignment block 350 in the correct orientation with respect to scaffold 300 and sagittal centering tool 250.

The side of body portion 352 opposite protrusion 356 defines lip 360 that rests on one of sides 309 defining entryway 308 of scaffold 300. Lip 360 acts as a stopping mechanism and rests flush with side 309 of scaffold 300. Centering apertures 358 are located on sides of body portion 352 adjacent to the sides that define protrusion 356 and lip 360.

When alignment block 350 is in place, centering apertures 358 are located at the cephalic and caudal aspects of the patient. In other words, they face the same direction as foot 304 and drill guide opening 305 of scaffold 300.

Alignment block 350 may optionally have a stopping mechanism 362 located inside aperture 354. This allows alignment block 350 to cooperate with a patterned or raised area on handle 260 of sagittal centering tool 250 to provide feedback that sagittal centering tool 250 is fully seated in the disc space. Note that this embodiment supplements the stopping action of lip 360.

The size of alignment block 350 is such that it fits into entryway 308 of scaffold 300, preferably the fit is relatively tight and without much play. Similarly, aperture 354 of the alignment block 350 fits over the shaft of the sagittal centering tool 250, preferably this fit is also relatively tight and without much play. The relatively tight fit of these components allows the entire assembly to be adjusted and braced as a single unit.

5) Machining Fixture Bracing System and Method

Figure 41A:
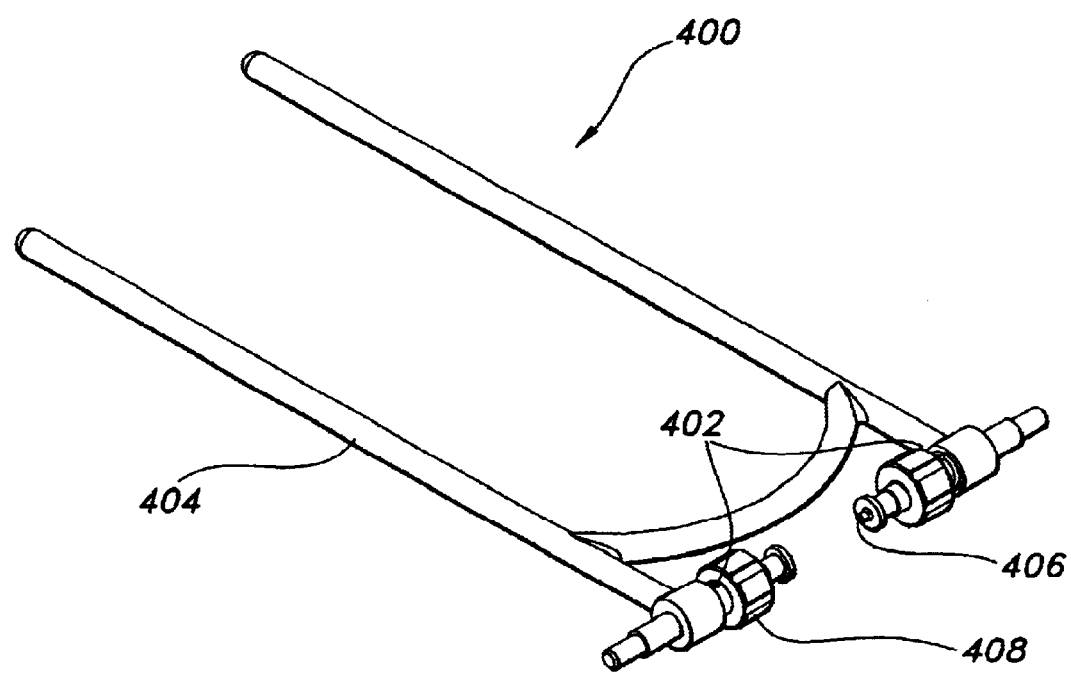
FIG. 41 is a perspective view (A) of one embodiment of a scaffold brace adapted to secure scaffold of FIG. 32 to the rigid frame shown in FIG. 9 and FIG. 10.
FIG. 41B is a cross-sectional view of the connectors 402 shown in FIG. 41A taken along the line B—B.
FIG. 41C is a exploded perspective view of the various components of connector 402.
FIG. 41D is a perspective view of connector 402 showing its various components combined.
Figure 41B:
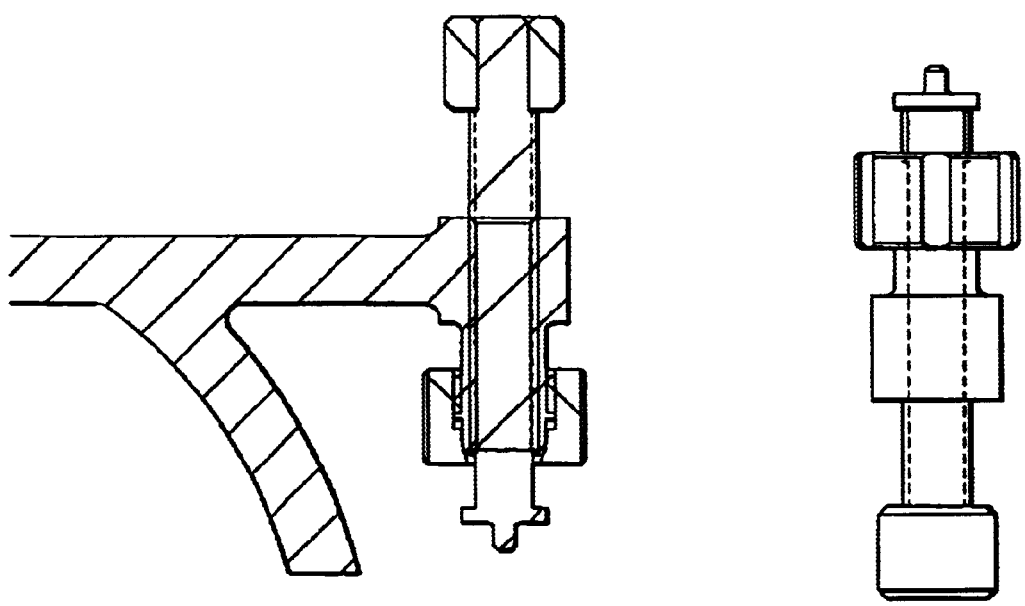

At some point before or after the placement of alignment block 350, scaffold 300 should be braced, or secured into position by scaffold brace 400, which is shown in FIG. 41. To secure scaffold 300, one end of scaffold brace 400 is connected to scaffold 300 and another end of scaffold brace 400 is attached to two Kunzler clamps 90 that are attached to rigid frame 60. The complete assembly is illustrated in FIG. 42.

In one embodiment, the instrument brace comprises at least one rigid support having distal end adapted to be releasably attached to the substantially horizontal rectangular open frame and a proximal end rigidly attached to at least one connector adapted to releasably and securely hold an instrument. Scaffold brace 400 shown in FIG. 41A is a device that has connectors 402 and supports 404. A preferred embodiment of connectors 402 is shown in greater detail in FIG. 41B, which provides a cross sectional view of connectors 402. Connectors may be retractable pins adapted to releasably insert into corresponding openings in the instrument. The retractable pins may comprise a threaded body disposed in a correspondingly threaded barrel or knob, and wherein turning of the body, barrel or knob advances or retracts the pin.

Figure 41C:
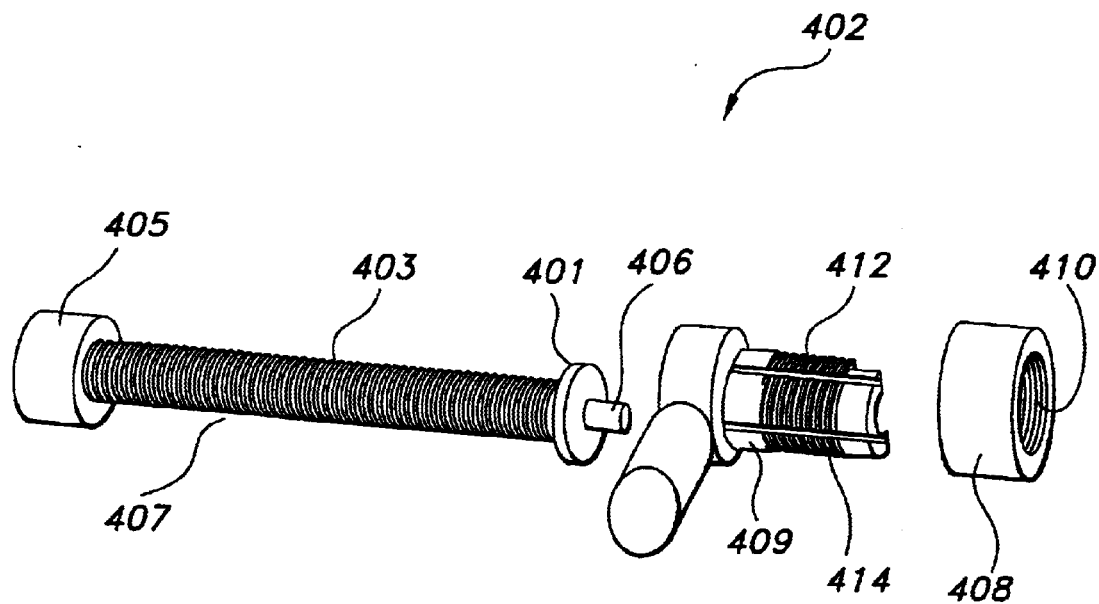
Figure 41D:
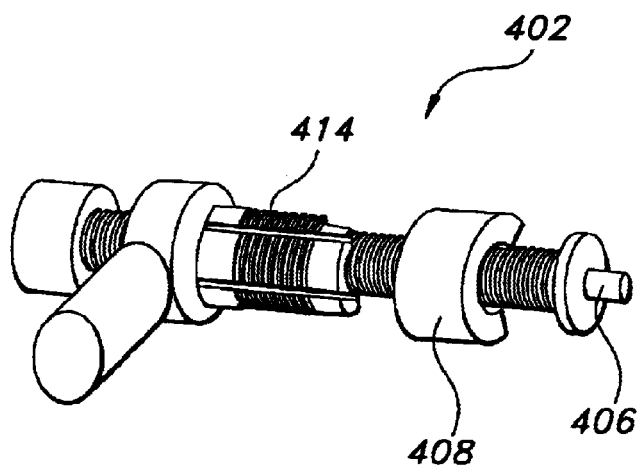
Figure 42:
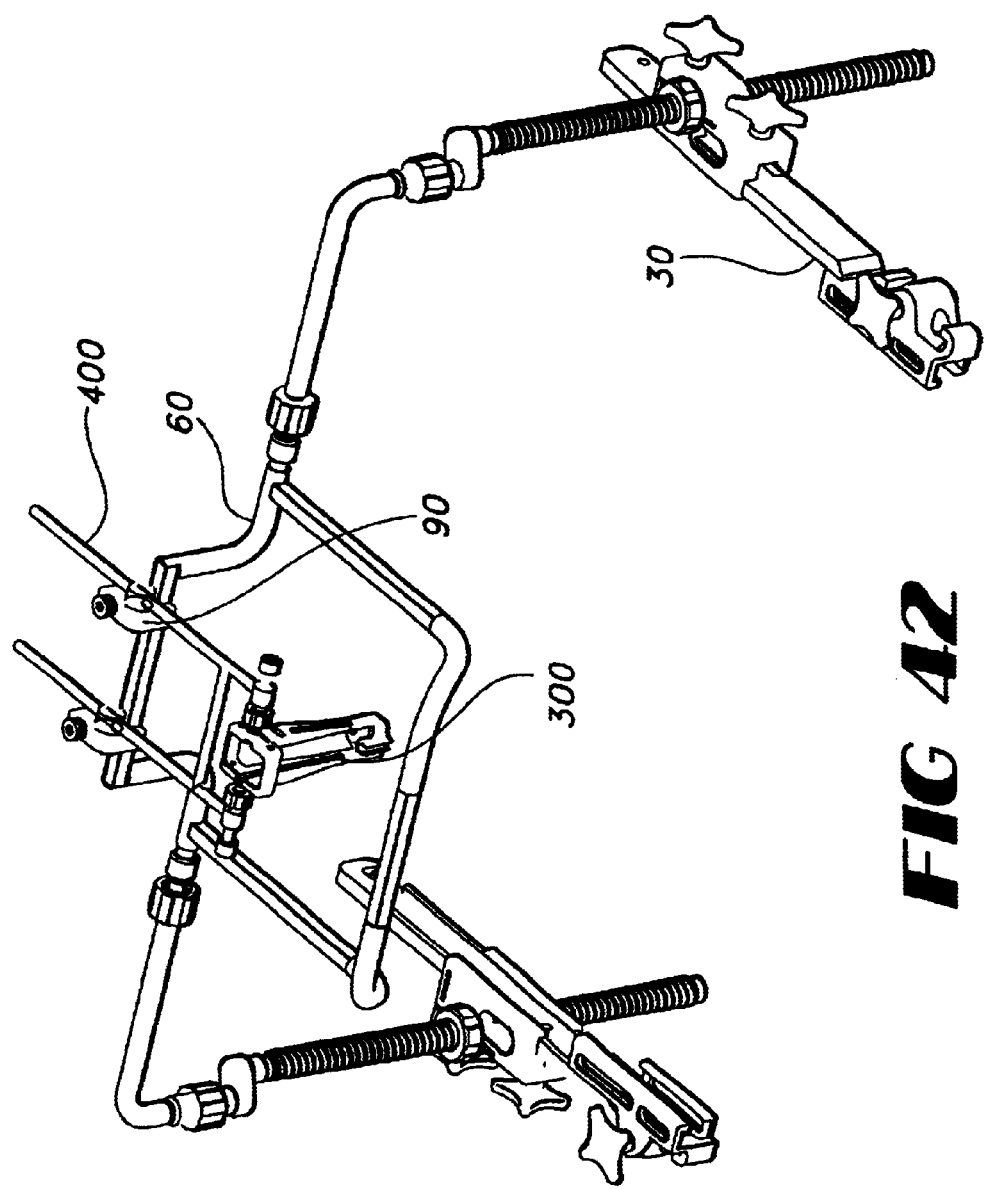
FIG. 42 is a perspective view illustrating how various components of the present invention interconnect with one another. In particular, a machining fixture, a machining fixture brace and a frame assembly are shown assembled together.

In addition, FIG. 41C shows the various components of connectors 402 separately, and FIG. 41D shows the various components of connectors 402 combined. Connectors 402 each include a screw 407, a locking portion 409 and locking nut 408. Screw 407 includes a screw knob 405, a threaded portion 403, a lip 401, and pin 406. Locking portion 409 includes external threaded section 412 (which may be tapered), an internal threaded conduit (not shown), and a plurality of slots 414 that extend from the outer surface of locking portion 409 to the internal conduit. The internal conduit of locking portion 409 is sized so that the treaded portion 403 of screw 407 fits within the internal conduit and the threads along the internal conduit mate with the threads along screw 407, as illustrated generally by FIG. 41D. Locking nut 408 includes internal threads 410 that are sized to mate with the threads along external threaded section 412 of locking portion 409. When connector 402 is assembled as shown in FIG. 41D, locking nut 408 can slide freely along screw 407 between lip 401 and locking portion 409. Lip 401 prevents locking nut 408 from being removed from the assembly. Pin 406 included at the tip of screw 407 interfaces with holes 316 of entryway sides 309 of machining fixture 300 (see FIG. 32 and FIG. 42). In use, pins 406 are aligned with the holes 316 on the machining fixture 300. The screw knob 405 is rotated thereby advancing pins 406 into holes 316 on both sides of machining fixture 300 until lip 401 tightly abuts the sides of machining fixture 300, thereby locking the machining fixture's position with respect to brace 400. Locking nut 408 is then screwed onto external threaded portion 412 of locking portion 409. As locking nut 408 is tightened, slots 414 allow the threaded portion 412 to compress onto screw 407, thereby binding the screw thread portion 403 and the internal threaded conduit of locking portion 409, and preventing the screw from loosened with respect to machining fixture 300.

In the embodiment shown, connectors 402 include pins 406 that are inserted into holes 316 in sides 309 of machining fixture 300. Alternatively, connectors 402 may include clamps that securely interface with scaffold 300, i.e. platforms that squeeze scaffold 300 like a vice, etc. Essentially, connectors 402 may be any form, as long as they provide a secure connection between machining fixture 300 and brace 400.

Supports 404 extend from connectors 402 and are shaped to be received in opening 112 of Kunzler clamp 90 (see FIG. 16). Kunzler clamp 90 is then attached to rigid frame 60 as described above and illustrated in FIG. 42.

6) Machining Fixture Centering System and Method

Before scaffold brace 400 is locked into place, the surgeon should adjust the angle formed by the shaft of sagittal centering tool 250 relative to a vertical line. The present invention provides a system for positioning the machining fixture 300 and tool 250 using an orienting device that is adapted to interface with and assist with the proper positioning of the instrument relative to a gravitational vector, comprising:

(a) a measuring component having indicia marked thereon that corresponds to various positions relative to the gravitational vector;

(b) a connecting component that allows the orienting device to cooperate with the instrument when the instrument is positioned within a surgical site; and (c) a leveling device associated therewith for determining the orienting device's position relative to the gravitational vector.

This system may also include or cooperate with the alignment block that interfaces with an fits over the instrument 250, with the block having an interfacing structure that allows the orienting device to cooperate with the instrument 250.

In accordance with one embodiment, the angle of the sagittal centering tool 250 is adjusted so that it is the same as the angle determined using the goniometer. In other embodiments, as described in greater detail below, it may be desirable to adjust the angle to a different angle.

Figure 43:
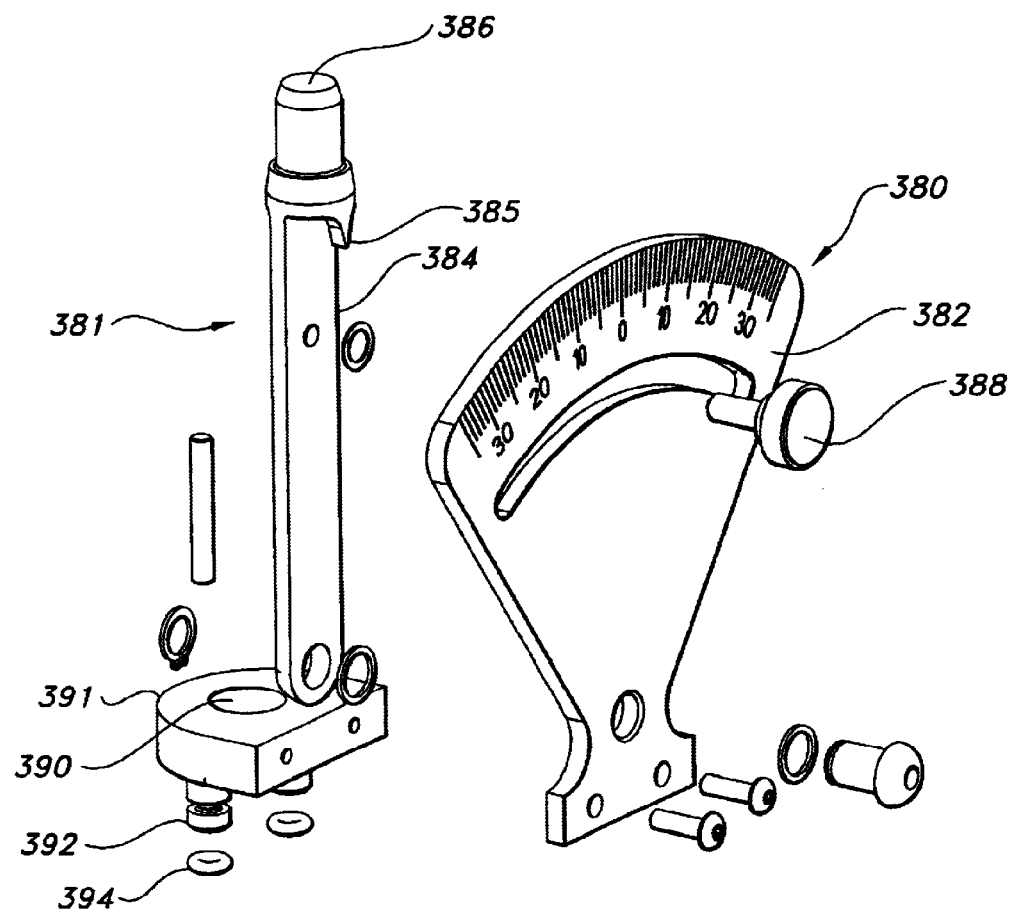
FIG. 43 is an exploded perspective view of one embodiment of a scaffold protractor of the present invention, showing generally a measuring component, a faceplate, and connectors. Scaffold protractor is adapted to fit with the centering apertures of the alignment block of FIG. 33.

An angle orienting instrument, such as scaffold protractor 380, shown in FIG. 43, is used to adjust the angle of the sagittal centering tool 250. In general, the orienting device is adapted to interface with and assist with the proper positioning of an instrument relative to a gravitational vector. The orienting device includes: a measuring component having indicia marked thereon that corresponds to various positions relative to the gravitational vector; a connecting component that allows the orienting device to cooperate with the instrument to be oriented when the instrument is positioned within a surgical site; and a leveling device associated therewith for determining the orienting device's position relative to the gravitational vector. More specifically, protractor 380 is adapted to be engaged with centering apertures 358 of alignment block 350 (see FIG. 40). Alternative embodiments simply fit over the end of the shaft of sagittal centering tool 250. This ensures that the axis around which scaffold 300 is disposed, and along which the surgical site preparation instruments will be inserted, passes through the predetermined point in the target disc space, and falls along a line that provides for optimal entry of the surgical instruments into the target disc space.

Scaffold protractor 380 has measuring component 381 and connecting component 391. Measuring component 381 comprises face plate 382, movable marker 384, marker point 385, securing knob 388, and centering level connector 386. Connecting component 391 comprises centering aperture connectors 392, with optional rings 394, and aperture 390.

More particularly, measuring component 381 has face plate 382 with a range of angles marked thereon. Face plate 382 has a 0° point with increasing degree ranges extending on both sides of the 0° point. Movable marker 384 is connected to face plate 382 and is adapted to move so that marker point 385 can precisely indicate a degree point on face plate 382. Movable marker 384 may be secured once marker point 385 indicates a degree that relates to the above-referenced degree by securing knob 388. Securing knob 388 has a securing mechanism that maintains marker point 385 in place with respect to face plate 382 and connecting component 391.

Once the correct angle is registered by measuring component 381, scaffold protractor 380 is placed on alignment block 350. Connecting component 391 of scaffold protractor 380 comprises centering aperture connectors 392 that cooperate with centering apertures 358 of alignment block 350 (see FIG. 40). The basic concept for centering aperture connectors 392 is that scaffold protractor 380 is balanced on alignment block 350.

Centering aperture connectors 392 have optional rings 394 attached at or near the ends of connectors 392 to facilitate the attachment of protractor 380 and block 350. Rings 394 may be rubber, foam, or other soft, buffering material that softens the connection and holds it more securely.

If sagittal centering tool 250 has handle 260 that would extend above body portion 352 of alignment block 350 and thus, interfere with the connection of alignment block 350 to scaffold protractor 380, connecting component 291 of scaffold protractor 380 may have an aperture 390 located therein. Aperture 390 would receive or otherwise cooperate with handle 260 of sagittal centering tool 250.

If, on the other hand, the sagittal centering tool 250 has a removable handle 260 or a short handle 260 that would not extend through body portion 352 of alignment block 350, then no aperture is needed, and the protractor can be disposed on the alignment block.

Figure 44:
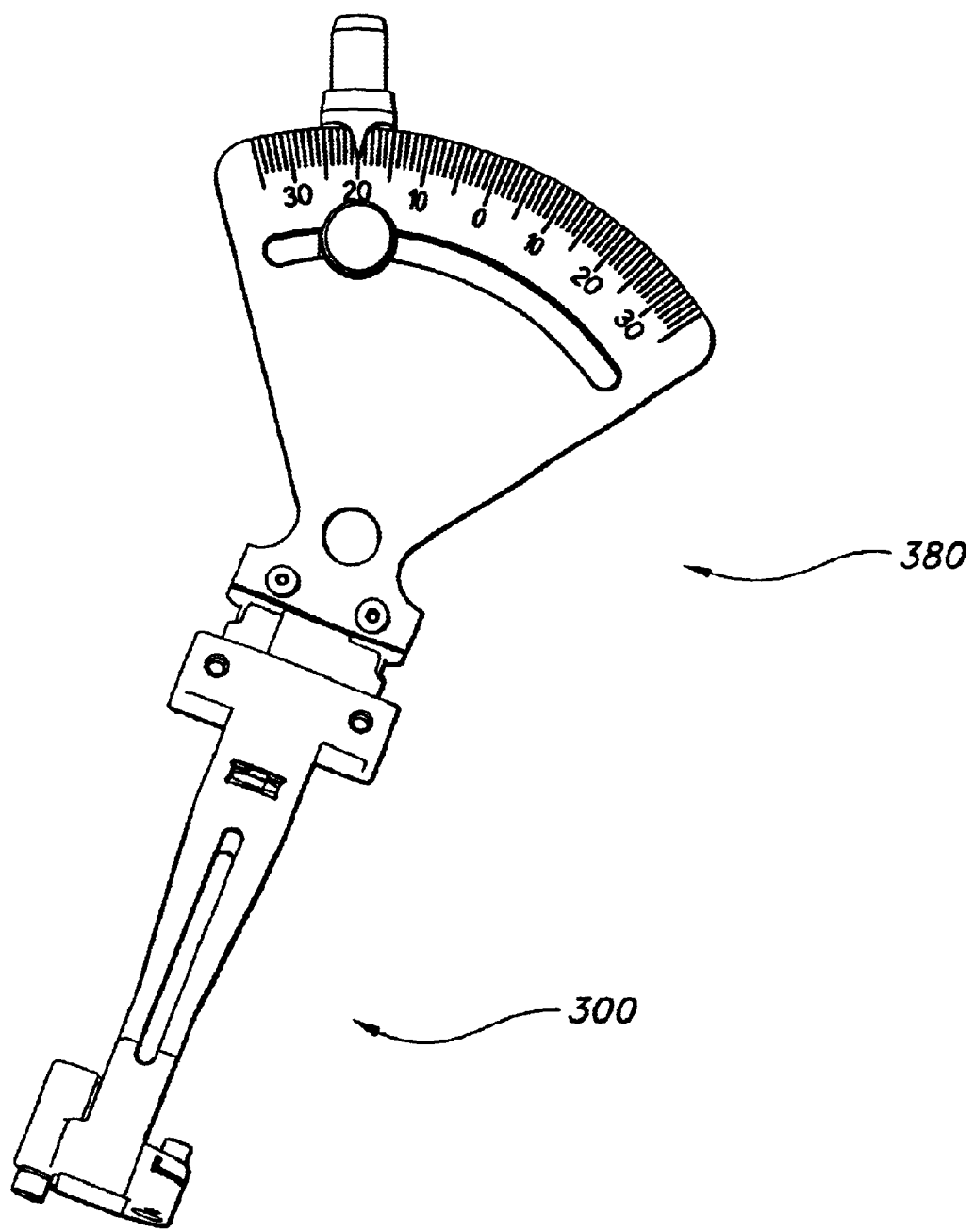
FIG. 44 is a side view of the scaffold protractor, centering block, and machining fixture in accordance with the present invention, and illustrates how these components are attached to one another.

Centering level 80 (shown in FIG. 12) is placed on top of scaffold protractor 380, and the surgeon adjusts the angle of the scaffold 300, sagittal centering tool 250, and alignment block 350 assembly so that the bubble of the level 80 is centered. As illustrated in FIG. 44, when the bubble level 80 is centered, movable marker 384 will be vertical and the scaffold 300 will be positioned at the desired angle relative to vertical indicated on the protractor.

Figure 45:
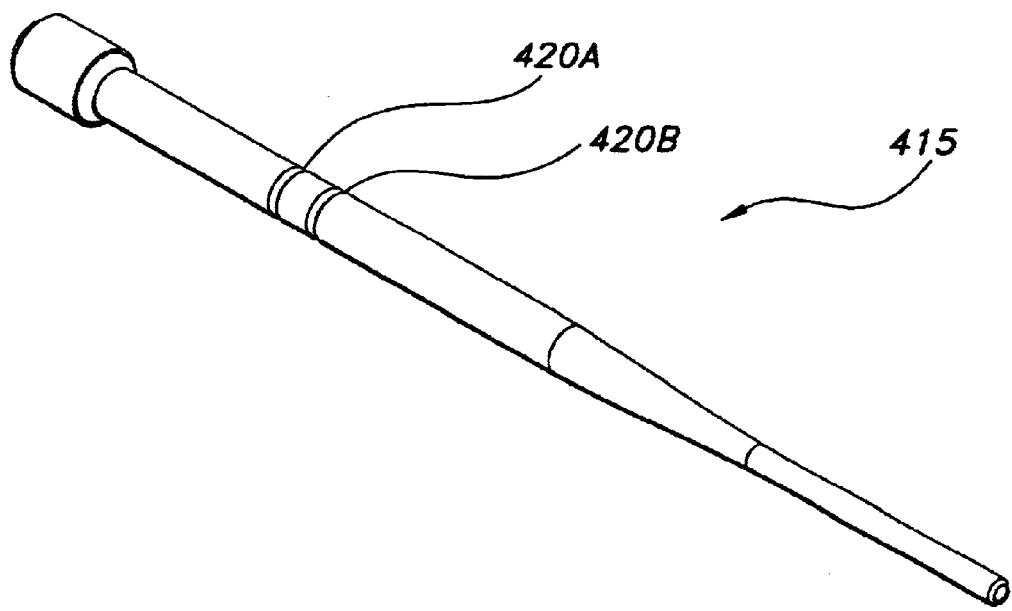
FIG. 45 is a side plan view of one embodiment of a cephalad contact pin of the present invention, which is adapted to fit through a centering aperture of the alignment block of FIG. 33 to measure the proper placement of the scaffold of FIG. 32. This figure shows two markings, indicating a range for the variable placement of the scaffold for the cephalad side.
Figure 46:
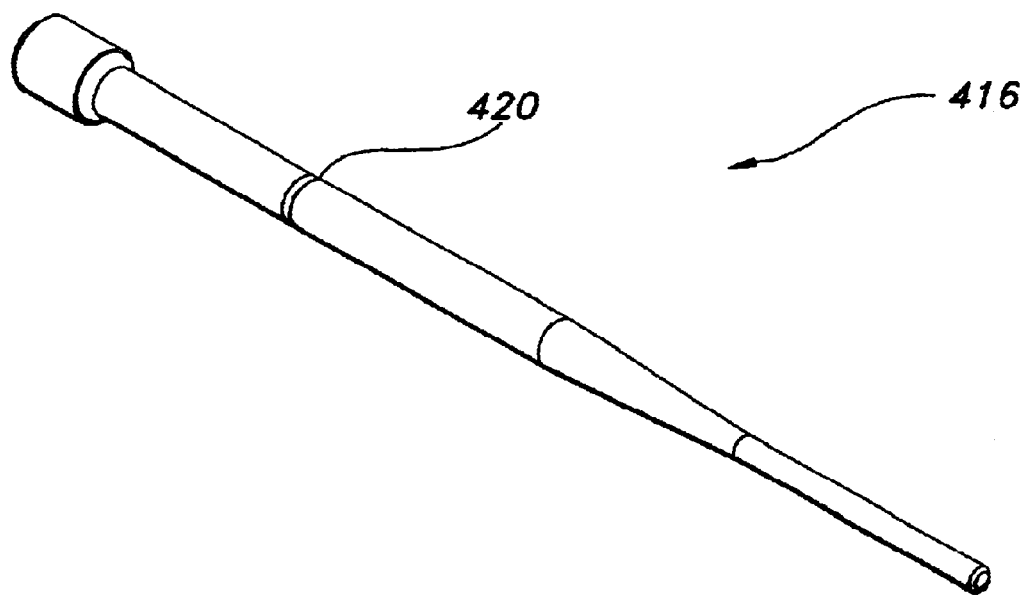
FIG. 46 is a side plan view of one embodiment of a caudal pin, which corresponds in use to that of the cephalad pin of FIG. 44, but that has only one marking, which in use, indicates the precise placement of the scaffold on the caudal side.

To ensure that scaffold 300 is properly placed and in contact with the vertebral bodies, pins 415 and 416 shown in FIG. 45 and FIG. 46 are inserted into respective centering apertures 358 of alignment block 350. The surgeon will know that scaffold 300 is correctly positioned on the anterior surfaces of the vertebral bodies based on two measurements. Marking 420 of caudal pin 416, shown in FIG. 46, should be flush with the top of centering aperture 358 on caudal side of alignment block 350. This alerts the surgeon that foot 304 is sitting directly on the anterior surface of the caudal vertebral body. Centering aperture 358 on cephalad side of alignment block 350 should fall between markings 420A and 420B of cephalad pin 415, shown in FIG. 45. Cephalad pin 415 has two markings that correspond to the adjustability of the drill guide. As long as the top of centering aperture 358 is between the two markings on cephalad pin 415, scaffold 300 is properly placed.

If a machining fixture 700 is being used (which is shown in FIG. 33 and is described in greater detail below), the machining fixture brace connectors 402 and clamp 90 may need to be loosened and adjusted to provide the appropriate positioning.

H. Drilling and Placing the Fixation Devices

Figure 39A:
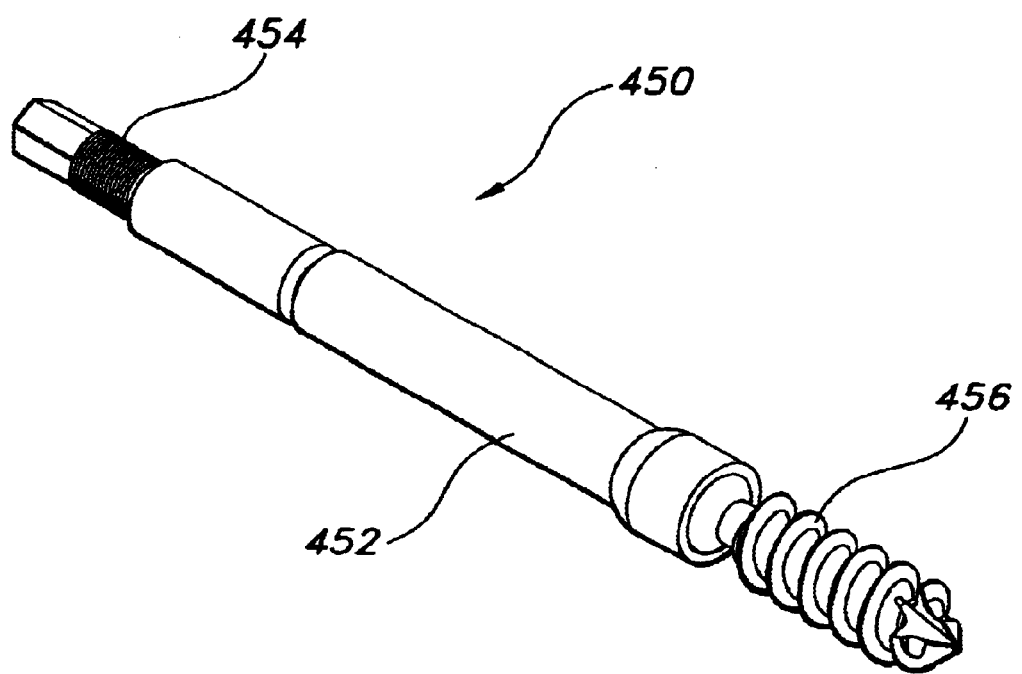
FIG. 39A shows two perspective views of one embodiment of a fixation device of the present invention, which is an anchor post adapted to fit through the foot and drill guide of the scaffold shown in FIG. 32.

After scaffold 300 has been placed, stabilized, and centered, it is secured to the vertebral bodies so that they can be prepared to receive the prosthetic implant. Generally, a fixation device is used to secure the scaffold 300. Referring to FIG. 39, in accordance with a preferred embodiment, the fixation device is a threaded anchor post 450. Preferably anchor posts 450 are secured through foot 304 and drill guide opening 305 of scaffold 300 and screwed into the vertebral bodies through pre-drilled holes. Any standard medical drill may be used to drill the holes, for instance, an Anspach® Black Max or an electric motor drill.

1) Placing Caudal Fixation Device

Figure 38:
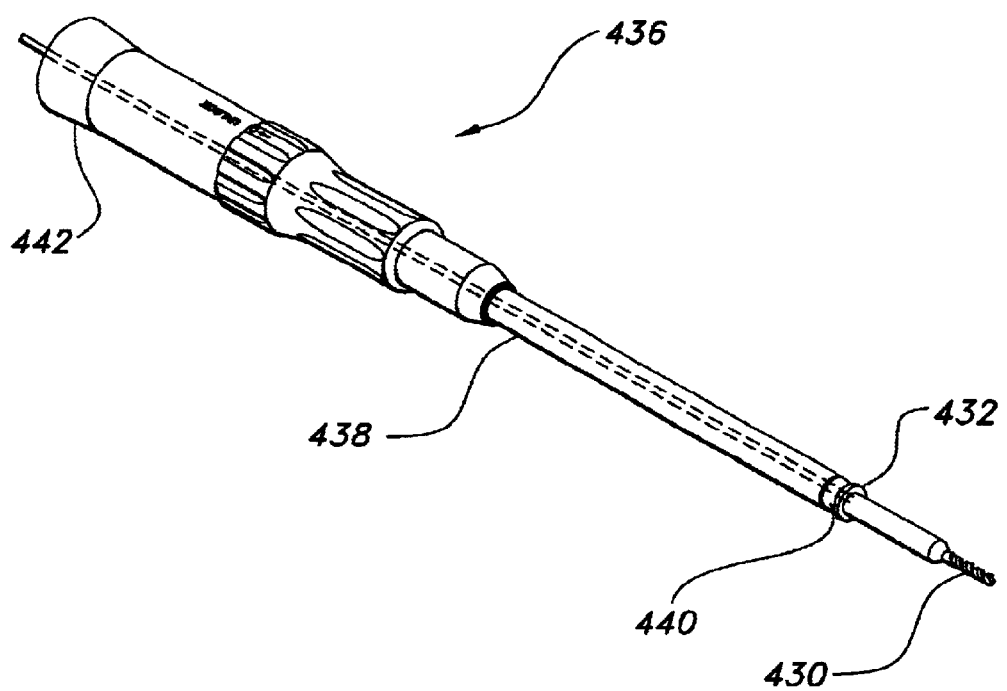
FIG. 38 is a side plan view of one embodiment of a drive attachment of the present invention, which is adapted to be inserted through a centering aperture of the alignment block of FIG. 40 and to abut the base of scaffold shown in FIG. 32. As illustrated, the drive attachment receives a drill bit for drilling the vertebral bodies in preparation for the insertion of the fixation device of FIG. 39.

While scaffold 300 still houses sagittal centering tool 250 and alignment block 350, a long drill bit 430 attached to drilling attachment 436, shown in FIG. 38, is introduced through centering apertures 358 of alignment block 350 (see FIG. 40). The drill bit is inserted into opening 440 of drilling attachment 436.

Drive attachment 436 has hollow shaft 438, opening 440, and drive connector 442, for interfacing with a standard medical drive mechanism. Drill bit 430 is adapted to be inserted into opening 440 of drive attachment and to extend through hollow shaft 438. Drill bit 430 has a shaft that is longer than the shaft 438 of drive attachment 436.

Hollow shaft 438 of drive attachment 436 can be inserted through centering aperture 358 of alignment block 350, and is held in place thereby. With drill bit 430 engaged, drive attachment 436 is advanced through centering aperture 358.

Figure 35C:
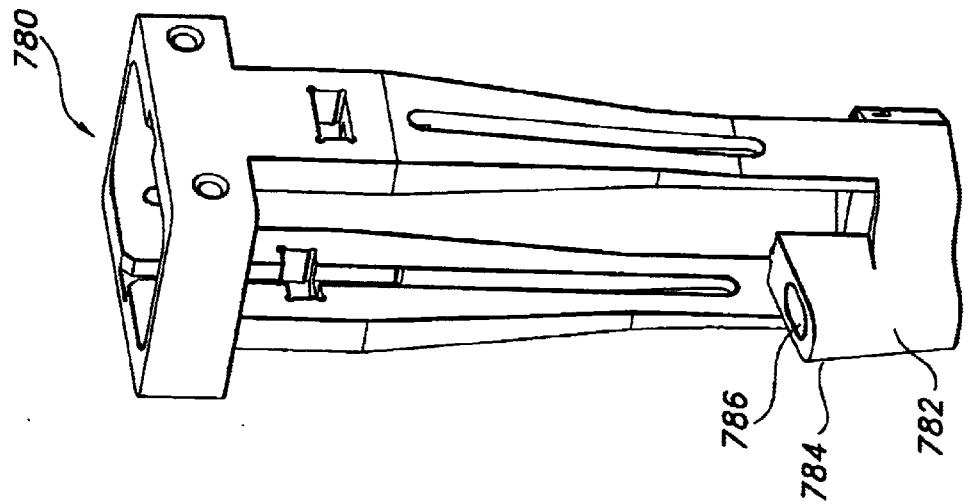
FIG. 35 is a lateral side view (A), a caudal-cephalad side view (B) and a perspective view (C) of an alternate embodiment of a multi-level machining fixture which includes an elongated slot adapted to receive the fixation device shown in FIG. 39.
Figure 35B:
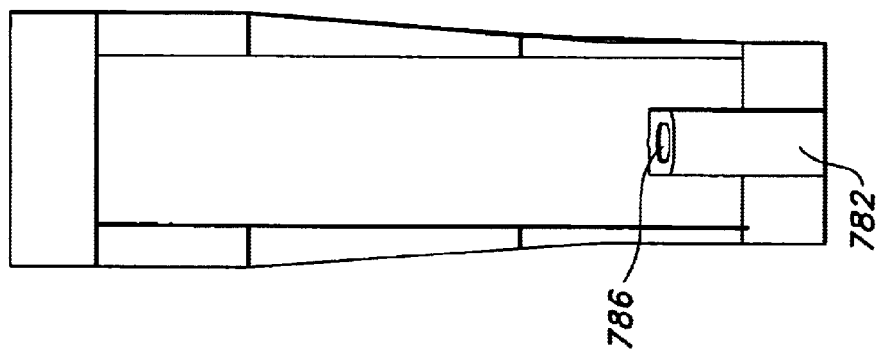
Figure 35A:
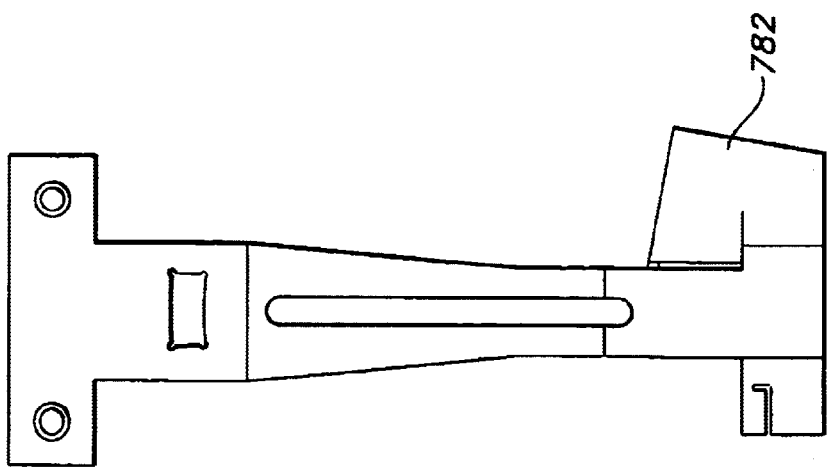

In accordance with alternative preferred methods of the present invention, if machining fixture 700 or machining fixture 780 is used (which are shown in FIG. 33 and FIG. 35, respectively, and are described in greater detail below), the surgeon should maintain drill bit 430 tip toward the center of the machining fixture 700 so that the hole is not made outside of open base portions 722 and 726 of machining fixture 700 or elongated base opening 786 of machining fixture 780.

In use, the surgeon inserts drill bit 430 into opening 440 (see FIG. 38). The surgeon then attaches drive connector 442 to the medical drive mechanism, and using a single continuous motion, advances drive attachment 436 through alignment block 350, scaffold 300, and foot 304 until the drill bit stop 432 contacts the upper surface of foot 304. After the hole is drilled, the surgeon should irrigate the area and apply suction to remove any particles of bone or other tissue.

Next, the surgeon places anchor post 450, shown in FIG. 39, in the hole that was created. Three embodiments of anchor post 450 are shown in FIG. 39—(A) a standard substantially rigid anchor post 450 shown in FIG. 39 A having a substantially rigid center section 452; (B) a flexible anchor post 1450 shown in FIG. 39B having a center section 1452 that is made from a substantially flexible material; and (C) a flexible anchor post 2450 shown in FIG. 39C having a center section 2452 that is scored to render it substantially flexible. Flexible anchor posts 1450 and 2450, and their use are described in greater detail below.

Anchor post 450 has screw threads 456 that engage the bone of the vertebral body. To place anchor post 450, the surgeon uses an anchor post driver (not shown) having a hollow shaft. The anchor post driver contains a structure, such as a rubber O-ring, that provides friction to hold the anchor post 450. This allows anchor post 450 to be advanced through scaffold 300, and as the surgeon drives anchor post 450 into place, the end of the anchor post driver contacts the top of foot 304. In accordance with one embodiment, the anchor post is self-releasing from the driver. In particular, as anchor post 450 penetrates into the bone, it starts to pull itself out of the driver until it reaches the proper depth. At this point, anchor post 450 completely disengages from the driver, which turns freely, communicating to the surgeon that anchor post 450 has achieved the appropriate depth. Alternatively, anchor post 450 is not self-releasing. In accordance with this embodiment, when the driver contacts the top of foot 304 and the anchor post 450 has reached its appropriate depth, the surgeon can simply pull the driver up and disengage it from anchor post 450.

Figure 47:
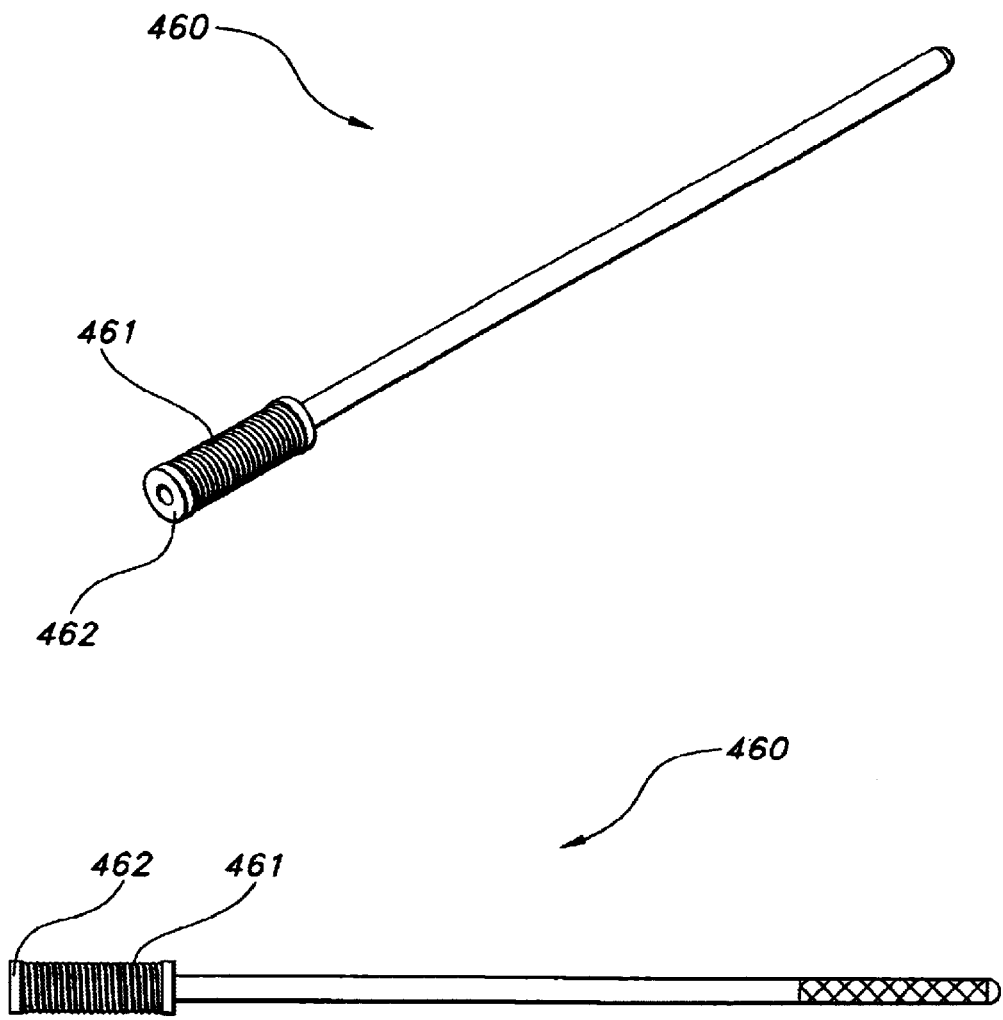
FIG. 47 is a side plan view of one embodiment of an anchor post nut of the present invention, showing generally an extension spring and a threaded bore, which is adapted to fit the anchor posts of FIG. 39.

The upper end of anchor post 450 contains threaded portion 454. Threaded portion 454 is adapted to receive a correspondingly threaded anchor post nut 460, shown in FIG. 47. The surgeon installs anchor post nut 460 over anchor post 450, and tightens anchor post nut 460, securing scaffold 300 to the vertebral body. In the embodiment shown, anchor post nut 460 has extension spring 461 connected to threaded bore 462. Spring 461 provides flexibility, and a convenient handle for tightening and loosening anchor post nut 460, which handle can be easily bent out of the way during other stages of the procedure.

2) Placing Cephalic Fixation Device

Once the anchor post 450 and anchor post nut 460 are inserted and secured in the caudal vertebral body, the anchor post 450 is inserted in the cephalic vertebral body. Because each individual vertebra may be angled differently relative to each other and the surgical tools being described, the anterior surface of the cephalic vertebral body may not be in the same anterior-posterior plane as the anterior surface of the caudal vertebral body. To account for these differences, it is desirable that drill guide opening 305 be adjustable. In the embodiment of scaffold 300 illustrated in FIG. 32C, drill guide opening 305 receives adjustable drill guide 470, shown in detail in FIG. 48, that in use extends from base 302 of scaffold 300.

Figure 48:
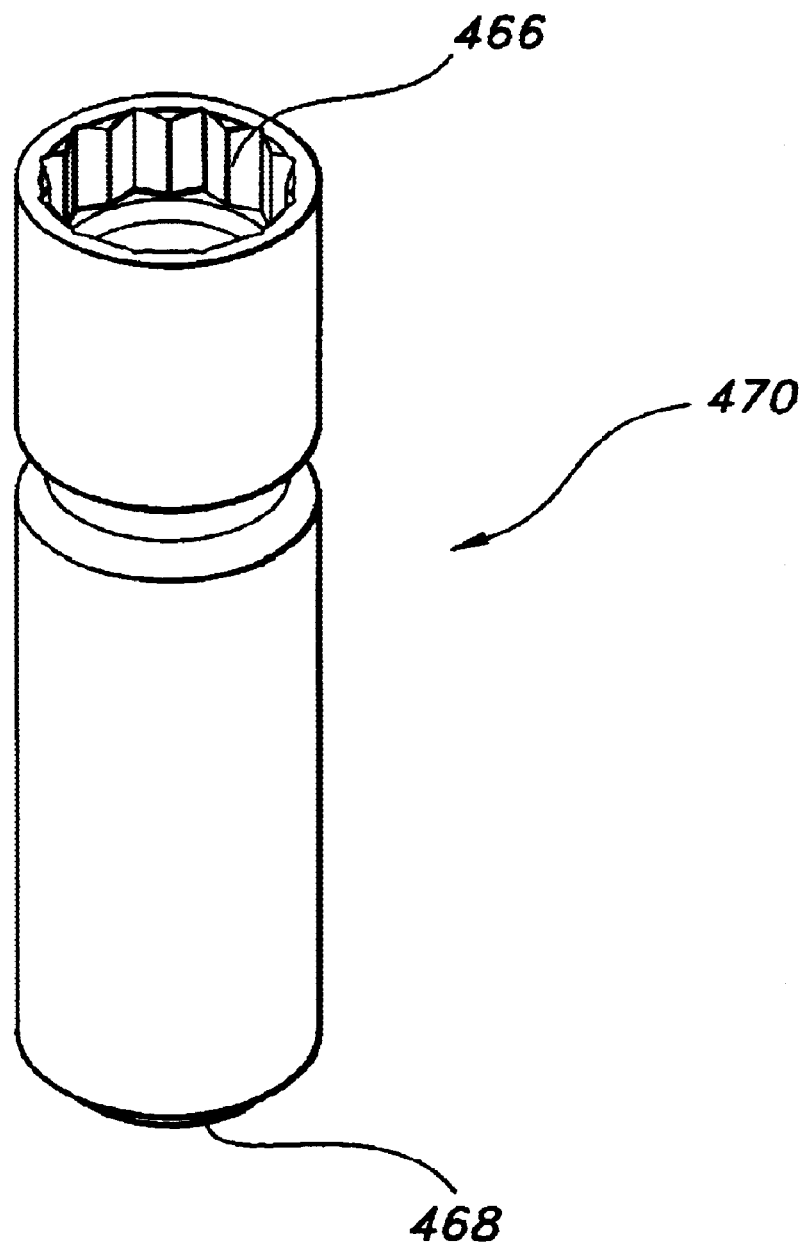
FIG. 48 is a perspective view of one embodiment of an adjustable drill guide of the present invention that is adapted to fit into the drill guide opening of the scaffold shown in FIG. 32.

As shown in FIG. 48, adjustable guide 470 is a small bushing that fits into opening 305 and which can be adjustably positioned to help facilitate stabilization of machining fixture 300 against the surface of a vertebral body and accommodate anatomic variations. In accordance with a preferred embodiment, machining fixture 300 is positioned such that adjustable guide 470 faces the cephalad direction. This positioning is merely arbitrary, but it is important that a direction be selected and consistently utilized if directional features such as keyways are incorporated into the various interfacing instruments.

In one embodiment, a wrench 672 (illustrated in FIG. 49) is used to raise or lower adjustable guide 470 until it contacts the anterior surface of the cephalad vertebral body. Adjustable guide 470 has a bore 466 that receives a wrench 672. Adjustable guide 470 has a substantially flat lower surface 468 that contacts the surface of the vertebral body. Although not shown, adjustable guide 470 is preferably threaded on the outside, and in use, cooperates with a corresponding threaded portion of guide opening 305 of machining fixture 300.

Once the surgeon is satisfied that machining fixture 300 is positioned appropriately, as described above, adjustable guide 470 may optionally be locked. Any conventional locking mechanism may be used. Referring again to FIG. 32C, in accordance with a preferred embodiment, guide 470 is locked in position by tightening an optional locking screw 472 located adjacent to guide opening 305 on machining fixture 300. As the surgeon tightens the locking screw 472, plates 471 formed in base 302 of machining fixture 300 are compressed together. The compression of the plates clamps the threads of adjustable guide 470, preventing it from moving relative to the machining fixture during subsequent procedures.

Note that if machining fixture 700 is used (which is shown in FIG. 33, and is described in greater detail below), connectors 402 securing machining fixture 700 to brace 400 are loosened, and machining fixture 700 is allowed to rotate in the opposite direction (i.e., if it is angled toward the cephalad direction, it is allowed to rotate in the caudal direction or vice versa). After the rotation, anchor post 450 that has been placed will no longer be collinear with the open base portion 720 or 726. An anchor post 450 and anchor post nut 460 are then inserted on the cephalad side (or caudal side) of the machining fixture using the systems and methods described above. In accordance with a preferred embodiment, the surgeon may re-confirm that the machining fixtures are positioned correctly by using the machining fixture protractor 380, a level, and the techniques and methods described above. For machining fixture 700, these measurements are optimally conducted when machining fixture 700 is at the center position, in other words, when connectors 402 of brace 400 secure machining fixture 700.

Those of skill in the art will recognize that the order in which anchor posts 450 are placed may differ, and that adjustable drill guides may be used on either the caudal side or the cephalad side of the scaffold, or both. In addition, anchor posts 450 may be self-tapping, thereby avoiding the need to predrill a hole.

Figure 50A:
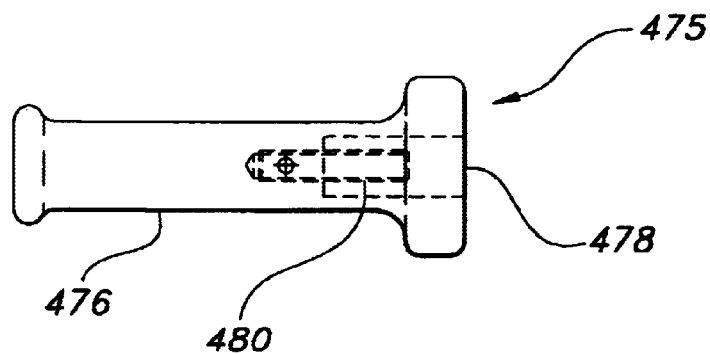
FIG. 50A is a side plan view of one embodiment of a centering tool puller of the present invention.
Figure 50B:
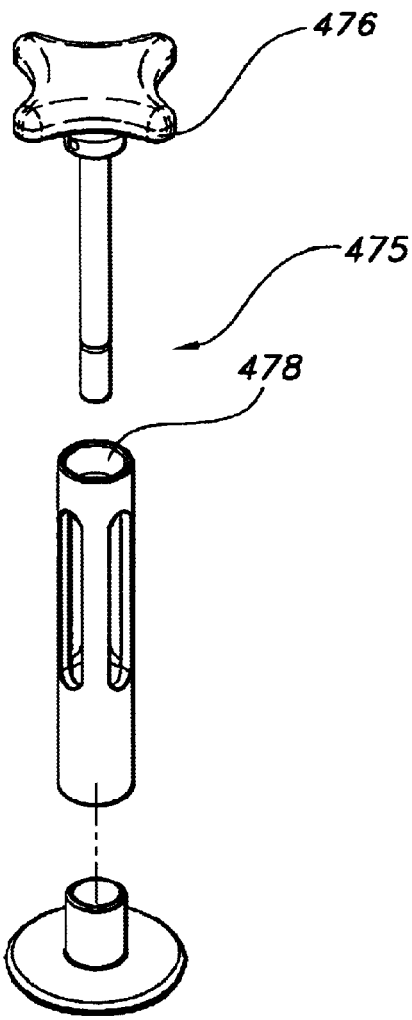
FIG. 50B is an exploded perspective view of another embodiment of a centering tool puller of the invention.

Once the scaffold is secured to the vertebral bodies and appropriately braced, sagittal centering tool 250, scaffold protractor 380, and alignment block 350 can be removed from scaffold 300. If necessary, the surgeon may use a sagittal centering tool puller 475 to remove sagittal centering tool 250. Alternative embodiments of puller 475 are shown in FIG. 50. In general, puller 475 has handle 476 and hollow cavity 478 with threaded screw 480 therein. Hollow cavity 478 is placed over threaded bore top portion 261 of sagittal centering tool 250. When the surgeon manipulates handle 476, threaded screw 480 cooperates with threaded bore top portion 261 and removes sagittal centering tool 250.

I. General Description of Site Preparation Instruments and Procedures

1) Determining the Appropriate Machining Angle

To this point the surgeon has precisely located machining fixture 300 with respect to the target site, and can now begin to prepare the target site to receive the implant. As previously noted, in accordance with a preferred embodiment, the techniques of the present invention are used to replace a spinal disc or fused bone segment with a functional endoprosthesis having two articulating outer shells. Such an endoprosthesis is described in co-pending application Ser. No. 09/783,910. In accordance with this embodiment, it is preferable that the implanted endoprosthesis shells be substantially parallel to one another when the spine is in its neutral position. As used herein the "neutral" position of the spine is hereby defined as the post-operative position that a spine assumes when the patient is standing without any flexion or extension, and takes into consideration the various angles of the vertebrae and the discs relative to one another. Alternatively, neutral position may also be defined as the position of the spine determined by extrapolating the pre-operative curvature of the spine at health spine levels to the curvature at non-health levels. Such placement of the endoprosthesis ensures that the endoprosthesis' maximum range of motion will be available to the patient as the patient's spine moves through its full range of flexion and extension.

In accordance with an alternative embodiment, the neutral position of the spine may be defined as the midpoint between full flexion and full extension of the spine while the patent is standing. If a patient has a greater range of flexion than extension (or vice versa), the midpoint will not be the position that a spine assumes when the patient is standing without any flexion or extension.

In determining the neutral position of the spine, the pre-operative position of the spine, including the various angles of among the vertebrae and the discs relative to one another, should be considered. In particular, a surgeon should consider any degradation of the target disc that may have occurred. If little or no degradation has occurred, the pre-operative positioning of the spine can be used to approximate the post-operative neutral position. However, in cases of significant pre-operative disc degeneration, or in a fusion revision case where a segment of fused bone is removed to create a target disc space, those skilled in the art may approximate the normal curvature of the spine by evaluating the height and curvature present at non-degenerated levels or non-fused levels and essentially extrapolate the spine's curvature along a healthy segment to a non-healthy segment.

Figure 51:
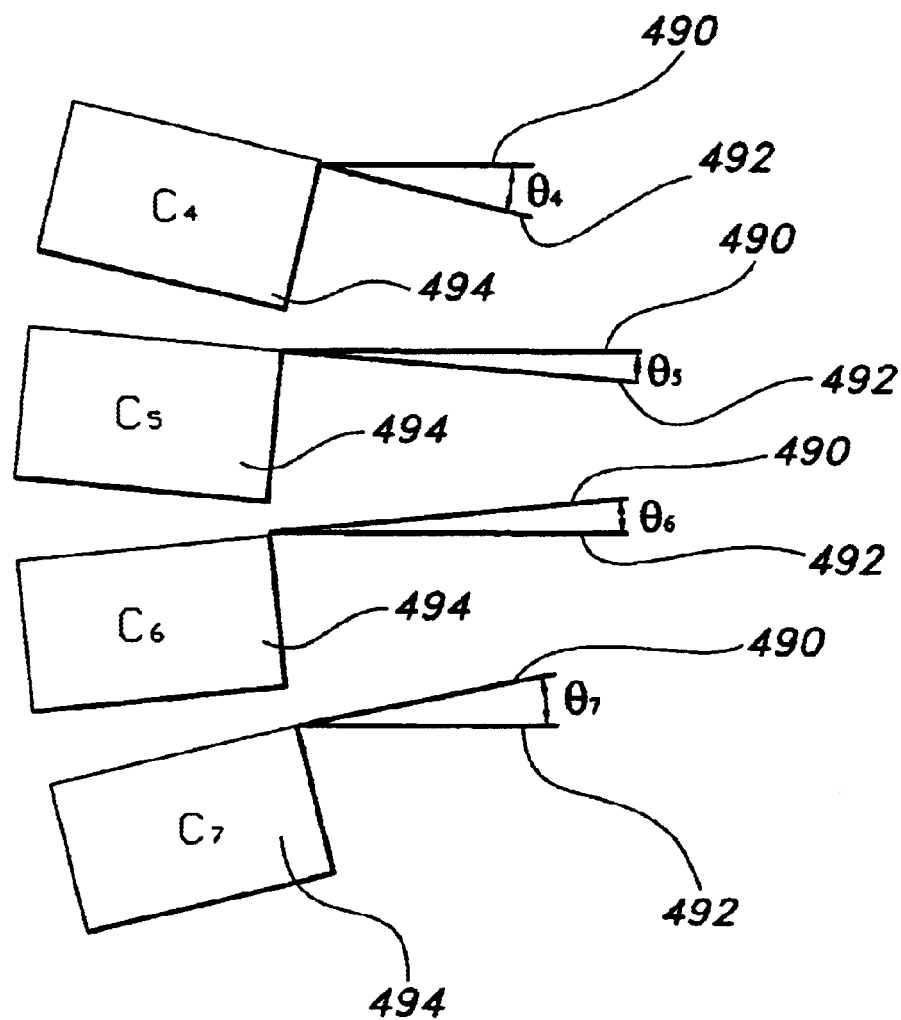
FIG. 51 is a schematic drawing illustrating a method of estimating the angle of a vertebral endplate relative to a reference line in accordance with the present invention.

FIG. 51 illustrates one method of approximating the normal curvature of the spine. Four cervical vertebrae 494 ($C_4$ to $C_7$) are shown in FIG. 51, and illustrate a possible preoperative configuration of the vertebrae. In accordance with this method, one measures the angle of the caudal vertebral endplates relative to a convenient reference axis, which can be either a horizontal line or one of the vertebral endplates. The reference line 490 (i.e. a horizontal line) is shown in FIG. 51 as the solid line. The dotted lines 492 shown in FIG. 51 illustrate the angle of the caudal vertebral endplates relative to the reference line 490. In accordance with this method, the surgeon assumes that the spine's curvature is equally dispersed over the various spine segments. Referring again to FIG. 51, if that angle at any given level is represented by $\theta$, and if, for example, $\theta_4=14°$ and $\theta_7=-13°$ (assuming that clockwise rotation is positive), then one could approximate the angles of the caudal endplates at levels $C_5$ and $C_6$ as follows:

$$\theta_5=[\tfrac{2}{3}(\theta_4-\theta_7)]+\theta_7$$

and $$\theta_6=[\tfrac{1}{3}(\theta_4-\theta_7)]+\theta_7$$

or $$\theta_5=5°$$

and $$\theta_6=-4°$$

A similar analysis could be made of the cephalad vertebral endplates, or of the intervertebral disc spaces. In addition, a similar analysis could be made for a spinal segment including more than four segments or only three spinal segments. In accordance with an embodiment, the fewest number of segments is used to approximate the preferred neutral position of any given degenerated segment. Thus, if the target disc space is level $C_5$–$C_6$, the surgeon could approximate the caudal endplate's angle as $\theta_6=\tfrac{1}{2}(\theta_5-\theta_7)+\theta_7$, which if we assume that $\theta_5=4°$ and $\theta_7=-13°$, then $\theta_6=-4.5°$.

In general, the extrapolation of the curvature of a spinal segment to a different spinal segment can be describe by the follow relationship:

$$\theta_x = \left[\left(\frac{y-x}{y-z}\right)(\theta_z - \theta_y)\right] + \theta_y$$

wherein $\theta$ represents the angle of a spinal anatomical plane relative to a reference plane, and x, y and z represent levels of the vertebrae wherein level x is between levels y and z, and level x is cephalad to level y. The spinal anatomical plane may be the general plane of an anterior surface of a vertebral body, a posterior surface of a vertebral body, a caudal surface of a vertebral body, a cephalad surface of a vertebral body, a disc, or a disc space. Preferably, the spinal anatomical plane is either a caudal or cephalad surface of a vertebral body. In addition, if level y is used as the reference plane, this relationship can be simplified as follows:

$$\theta_x = \left[\left(\frac{y-x}{y-z}\right)(\theta_z - \theta_y)\right]$$

Ultimately, it is within the skill of the surgeon to approximate which method will most closely approximate the neutral position of the spine based on clinical assessment of the spine and any degradation thereof.

Once the surgeon determines the appropriate angle of the target disc space and its adjacent vertebral body endplates relative to one another when the spine is in its neutral position, the surgeon can then use the instrumentation and methods provided herein to place a disc prosthesis such that its shells will be parallel when the spine assumes its neutral position.

Figure 52:
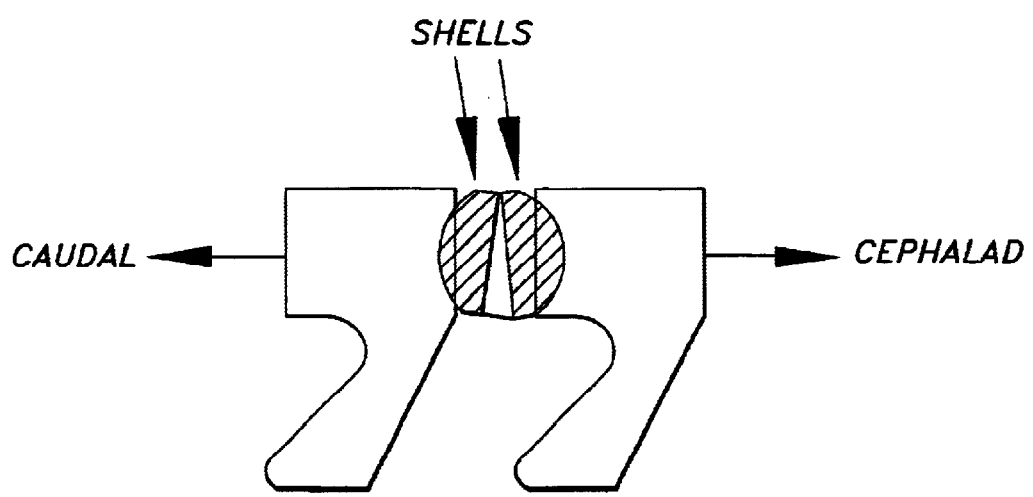
FIG. 52 is a schematic drawing showing an endoprosthesis that is placed in a position other than parallel. This placement is not always preferred, and the structures of FIG. 33, FIG. 36, and FIG. 36 seek to improve this placement.

FIG. 52 illustrates one less-preferential result that may occur during placement of the endoprosthesis. If the vertebral bodies that receive the prosthesis are not prepared appropriately, there is a possibility that the shells will not be positioned optimally relative to each other. In this example, the endoprosthesis is placed in the disc space such that the shells are not be parallel to one another. That is, the anterior portions of the shells are closer and the posterior portions of the shells are spread further away from one another. It is optimal for the shells of the endoprosthesis to be at least substantially parallel to one another when the patient's spine is in a neutral position. In some cases, it is necessary to compensate for the angulation of the vertebral bodies that is present during surgery. One may compensate for this by machining the vertebral bodies at various angles. The following discussion summarizes how such angles should be determined.

Each spinal disc space is defined by opposing vertebral body endplates into which the endoprosthesis shells will be embedded in accordance with the techniques described herein. Since the spine usually has a natural curve (either lordotic or kyphotic), the angle of the various endplates relative to their adjacent disc space when the spine is in the neutral position will generally vary between individuals. As used in this patent, references to the plane of the disc space refer to a bisector of the disc space or a hypothetical plane passing generally through the caudal-cephalad center of the disc space, and which is substantially parallel to the disc space. Alternatively, the plane of the disc space may be defined as analogous to the reference line referred to above that is normal to a line connecting the image of the posterior inferior edge of the caudal vertebral body adjacent the target disc space, and the posterior superior edge of the cephalad vertebral body adjacent the target disc space. In addition, those skilled in the art will appreciate that the endplates of the vertebral bodies are not generally flat surfaces. Therefore references herein to the angle of the endplate relative to surgical instruments, implants, or other anatomic structures generally refer to a plane that substantially approximates the surface of the endplate.

Figure 53:
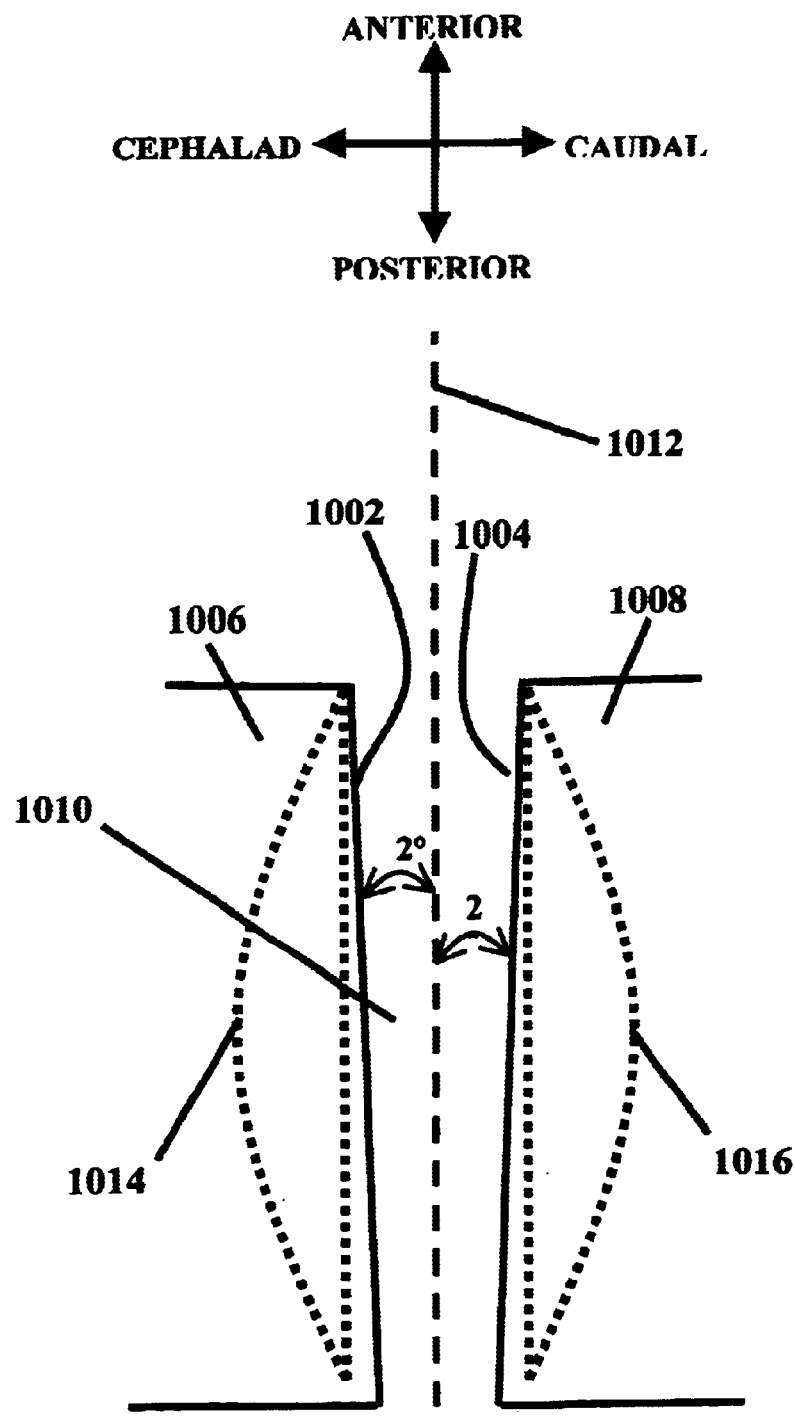
FIG. 53 is a schematic drawing of an intervertebral disc space and illustrates a preferred method of determining the appropriate position of a spinal disc prosthesis.

Referring to FIG. 53, a schematic drawing of the endplates 1002, 1004 of two vertebral bodies 1006, 1008, respectively, are shown in their neutral position. The endplates 1002, 1004 define a disc space 1010. The dotted line 1012 represents the plane of the disc space 1010. As shown in FIG. 53 the endplates 1002, 1004 are not parallel. Nor is either of the endplates 1002, 1004 parallel to the disc space 1010. Instead, lordotic curvature is present and the endplates 1002, 1004 are angled by approximately 2° relative to the disc space. As a convenient frame of reference, we have chosen to assign positive values to lordotic angles and negative values to kyphotic angles.

Since the endplates and the disc space are not parallel when the spine is in its neutral position, the articulating shells of the endoprosthesis are preferably implanted at angles relative to the endplates. In accordance with an embodiment of the present invention, the preferable prosthesis positioning would be such that the shells are parallel to the disc space when the spine is in its neutral position, which would result in parallel shell positions when the spine is in its neutral position. In the example shown in FIG. 53, the dotted lines 1014, 1016 illustrate the preferred positioning of the endoprosthesis shells relative to the endplates 1002, 1004, and the disc space. In this example, each endoprosthesis shell is parallel to the plane of the disc space, but is angled at approximately 2° relative to its respective endplate.

In accordance with the preferred techniques described herein, cavities closely matching the geometry of the endoprosthesis shells are formed in each vertebral body endplate. Therefore, dotted lines 1014, 1016 also illustrate the preferred positions for such cavities. Since the vertebral bodies may not be in their neutral positions when the cavities are formed, the present invention provides instrumentation and techniques to precisely form the cavities in a manner that ensures that the endoprosthesis shells placed within the cavities will be substantially parallel to one another when the spine assumes its neutral position, regardless of the patient's position during surgery.

Figure 54:
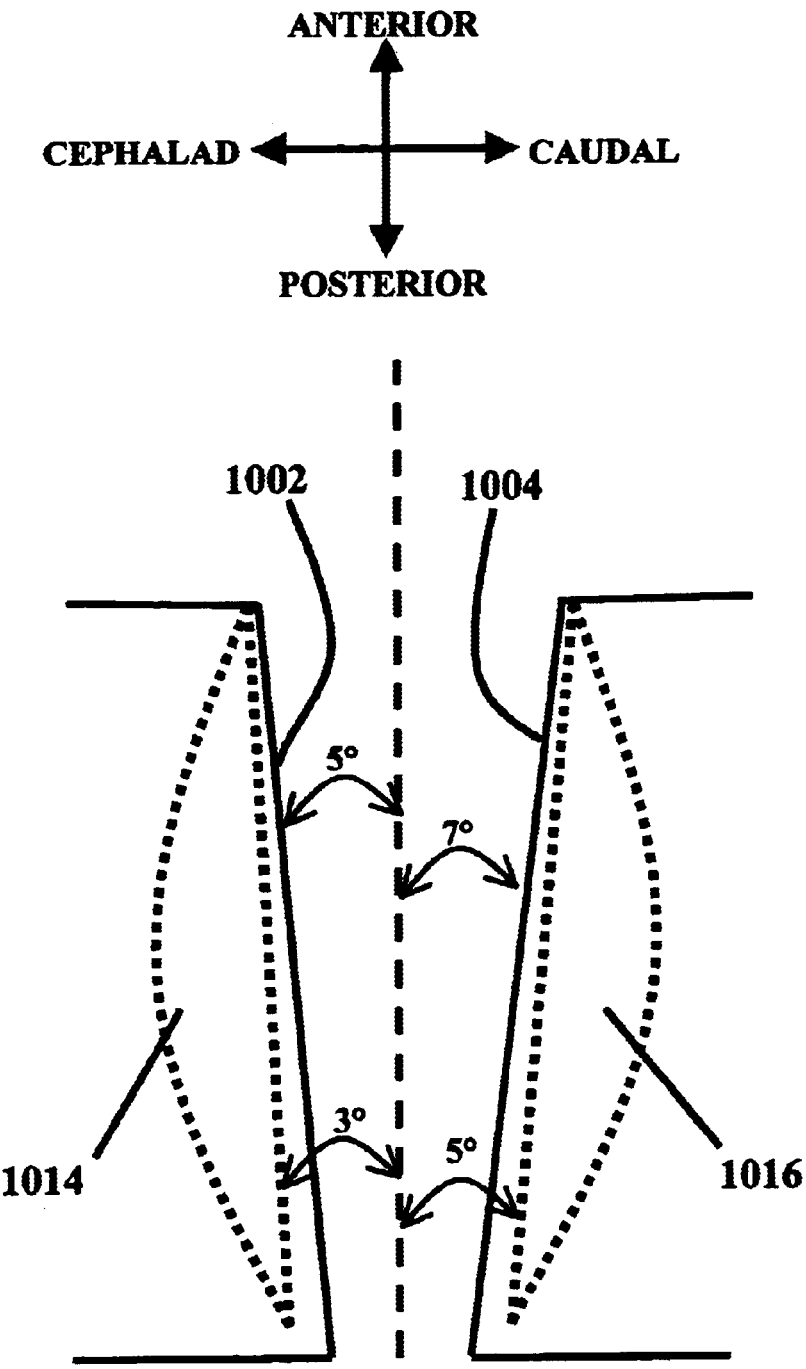
FIG. 54 is another schematic drawing of an intervertebral disc space, and also illustrates a preferred method of determining the appropriate position of a spinal disc prosthesis.

In accordance with the preferred methods described herein, the patient is carefully positioned on the operating table to mimic as closely as possible the neutral position of the spine at the target level(s). As also described hereinabove, prior to forming the cavities in the endplates, the vertebral bodies are distracted to enhance access to the disc space and the endplates. Following the distraction of the vertebral bodies, the angle of endplates relative to the target disc space may not closely mimic their neutral position. FIG. 54 provides an example of how the endplates of FIG. 53 might be positioned following distraction. Cephalad endplate 1002 is shown at a 5° angle relative to the target disc space, and caudal endplate 1004 is shown at a 7° angle relative to the target disc space. To achieve neutral parallel shell positions in this example, the prosthesis shell must be positioned in the caudal endplate at a 5° angle relative to the disc space, which would be the equivalent of a 2° angle relative to the caudal endplate. Similarly, the prosthesis shell must be positioned in the cephalad endplate at a 3° angle relative to the disc space, which would be the equivalent of a 2° angle relative to the cephalad endplate. Accordingly, the cavities 1014 and 1016 that are machined into the endplates must be formed at these preferred angles as illustrated in FIG. 54.

Figures 55A, 55B:
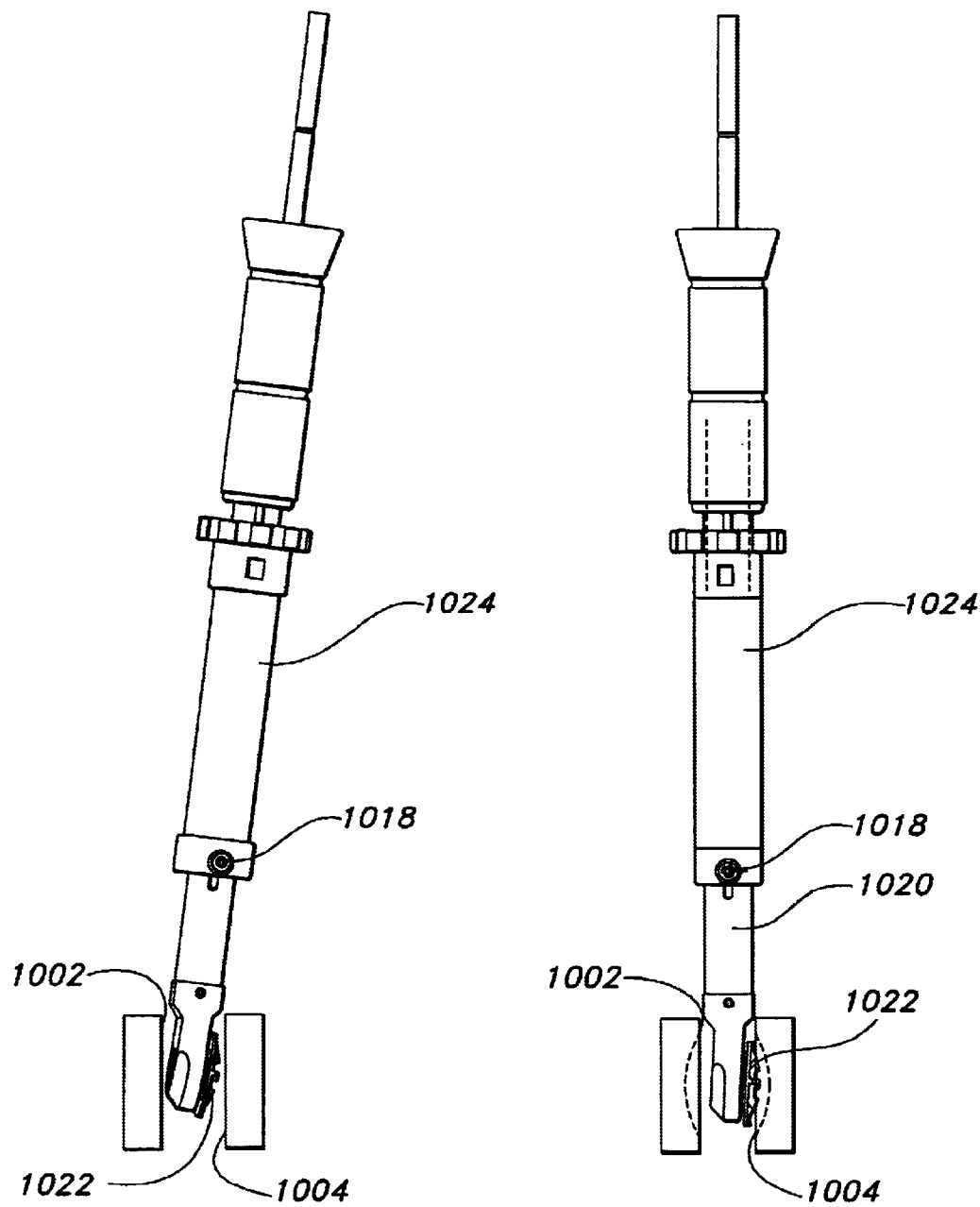
FIG. 55 includes two side views of a milling attachment of FIG. 70 having a milling cutter of FIG. 69 mounted thereon, and illustrates two positions of the milling attachment within the intervertebral disc space.
Figure 56:
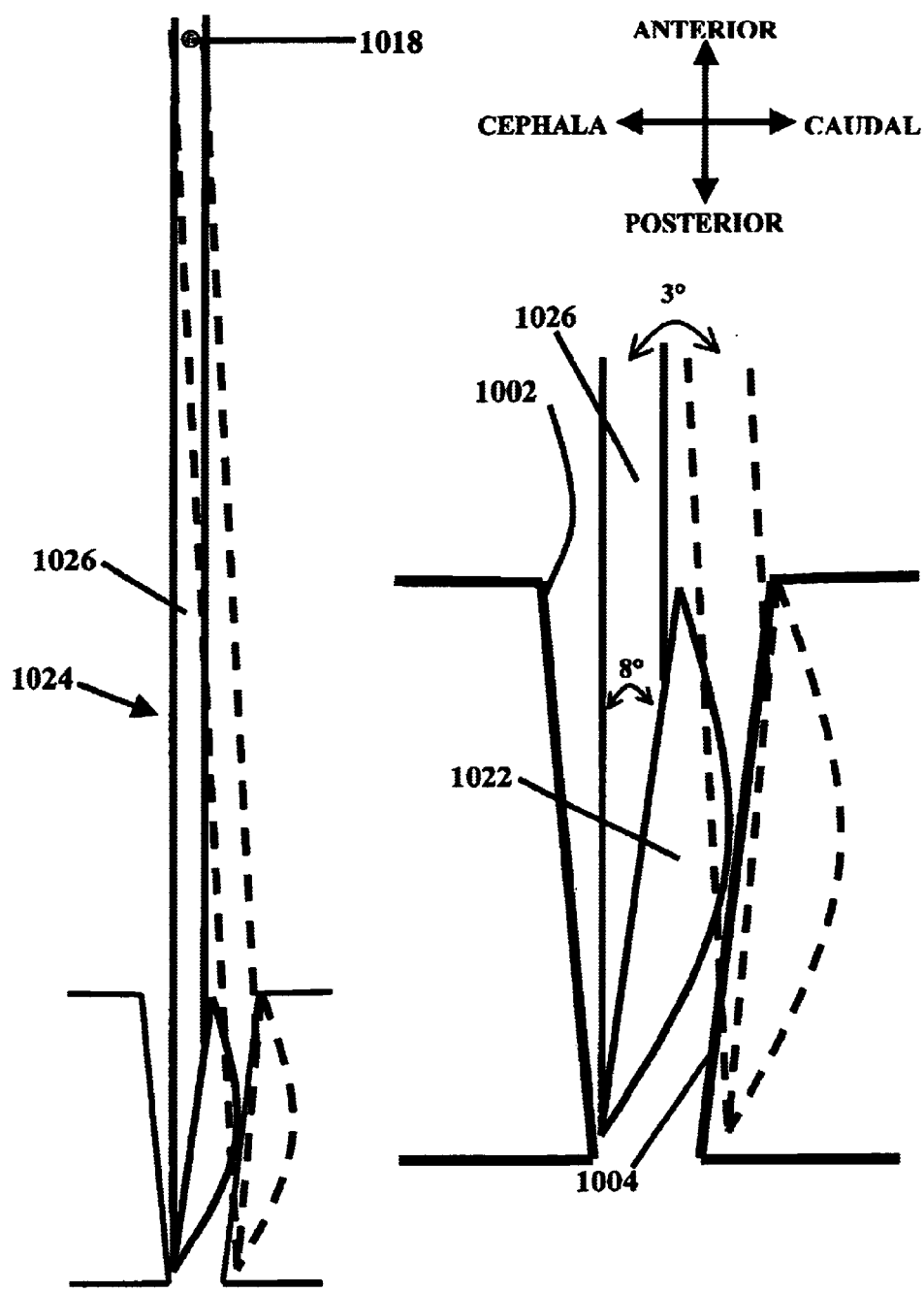
FIG. 56 is as schematic drawing illustrating the two positions shown in FIG. 55 of the milling attachment and milling cutter.

In accordance with the current invention, as shown in FIG. 55A and FIG. 55B, the machining element 1022 is attached to a machining tool 1024. The machining element 1022 is brought into contact with the endplate by rotating the machining tool 1024 about a pivot point 1018 above the disc space. In general, the machining element 1022 is first inserted into the disc space into the position shown in FIG. 55 A. As shown in FIG. 55B, the machining element 1022 is then brought into contact with the vertebral endplate 1004 by rotating the machining tool 1024 about a pivot pin 1018, which is positioned within a machining jig that is not shown. The arrow 1020 illustrates the movement of the machining tool 1024. As illustrated schematically in FIG. 56, the angle of the machining element 1022 relative to the vertebral endplate 1004 will change as the machining tool 1024 is rotated about pivot pin 1018, and as the machining element 1022 is moved toward the endplate 1004. Consequently, the machining element 1022 is preferably angled relative to the arm 1026 of the tool to compensate for the angling that will result from the rotation of the machining tool 1024. For example, in the embodiment shown in FIG. 56, the machining instrument is designed to rotate 3° between the two positions shown therein. As noted above, in this example it is preferable to machine the caudal endplate at a 5° angle relative to the distracted disc space, which would be the equivalent of machining at a 2° angle relative to the caudal endplate. Since the machining tool 1024 will be rotated 3° during the machining process, the machining element 1022 must be introduced into the disc space at an angle of 8° relative to the disc space or 5° relative to the caudal endplate in order to actually machine the caudal endplate at the requisite angle. In accordance with a preferred embodiment of the present invention, this 8° angle is achieved by either: (1) angling the machining element 1022 relative to the arm 1026 of the machining tool 1024; or (2) inserting the machining tool 1024 into the disc space at an angle; or (3) a combination of (1) and (2). In the example shown in FIG. 56, the 8° machining element insertion angle is achieved by angling the machining element 1022 8° relative to the arm 1026, and as a result the machining instrument arm 1026 is inserted into the disc space such that it is parallel to the disc space.

One should note however, that the dimensions of the target disc space might limit the extent to which the machining element 1022 can be angled relative to arm 1026. Higher angles will increase the cephalad-caudal width of the distal end of the machining tool 1024, and therefore require a larger target disc space to accommodate the insertion of the tool into the disc space. Similarly, the amount of rotation of the machining tool 1024, e.g. the 3° rotation in the example above, might also be limited by the dimensions of the disc space. The cephalad-caudal translation of the distal tip of the machining tool 1024 increases as the rotation of the machining tool 1024 increases.

In summary, in accordance with the present invention three factors are considered in determining the angle at which a machining element should be introduced into the vertebral disc space relative to either the disc space or the target endplate. Those factors include: (1) the angle of the target endplate relative to the disc space when the spine is in its neutral position ($\alpha$); (2) the angle of the target endplate relative to the disc space immediately prior to machining the target endplate ($\beta$); (3) any rotation that the machining tool will undergo in advancing toward the target endplate ($\delta$). In general, the following equation may be applied:

Machining Element Angle Upon Insertion Relative to the Target Disc Space ($\phi$)=$\beta$−$\alpha$+$\delta$ As noted above, the machining element angle relative to the target disc space ($\phi$) may be achieved by either: (1) angling the machining element 1022 relative to the arm 1026 of the machining tool 1024; or (2) inserting the machining tool 1024 into the disc space at an angle; or (3) a combination of (1) and (2). If the angle of the machining element relative to the machining tool arm is $\lambda$, and if the angle relative to the target site at which the machining tool arm is inserted into the disc space is $\theta$. The following relationship exists:

$\phi = \lambda + \theta = \beta - \alpha + \delta$

In accordance with another embodiment of the present invention, the machining element may be brought into contact with the endplate by translational movement without rotating it about a pivot point. In accordance with this embodiment $\delta$=0, and the above equation would still apply.

As a practical matter, $\beta$ & $\alpha$ will vary among patients. In addition, there are advantages to providing a relatively simple surgical technique that relies on relatively simple instrumentation. Therefore, in accordance with a simplified embodiment of the present invention, we have determined that introducing a machining element into the cervical spine at an angle of 3°+$\delta$ to 5°+$\delta$, and more preferable 4°+$\delta$, will in the majority of patients result in a substantially parallel shell placement when the spine assumes its neutral position. Similarly, introducing a machining element into the lumbar spine at an angle of between about 0°+$\delta$ to about 19°+$\delta$, will in the majority of patients result in a substantially parallel shell placement when the spine assumes its neutral position. More specifically the following preferred machining element angles should be used at the indicated lumbar levels:

| Level | PREFERRED | Most Preferred |
|-------|-----------|----------------|
| L1–L2 | ~7.4° + $\delta$ to ~9.6° + $\delta$ | ~8.5 + $\delta$ |
| L2–L3 | ~8.4° + $\delta$ to ~11.6° + $\delta$ | ~10 + $\delta$ |
| L3–L4 | ~10.4° + $\delta$ to ~13.8° + $\delta$ | ~12.1 + $\delta$ |
| L4–L5 | ~11.2° + $\delta$ to ~16.4° + $\delta$ | ~13.8 + $\delta$ |
| L5–S1 | ~12.4° + $\delta$ to ~19° + $\delta$ | ~15.7 + $\delta$ |

Finally, it should be noted that in applying the present invention to implanting a cervical prosthesis, preferably $\delta$ is between about 0° to about 5°, and most preferably about 3°. With regard to implanting a lumbar prosthesis, preferably $\delta$ is between about 0° to about 10°, and most preferably about 5°.

1) Instrumentation Facilitating Angled Machining

The present invention provides methods and instrumentation that allow machining of the vertebral body endplates at a controlled or predetermined angle. The following discussion describes the instrumentation within the present invention for achieving above-described angles.

In one embodiment, there is provided machining instruments having an angled arm. The angle is preferable toward the distal end of the instruments (i.e. the machining end). In particular, the compensating angle may be built into the head of the machining device as described below. This angle may be fixed at anywhere from 3° to 10°, or alternatively the angle may be adjustable from 3° to 10°. In use, when the angled machining instrument is inserted through the machining fixture and brought into contact with the vertebral body endplate, the vertebral body endplate will be machined at the appropriate angle.

Other embodiments for ensuring the appropriate machining for preparation of the vertebral body endplates include providing support beneath the patient's neck to better position the spine in its neutral position, providing a conical shaped machining tool which will create a more angled surface, varying the distraction of the vertebral bodies using a special sagittal centering tool illustrated in FIG. 30, more aggressive osteophyte removal to provide a flatter endplate surface, holding the distraction of the vertebral bodies longer in order to relax the soft tissues (for example, for approximately 60 seconds) so that when the surgeon releases the distraction between the vertebral bodies, there is less tendency to return to the undistracted orientation.

In addition to providing angled machining instruments and/or in combination with the other embodiments described above, the invention also provides adjustable machining fixtures, such as a rotatable machining fixtures shown in FIG. 33, multi-track machining fixture shown in FIG. 36, and pivoting machining fixture shown in FIG. 36.

Figure 33A:
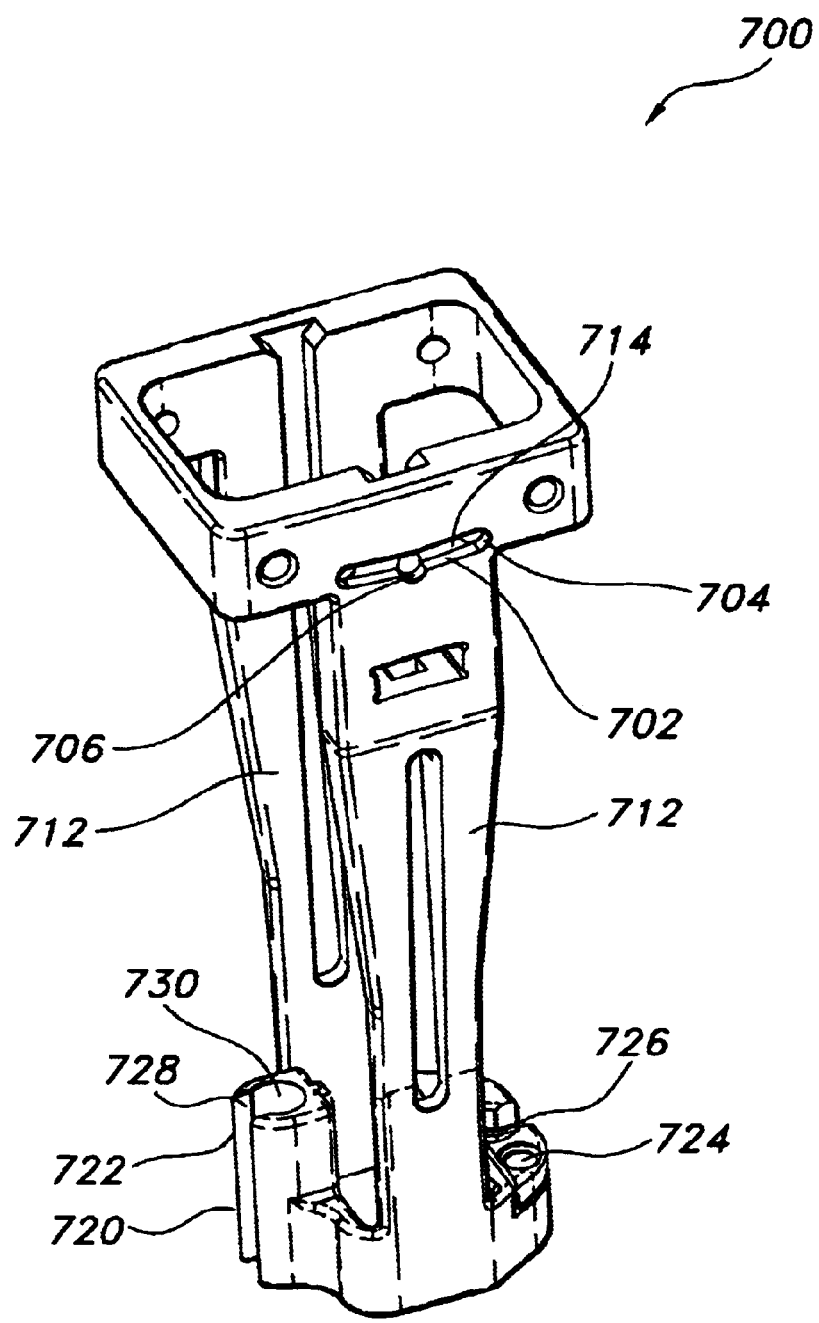
FIG. 33 is a perspective view (A) and side view (B) of a special machining fixture or machining jig, adapted to be maneuvered in order to position instrumentation to allow for angled machining so that when the vertebral body endplates are prepared and an endoprosthesis is implanted, the shells of the endoprosthesis are substantially parallel when the patient's spine is in a neutral position while the patient is standing.
Figure 33B:
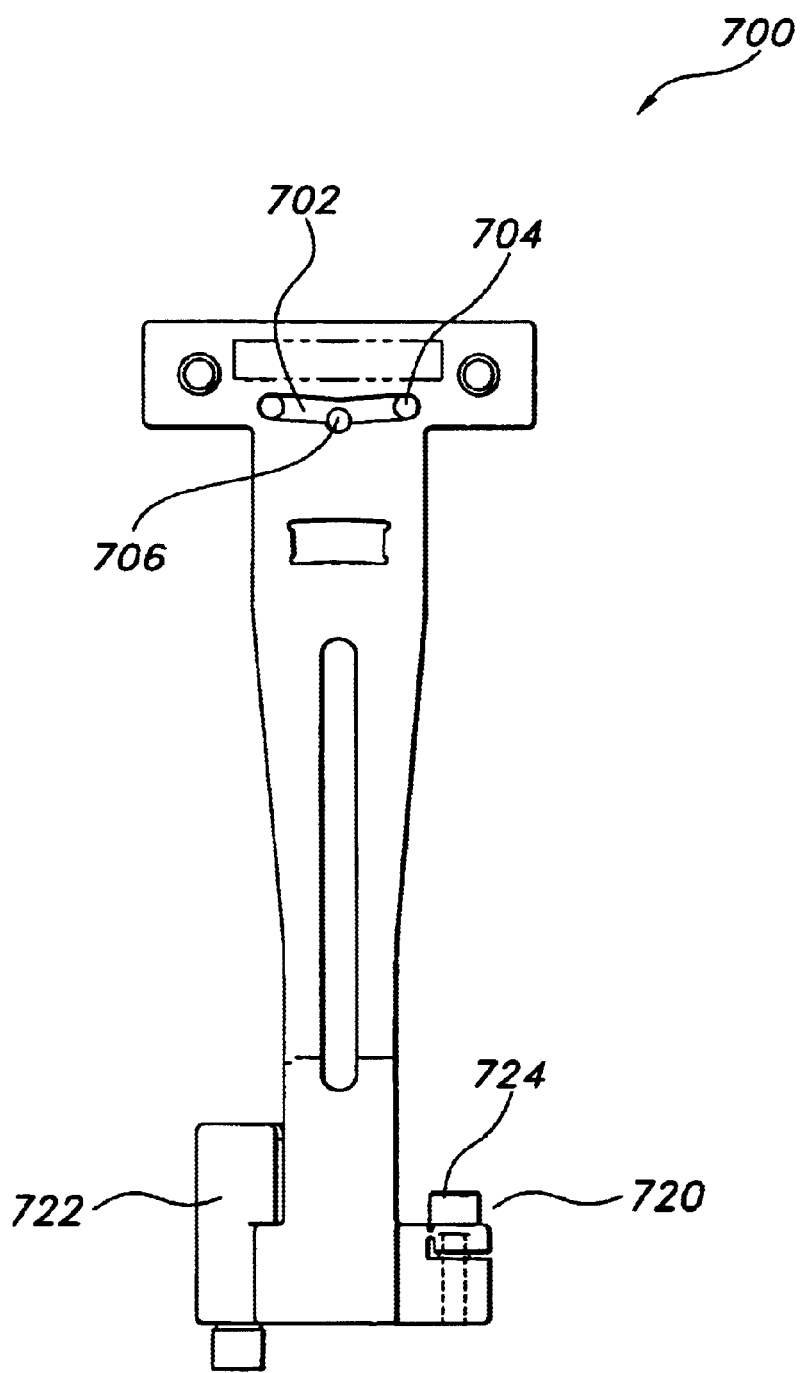

Rotatable machining fixture 700, shown in FIG. 33A and FIG. 33B has a number of features corresponding to machining fixture 300 described above and shown in FIG. 32A and FIG. 32B. The general concept of rotatable machining fixture 700 is that it has a rotation facilitating section 702 and a base 720 that are adapted to allow rotational movement of machining fixture 700, while also being adapted to provide secure placement and fixation of machining fixture 700. Rotation facilitating section 702 may allow rotational variations from a plane substantially parallel to the target disc space between about 0 and about 10 degrees, preferably between about 3 and about 4 degrees, and most preferably at about 4 degrees.

Rotation facilitating section 702 is provided such that machining fixture 700 may be rotated toward the cephalad direction or toward the caudal direction when in use. Machining fixture 700 is secured to machining fixture brace 400 (described in more detail below) at the rotation facilitating sections 702 that are located on both sides 712 of machining fixture 700. Connectors 402 shown in FIG. 41A of machining fixture brace 400 are adapted to interface with rotation facilitating sections 702 to secure machining fixture 700 to frame 60 as illustrated with machining fixture 300 in FIG. 42.

Figure 57C:
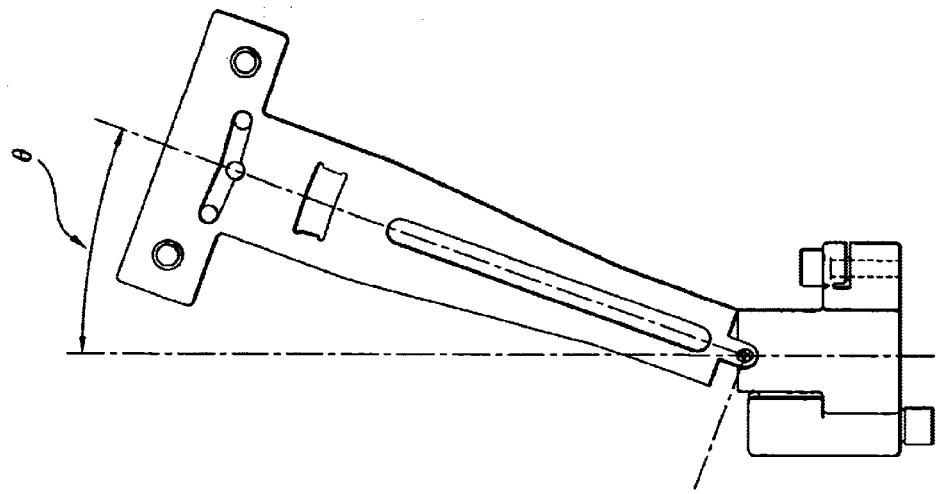
FIG. 57 includes side views of various embodiments of machining fixtures capable of orienting instruments inserted therein at various angles relative to the target disc space.
Figure 57A:
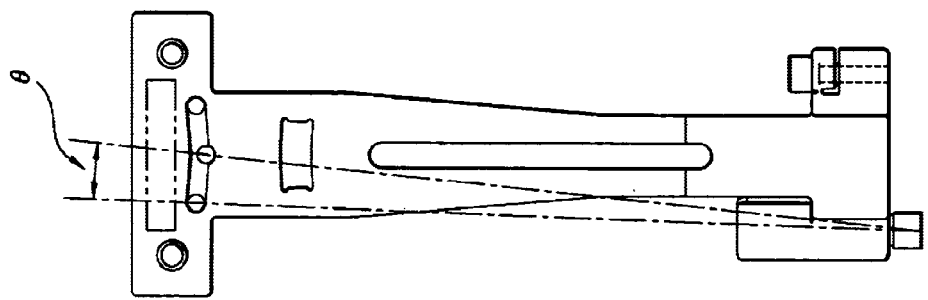

In a more preferred embodiment, rotation facilitating sections 702 each consist of a slot or groove 714 extending along the lateral and the medial sides 712 of the machining fixture in the caudal-cephalad direction. In use, machining fixture 700 is secured by inserting the pins 406 of brace 400 into the slot 714, and locking them into place by rotating knobs 408 of brace 400. The angle of the machining fixture is determined by the position of connectors 402 along the slot 714. In general, if the connectors 402 are positioned within the slots 714 at the center point of the slots in the caudal-cephalad direction, the machining fixture would be aligned parallel to the target disc space and would not be rotated. As the connection point for the connectors 402 moves away from this central point, either in the caudal or the cephalad direction, the angle of the machining fixture relative to the target disc space increases. The actual angle can be determined by a basic geometric analysis of the a hypothetical triangle formed by the connection point for connector 402, the caudal-cephalad central point of the machining fixture slot 714 and the center of rotation of the machining fixture. This hypothetical triangle is shown in FIG. 57A, and the angle of rotation is indicated by the angle θ. Preferably the slot 714 is configured such that it is possible to rotate the machining fixture between about 0 and about 10 degrees, and preferably between about 3 and about 4 degrees, most preferably about 4 degrees. Preferably the slot 714 is essentially "V"-shaped, and is centrally located along the side 712 of the machining fixture in the caudal-cephalad direction. In accordance with this embodiment of the invention, the lowest point of the slot represents the position that connectors 402 should be located to correctly position the machining fixture with 0° rotation relative to the target disc space. The configuration facilitates the quick and easy locating of this neutral 0° position for the machining fixture. Alternatively, slot 714 could be substantially arc-shaped, substantially u-shaped, substantially a straight line, or substantially a zigzag line.

The slot may include position locators to aid the surgeon in positioning the connector 402 at a given point along the slot and thus at a specific amount of rotation. Preferably the position locator can include a detent, groove, notch, threaded member, or other mechanical interface. In accordance with one embodiment, detents 704 are located at either end of the slot 714 and/or positioned along the slot 714. These detents 704 provide positive position locating points for connectors 402. The detents 704 are preferably positioned along the slot at points that define specific predetermined positioning angles for the machining fixture relative to the target disc space.

In a preferred embodiment, slot 714 includes a central detent that allows for neutral positioning of the machining fixture, and further includes a series of detents positioned along the slot that corresponding to rotations of between 0°–16°, more preferably between 0°–13°, and most preferably between 0°–10°. More preferably, the machining fixture of the present invention includes a slot having: (1) a central detent that allows for neutral positioning of the machining fixture; (2) a first pair of detents essentially equally positioned in opposite directions away from the central detent and both of which allow for positioning the machining fixture at an angle of substantially 3° relative to the target disc space; and (3) a second pair of detents essentially equally positioned in opposite directions away from the central detent and positioned further from the central detent than the first pair, wherein each of the second pair of detents allows for positioning the machining fixture at an angle of substantially 4° relative to the target disc space. In yet another embodiment of the present invention, a third pair of detents can be added to the slot that are positioned further from the central detent than the second pair, and which allow for positioning the machining fixture at an angle of substantially 5°.

It is also possible to provide multiple rotation facilitating sections 702 that are placed at various anterior-posterior positions and that provide various angling options for the surgeon. For example, the machining fixture may include two tilting facilitating sections on each side that allow two angulations of the machining fixture. In accordance with this embodiment, a machining fixture has two slots of different lengths on each side 712. Preferably, when the connectors 402 are positioned at either end of the shorter slot the machining fixture has a rotation of substantially 3°. When the connectors 402 are positioned at either end of the longer slot the machining fixture has a rotation of substantially 4°. Furthermore, additional longer or shorter slots can be added. For example, a third longer slot could be added that allows for rotation of substantially 5°.

The lateral-medial position of the rotation facilitating section 702 on machining fixture 700 is not critical. For instance, if a facilitating section 702 is higher (or more anteriorly located) on the machining fixture 700, it may be necessary for the tilting facilitating section 702 to be longer to provide the desired angulation. Alternatively, facilitating section 702 may be located closer to the base section 702 of machining fixture 700 and therefore may be shorter, while providing the same angulation. Furthermore, as described in greater detail below, the clamps 90 (shown in FIG. 42) allow the machining fixture brace 400 to be position at virtually any anterior-posterior position to allow the surgeon to attach the connectors 402 to the rotation facilitating sections 702.

The general purpose of machining fixture 700 is to control the angulation at which the vertebral bodies are machined. The machining fixture 700 positions surgical instruments relative to a surgical site and the patient's anatomy, and comprises features adapted to allow instruments cooperating with the machining fixture to prepare the anatomy of the vertebral bodies at specified angular positions relative to the target disc space or to the endplates adjacent the target disc space. When machining fixture 700 is positioned at an angle, the instruments placed therein will interface with the vertebral body endplates at the desired specified angles. These desired specified angles may be achieved by the rotation of the machining fixture alone, or may be a function of a combination of the rotation of the machining fixture and angles designed within the instruments themselves as described above.

The base 720 of machining fixture 700 is provided with an open portion 722. Open base portion 722 corresponds generally to foot 304 of machining fixture 300, with the exception that open base portion 722 has an aperture 730 that includes an open section 728 along its length. When an anchor post is placed within aperture 730 to secure the machining fixture 700 to the vertebral body, open section 728 allows the anchor post to move within aperture 730 when the machining fixture 700 is rotated. Depending on the extent of rotation, the anchor post may at least partially protrude from open base portion 720. This allows the surgeon to secure machining fixture 700 with an anchor post (described below), while allowing the surgeon to rotate machining fixture 700. The purpose of open base portion 722 is to provide an aperture 730, shown in FIG. 33A as a "C" shaped aperture, that at least partially retains a portion of an anchor post and at least partially allows a portion of the anchor post to escape or otherwise protrude from open base portion 722.

In another embodiment, it is possible to provide an open base portion 722 having an elongated aperture that is closed, i.e. that does not include open section 728, similar to elongated opening 786 shown in FIG. 35. In this embodiment the elongation of the aperture allows movement of the anchor post within the aperture during rotation of the machining fixture.

Any embodiment that allows securing an anchor post while allowing the machining fixture and anchor post some degrees of rotational motion relative to each other when the machining fixture 700 is rotated is usable and encompassed by the present invention.

Base 720 of machining fixture 700 is also provided with a drill guide opening 724 which corresponds to drill guide opening 305 of machining fixture 300. Note also that the side of machining fixture 700 that has drill guide opening 724 is also provided with an open base portion 726 which provides the same functions as open base portion 722, i.e., that of providing maneuverability and additional options for the receiving and exiting of an anchor post.

Figure 36B:
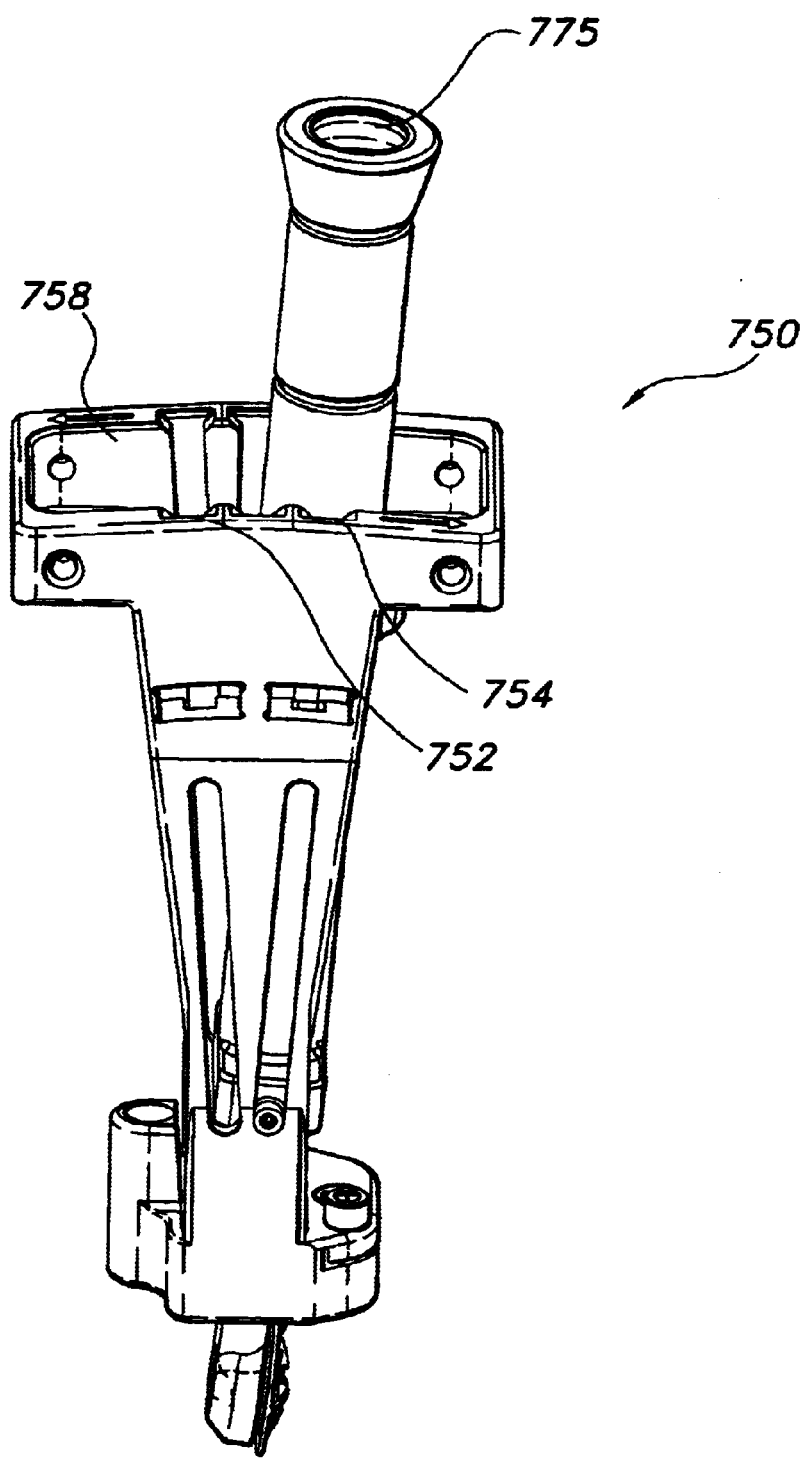
FIG. 36B is a side perspective view of the multi-track machining fixture of FIG. 36A having an instrument inserted therethrough.

Another embodiment providing angulation options for the instruments described herein is a multi-track machining fixture 750, shown in FIG. 36. Multi-track machining fixture 750 also has elements corresponding to machining fixture 300, but also provides multiple tracks 752 and 754 that are adapted to allow various instruments to interface with multi-track machining fixture 750 such that the instruments enter the target disc space at an angle relative thereto. As shown best in FIG. 36, angled tracks 752 and 754 include similar elements as those included in the sides 709 of machining fixture 700, such as key 760, slots 762, pivot arc slot 764, and holes 756. In the embodiment shown in FIG. 36A-FIG. 36D, tracks 752 and 754 are angled in opposite directions and generally mirror one another. Alternatively, machining fixture 750 may include multiple tracks that are all angled in the same direction, or a combination of multiple tracks wherein some are angled in the same direction and others are angled in an opposite direction. Entryway 758 of multi-track machining fixture 750, in some embodiments, may be larger than entryway 308 of machining fixture 300.

The multi-track machining fixture 750 is used in accordance with the present invention as follows. When the various instruments described below are interfaced with multi-track machining fixture 750, the surgeon will select which track to employ in order to achieve the desired positioning of the instrument relative to the target disc space. For example, a surgeon may utilize track 752 to prepare the cephalad vertebral body, and then track 754 to prepare the caudal vertebral body.

Tracks 752 and 754 may be configured to allow similar instrument positions relative to the target disc space as those provided by machining fixture 700. The positions may include anywhere from between about 0 degrees to about 13 degrees of rotation relative to the target disc space, and are preferably between about 0 degrees to about 10 degrees, more preferably between about 3 degrees and about 6 degrees, and are most preferably about 4 degrees. It may be desirable to include angles up to about 16 degrees, depending upon various surgical considerations.

Figure 57B:
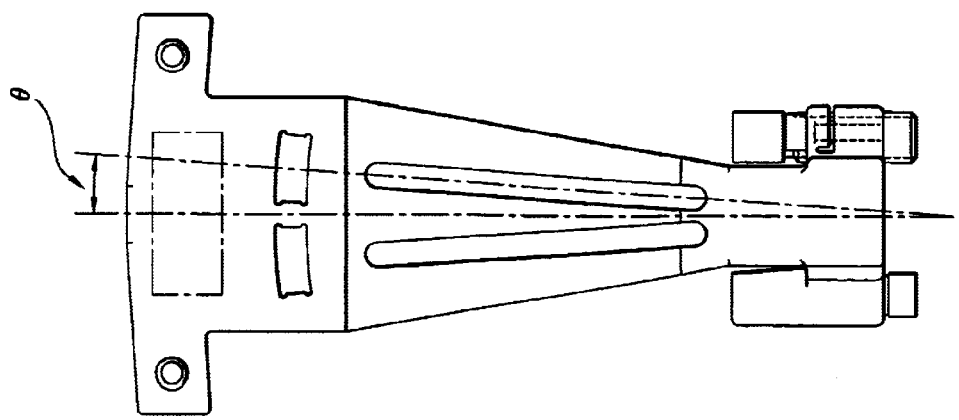
Figure 57D:
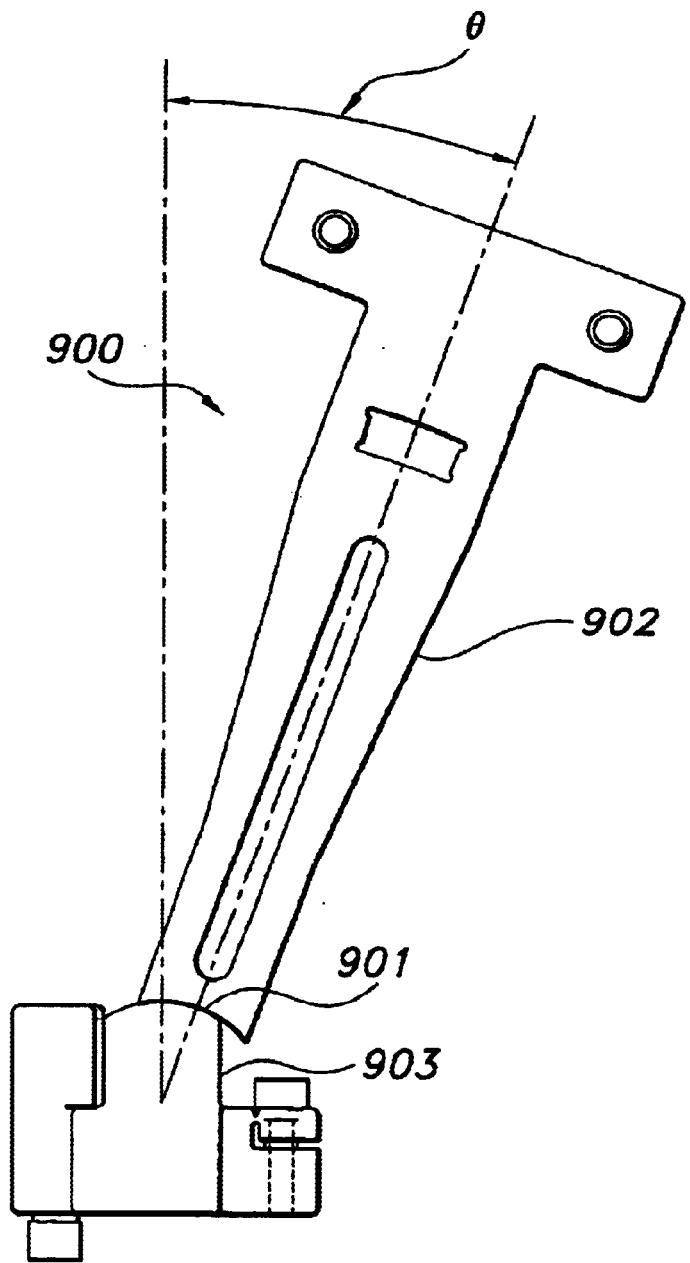

These angles are measured between the angled track and a line passing through the caudal-cephalad central point of the machining fixture, taking into account the center of rotation of the machining fixture. This angle is illustrated in FIG. 57B, and is represented by the angle θ. In other words, there is a range in the most preferred embodiment, of about 8 degrees between angled tracks 752 and 754. FIG. 36B shows an exemplary instrument 775 inserted through entryway 758 of multi-track machining fixture 750. FIGS. 36C and D show additional perspective side views of one embodiment of a multi-track machining fixture 750.

There is also provided a machining fixture 800 embodiment, shown in FIG. 34 and machining fixture 780 shown in FIG. 35, both of which are described further below. These machining fixtures facilitate placement of a prosthesis at an intervertebral disc space level that is adjacent to a level that already has a prosthesis.

Figures 37A, 37B:
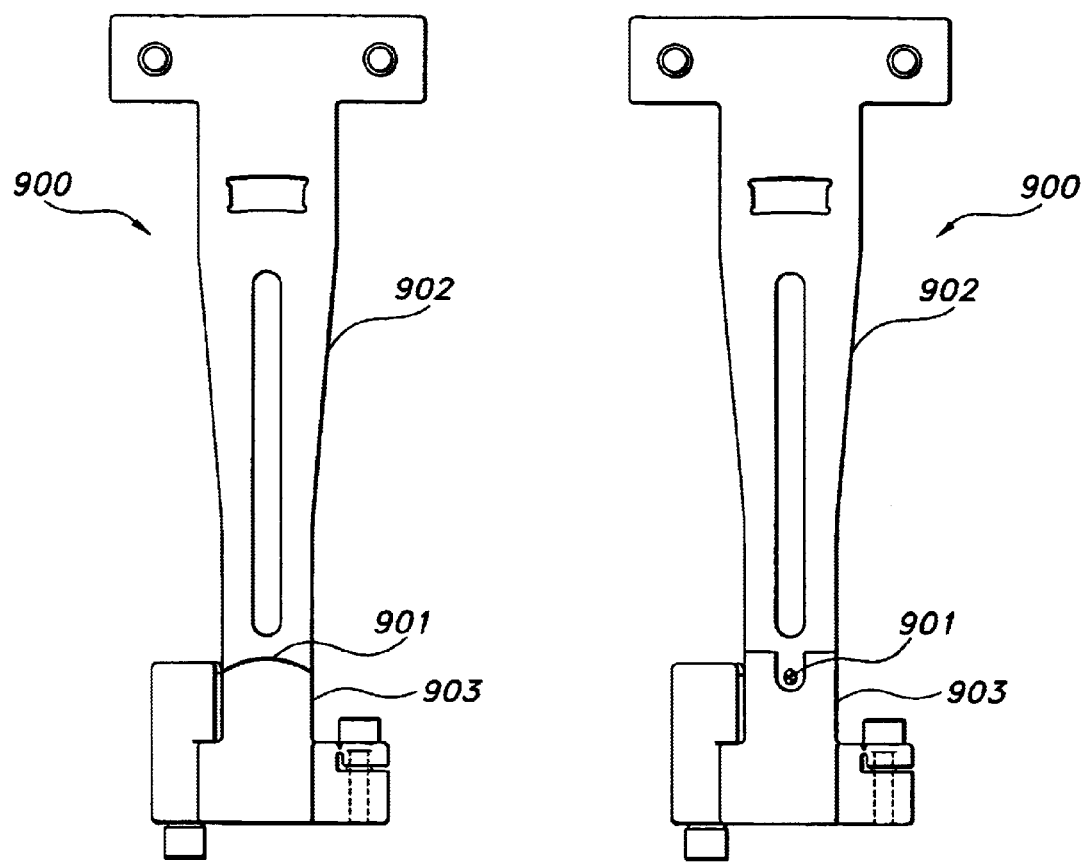
FIG. 37A and B are side views of two embodiments of a machining fixture that include a pivot joint to facilitate positioning the machining fixture at various angles relative to a target implant site.

Referring now to FIG. 36, another embodiment of the present invention for providing angulation options for the instruments described herein is a machining fixture 900 that includes a pivot joint 901. Machining fixture 900 includes the same features included in machining fixture 300, including those features for aligning and controlling the position and movement of various machining instruments. In accordance with this embodiment, however, the machining scaffold includes an upper section 902 and a lower section 903. Joint 901 may be a pivot point as shown in FIG. 37B or it may be an arcuate interface as shown in the embodiment illustrated in FIG. 37A. The upper section and lower section are interconnected with a joint 901 that allows the upper section to be angled relative to the lower section. In use the lower section 903 is aligned with and attached to the target site in the same manner described above with regard to machining fixture 300. Since the machining tool aligning features are included on the upper section, adjusting the angle of the upper section 902 relative to the lower section 903 can change the angle at which the machining tools are introduced into the target site.

2) Frame of Reference for Angle Measurements

It should be noted that the frame of reference for the various angle-accommodating machining fixtures may vary. One skilled in the art may readily calculate these angles by applying basic geometric principles. For purposes of clarity, the reference points that have been used for determining the machining fixture's angle relative to the target site (θ) for the various machining fixture preferred embodiments are shown in FIG. 57.

3) Other Features of Machining Instruments

In accordance with another embodiment of the present invention, the machining fixture may include a modified low-profile anterior configuration to avoid interference with the patient's anatomy such has the patient's chin or manubrium sterni. This is particularly useful in the rotating machining fixture embodiment.

Furthermore, as described in greater detail below, one common aspect of most of the instruments described herein is that they contain structures that cooperate with structures on the machining fixture 300 that limit the range of motion, depth penetration, etc. of the instruments to those necessary and desirable for the preparation of the target disc space. These features generally includes upper notches and lower notches on the scaffold, and a series of pins located on the instruments that fit within the notches and are stopped by the ends of the notches when the instrument has reached the end of its desired range of motion. In particular, lower keys on various instruments are "caught" by the bottom of slots 312 of scaffold 300. This secures those instruments in the same location in relation to scaffold 300 every time they are inserted through scaffold 300. The lower keys precisely locate the instruments in the anterior-posterior direction, and prevent the instruments from being inserted too far into the target disc space. In addition, upper keys interface with pivot arc slots 314 of scaffold 300, which allow the instrument to be rotated slide back and forth in pivot arc slots 314 in a limited motion in the sagittal direction. These general concepts will be described with more particularity for each instrument below.

B. Machining the Vertebral Body Endplates and Within the Disc Space

As noted above, the current invention provides precision instrumentation for machining the vertebral body endplates to form a cavity therein that closely matches the geometric profile of a prosthesis. This machining step is referred to herein as the endplate profile machining operation. Prior to the endplate profile machining operation, however, a preliminary machining operation must be done to create sufficient space to allow insertion of the profile machining instrumentation. This preliminary operation is referred to herein as a transverse burring operation. Prior to either transverse burring or the profile machining of the vertebral body endplates, however, the surgeon must first (1) determine the posterior limits for transverse burring within the intervertebral space, and (2) locate the preferred anterior-posterior position for the prosthesis which will determine where the endplate profile machining should be done. In accordance with a preferred embodiment of the present invention, the surgeon should first locate the preferred prosthesis anterior-posterior position. This is preferably done prior to transverse burring since it is possible that landmarks used to locate the preferred anterior-posterior prosthesis position may be removed during transverse burring.

1) Locating the Preferred Anterior-Posterior Prosthesis Position

Figure 58:
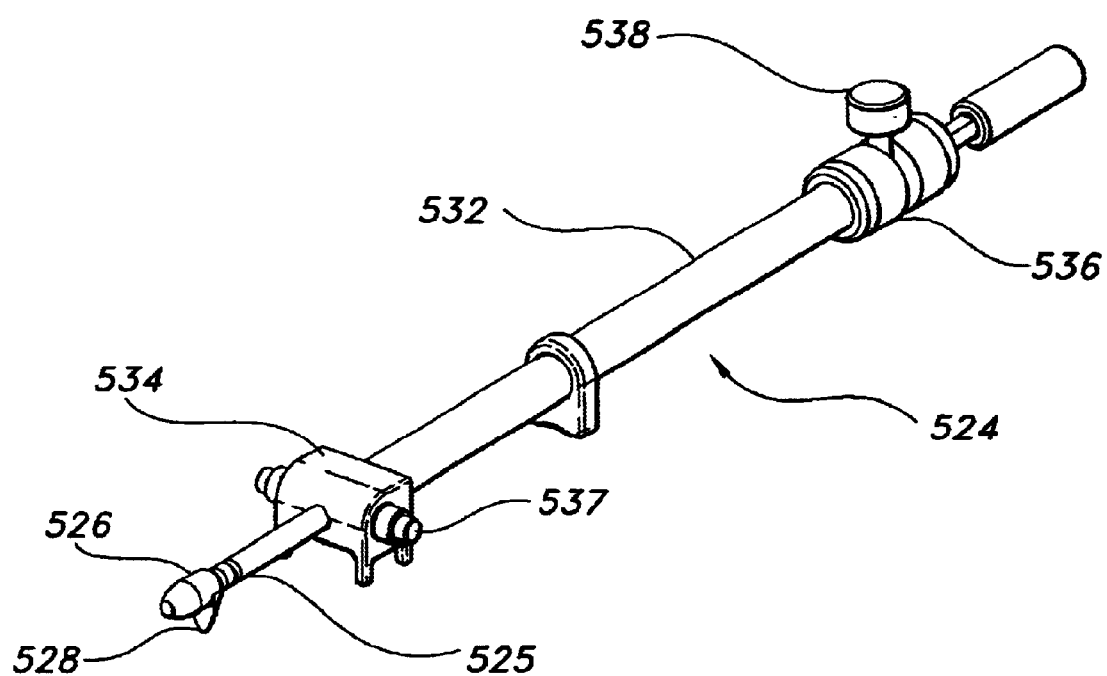
FIG. 58 is a perspective view of one embodiment of a milling cutter depth gauge, showing generally a foot that measures how deep into the space the vertebral bodies will be milled and a saddle that is used to couple milling cutter depth gauge to the milling attachment of FIG. 70.

Referring to FIG. 58, gauge 524 is used locate the preferred anterior-posterior position in which the prosthesis should be placed. The location of the preferred prosthesis position determines where the vertebral body endplates should be milled. In accordance with a preferred embodiment, the preferred anterior-posterior prosthesis position is illustrated schematically in FIG. 59, and is such that the prosthesis' anterior edge is tangent to the anterior edge of the anterior superior vertebral body. Such prosthesis positioning is preferred because it prevents machining too close to the spinal canal or locating the prosthesis too anteriorly or outside the disc space. This also facilitates optimizing sizing of the device in the intervertebral space.

Gauge 524 is designed to locate the position of the anterior superior vertebral body. Gauge 524 has hollow shaft 532 that has saddle 534 mounted thereon. Saddle 534 has pins 537 that cooperate with slots 312 in machining fixture 300 shown in FIG. 32. When pins 537 are fully seated at the end of slots 312, pins 537 position gauge 524 at a predetermined distance from the anterior surface of the vertebral bodies. Hollow shaft 532 also houses extendible rod 525. At the end of extendible rod 525 is foot 526, which is described in more detail below. Gauge 524 also has depth-securing portion 536 with adjustable locking portion 538.

In use, the gauge 524 is inserted into the entryway 308 of the scaffold 300 (see FIG. 32) until the pins 537 of the gauge 524 contact the bottom of the scaffold slots 312. The extendable rod 525 of the gauge 524 is then moved posteriorly until the contact surface 528 of foot 526 contacts the more anterior surface of the two vertebral bodies adjacent the target disc space. The adjustable locking portion 538 is then locked in place to prevent extendable rod 525 from moving. Gauge 524 is used later in the process to configure the profile milling instrumentation.

2) Transverse Burring—Determining Proper Posterior Depth for Burring Within the Target Disc Space After the preferred anterior-posterior prosthesis position has been located, the surgeon should verify the maximum anterior-posterior depth for transverse burring. As previously noted, the purpose of transverse burring is to ensure adequate space for insertion of the profile machining instruments. In essence, the transverse burring process creates an essentially quadrahedron-like opening within the target disc space.

Figure 60:
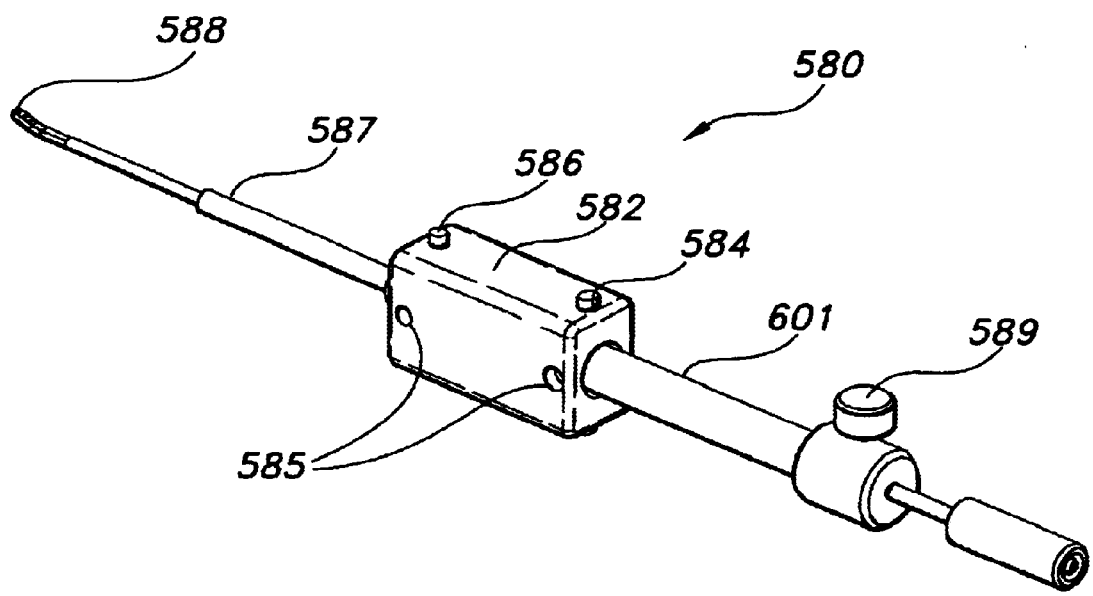
FIG. 60 is a perspective view of one embodiment of a transverse burring depth gauge of the present invention, showing generally a gauge tip, positioning portion, and a gauge screw. Transverse burring depth gauge is adapted to be inserted through the burring block of FIG. 61 to measure the proper burring depth.

Before the surgeon begins the transverse burring process, however, burring gauge 580, shown in FIG. 60 is used to verify the maximum posterior position to which the burring instrumentation should reach. In accordance with a preferred embodiment, the posterior limit for the transverse burring operation should be set at a position that is anterior to the posterior ligament of the intervertebral space or the posterior margins of the vertebral body.

Figure 61:
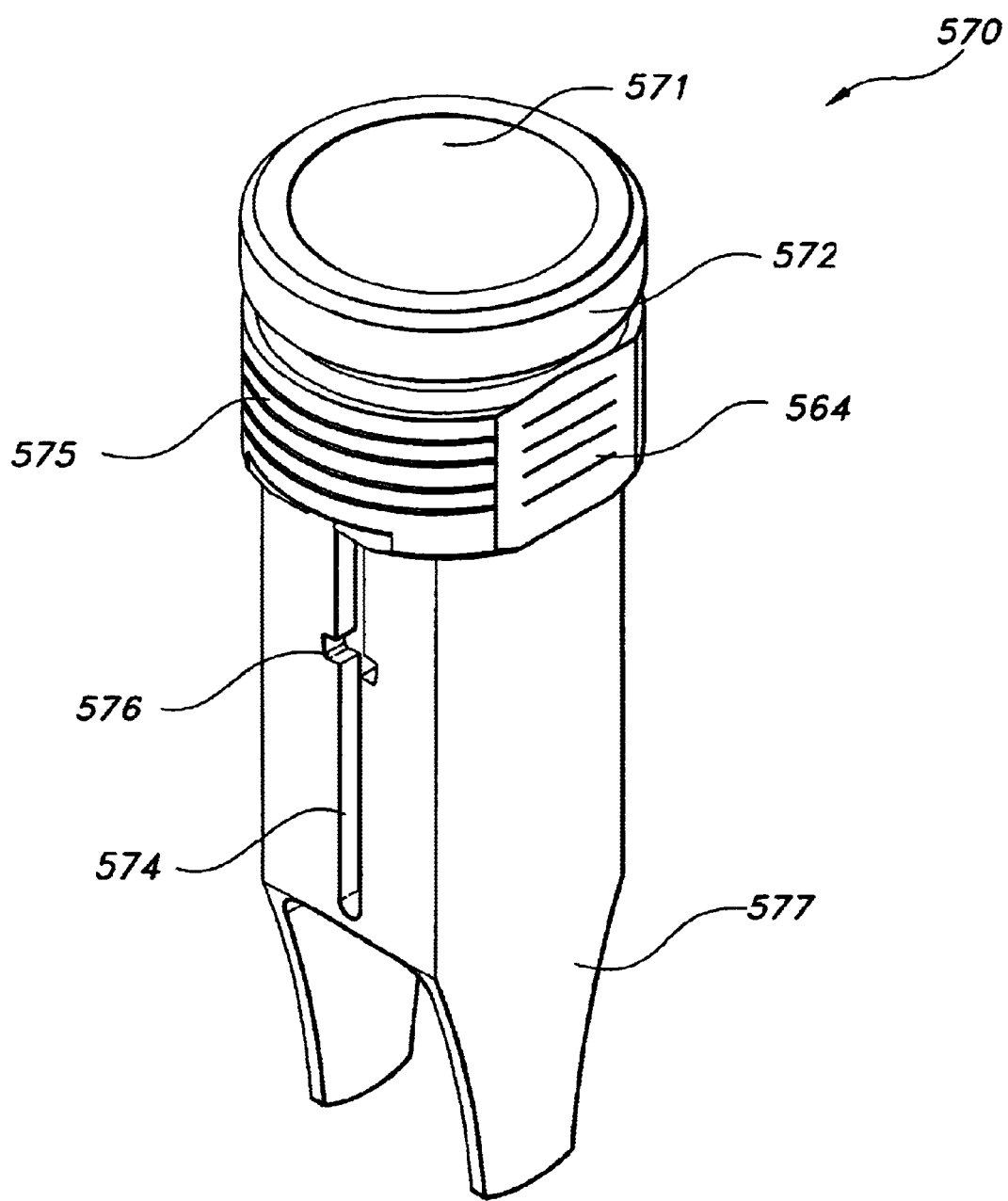
FIG. 61 is a perspective view of one embodiment of a burring block that is adapted to fit with the scaffold of FIG. 32.

Referring to FIG. 60, burring depth gauge 580 has positioning portion 582 that includes proximal pins 584 (also called positioning stops) and distal pins (also called positioning strips) 586 that interface with anterior-posterior slots 574 and lateral slots 576 of burring block 570, which is shown in FIG. 61 and is discussed greater detail in below. It should be noted that position portion 582 includes similar proximal and distal pins 584, 586 on the side opposite those shown in FIG. 60. Burring depth gauge 580 also has tip 588 at the end of extendable shaft 587. The shaft 587 is movably positioned within a conduit extending through the body 601 of the gauge 580. The gauge also includes an adjustable locking portion 589 that when tightened will interface with shaft 587 within the conduit, and thereby prevent movement of shaft 587 along the conduit. The tip 588 is adapted to allow the surgeon to feel or view the posterior ligament of the intervertebral space or posterior margins of the vertebral body. This allows the surgeon to determine the most posterior part of the target space into which he intends to burr.

Figure 62:
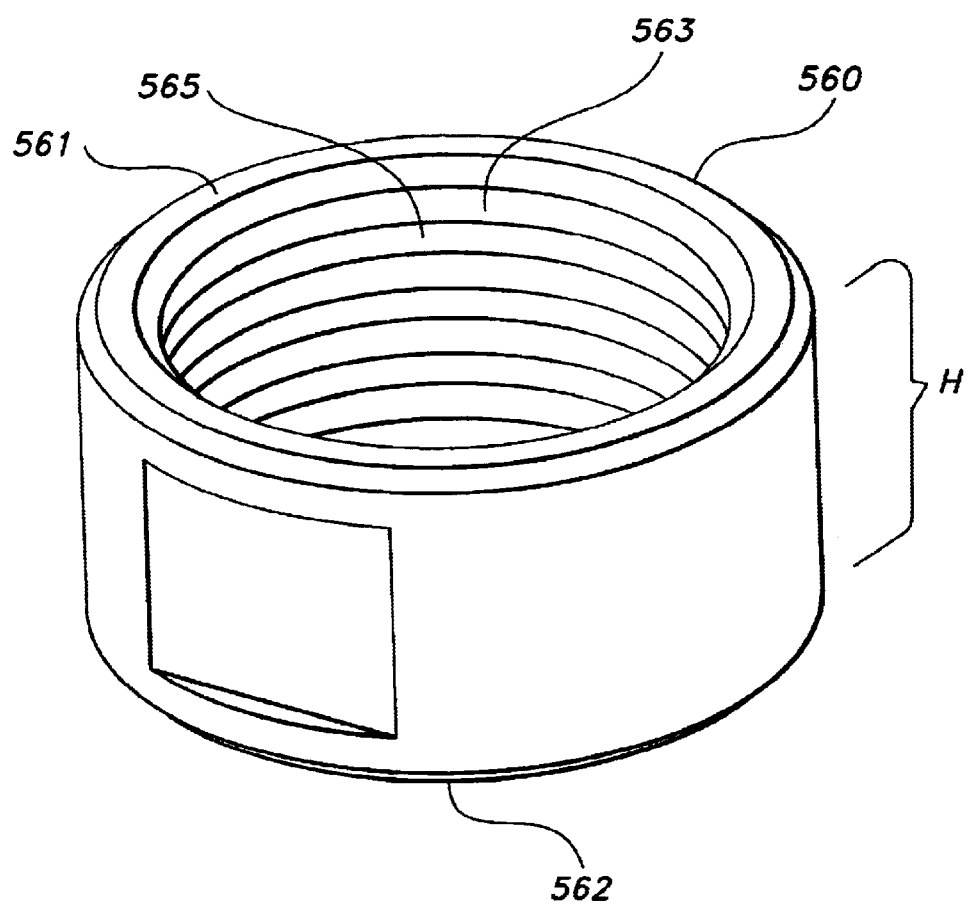
FIG. 62 is a perspective view of a burring depth control ring that is used in conjunction with the burring block shown in FIG. 61.

In use, burring gauge 580 is inserted into a burring positioning system, which includes burring adjustment ring 560, shown in FIG. 62, and burring block 570, shown in FIG. 61. In accordance with a preferred embodiment, in forming the burring positioning system the surgeon first selects a burring adjustment ring 560 and burring block 570 from a plurality of burring adjustment rings and blocks. The selected ring and block correspond in size to the pre-selected disc prosthesis size to be implanted. In accordance with a preferred embodiment, the surgical instrument system of the present invention is designed to prepare the disc space to accept one of five substantially circular prosthesis sizes including 14 mm, 15 mm, 16 mm, 17 mm, and 18 mm prostheses, wherein the prosthesis' size corresponds to the diameter of the prosthesis. In accordance with this preferred system, two burring blocks 570 are provided—one designed for use in preparing the disc space to accept either the 14 mm, 15 mm, or 16 mm prosthesis, and a second designed for use in preparing the disc space to accept either the 17 mm or 18 mm prosthesis. In addition, in accordance with this preferred system, five burring adjustment rings 560 are provided, wherein each is designed for use in preparing the disc space to accept one of the five prosthesis sizes. The relationship of the dimensions of the various burring adjustment rings 560, the burring blocks 570, and the prosthesis sizes is explained in greater detail below.

As shown in FIG. 61, burring block 570 includes a proximal opening 571, a distal end 577, a flange 572 located at its proximal end, a distal threaded portion 575 with an opening therein, indicia 564, anterior-posterior positioning slots 574, and lateral positioning slots 576. Slot 574 actually acts as stop to position a burring tool in the anterior-posterior direction and slots 576 actually act as a lateral positioning stop adapted to limit lateral movement of burring tool. It should be noted that similar slots 574 and 576 are present on the opposite side of block 570, but are not shown in FIG. 61. In accordance with a preferred embodiment shown in FIG. 61, slots 574 and 576 are intersecting, and are otherwise similar in design and function to slots 312 and 314 of the machining fixture 300 shown in FIG. 32 (which are not intersecting). As described in greater detail below, the block 570 provides a cephalad-caudal pivot axis for transverse burring and provides a means for controlling the extent and the rate of the transverse burr's dissent into the target disc space.

Burring adjustment ring 560 includes an opening 565 that is surrounded by interior threads 563 which is a threaded portion corresponding to the threaded portion of the burring block. Opening 565 is sized to accept threaded portion 575 of block 570, and ring threads 563 are sized to correspond to the threads of block threaded portion 575. Ring 560 also includes upper surface 561 and lower surface 562. Lower surface 562 defines in part a proximal edge adapted to cooperate with the machining fixture.

The surgeon assembles the burring positioning system as follows. Upon selecting the appropriate size burring adjustment ring 560 and burring block 570, ring 560 is screwed onto threaded portion 575 of burring block 570, thus forming the burring positioning system. Ring 560 is screwed completely onto the burring block 570 until upper surface 561 of ring 560 meets flange 572 of block 570.

Prior to inserting burring gauge 580 into the burring positioning system, the burring positioning system is placed into the machining fixture 300. In particular, the distal end 577 of burring block 570 is inserted into entryway 308 of machining fixture 300 until the lower edge 562 of ring 560 contacts upper surface 311 of machining fixture 300 (See FIG. 32, FIG. 61, and FIG. 62). Thereafter, gauge 580 is inserted into proximal opening 571 such that distal pins 586 on gauge 580 travel along slots 574 on block 570 until distal pins 586 contact the distal end of slots 574. Gauge screw 589 is loosened to allow shaft 587 to move freely. Shaft 587 may then be adjusted so that gauge tip 588 is positioned at the level of the most posterior position that the surgeon wishes to burr in the target space. This position may be at the level of the posterior longitudinal ligament. Once the surgeon believes that gauge 588 is in the desired position, he locks position of shaft 587 by rotating gauge screw 589. After shaft 587 is locked and set, the surgeon can confirm the desired positioning of gauge tip 588 using a fluoroscopic x-ray machine. Gauge 580 is then removed from the burring assembly.

3) Transverse Burring—Verifying Proper Posterior Depth of Burring Instrumentation As described in greater detail below, the instrumentation used in the transverse burring operation includes two burring handpieces 550 and 551, shown in FIG. 63 and FIG. 64, respectively. As illustrated only in FIG. 63, a fluted burr 555, which will be used to machine the space between the vertebral bodies, is inserted into burring handpiece 550 (which may also be referred to as a longitudinally extending barrel), and the handpiece 550 is attached to a power source (not shown) such as an electric or air-powered motor. Burring handpieces 550, 551 have drive connecting portions 552 for attachment to the power source. They also include positioning portions 554 and hollow shafts 559 which may be a rotatable burring shaft disposed with the longitudinally extending barrel. Each positioning portion 554 has proximal pins or stops 556 and distal pins 558.

Figure 63A:
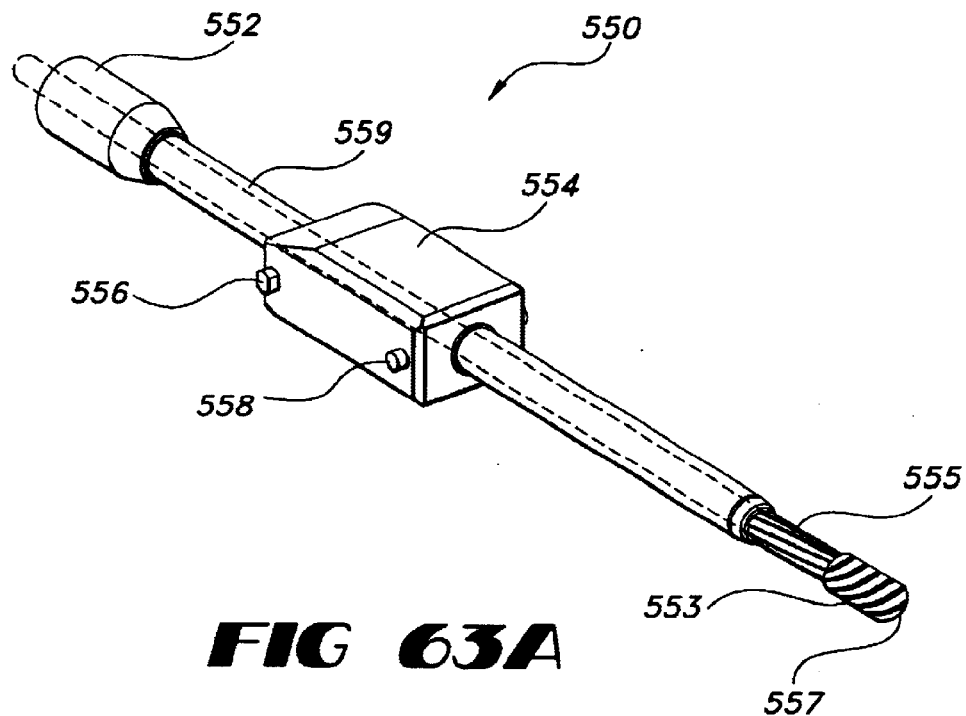
FIG. 63 is a perspective view (A), side plan view (B), and top view (C) of one embodiment of a centered burring attachment of the present invention, showing generally a burring attachment having a positioning portion that interfaces with slots of the scaffold shown in FIG. 32. Centered burring attachment is used to burr the target space and allow it to receive head of the milling attachment of FIG. 70 and a spinal prosthesis.
Figure 63B:
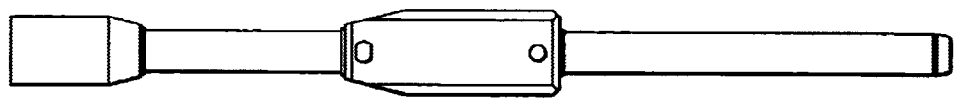
Figure 63C:
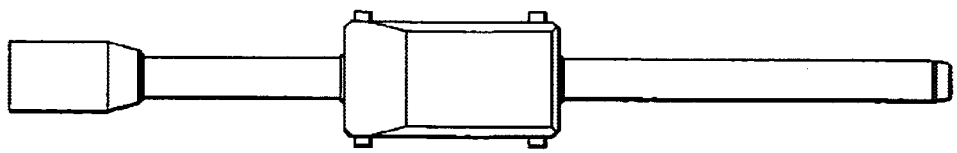
Figure 65:
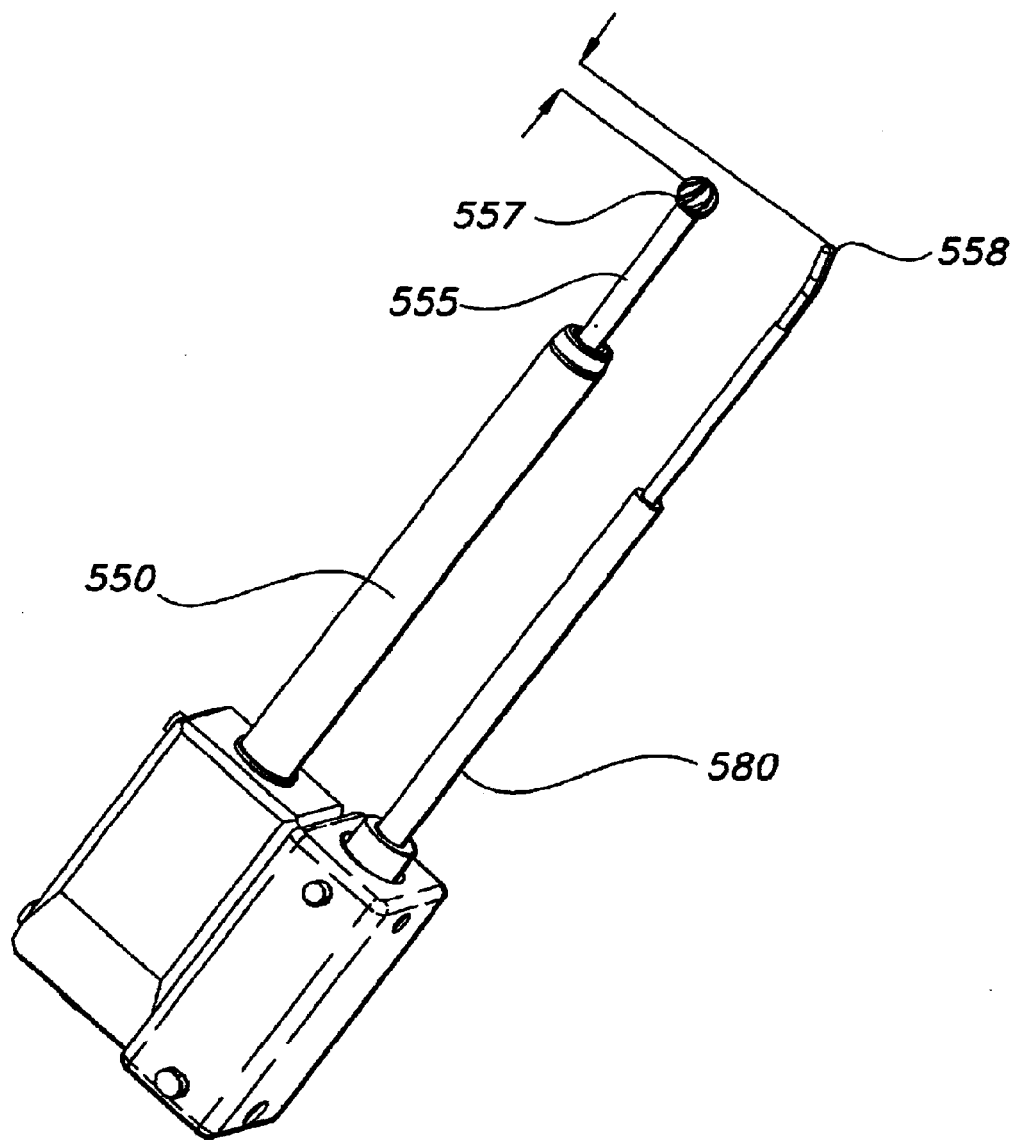
FIG. 65 is an illustration of a transverse burring attachment appropriately positioned adjacent to a gauge.

As illustrated in FIG. 65, after gauge 580 is adjusted as outlined above, it is positioned next to burring handpiece 550 with the burr 555 installed, so that the holes 585 on the gauge meet the pins 556, 558 on the burring handpiece 550 shown in FIG. 63 (not shown in FIG. 65 because the pins and holes engage one another in use.) The surgeon will then visually confirm that the tip 557 of burr 555 does not extend past tip 588 of gauge 580. This confirms that the burr will not penetrate past the posterior margin of either vertebral body. Optimally, the distal tip 557 of the burr 555 is located shorter than the tip 588 of burring depth gauge 580 by about 1 mm. If tip 557 extends beyond depth gauge tip 588 damage may result to the posterior soft tissues, and the surgeon should reevaluate the appropriate size prosthesis for the patient. This may indicate that the pre-selected prosthesis size is too large, and that a smaller prosthesis should be implanted.

4) Transverse Burring Within the Target Disc Space

Once the proper depth for the burring of the target space has been confirmed, the surgeon is then ready to begin burring. Generally, first a central portion of the space will be burred using a centered burring handpiece 550, wherein the center line of the positioning portions coincident with the center line of the longitudinally extending barrel, which is shown in FIG. 63. Thereafter, the caudal and cephalad extremities of the disc space will be burred using an offset burring handpiece 551, wherein the center line of the portion is not coincident with the center line of the longitudinally extending barrel, which is shown in FIG. 64.

Referring to FIG. 63, the centered burring handpiece 550 includes positioning portion 554, which is centered on shaft 559. In other words, the centerline of positioning portion 554 is coincident with the axis of shaft 559. Referring to FIG. 64, the offset handpiece 551 includes position portion 554, which is offset with respect to shaft 559.

Figure 64A:
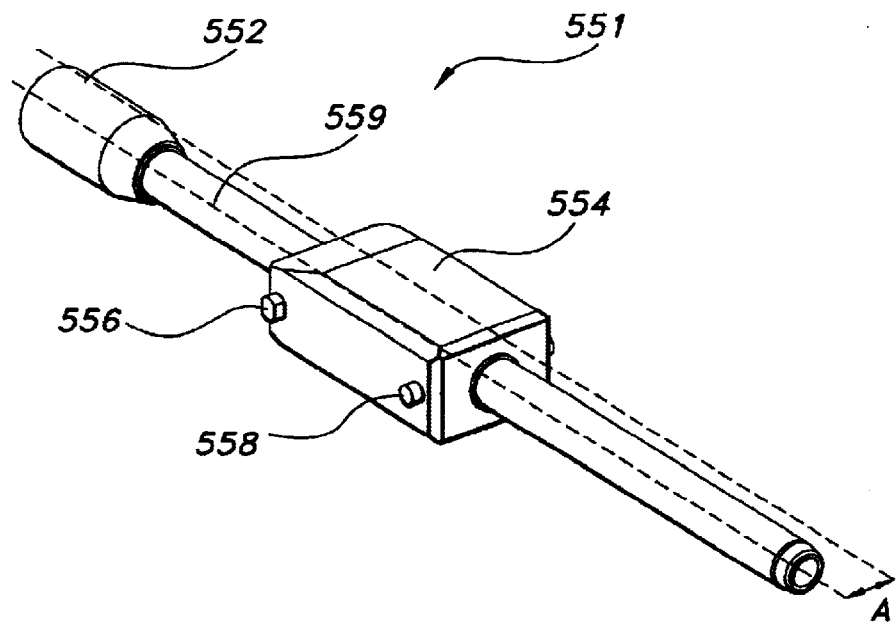
FIG. 64 is a perspective view (A), side plan view (B), and top view (C) of one embodiment of an offset burring attachment of the present invention, having the same features of the centered burring attachment of FIG. 59, but with an offset positioning portion.
Figure 64B:
Figure 64C:
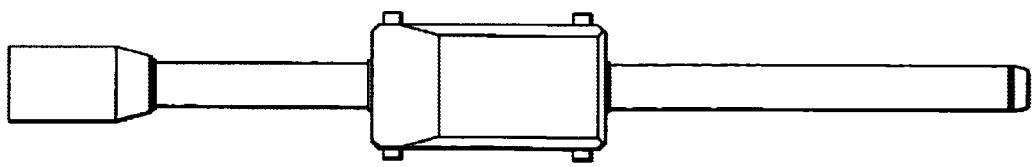

The offset is shown in FIG. 64 by distance A. This offset may be about 1.75 to about 2.5 mm, more particularly about 2 to about 2.25 mm, for a 4 mm burr. Providing both a centered and an offset positioning portion 554 allows the surgeon to burr the central portion of the intervertebral space, and then burr on either side of the central portion (superiorly and inferiorly), as will be described in more detail below. In accordance with an alternative embodiment of the method of the present invention, a single central transverse burring operation may be done with a single larger burr.

The burring positioning system, i.e. the assembled burring block 570 and ring 560, is removed from opening 308 of machining fixture 300, and ring 560 is repositioned along threaded portion 575 to a burring starting position. Burring block 570 includes indicia 564 that indicate the appropriate start position for the upper edge 561 of ring 560 depending upon the prosthesis size to be implanted. In accordance with the preferred system outlined above, one burring block 570 would include indicia 564 for 17 mm and 18 mm, and the second burring block 570 would include indicia 564 for 14 mm, 15 mm, and 16 mm. Upon adjusting ring 560 to the appropriate start position, the burring positioning system is reinserted into opening 308 of machining fixture 300 (see FIG. 32) until lower edge 562 of ring 560 contacts upper surface 311 of machining fixture 300.

Referring to FIG. 63 and FIG. 61, centered burring handpiece 550, having a burr inserted therein and being attached to a power source, is then inserted into opening 571 of block 570 such that pins 556, 558 are aligned with and travel along slot 574 in block 570. Handpiece 550 is inserted until lower pins 558 are seated at the distal end of slot 574 and upper pins 556 are aligned with pivot slots 576. The surgeon then burrs the center portion of the disc space by simultaneously (1) moving handpiece 550 back and forth in the lateral direction, and (2) rotating the burring ring 560. As the surgeon moves handpiece 550 back and forth, upper pins 556 travel back and forth to the lateral ends of slot 576 in block 570. Slots 576 provide burring handpiece 550 with the correct range of motion. This motion causes the burr to move laterally back and forth across the center of the disc space. The ring 560 is rotated in the direction that causes the upper surface 561 of ring 560 to move toward flange 572 of block 570. As the ring 560 is rotated in this manner, block 570 is lowered with respect to the machining fixture 300. When upper surface 561 of ring 560 reaches flange 572 the burr is positioned at the previously determined maximum posterior location, and the centered burring is completed. Ring 560 therefore controls the anterior-posterior position within the disc space of burr cutting element 553. The combined lateral movement and anterior-posterior movement of burr cutting element 553 allows it to machine out a substantially quadrahedron-like pattern within the center of the disc space. During the burring process, continuous sterile saline irrigation and suction are used to keep the bone surface cool and clear of debris.

Next, offset burring handpiece 551 is inserted into block 570 and used to burr the caudal and cephalad extremities of the disc space, including if necessary the endplates of the vertebral bodies. Upper edge 561 of burring ring 560 is reseated against flange 572 of block 570, and the posterior limit for transverse burring is reconfirmed. The limit is reconfirmed by: (1) reinserting the burring depth gauge 580 into the burring block assembly, (2) recoupling the depth gauge 580 with offset burring handpiece 551, and (3) verifying that the gauge tip 588 extends more posteriorly than the burr. Burring ring 560 is then repositioned to its starting position indicated by indicia 564. The offset burring handpiece 551 is then inserted into the burring assembly and the burring process described above is repeated with the offset burring handpiece 551. Offset burring handpiece 551 is removed, rotated 180 degrees and replaced into the burring block 570 so that burring occurs on the opposite side of the disc space. The target space is then burred again as described above. The burring handpiece and the transverse burring block assembly are then removed from scaffold 300.

In accordance with an alternative method of the present invention, a single central burring operation can be performed. In accordance with this method a larger burr, preferably about 8 mm is placed in centered milling attachment 550, and positioned within burring block 570 with ring 560 positioned at the appropriate start position. In accordance with this technique, the surgeon can either use the laterally oscillating motion as described above, or alternatively use a modified technique. In accordance with the modified technique, the surgeon positions attachment 550 such that upper pins 556 are positioned at one end of slot 576 in block 570. The motor is activated and the surgeon rotates ring 560 while maintaining the attachment's lateral positioning. When ring 560 reaches flange 572, attachment 550 is repositioned such that upper pins 556 are positioned at the opposite end of slot 576 in block 570. The ring is rotated in the opposite direction until it reaches its start position, and the burring operation is completed.

Figure 49A:
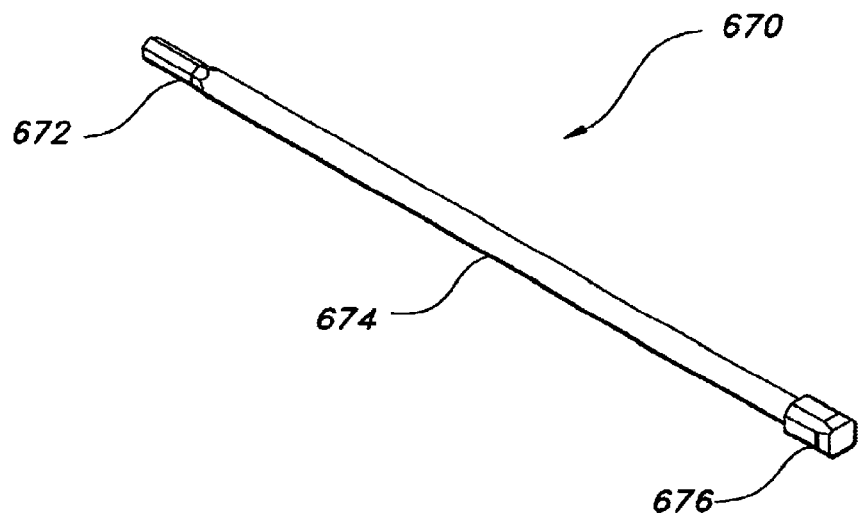
FIG. 49 is a perspective view (A) and side view (B) of a gauge-wrench instrument used to adjust the adjustable drill guide of FIG. 48, and used to check the caudal-cephalad dimension of the target disc space in accordance with the present invention.
Figure 49B:
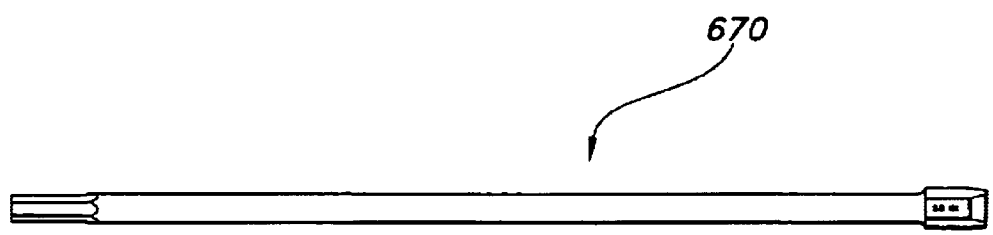

Following transverse burring, the surgeon should confirm that a correct opening has been prepared between the endplates. In accordance with a preferred embodiment, this opening should be at least about 8.5 mm. This is preferably confirmed by using a gauge-wrench instrument, which is shown in FIG. 49. Gauge-wrench instrument 670 includes wrench end 672 and gauge end 676 interconnected by shaft 674. Wrench end 672 is configured for use in adjusting the adjustable drill guide 470, shown in FIG. 48. Gauge end 676 consists of a square block that is sized to equal the preferred minimum caudal-cephalad height of the disc space following transverse burring. In accordance with a preferred embodiment, the width and height of gauge end 676 is 8.5 mm. Following transverse burring, gauge end 676 is inserted into the disc space to confirm that the caudal-cephalad height of the created quadrahedron-like opening is at least 8.5 mm. If it is not, the transverse burring operation should be repeated.

Figure 66:
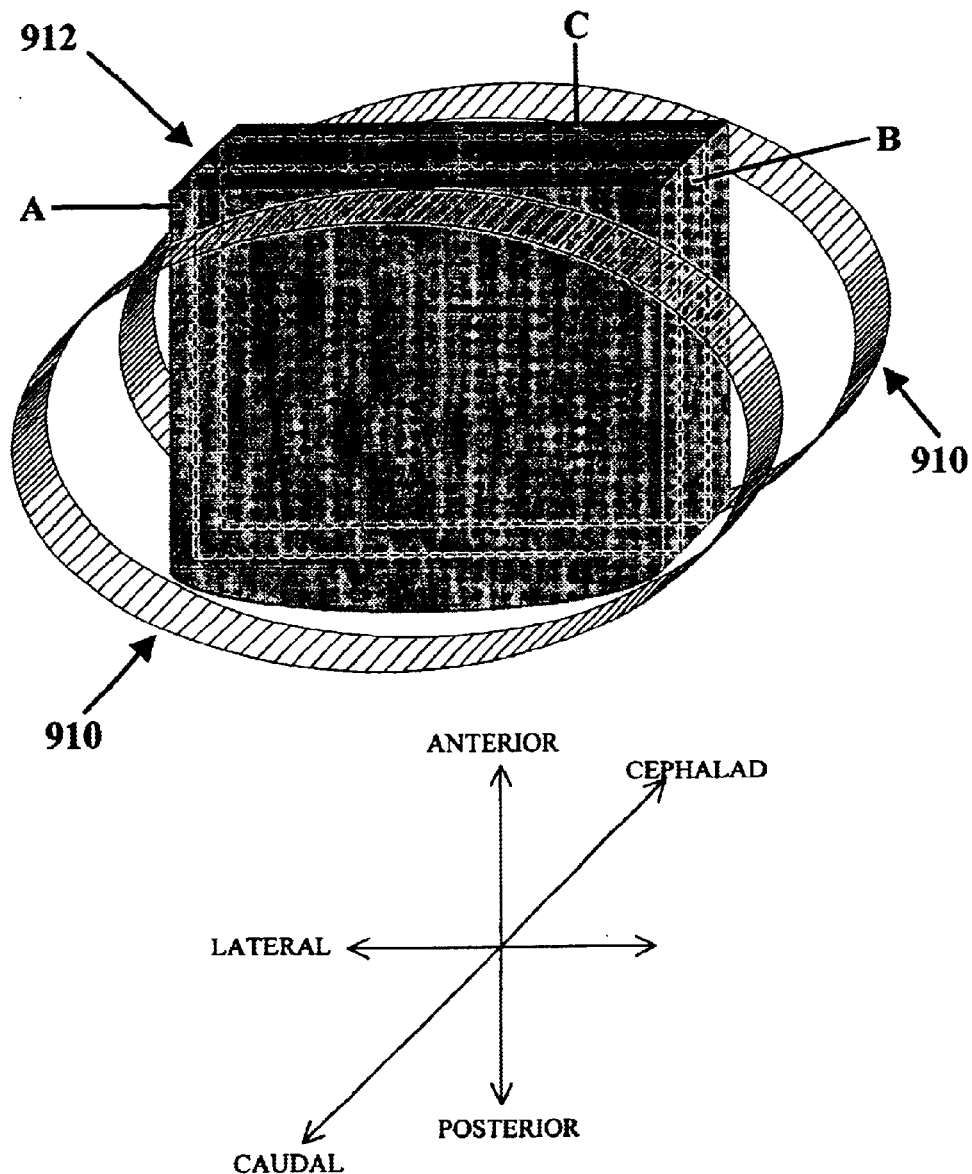
FIG. 66 is a schematic drawing that illustrates the quadrahedron-like opening that is created between two vertebrae during the transverse burring procedure in accordance with the present invention.

As noted above, in accordance with a preferred embodiment of the present invention there is a relationship among the dimensions of the various burring adjustment rings 560, the burring blocks 570, and the prosthesis sizes. These dimensional relationships define the dimensions of the quadrahedron-like opening that is created in the disc space during transverse burring. Referring now to FIG. 66, a schematic drawing is provided to illustrate the quadrahedron-like opening (represented by blocked region 912) that is created between two vertebrae 910 during the transverse burring procedure. One skilled in the art will appreciate that the opening 912 is not a true quadrahedron. Because of the pivoting motion of the burr, the posterior edge of the opening is rounded. As illustrated in FIG. 66, opening 912 can be characterized in three sections. Caudal and cephalad sections, A and C respectively, are created during the offset transverse burring operation. Center section B is created during the center transverse burring operation.

The dimensions of opening 912 are determined as follows. The width of slot 576 in block 570 (see FIG. 61) determines in the lateral dimension of opening 912. As noted above, in accordance with a preferred instrument system, two blocks 570 are provided—one for use in implanting a 14 mm, 15 mm, or 16 mm prosthesis, and one for use in implanting a 17 mm or 18 mm prosthesis. These blocks are identical except that slot 576 in the 17/18 block 560 is longer than slot 576 in the 14/15/16 block 560. In accordance with this preferred embodiment, slot 576 is sized such that the lateral dimension of opening 912 will be 18 mm when the 17/18 block 560 is used, and 16 mm with the 14/15/16 block 560 is used. As a result opening 912 will be slightly oversized for the 17 mm, 15 mm and 14 mm prostheses. This is not critical, however, since the profile milling operation will follow during which a more precisely sized cavity will be formed. Alternatively, the system may include a block 560 corresponding to each implant size included in the system.

The offset distance "A" of attachment 551 (see FIG. 64) and the diameter of the burr determine the caudal-cephalad dimension of opening 912. Finally, as described in greater detail below, the distance between indicia 564 and flange 572 on block 570 (see FIG. 61) determines the anterior-posterior dimension of opening 912.

Figure 67:
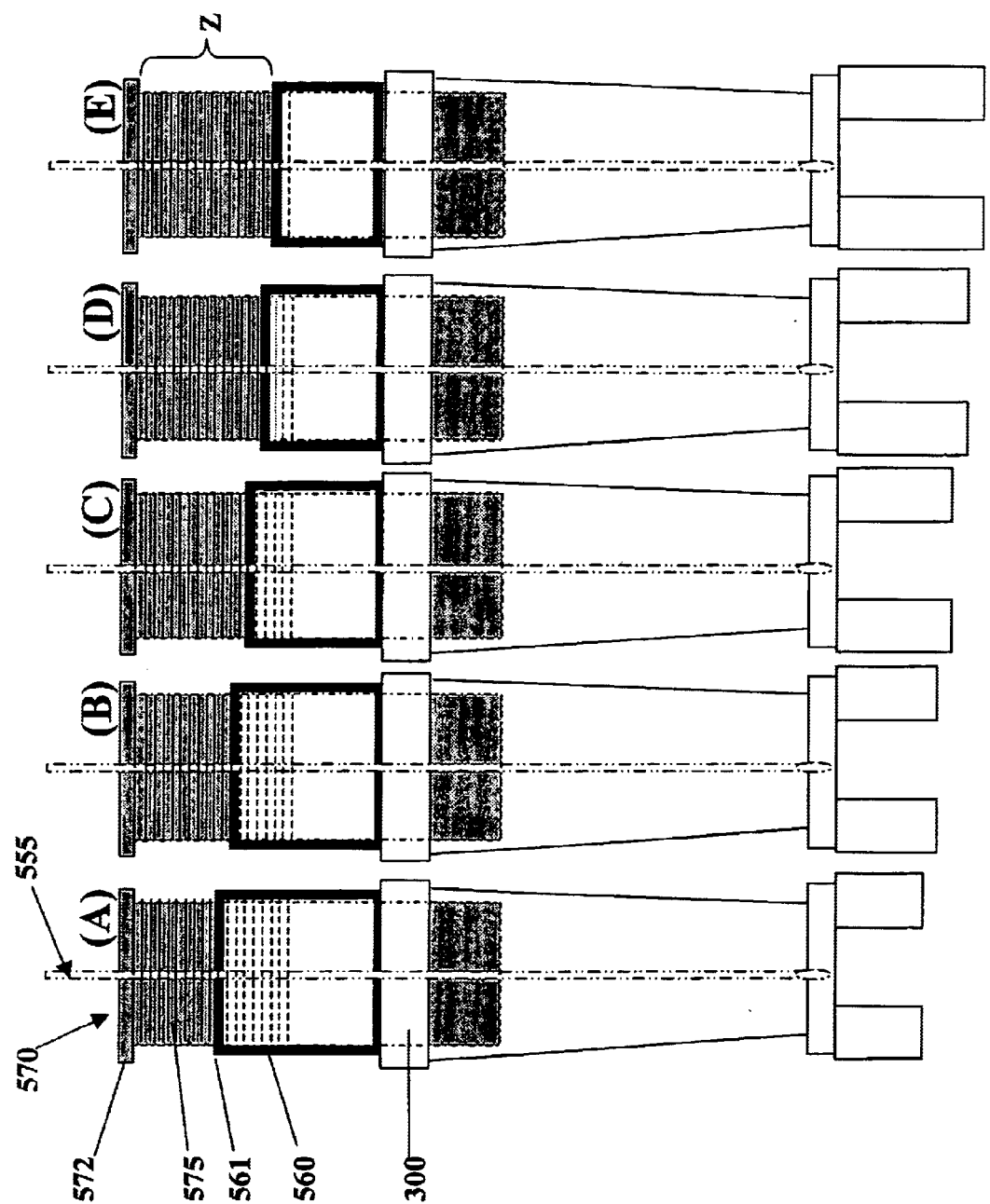
FIG. 67 is a schematic drawing of a system of an instrument positioning system in accordance with the present invention, and illustrates the relative starting positions of a burring block, a burring ring, a machining fixture, a drill bit, and a target disc space.
Figure 68:
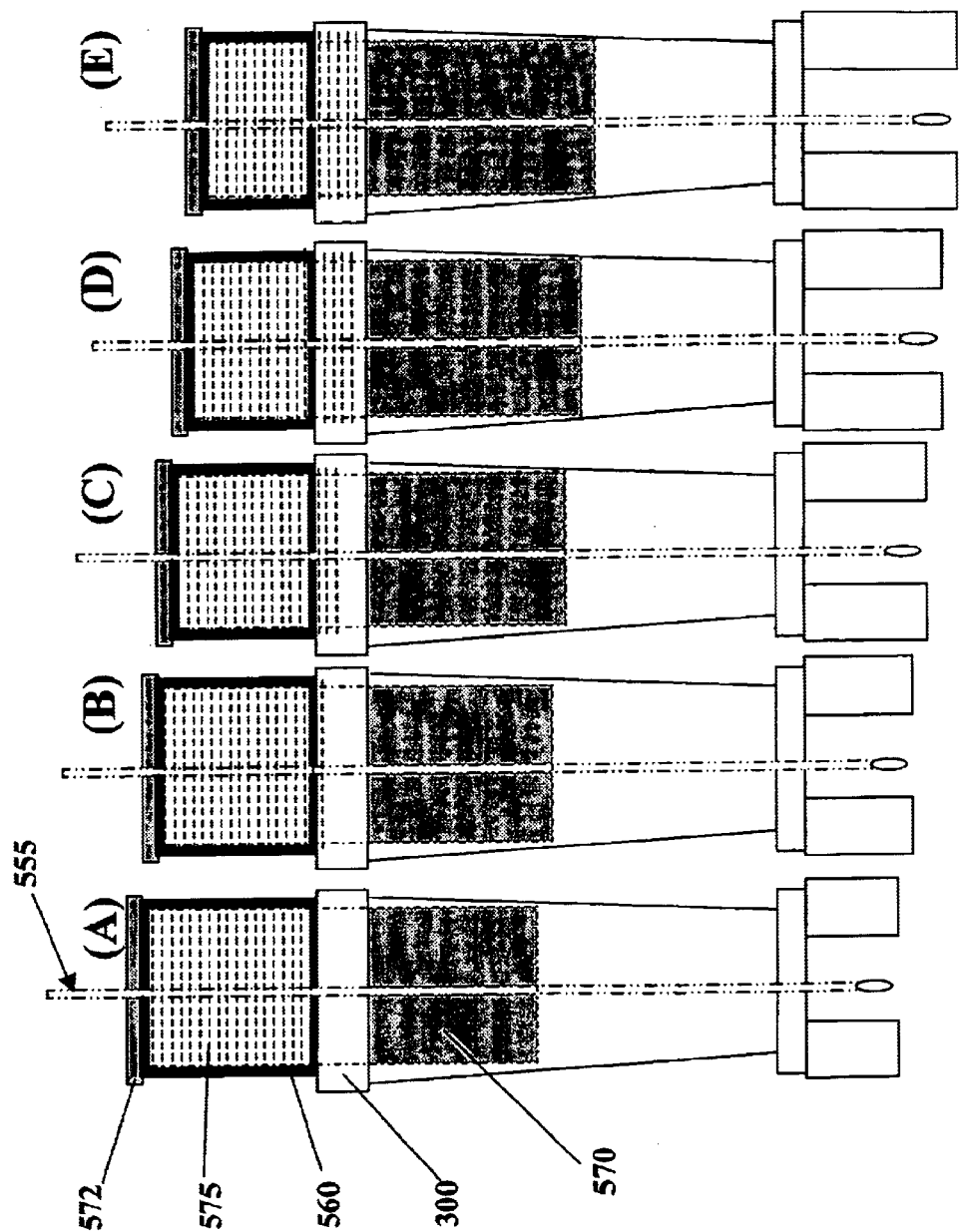
FIG. 68 is a schematic drawing of the system shown in FIG. 67, and illustrates the relative end positions of the various instruments.

Reference will now be made to FIG. 67 and FIG. 68 to describe how the distance between indicia 564 and flange 572 on block 570 (see FIG. 61) determine the anterior-posterior dimension of opening 912 illustrated in FIG. 66. As described above, preferably the system includes five rings 560 with each ring 560 corresponding to one of five prosthesis sizes. A preferred system includes up to five prosthesis sizes ranging in 1 mm increments from 14 mm to 18 mm. In accordance with an alternative embodiment, the system may include seven prosthesis sizes ranging in 1 mm increments from 12 mm to 18 mm. The rings 560 corresponding to each prosthesis size differ only in their height (H) dimension (see FIG. 62). All other dimensions, including the ring diameters and the thread dimensions, are the same on each ring. The height (H) of rings 560 increases in 1 mm increments going from the shortest ring corresponding to the 18 mm prosthesis (FIG. 67E) to the tallest ring corresponding to the 14 mm prosthesis (FIG. 67A). One skilled in the art will appreciate that the actual height (H) of the ring is a function of the length of the distance between the burr tip 557 and upper pin 556.

FIG. 67 illustrates a system wherein five rings 560 are positioned on burring blocks 570 at five different starting positions. The starting position for each block 560 is defined by indicia 564 (shown in FIG. 61, but not shown in FIG. 67). The upper surface 561 of each block 560 is aligned with its appropriate starting position indicia corresponding to the prosthesis size that will be implanted. As illustrated in FIG. 67, because the height (H) of each block varies, the relative starting positions of block 560, machining fixture 300 and burr 555 (including the burring attachment which is not shown) is the same for each prosthesis size configuration. FIG. 68 illustrates the final burring positions corresponding to the embodiments illustrated in FIG. 67, and represents the relative positions of the various instruments once the block 560 has been rotated about threaded section 575 until the upper surface 561 of block 560 abuts flange 572. Thus, FIG. 67 with reference to FIG. 68 illustrates that the distance "z" (indicated in FIG. 67E) defines the anterior-posterior dimension of opening 912 created within the disc space during the transverse burring operation. The distance "z" is the distance between the starting position indicia and the flange 572, Referring now to FIG. 33, if machining fixture 700 is being used, the machining fixture is first oriented with respect to one vertebral body, and the transverse burring operation outlined above is perform. Immediately thereafter, the endplate profile machining as outlined in the following section is done on the vertebral body to which the machining fixture 700 has been oriented. Machining fixture 700 is then reoriented with respect to the other vertebral body, i.e. connectors 402, shown in FIG. 41, securing machining fixture 700 to brace 400 are loosened, and machining fixture 700 is allowed to tilt in the opposite direction (i.e., if it is first tilted toward the cephalad direction, it is allowed to tilt in the caudal direction or vice versa). A transverse burring operation as outlined above is repeated, and thereafter the second endplate is machined in accordance with the procedure outlined below.

Alternatively, if the surgeon is using a multi-track machining fixture 750, which is shown in FIG. 36A, the transverse burring and endplate profile machining are done for each vertebral body endplate through tracks 752 and 754, respectively.

5) Endplate Profile Machining—Configuring the Instrumentation

Once the surgeon completes the transverse burring operation, the surgeon can perform the endplate profile machining operation. As described above, prior to the transverse burring operation, gauge 524 is adjusted to indicate the proper anterior-posterior position for the implant, and thus the proper position for the endplate profile machining. Gauge 524 can now be used to configure the profile machining instrumentation. The profile machining instrumentation includes milling cutter (also called milling head) 500 shown in FIG. 69 and milling attachment (also called milling tool) shown in FIG. 70.

Figure 69:
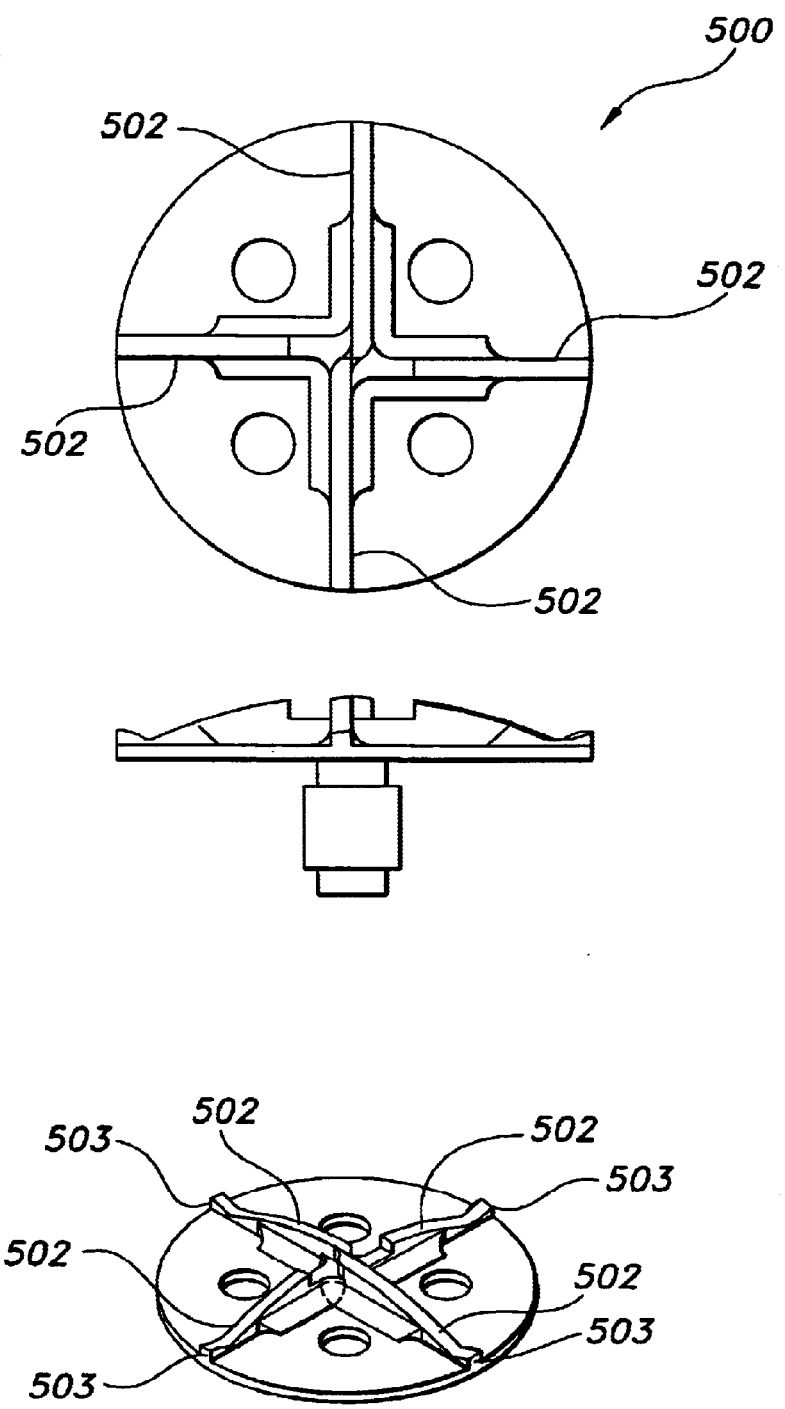
FIG. 69 is a top plan view (A), side plan view (B), and perspective view (C) of one embodiment of a milling cutter that is adapted to fit on the milling attachment shown in FIG. 70.
Figure 70A:
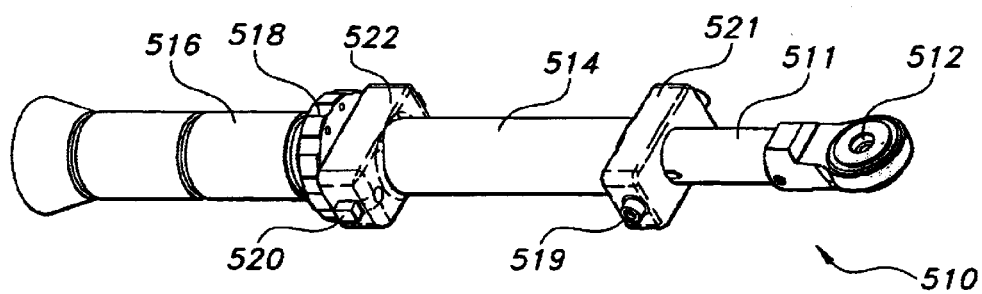
FIG. 70 is a perspective view (A), bottom plan view (B), side plan view (C), top plan view (D) and exploded perspective view (E) of one embodiment of a milling attachment of the present invention, showing generally, a head, securing block, an adjustable nut, and a drive connecting portion. The milling attachment is used to mill a precise concavity in a vertebral body.
Figure 70B:
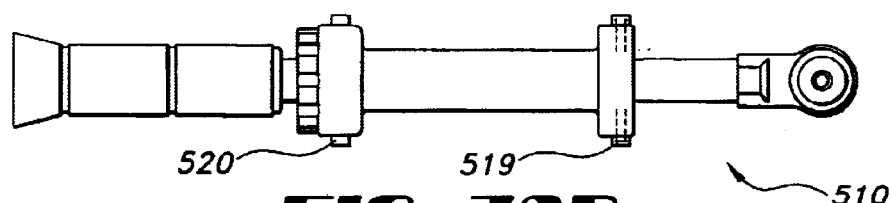
Figure 70C:
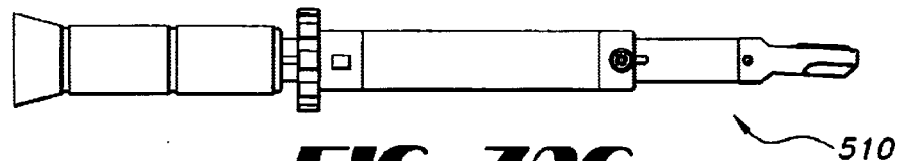
Figure 70D:
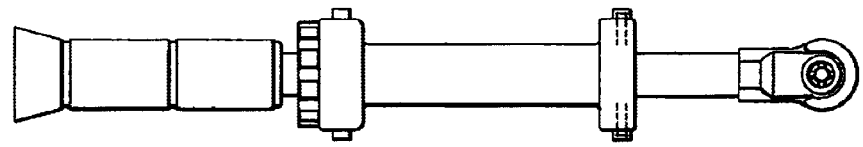
Figure 70E:
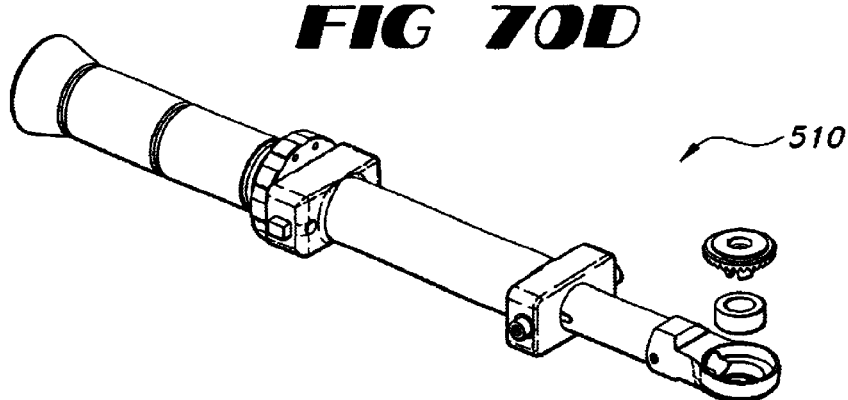

Referring now to FIG. 69, a milling cutter or milling head 500 is selected that corresponds to the size of the disc prosthesis (whose size was estimated before the surgery began and subsequently confirmed or adjusted during surgery). Milling cutter 500 is preferably circular and includes a cutting head with cutting blades or radially extending cutting flutes 503. Each flute 503 includes a leading edge that has a cutting surface 502. Cutting surfaces 502 are preferably along the center lines of the cutter 500, and in use make a concave shape in the endplates of the vertebral bodies that matches the convex shape of the implant. Other shapes or other profiles can be used, depending upon the shape or profile of the implant to be inserted.

Milling cutter 500 is designed to minimize heat generation in the bone surface that can kill local osteoblasts. Minimizing heat generation increases the likelihood of bony ingrowth into the subsequently implanted prostheses. In particular, the presence of a limited number of cutting surfaces with space between such surfaces, as well as openings 504 in the cutter, allow cooling of the bone surfaces and debris removal by facilitating access of circulating saline. This limits the temperature increase of the bone during milling, and minimizing the threat of thermal necrosis. Milling cutter 500 is typically made of stainless steel, but can be made of other materials, such as ceramics.

Milling cutter 500 is mounted onto a drive mechanism that includes milling attachment 510, shown in FIG. 70. The milling attachment or milling tool 510 has head 512, handle 514, telescoping shaft 511, drive connecting portion 516 and lower block 521 with lower pins 519 that cooperate with slot 312 of machining fixture 300. Handle 514 has an adjusting wheel 518, and an upper block 522 with keys 520 that cooperate with slots 314 of machining fixture 300 shown in FIG. 32 to control the range of motion in the sagittal direction. Adjusting wheel 518 allows the surgeon to extend or retract telescoping shaft 511 within handle 514 to adjust the position of machining in the anterior-posterior direction based upon the determination of the correct location that was made with gauge 524, and the size of the milling cutter 500. Head 512 is desirably angled with respect to handle 514, so that as the milling tool is moved in the sagittal direction during milling, cutting head 502 will be positioned appropriately with respect to the vertebral body endplates when keys 520 contact the ends of slots 314 shown in FIG. 32.

Block 521 may be located near head 512 of milling attachment 510, and may include pins 519 adapted to cooperate with saddle 534 of depth gauge, shown in FIG. 58. Pins 519 also cooperate with and contact the bottom of slots 312 of machining fixture 300 shown in FIG. 32 to locate milling attachment head 512 at the correct position within the intervertebral space.

Milling cutter 500 is secured to milling attachment head 512 using threads or other suitable methods. A wrench and driver are tools that are adapted to receive cutter 500 and assist in securing it to milling attachment head 512. Drive connecting portion 516 cooperates with a standard surgical drive mechanism or power source.

Figure 71:
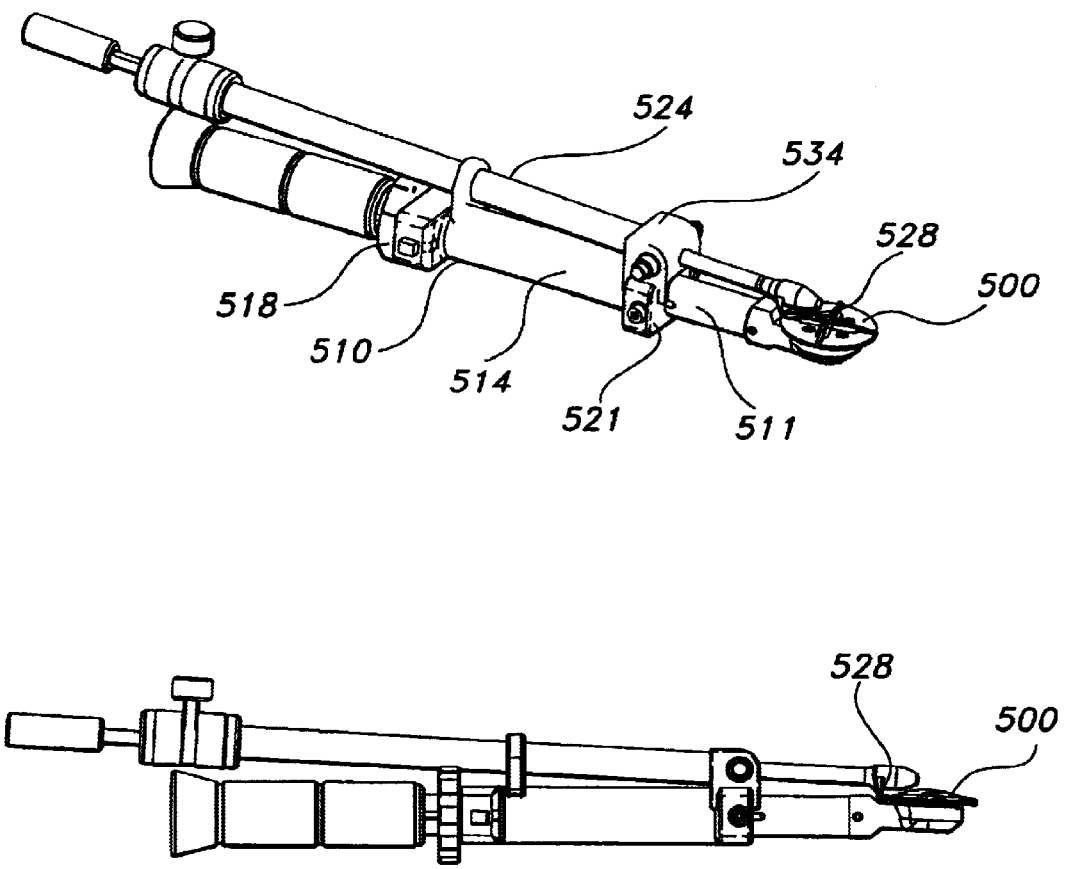
FIG. 71 is a perspective view (A) and a side view (B) of a milling attachment appropriately positioned adjacent to a gauge.

When the milling tool is assembled with the correct size cutting disc, the surgeon uses a gauge 524 shown in FIG. 58 to measure and set the correct machining position in the anterior-posterior direction. As illustrated in FIG. 71, depth gauge 524 is placed on milling attachment 510 so that saddle 534 engages lower block 521 on the milling attachment 510. Milling attachment 510 can then be adjusted by turning adjusting wheel 518 so that telescoping shaft 511 moves in or out of shaft 514 until contact surface 528 is in line with or contacts the outer diameter of cutting disc 500 as shown in FIG. 71. Because of this adjustment, the milling cutter 500 will machine the endplate tangent to the most anterior aspect of the most anterior vertebral body endplate and create the preferred machined profile illustrated in FIG. 59.

6) Machining the Vertebral Body Endplates

Prior to machining the vertebral body endplates, the surgeon should preferably again verify that the transverse burring operation created a sufficient space to accommodate insertion of the milling attachment and cutter into to the target disc space with disc 500 (shown in FIG. 69 and FIG. 70) oriented in each of the caudal and cephalic directions (without activating the power source). If the attachment 510 cannot be fully inserted, the surgeon may repeat the burring operation, or may attempt powered insertion of the milling tool.

Milling attachment 510 is then connected to the surgical power source, and inserted into machining fixture 300 and into the burred target disc space until pins 520 reach the distal ends of slots 314. Using continuous saline irrigation and suction, the surgeon mills a concavity in each vertebral body endplate by pivoting milling attachment 510 back and forth in a pecking motion within the limits defined by slots 314. The surgeon mills one vertebral body, removes milling attachment 510 and rotates it 180° and then mills the other vertebral body.

Again, if a tilting scaffold 700 embodiment is being used, after the first vertebral body has been milled, the connectors 402 securing scaffold 700 to brace 400 are loosened, and scaffold 700 is allowed to tilt in the opposite direction (i.e., if it is tilted toward the cephalad direction, it is allowed to tilt in the caudal direction or vice versa) and the opposite vertebral body is milled. Alternatively, if the surgeon is using a multi-track scaffold 750, the milling is done for each vertebral through angled tracks 752 and 754, respectively.

C. Placing The Prosthesis

Once the vertebral bodies have been prepared, the surgeon places the prosthesis in the machined disc space. During insertion, the space between the vertebral bodies must be maintained. If entryway 308 of machining fixture 300 is sized to receive prosthesis and prosthesis inserter, the steps below can be omitted. If entryway 308 of machining fixture 300 is not sized to receive these items, then the surgeon needs to remove machining fixture 300 before inserting the prosthesis, while maintaining the separation between the vertebral bodies. Additionally, the ability to insert the prosthesis without machining fixture 300 in the way provides the surgeon with a clearer view of the target space.

Figure 72A:
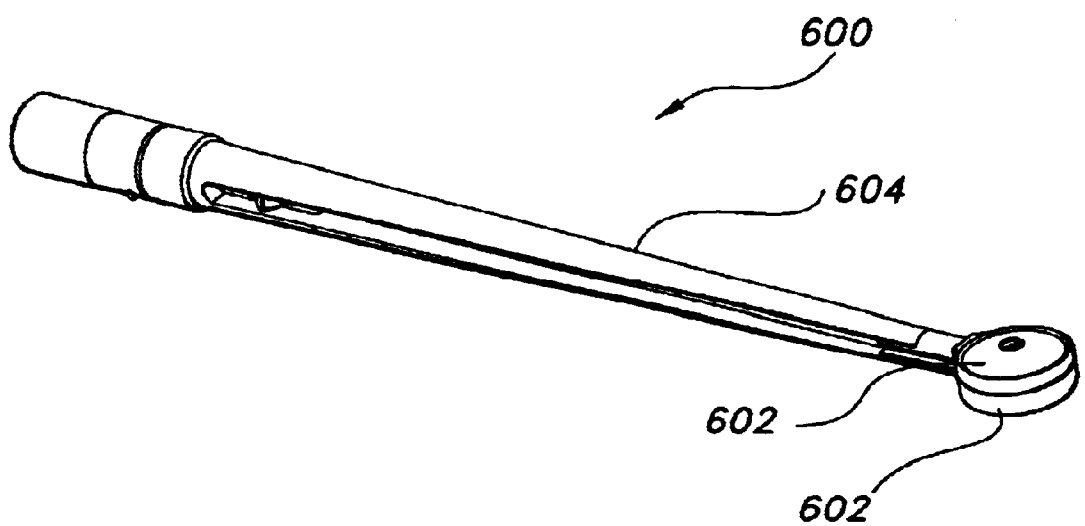
FIG. 72 A is a perspective view of one embodiment of a profile-matching distractor of the present invention, showing generally discs that correspond to the size of the milling cutter of FIG. 69.
FIG. 72B is two perspective views of an alternative embodiment of profile-matching distractor having a modified multi radius head profile. These distractors are used to maintain the space between the distracted and milled vertebral bodies.
FIGS. 72C and 72D are additional views of the embodiment shown in FIGS. 72A and 72B.
Figure 72B:
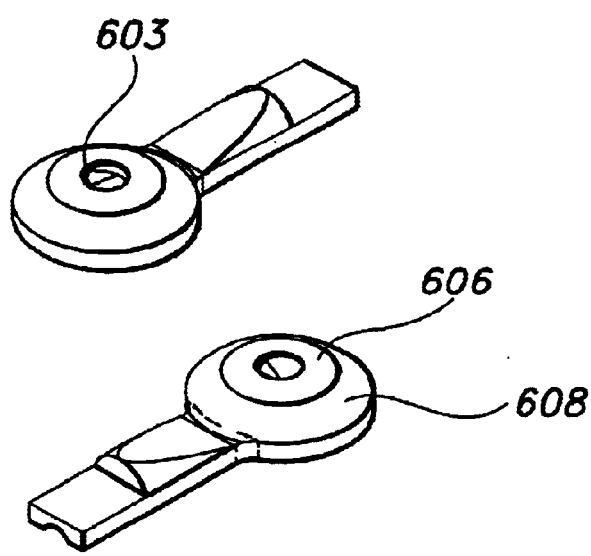
Figure 72C:
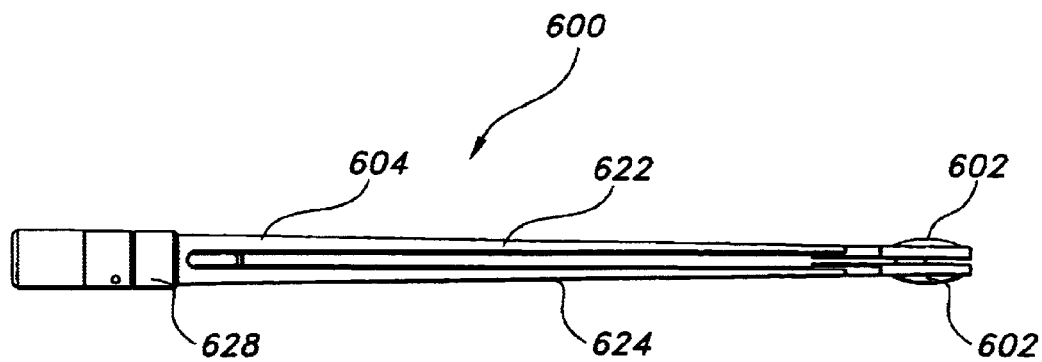
Figure 72D:
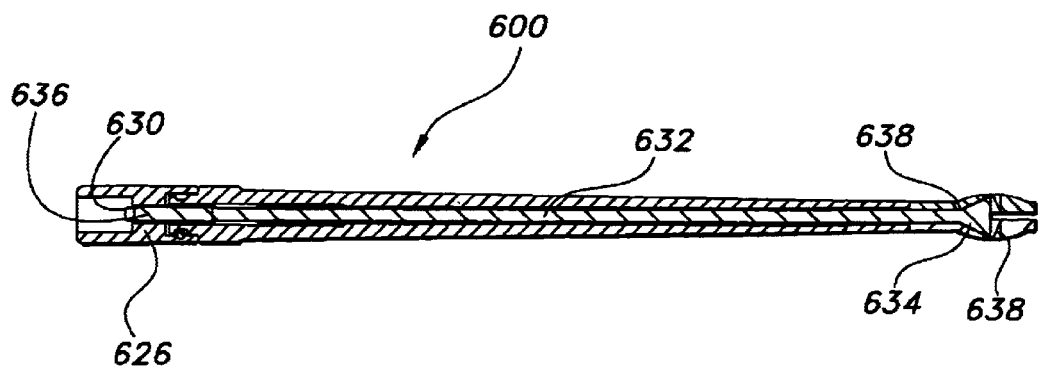
Figure 73:
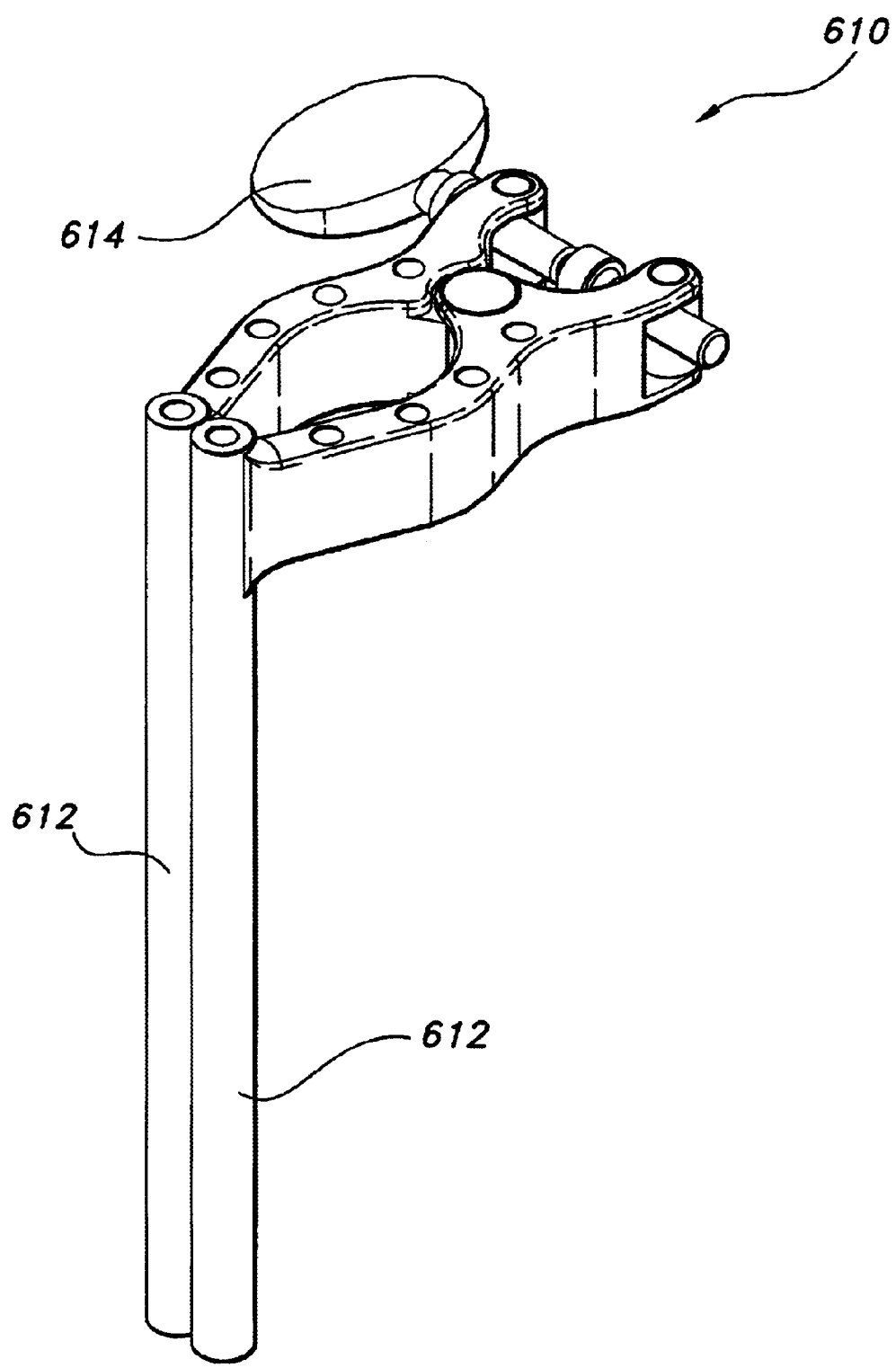
FIG. 73 is a perspective view of one embodiment of a tubular separator of the present invention, showing generally tubes that receive the anchor posts shown in FIG. 39, a thumbscrew that is used to tighten the tubular separator at the correct position, and locking mechanism to maintain distraction.

To remove machining fixture 300 and maintain spacing, the surgeon employs a space maintaining system, including machined endplate profile-matching distractor 600, shown in FIG. 72, and tubular separator 610, shown in FIG. 73. In accordance with a preferred embodiment, profile-matching distractor 600 includes first and second discs 602, a handle 604, an actuating nut 626, and an actuating shaft 632. Handle 604 includes a base portion 628 and first and second extensions 622, 624 that extend from base portion 628, wherein first and second extensions 622, 624 are attached to first and second discs 602 respectively. First and second discs (602) include tapered cavities 638 in their facing surfaces. The actuating nut 626 is rotatably mounted on the base portion and includes a threaded opening 630 therein. Actuating shaft 632 has a conically tapered end 634 and a threaded end 636, and is positioned between first and second extensions 622, 624 such that its threaded end 636 is positioned within the threaded opening 630 of the actuating nut 626 and its tapered end 634 is positioned within said tapered cavities 638 of first and second discs 602. In use, as actuating nut 626 is rotated, tapered end 634 of the actuating shaft 632 translates longitudinally, and as the enlarged portion of the taper moves out of the tapered cavities 638 first and second discs are pushed away from one another. In accordance with the embodiment shown in FIGS. 72C and D, discs 602 have outer geometries that are substantially similar to the geometry of the concavity milled in each vertebral body. Alternatively, in accordance with the embodiment shown in FIG. 72B, only a segment of the outer geometry of discs 603 approximately matches the geometry of a corresponding segment of the milled vertebral body cavity.

In accordance with one embodiment of the present invention, a plurality of profile-matching distractors 600 are provided, each one having circular discs 602 corresponding to the one of the various sizes of prosthesis. A profile-matching distractor is positioned within the prepared cavities within the prepared cavities, wherein the profile-matching distractor includes first and second discs (602), each having a segment whose geometry approximately matches the geometry of at least a portion of the corresponding cavity. Alternatively, one size is provided corresponding to the smallest prosthesis in the system.

Yet in accordance with another embodiment, a profile matching distractor 600 is provided wherein the discs 603 include multiple segments having difference curvature radii.

As shown in FIG. 72B, this embodiment includes disc 603 including a section having a first radius 606 and a second section having a second radius 608. Multiple radii enable the distractor disc to match the profile of more than one prosthesis size, and eliminate the need to have multiple distractors. Note that although two radii are shown, it is possible to have a plurality of radii on profile distractor 600. Alternatively, it is believed that two radii may be sufficient to distract vertebral bodies prepared to receive any of the various prosthesis sizes. In other words, the specific radii 608 need not perfectly match the size of the prosthesis to be implanted.

Circular discs 602 are attached to handle 604, and separate from each other a pre-determined distance. With circular discs collapsed, profile-matching distractor 600 is inserted through entryway 308 of machining fixture 300, and the circular discs are separated until they just touch the machined endplates. Once profile-matching distractor 600 is in place, circular discs 602 hold the vertebral bodies and keep the intervertebral space from closing. The surgeon can then remove brace 400, anchor post nuts 460, and machining fixture 300, leaving anchor posts 450 in place.

Tubular separator 610 shown in FIG. 73 has two tubes 612 that are adapted to engage anchor posts 450. Specifically, in one embodiment, tubular separator 610 is a skeletal joint distractor, comprising:

a. first and second tubes adapted to receive first and second anchors, respectively, that are positioned within tissue adjacent said joint;

b. a first arm having a distal end attached to said first tube and a second arm having a distal end attached to said second tube, wherein said first and second arms are movably connected to one another such said distal ends of said arms can be moved relative to each other; and c. an adjuster that controls the movement of said first and second arms relative to each other.

The separator or distractor may also have an adjusting screw attached to the first and second arms. Additionally or alternatively, the first and second arms are pivotally attached to one another between the adjusting screws. The surgeon rotates adjusting screw 614 to move the tubes 612 a distance apart that corresponds to the distance between the anchor posts. The surgeon then places tubes 612 of the tubular separator 610 over anchor posts 450. Profile-matching distractor 600 can then be collapsed and removed from the disc space.

A prosthesis may then be prepared for insertion into the disc space that has been prepared. The following description describes an exemplary implant embodiment and method in which the implant may be prepared for placement into the disc space. This method provides a preferred lubricated implant, but it should be understood that any acceptable prosthesis or insertion method may be used.

An exemplary prosthesis contains two rigid opposing shells, each having an outer surface adapted to engage the surfaces of the bones of a joint in such a way that frictional forces resist movement of the shells relative to the bone surface. The outer surfaces are sufficiently textured or rough so that frictional forces resist any relative motion between the prosthesis' outer surfaces and the bone surfaces within which the prosthesis is implanted. In addition to providing surface roughness, the outer surfaces may be adapted to allow for bone ingrowth, which over time provides further resistance to motion of the shells. The inner surfaces of the shells are relatively smooth, and adapted to conform to and slide easily across a portion of the outer surface of a deformable, resilient central body disposed between the shells. The central body has a shape that cooperates with the shape of the inner surface of the shell so as to provide a range of motion similar to that provided by a normal joint. This form of prosthesis is described more fully in copending U.S. patent application Ser. No. 09/783,910, filed Feb. 13, 2001, the entire contents of which are incorporated by reference.

Figure 74:
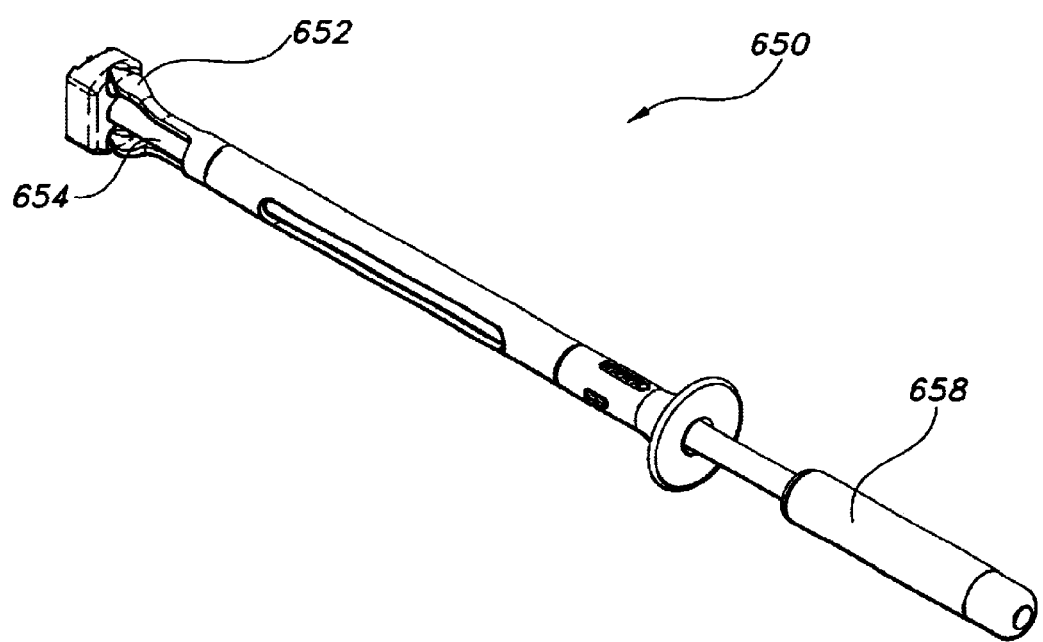
FIG. 74 is a perspective view of one embodiment of a prosthesis inserter of the present invention, which is adapted to insert a prosthesis into a prepared space using the methods of the present invention. Prosthesis inserter is shown having fingers that hold a prosthesis, a locking arm, and an ejector.

Once the prosthesis is prepared, it is attached to a prosthesis inserter 650. As shown in FIG. 74, prosthesis inserter 650 includes a locking arm (654); at least two fingers (652) extending from a distal end of said locking arm (654), and adapted to cooperate with openings in the prosthesis; and an ejector (658) movably mounted between said fingers having a pushing surface that can be positioned distal to said fingers (652) (extended position) and proximal to said fingers (652) (retracted position). Preferably ejector (658) is spring biased such that the pushing surface is biased to its extended position. In addition, preferably the device includes a locking mechanism allowing the pushing surface to be locked in either its extended position or its retracted position.

Prosthesis inserter 650 is then advanced toward the target intervertebral disc space, and the prosthesis is placed into the target space that is, the prosthesis is placed within the prepared cavities. If necessary, adjusting screw 614 of tubular separator 610 may be manipulated to widen the space.

To disengage the prosthesis from the inserter after it is positioned within the disc space, the surgeon activates ejector 658 and the fingers 652 release the prosthesis. Once the prosthesis is properly seated, the surgeon may confirm that the surfaces of the milled vertebral bodies fit substantially tightly against the convex surfaces of the inserted prosthesis. Once he is satisfied, he removes the tubular separator 610 and completes the surgery using standard closure procedures. The surgeon may do a final verification that prosthesis is placed properly using fluoroscopy.

In summary, one embodiment of the invention provides a method of inserting a prosthesis into a target intervertebral space comprising:

(a) forming a first cavity within a first vertebral body endplate adjacent the disc space;

(b) forming a second cavity within a second vertebral body endplate adjacent the disc space;

(c) positioning a profile-matching distractor within said first and second cavities, wherein said profile-matching distractor includes first and second discs, and said first disc has a segment whose geometry approximately matches the geometry of a portion of said first cavity, and said second disc has a segment whose geometry approximately matches the geometry of a portion of said second cavity;

(d) positioning a tubular distractor on first and second anchors extending from the adjacent vertebral bodies, wherein said tubular distractor includes: (1) first and second tubes adapted to receive said anchors, (2) a first arm having a distal end attached to said first tube and a second arm having a distal end attached to said second tube, wherein said first and second arms are movably connected to one another such said distal ends of said arms can be moved relative to each other, and (3) an adjuster that controls the movement of said first and second arms relative to each other;

(e) removing said profile-matching distractor (600) from the disc space;

(f) inserting said prosthesis into the disc space; and (g) removing said tubular distractor.

2. MULTI-LEVEL PROCEDURE

In some cases, the surgeon may desire to perform another disc implantation procedure at a disc space adjacent to the first procedure location. Accordingly, this invention also provides a method of implanting a first intervertebral disc prosthesis in a first intervertebral disc space of a patient and implanting a second intervertebral disc prosthesis in a second intervertebral disc space of the patient, wherein the first and second disc spaces are adjacent and are separated by a linking vertebral body, comprising:

(1) positioning a first fixture relative to the first disc space;

(2) securing the first fixture's position by attaching a fixation device to the first fixture and the linking vertebral body, wherein the fixation device includes a threaded lower portion that is threaded into the linking vertebral body and an upper portion adapted to extend through an aperture in the fixture and engage a locking mechanism;

(3) using the first fixture to position at least one instrument within the first disc space to prepare the first disc space to receive the first prosthesis;

(4) removing the first fixture from the upper portion of the fixation device, while leaving the lower portion of the fixation device threaded into the linking vertebral body;

(5) positioning a second fixture relative to the second disc space, wherein said second fixture includes a movable base having an open portion adapted to receive the upper portion of the fixation device;

(6) securing the second fixture's position by moving the movable base to capture the upper portion of the fixation device in the open portion of the movable base and securing a locking mechanism to the fixation device; and (7) using the second fixture to position at least one instrument within the second disc space to prepare the second disc space to receive the second prosthesis.

The invention also provides a method of implanting a second intervertebral disc prosthesis in a second intervertebral disc space of a patient, wherein the second intervertebral disc space is adjacent to a first intervertebral disc space having a first prosthesis previously implanted therein, and said first and second disc spaces are separated by a linking vertebral body, comprising:

(1) positioning a fixation device in an opening in the linking vertebral body, wherein said opening was initially formed to position an instrument for use in implanting the first prosthesis;

(2) positioning a fixture relative to the second disc space, wherein said second fixture includes a movable base having an open portion adapted to receive a portion of the fixation device;

(3) securing the second fixture's position by moving the movable base to capture the fixation device in the open portion of the movable base and securing a locking mechanism to the fixation device; and (4) using the second fixture to position at least one instrument within the second disc space to prepare the second disc space to receive the second prosthesis.

Figure 34A:
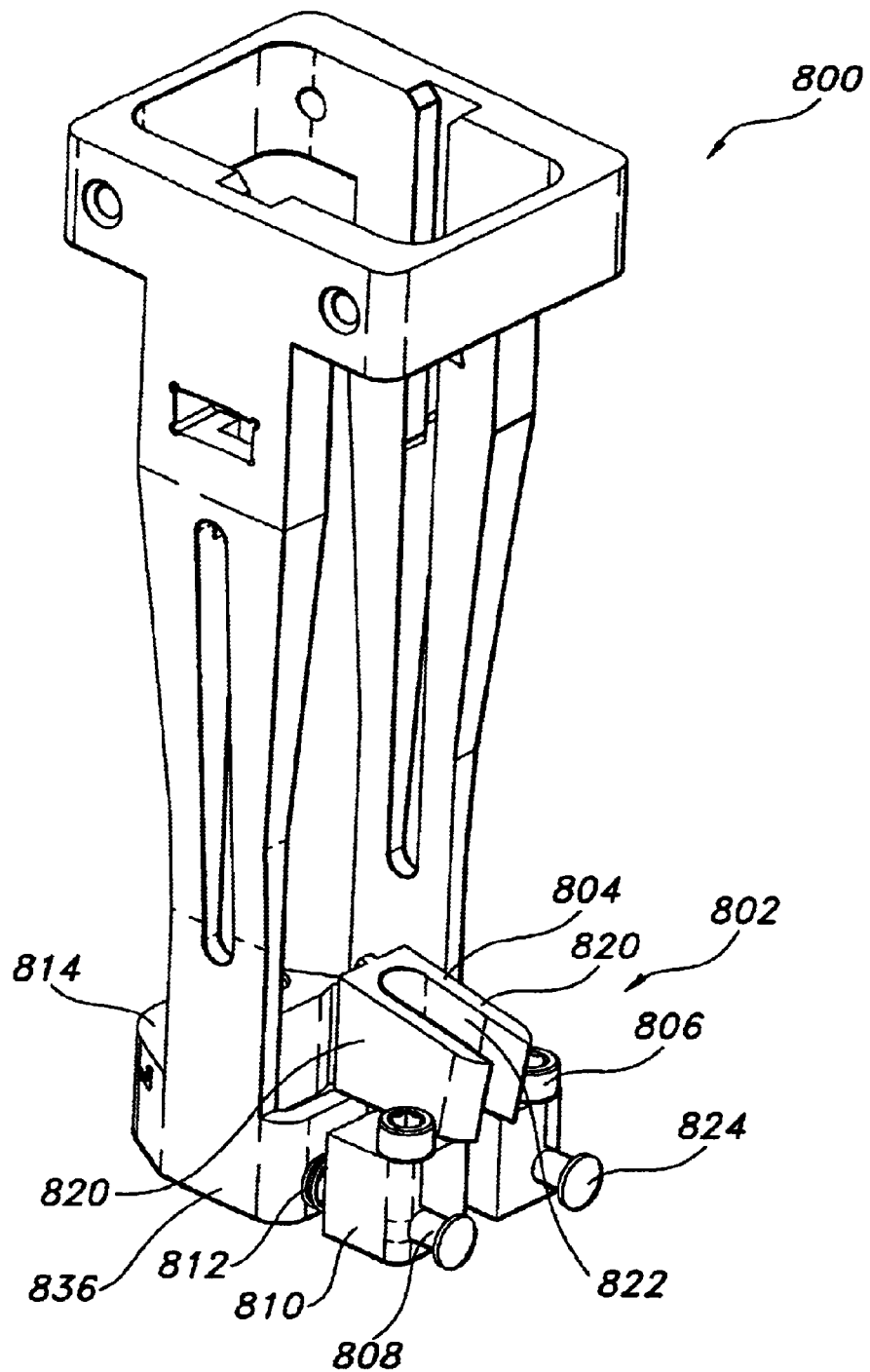
FIG. 34A is a top perspective view of one embodiment of a multi-level machining fixture that is adapted to receive, align, and secure various surgical instruments for use with a multi-level adjacent procedure, which is performed after a first prosthesis is placed in the first target disc space. During the multi-level adjacent procedure, a second prosthesis is placed in the disc space immediately adjacent to the first target disc space.
Figure 34B:
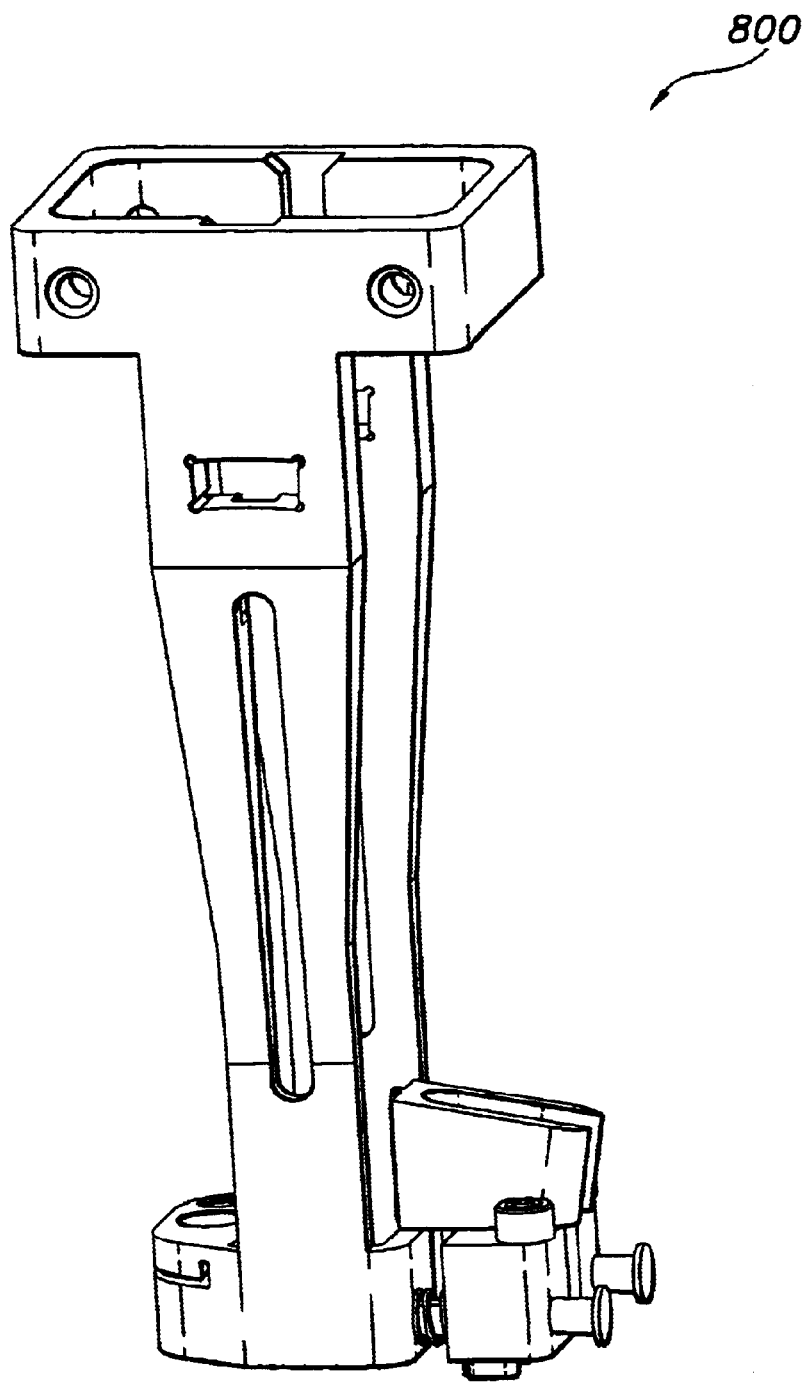
FIG. 34B shows a bottom perspective view of the machining fixture of FIG. 34A, showing more particularly the base adapted to adjustably receive a fixation device.
Figure 34C:
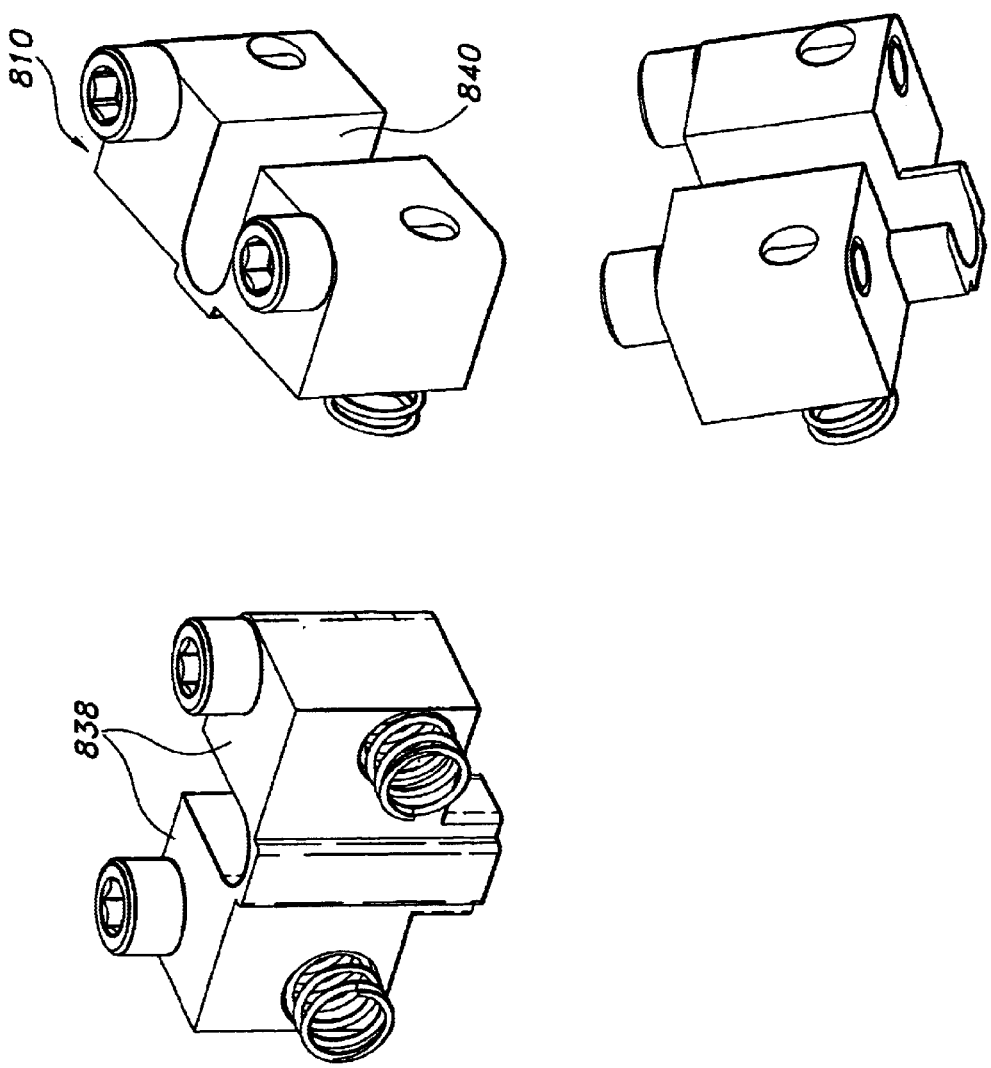
FIG. 34C is a perspective view of the movable base included in the machining fixture shown in FIG. 34A.

In order to accommodate this method, the present invention also provides a machining fixture 800 shown in FIG. 34A and FIG. 34B, and an alternative design machining fixture 780 shown in FIG. 35. Multi-level machining fixtures 800 and 780 are used to perform adjacent level procedures, i.e. procedures of the type described herein that are done at a spine disc space level that is adjacent to a spine level that already has a disc prosthesis implanted. The multi-level machining fixture can be used as part of a single surgical procedure where multiple prostheses are implanted at adjacent levels, or as part of a subsequent surgery where a prosthesis is implanted at a level that is adjacent to a prosthesis implanted during an earlier procedure.

Adjacent disc spaces share one common vertebral body that is located between them. Removing the machining fixture from the first disc space and removing the anchor post that has been placed in the common vertebral body leaves a hole in the vertebral body. If the surgeon desires to perform an adjacent level procedure, the surgeon will need to appropriately and precisely position the machining fixture relative to the second disc space. In doing so, the surgeon will necessarily need to use either the existing anchor post hole in the common vertebral body, or drill a new hole. The structural integrity of the new hole may be compromised if it overlaps with, or essentially merges with, or merely enlarges the existing hole. Such a compromised anchor post hole will result in a weak attachment of the anchor post to the vertebral body and inadequate fixation of the machining fixture. Therefore, it is desirable to lock the machining fixture in place using an anchor post that uses the previously created anchor post hole in the common vertebra. The base of the multi-level machining fixture must be adapted to allow both (1) adjustment and proper positioning of the machining fixture relative to the target disc space, and thereafter (2) fixation of the machining fixture using a previously positioned anchor post.

Accordingly, it is desirable to provide a multi-level machining fixture having a specifically configured base 802. As illustrated best in FIG. 34A, the base of multi-level machining fixture 800 includes an adjustable mounting device 830. The adjustable mounting device 830 enables the surgeon to properly position machining fixture 800 relative to a target disc space, and then lock the machining fixture into that position by using a previously positioned fixation apparatus. Adjustable mounting device 830 comprises receiving structure 804, movable base 810, base mounting member 808, biasing member 812, and position locker 806.

In accordance with the preferred embodiment shown in FIG. 34A, receiving structure 804 includes sides 820 that define an entryway 822 for receiving a fixation device such as an anchor post. In addition, receiving structure 804 is integrally mounted to fixed base 836. Movable base 810 is movably mounted on base mounting members 808, and is outwardly biased by the biasing member 812. The position locker 806 interfaces with movable base 810 and base mounting member 808 such that it can be configured to either allow or prevent motion between base 810 and mounting member 808. As shown best in FIG. 34C, movable base 810 is substantially U-shaped and includes sides 838 that define a second entryway 840. Second entryway 840 is generally aligned with entryway 822 in receiving structure 804.

In accordance with a preferred embodiment shown in FIG. 34A and FIG. 34B, base mounting member 808 is a pin extending outward from fixed base 836 of machining fixture 800. Movable base 810 is slideably mounted on pin 808. The biasing member 812 is a helical spring that encircles pin 808, and is positioned between fixed base 836 and movable base 810, and thereby biases movable base 810 in an outward direction. The position locker 806 is a setscrew positioned within a threaded opening that extends from an exterior surface of movable base 810 to pin 808.

After the surgeon has performed a single level procedure as described herein, he may desire to remove the machining fixture 300 and perform a second prosthesis implantation procedure using multi-level machining fixture 800. However, one skilled in the art will appreciate that it is also possible to use multi-level machining fixture 800 to perform a single level procedure as described herein with reference to machining fixture 300. In performing the second level implantation procedure, the surgeon will perform the same steps described above in the single level procedure until the surgeon reaches the point where the machining fixture is positioned over the sagittal centering tool. At that point the surgeon will configure the adjustable mounting device 830 such that the movable base 810 is locked in a position as close as possible to the fixed base 836. The surgeon will then position machining fixture 800 over the sagittal centering tool such that entryway 822 is directed toward the level of the previously implanted prosthesis. Machining fixture 800 is then loosely attached to machining fixture brace 400 (in the manner similar to that illustrated in FIG. 42 with reference to machining fixture 300), which generally holds the machining fixture in place, but allows for the final machining fixture positioning. Using the same technique described above with regard to the single level procedure, the surgeon will properly position the machining fixture 800 relative to the target disk space using an alignment block and machining fixture protractor or other appropriate apparatus. In addition to properly positioning the machining fixture relative to the target disc space, the surgeon must also make sure that the entryway 822 is generally aligned with the existing anchor post hole in the common vertebral body. When the machining fixture position is achieved, the surgeon places an anchor post through anchor post receiving portion 814 in the non-common vertebral body as described above with respect to machining fixture 300. If an anchor post is not already in the preexisting hole, an anchor post is also placed in that location. The position locker 806 is then released and the biasing member 812 advances the movable base 810 toward the anchor post in the common vertebral body until the anchor post is positioned within the receiving portion 840, and preferably completely within the receiving portion 840. The machining fixture is then locked in position using anchor post nuts and the machining fixture brace. The procedure is then completed in accordance with the steps outlined above with reference to machining fixture 300.

FIG. 35 illustrates an alternative embodiment of the multi-level machining fixture 780 of the present invention. In this embodiment adjustable mounting device 784 consists of a completely enclosed receiving structure 782 located preferably only on one side of the machining fixture 782. Enclosed receiving structure 782 includes an elongated opening 786 therein. Receiving structure 782 is integral with the base of the machining fixture 780, and it is not movable relative to thereto. With the exception of receiving structure 782, machining fixture 780 is the same as machining fixture 300 in all other respects.

In use, an anchor post is first positioned in the common vertebra, i.e. positioned in the same manner that it was positioned to secure the machining fixture during the first prosthesis implantation. Alternatively, if endoprostheses are being implanted at multiple levels during a single procedure, the anchor post could remain in position following the first procedure. Machining fixture 780 is then positioned over the common vertebral body anchor post such that the anchor post is received in the elongated opening 786.

Since the common vertebral body anchor post is originally positioned relative to the first disc space, it will generally be improperly angled relative to the second disc space. Therefore, in accordance with a preferred embodiment, the anchor post used in the common vertebral body is a flexible such that its nut attachment end can be angled relative to the bone attachment end. Two preferred embodiments of flexible anchor posts 1450 and 2450 are shown in FIG. 39B and C, respectively. Flexible anchor posts 1450 and 2450 include elements analogous to anchor post 450 including threaded portions 1454 and 2454, and screw threads 1456 and 2456. However, flexible anchor posts 1450, 2450 also include flexible segment 1452 and 2452 that interconnects the flexible anchor post's threaded portion and the screw threads. Flexible segment 1452 derives its flexibility primarily from the material characteristics of the segment. Flexible segment 1452 may be made from any flexible material such a rubber, a polymer or a flexible metal. Flexible segment 2452 derives its flexibility primarily from the mechanical design of the segment. In the specific example illustrated in FIG. 39C, flexible segment 2452 is made from a relatively rigid material, but includes scoring 2453 that allows segment 2452 to be flexible. In accordance with yet another embodiment of the present invention, the flexible segment of the anchor post may derive its flexibility from a combination of both material characteristics and mechanical design features.

The elongated and angled nature of opening 786 and the use of the flexible anchor post facilitates the placement of the machining fixture over the anchor post, and allows the surgeon to rotate the machining fixture in the caudal-cephalad direction until the proper positioning relative to the second target disc space is achieved in the manner described above with reference to machining fixtures 800 and 300. Once the machining fixture is properly positioned, it is locked in place using anchor post nuts and the machining fixture brace in the same manner described above. The procedure is then completed in accordance with the steps outlined above with reference to machining fixture 300.

In accordance with yet another embodiment of the present invention, a flexible anchor post is also used with multi-level machining fixture 800. More particularly, once a first anchor post 450 has been placed as described above for the non-shared vertebral body, a flexible anchor post 1450 or 2450, shown in FIG. 39, is inserted into the existing fixation post location of the common body. The flexible anchor post 1450, 2450 is then used to stabilize the machining fixture 800. Flexible anchor post 1450, 2450 is received through entryway 822, and moveable base 810 is adapted to be maneuvered along slides 808 to engage anchor post 1450, 2450. Optional springs 812 are provided because often, multi-level machining fixture 800 will be placed where there is tissue or other material that inhibits the ease of movement of movable base 810. Springs provide a means to move the movable base to an appropriate position, but it should be understood that the function provided by springs 812 may be provided by any structure that will bias movable base from base 802. In other words, a wedge or cam type instrument may be used to slide movable base 810 along slides 808, and other embodiments for moving movable base 810 would be obvious and apparent to those skilled in the art.

Once movable base 810 has been maneuvered such that it engages anchor post 1450, 2450, locking screws 806 are engaged to secure movable base 810. It is preferable for slides 808 to have stops 824 which maintain movable base 810 on slides 808 so that movable base is not removed from multi-level machining fixture 800 unnecessarily or unintentionally.

In summary, this embodiment of a multi-level machining fixture 800 provides a machining fixture for performing adjacent level procedures. Machining fixture 800 comprising a receiving structure 804 defining an entryway 822, a movable base 810 and a locking screw 806, wherein the entryway 822 of receiving structure 804 receives an anchor post 450, 1450, 2450, and the movable base 510 and locking screw 806 secure the anchor post 450, 1450, 2450 to secure the machining fixture 800 in place.

The particular embodiments of the invention having been described above are not limiting of the present invention, and those of skill in the art can readily determine that additional embodiments and features of the invention are within the scope of the appended claims and equivalents thereto.

What is claimed is:

1. A method for locating a preferred positioning for a prosthesis in a target implant location, comprising:
    (a) surgically exposing a skeletal joint;
    (b) locating a first plane within the target location in the transverse direction; and
    (c) locating a second plane within the target location in the sagittal direction,
    wherein the first and second planes intersect to define a line along which a preferred position for locating the prosthesis can be determined.

2. The method of claim 1 further comprising positioning a fixture such that it is collinear with the line, and such that said fixture may be used to position instruments for preparation of the target location for implantation of the prosthesis at the preferred position.

3. The method of claim 1, wherein the locating the first second planes further comprises:
    (a) using anatomical features as reference points to position a first tool to locate the first plane which defines the preferred transverse position for the center of the prosthesis;
    (b) positioning a second tool with respect to the preferred transverse position; and
    (c) using the second tool to locate second plane which define the preferred sagittal position for the center of the prosthesis, wherein the intersection of the preferred transverse position and the preferred sagittal position defines the line along which a preferred position for locating the center of the prosthesis can be determined.

4. The method of claim 3 wherein said anatomical features border the surgical site.

5. The method of claim 3 wherein said second tool is positioned with respect to the preferred transverse position by marking the preferred transverse position and using said mark to guide the positioning of the second tool.

6. The method of claim 3 wherein said first and second tools are the same instrument.

7. The method of claim 3 wherein the prosthesis is an intervertebral disc prosthesis and the preferred positioning of the center of the prosthesis is the lateral and caudal-cephalad anatomical center of the intervertebral disc space.

8. The method of claim 3 wherein the prosthesis is an intervertebral disc prosthesis and said method further comprises determining the preferred position for the center of the prosthesis by identifying a position along the line that positions the anterior edge of the prosthesis substantially tangent to the anterior edge of one of the adjacent vertebral bodies.

9. The method of claim 3 wherein the prosthesis is an intervertebral disc prosthesis and said method further comprises determining the preferred position for the center of the prosthesis by identifying a position along the line that positions the posterior edge of the prosthesis at least 1 mm anterior to the posterior edge of the disc space.

10. A system for positioning instruments within a patient's intervertebral disc space relative to a reference line, comprising:
    (a) a first instrument for locating and marking a transverse center of the disc space;
    (b) a second instrument for determining a sagittal center of the disc space that intersects with the transverse center;
    (c) an angle orienting instrument for adjusting the second instrument to be collinear with the reference line, which is positioned at a predetermined angle relative to a gravitational vector; and
    (d) a machining fixture that is positioned with the second instrument relative to the reference line, and which is adapted to position additional instruments relative to the reference line.

11. A system for positioning instruments relative to a line during spinal surgery, comprising:
    (a) a first instrument for determining a first point in a first plane and for indicating the position of the first point by marking a surgically exposed vertebral body;
    (b) a second instrument adapted to be positioned relative to the mark for adapted for locating a second plane substantially perpendicular to the first plane, wherein the first and second planes intersect to form a line;
    (c) a fixture adapted to be temporarily affixed to a vertebral body such that it is collinear with the reference line, and adapted to position site preparation instruments relative the line.

12. A method for locating a preferred implant location for a spinal intervertebral disc prosthesis and for preparing the spinal disc space for receiving the prosthesis, comprising:
    (a) determining an angle that defines the relation of the disc space relative to a gravitational vector;
    (b) stabilizing a frame over a general area of the disc space using an operating room table as a fixed base;
    (c) determining a preferred transverse position for locating the prosthesis within the disc space using a transverse positioning tool;
    (d) marking the preferred transverse position of the disc space;
    (e) determining the preferred sagittal position for locating the prosthesis within the disc space, comprising:
        (1) aligning a sagittal positioning tool with respect to the marked transverse position;
        (2) determining the preferred location of the sagittal positioning tool, which is the location at which an axis of the sagittal positioning tool is at an angle relative to the gravitational vector that is substantially equal to the angle that defines the relation of the disc space relative to the gravitational vector;
    (f) orienting a guide with respect to the preferred location of the sagittal positioning tool such that an axis of the guide is substantially parallel to said axis of the sagittal positioning tool;
    (g) anchoring the guide to the frame and to the vertebral bodies bordering the disc space; and
    (h) inserting site preparation tools through the guide to prepare the disc space for receiving a prosthesis, wherein the guide interfaces with the site preparation tools to control their position relative to the disc space and the adjacent vertebral bodies.

13. The method of claim 12 further comprising using a bubble level in cooperation with the transverse and sagittal positioning tools to locate the preferred positions for said tools.

14. The method of claim 12 wherein the guide has a connecting interface that corresponds to a connecting interface of the sagittal positioning tool and of the site preparation tools.

15. The method of claim 12, wherein the guide is anchored to the frame using clamps and anchored to the disc space by screws inserted at holes at a base of the guide.

16. A method for positioning one or more instruments for preparing a space between two vertebral bodies to receive an articulable prosthesis, the method comprising:

surgically exposing at least a portion of the space between the two vertebral bodies into which the articulable prosthesis will be placed;

inserting a first tool into the space for locating a first plane through the space in an axial direction;

inserting a second tool into the space for locating a second plane through the space in a sagittal direction;

positioning a fixture collinear with a reference line defined by the intersection of the first and second planes, wherein the fixture is adapted for positioning the one or more instruments relative to the reference line.

17. The method of claim 16 wherein the first and second tools are the same tool.

18. The method of claim 16 wherein locating the first plane comprises marking an anterior surface of one of the two vertebral bodies.

19. The method of claim 18 wherein marking the anterior surface of one of the two vertebral bodies includes marking the anterior surface of one of the two vertebral bodies with a pointed pin.

20. The method of claim 18 wherein marking the anterior surface of one of the two vertebral bodies includes marking the anterior surface of one of the two vertebral bodies with sterile ink.

21. The method of claim 16 further comprising removing bone from one of the vertebral bodies with the one or more instruments to prepare the vertebral body for receiving the articulable prosthesis.

* * * * *